US012163148B2

(12) United States Patent
Yeo et al.

(10) Patent No.: US 12,163,148 B2
(45) Date of Patent: Dec. 10, 2024

(54) DIRECTED EDITING OF CELLULAR RNA VIA NUCLEAR DELIVERY OF CRISPR/CAS9

(71) Applicant: The Regents of the University of California, La Jolla, CA (US)

(72) Inventors: Eugene Yeo, La Jolla, CA (US); Kristopher Brannan, La Jolla, CA (US); Ryan Marina, La Jolla, CA (US); David Nelles, La Jolla, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 17/811,626

(22) Filed: Jul. 11, 2022

(65) Prior Publication Data

US 2023/0053915 A1 Feb. 23, 2023

Related U.S. Application Data

(62) Division of application No. 15/975,728, filed on May 9, 2018, now Pat. No. 11,453,891.

(60) Provisional application No. 62/504,497, filed on May 10, 2017.

(51) Int. Cl.

| | |
|---|---|
| ***C12N 15/00*** | (2006.01) |
| ***A61P 21/00*** | (2006.01) |
| ***C12N 9/22*** | (2006.01) |
| ***C12N 15/11*** | (2006.01) |
| ***C12N 15/113*** | (2010.01) |
| ***C12N 15/85*** | (2006.01) |
| *A61K 48/00* | (2006.01) |

(52) U.S. Cl.

CPC .............. *C12N 15/85* (2013.01); *A61P 21/00* (2018.01); *C12N 9/22* (2013.01); *C12N 15/11* (2013.01); *C12N 15/113* (2013.01); *A61K 48/00* (2013.01); *C12N 2310/20* (2017.05); *C12N 2740/16043* (2013.01); *C12N 2750/14143* (2013.01)

(58) Field of Classification Search

CPC .......... C12N 15/85; C12N 9/22; C12N 15/11; C12N 15/113; C12N 2310/20; C12N 2740/16043; C12N 2750/14143; A61P 21/00; A61K 48/00

See application file for complete search history.

(56) References Cited

U.S. PATENT DOCUMENTS

| | | | |
|---|---|---|---|
| 3,687,808 | A | 8/1972 | Merigan et al. |
| 5,034,506 | A | 7/1991 | Summerton et al. |
| 5,166,315 | A | 11/1992 | Summerton et al. |
| 5,185,444 | A | 2/1993 | Summerton et al. |
| 5,214,134 | A | 5/1993 | Weis et al. |
| 5,216,141 | A | 6/1993 | Benner |
| 5,235,033 | A | 8/1993 | Summerton et al. |
| 5,264,562 | A | 11/1993 | Matteucci |
| 5,264,564 | A | 11/1993 | Matteucci |
| 5,405,938 | A | 4/1995 | Summerton et al. |
| 5,434,257 | A | 7/1995 | Matteucci et al. |
| 5,466,677 | A | 11/1995 | Baxter et al. |
| 5,470,967 | A | 11/1995 | Huie et al. |
| 5,489,677 | A | 2/1996 | Sanghvi et al. |
| 5,539,082 | A | 7/1996 | Nielsen et al. |
| 5,541,307 | A | 7/1996 | Cook et al. |
| 5,561,225 | A | 10/1996 | Maddry et al. |
| 5,596,086 | A | 1/1997 | Matteucci et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,618,704 | A | 4/1997 | Sanghvi et al. |
| 5,623,070 | A | 4/1997 | Cook et al. |
| 5,633,360 | A | 5/1997 | Bischofberger et al. |
| 5,663,312 | A | 9/1997 | Chaturvedula |
| 5,677,437 | A | 10/1997 | Teng et al. |
| 5,677,439 | A | 10/1997 | Weis et al. |
| 5,714,331 | A | 2/1998 | Buchardt et al. |
| 5,719,262 | A | 2/1998 | Buchardt et al. |
| 6,013,639 | A | 1/2000 | Peyman et al. |
| 6,461,864 | B1 | 10/2002 | Soriano et al. |
| 6,471,996 | B1 | 10/2002 | Sokoll et al. |
| 6,472,375 | B1 | 10/2002 | Hoon et al. |
| 7,074,596 | B2 | 7/2006 | Darzynkiewicz et al. |
| 7,078,387 | B1 | 7/2006 | Leiden et al. |
| 8,304,529 | B2 | 11/2012 | Kore et al. |
| 8,697,359 | B1 | 4/2014 | Zhang |

(Continued)

FOREIGN PATENT DOCUMENTS

| | | | |
|---|---|---|---|
| CA | 3093580 | A1 | 9/2019 |
| CN | 106103705 | | 11/2016 |

(Continued)

OTHER PUBLICATIONS

GenBank Accession No. NP 001124150.1, "eukaryotic translation initiation factor 4E isoform 3 [*Homo sapiens*], " Sep. 3, 2019, 3 pages.

(Continued)

*Primary Examiner* — Catherine S Hibbert

(74) *Attorney, Agent, or Firm* — Fish & Richardson P.C.

(57) ABSTRACT

Disclosed herein is a technology to perform programmable RNA editing at single-nucleotide resolution using RNA-targeting CRISPR/Cas9. This approach, which Applicants have termed "Cas9-directed RNA editing" or "CREDIT," provides a means to reversibly alter genetic information in a temporal manner, unlike traditional CRISPR/Cas9 driven genomic engineering which relies on permanently altering DNA sequence.

11 Claims, 14 Drawing Sheets

Specification includes a Sequence Listing.

(56) References Cited

U.S. PATENT DOCUMENTS

| | | | | |
|---|---|---|---|---|
| 9,074,199 | B1 | 7/2015 | Chavez et al. | |
| 11,453,891 | B2 | 9/2022 | Yeo et al. | |
| 11,667,903 | B2 | 6/2023 | Yeo et al. | |
| 2002/0068709 | A1 | 6/2002 | Orum et al. | |
| 2015/0056702 | A1 | 2/2015 | Conway | |
| 2015/0056705 | A1 | 2/2015 | Conway et al. | |
| 2015/0071899 | A1 | 3/2015 | Liu et al. | |
| 2015/0232844 | A1 | 8/2015 | Ozsolak | |
| 2015/0353905 | A1 | 12/2015 | Weiss | |
| 2016/0138012 | A1 | 5/2016 | Wickens et al. | |
| 2016/0214276 | A1 | 7/2016 | Liu | |
| 2016/0215276 | A1 | 7/2016 | Liu et al. | |
| 2016/0238593 | A1 | 8/2016 | Biyden et al. | |
| 2016/0289659 | A1 * | 10/2016 | Doudna | C12P 19/34 |
| 2016/0304846 | A1 | 10/2016 | Liu et al. | |
| 2016/0362667 | A1 | 12/2016 | Donohue et al. | |
| 2017/0073670 | A1 | 3/2017 | Nishida et al. | |
| 2018/0073012 | A1 | 3/2018 | Liu et al. | |
| 2018/0208924 | A1 | 7/2018 | Fukuda et al. | |
| 2018/0273576 | A1 | 9/2018 | Hogrefe et al. | |
| 2019/0062724 | A1 | 2/2019 | Hsu et al. | |
| 2020/0239863 | A1 | 7/2020 | Yeo | |
| 2021/0079366 | A1 | 3/2021 | Zhang et al. | |
| 2021/0332344 | A1 | 10/2021 | Yeo et al. | |
| 2021/0340197 | A1 | 11/2021 | Yeo et al. | |
| 2022/0127621 | A1 | 4/2022 | Yeo et al. | |
| 2022/0204978 | A1 | 6/2022 | Yeo et al. | |
| 2022/0220473 | A1 | 7/2022 | Yeo et al. | |
| 2023/0365951 | A1 | 11/2023 | Yeo et al. | |

FOREIGN PATENT DOCUMENTS

| | | | | |
|---|---|---|---|---|
| CN | 108103090 | | 6/2018 | |
| CN | 110055284 | | 7/2019 | |
| JP | 2015-506669 | | 3/2015 | |
| JP | 2019-500899 | A | 1/2019 | |
| WO | WO 1998/39352 | | 9/1998 | |
| WO | WO 1999/14226 | | 3/1999 | |
| WO | WO 2000/066604 | | 11/2000 | |
| WO | WO 2009/066758 | | 5/2009 | |
| WO | WO 2009/149253 | | 12/2009 | |
| WO | WO 2001/75097 | | 10/2011 | |
| WO | WO 2012/068627 | | 5/2012 | |
| WO | WO 2013/058404 | | 4/2013 | |
| WO | WO 2013/082548 | | 6/2013 | |
| WO | WO 2013/130684 | | 9/2013 | |
| WO | WO 2014/093622 | | 6/2014 | |
| WO | WO 2014/093635 | | 6/2014 | |
| WO | WO 2014/093661 | | 6/2014 | |
| WO | WO 2014/113493 | | 7/2014 | |
| WO | WO 2014/191518 | | 12/2014 | |
| WO | WO 2014/191521 | | 12/2014 | |
| WO | WO 2015/006294 | | 1/2015 | |
| WO | WO 2015/048690 | | 4/2015 | |
| WO | WO 2015/089277 | | 6/2015 | |
| WO | WO 2015/089351 | | 6/2015 | |
| WO | WO 2015/089354 | | 6/2015 | |
| WO | WO 2016/019655 | | 2/2016 | |
| WO | WO 2016/097212 | | 6/2016 | |
| WO | WO 2016/106236 | | 6/2016 | |
| WO | WO-2016097212 | A1 * | 6/2016 | C12N 15/11 |
| WO | WO 2016/183402 | | 11/2016 | |
| WO | WO 2016/191684 | | 12/2016 | |
| WO | WO 2016/196655 | | 12/2016 | |
| WO | WO 2016/196805 | | 12/2016 | |
| WO | WO 2016/201138 | | 12/2016 | |
| WO | WO-2016201138 | A1 * | 12/2016 | C12N 9/22 |
| WO | WO 2017/010556 | | 1/2017 | |
| WO | WO 2017/053297 | | 3/2017 | |
| WO | WO 2017/053312 | | 3/2017 | |
| WO | WO-2017053312 | A1 * | 3/2017 | B82Y 5/00 |
| WO | WO 2017/091630 | | 6/2017 | |
| WO | WO 2017/219027 | | 12/2017 | |
| WO | WO 2018/002697 | | 1/2018 | |
| WO | WO 2018/027078 | | 2/2018 | |
| WO | WO 2018/075827 | | 4/2018 | |
| WO | WO 2018/154387 | | 8/2018 | |
| WO | WO 2018/183703 | | 10/2018 | |
| WO | WO 2019/006471 | | 1/2019 | |
| WO | WO 2019/040664 | | 2/2019 | |
| WO | WO 2019/060746 | | 3/2019 | |
| WO | WO 2019/204828 | | 10/2019 | |

OTHER PUBLICATIONS

Adamala et al., "Programmable RNA-binding protein composed of repeats of a single modular unit," Proceedings of the National Academy of Sciences, May 10, 2016, 113(19):E2579-E2588.

Akerstrom et al., "A physicochemical study of protein G, a molecule with unique immunoglobulin G-binding properties," J. Biol. Chem., 1986, 261: 10,240-10,247.

Allocca et al., "Novel adeno-associated virus serotypes efficiently transduce murine photoreceptors," Journal of virology, Oct. 15, 2007, 81(20):11372-11380.

Anant et al., "Molecular mechanisms of apolipoprotein B mRNA editing,"Current opinion in lipidology, Apr. 1, 2001, 12(2):159-165.

Asokan et al., "The AAV vector toolkit: poised at the clinical crossroads," Molecular Therapy, Apr. 1, 2012, 20(4):699-708.

Bashor et al., "Using engineered scaffold interactions to reshape MAP kinase pathway signaling dynamics, " Science, 2008, 319(5869):1539-1543.

Basolo et al., "RET protein expression has No. prognostic impact on the long-term outcome of papillary thyroid carcinoma," European journal of endocrinology, Nov. 1, 2001, 145(5):599-604.

Batra et al., "Elimination of Toxic Microsatellite Repeat Expansion RNA by RNA-Targeting Cas9," Cell, 2017, 170(5):889-912.e10, 34 Pages.

Batra et al., "Loss of MBNL Leads to Disruption of Developmentally Regulated Alternative Polyade in RNA-Mediated Disease," Mol. Cell, Oct. 2014, 56(2):311-322.

Bennett et al., "RNA targeting therapeutics: molecular mechanisms of antisense oligonucleotides as a therapeutic platform," Anmi Rev Pharmacol Toxicol, 2010, 50: 259-293.

Bertrand et al., "Localization of ASHI mRNA particles in living yeast," Molecular cell, Oct. 1, 1998, 2(4):437-445.

Beuth et al., "Structure of a *Mycobacterium tuberculosis* NusA-RNA complex," The EMBO journal, Oct. 19, 2005, 24(20):3576-3587.

Bjerke et al., "Recent Advances in CRISPR Base Editing: From A to RNA," Biochemistry, Jan. 26, 2018, vol. 57, pp. 886887.

Bjorck et al., "Purification and some properties of streptococcal protein G, a novel IgG-binding reagent," J. Immunol., 1984, 133:969-974.

Blanc et al., "C-to-U RNA editing: mechanisms leading to genetic diversity," Journal of Biological Chemistry, Jan. 17, 2003, 278(3):1395-1398.

Borghardt et al., "Inhaled Therapy in Respiratory Disease: The Complex Interplay of Pulmonary Kinetic Processes," Canadian Respiratory Journal, 2018, 1-11.

Braasch et al., "Novel antisense and peptide nucleic acid strategies for controlling gene expression," Biochemistry, Apr. 9, 2002,41(14):4503-4510.

Braddock et al., "Structure and dynamics of KH domains from FBP bound to single-stranded DNA," Nature, Feb. 2002, 415(6875):1051-1056.

Brezgin et al., "Dead Cas systems: types, principles, and applications," International journal of molecular sciences, Jan. 2019, 20(23):6041, 26 pages.

Buchan et al., "Eukaryotic stress granules: the ins and outs of translation," Molecular cell, Dec. 24, 2009, 36(6):932-941.

Buxbaum et al., "Single β-actin mRNA detection in neurons reveals a mechanism for regulating its translatability," Science, Jan. 24, 2014, 343(6169): 5 Pages.

Cai et al., "Quantitative assessment of mRNA cap analogues as inhibitors of in vitro translation," Biochemistry, Jun. 29, 1999, 38(26):8538-8547.

(56) References Cited

OTHER PUBLICATIONS

Cao et al., "A universal strategy for regulating mRNA translation in prokaryotic and eukaryotic cells," Nucleic acids research, Apr. 30, 2015 43(8):4353-4362.
Cencic et al., "Protospacer adjacent motif (PAM)-distal sequences engage CRISPR Cas9 DNA target cleavage," PloS one, Oct. 2, 2014, 9(10):e109213, 13 Pages.
Chen et al., "Dynamic imaging of genomic loci in living human cells by an optimized CRISPR/Cas system," Cell, Dec. 19, 2013, 155(7):1479-1491.
Chen et al., "Structure-guided design, synthesis, and evaluation of guanine-derived inhibitors of the eIF4E mRNA-cap interaction," Journal of medicinal chemistry, Apr. 26, 2012, 55(8):3837-3851.
Cheong et al., "Engineering RNA sequence specificity of Pumilio repeats," Proceedings of the National Academy of Sciences, Sep. 12, 2006, 103(37):13635-13639.
Cho et al., "Targeted genome engineering in human cells with the Cas9 RNA-guided endonuclease," Nature biotechnology, Mar. 2013, 31(3): 230-232.
Chou et al., "Picky: oligo microarray design for large genomes," Bioinformatics, 2004, 20(17):2893-28902.
Choudhury et al., "Engineering RNA endonucleases with customized sequence specificities," Nature communications, Oct. 23, 2012, 3(1):1-18.
Cichowski et al., "NF1 tumor suppressor gene function: narrowing the GAP," Cell, Feb. 23, 2001, 104(4):593-604.
Cokol et al., "Finding nuclear localization signals," EMBO reports, Nov. 1, 2000, 1(5):411-415.
Cong et al., "In Vivo Genome Engineering With AAV Vector Carrying CRISPR-Cas9 System," InMolecular Therapy, May 1, 2014, 22(1): S214, Abstract 551.
Cong et al., "Multiplex genome engineering LJsing CRISPR/Cas systems," Science, Feb. 15, 2013, 339(6121): 6 Pages.
Cooke et al., "Targeted translational regulation using the PUF protein family scaffold," Proceedings of the National Academy of Sciences, Sep. 20, 2011, 108(38):15870-15875.
Cox et al., "RNA editing with CRISPR_Cas13," Science, 2017, 358(6366):1019-1027.
De Mesmaeker et al., "Antisense oligonucleotides," Accounts of Chemical Research, Sep. 1, 1995, 28(9):366-374.
De Zoysa et al., "Posttranscriptional RNA pseudouridylation," The enzymes, Jan. 1, 2017, 41:151-167.
Deer et al., "High-level expression of proteins in mammalian cells using transcription regulatory sequences from the Chinese hamster EF-1α gene, " Biotechnology progress, 2004, 20(3):880-889.
DeJesus-Hernandez et al., "Expanded GGGGCC hexanucleotide repeat in noncoding region of C9ORF72 causes chromosome 9p-linked FTD and ALS," Neuron, Oct. 20, 2011, 72(2): 245-256.
Delebecque et al., "Organization of intracellular reactions with rationally designed RNA assemblies," Science, Jul. 22, 2011 333(6041): 7 Pages.
Deyle et al., "Adeno-associated virus vector integration," Current opinion in molecular therapeutics, Aug. 2009, 11(4):442-447.
Doench et al., "Rational design of highly active sgRNAs for CRISPR-Cas9-mediated gene inactivation," Nature biotechnology, 2014, 32(12): 8 Pages.
Dong et al., "Quantitative analysis of the packaging capacity of recombinant adeno-associated virus," Human gene therapy, Nov. 10, 1996, 7(17):2101-2112.
Donnelly et al., "Limited availability of ZBP1 restricts axonal mRNA localization and nerve regeneration capacity," The EMBO journal, Nov. 16, 2011, 30(22):4665-4677.
Dow et al., "Inducible in vivo genome editing with CRISPR-Cas9," Nature biotechnology, Apr. 2015, 33(4): 7 Pages.
Du et al., "m 6 A RNA methylation controls neural development and is involved in human diseases," Molecular neurobiology, Mar. 2019, 56(3):1596-1606.
Dueber et al., "Synthetic protein scaffolds provide modular control over metabolic flux," Nature biotechnology, Aug. 2009, 27(8): 9 Pages.
Durand et al., "The inside out of lentiviral vectors," Viruses, Feb. 2011, 3(2):132-159.
Durocher et al., "High-level and high-throughput recombinant protein production by transient transfection of suspension-growing human 293-EBNA1 cells," Nucleic Acids Research, 2002, 30(2), 9 pages.
Eliasson et al., "Chimeric IgG-binding receptors engineered from staphylococcal protein A and streptococcal protein G," J. Biol. Chem., 1988, 263:4323-4327.
Encode Project ConsortiL. 1m, The; "An integrated encyclopedia of DNA elements in the human genome," Nature, 2012, 489(7414): 57-74.
Englisch et al., "Chemically modified oligonucleotides as probes and inhibitors," Angewandte Chemie International Edition in English, Jun. 1991, 30(6):613-629.
Esakova et al., "Of proteins and RNA: the RNase P/MRP family," Rna, Sep. 1, 2010, 16(9):1725-1747.
Esvelt et al., "Orthogonal Cas9 proteins for RNA-guided gene regulation and editing," Nature methods, Nov. 2013, 10(11): 8 Pages.
Extended European Search Report in EP Appln. No. 18799398, dated May 15, 2020, 11 pages.
Extended European Search Report in EP Appln. No. 19788702.9, dated Oct. 13, 2021, 11 pages.
Fernanda et al., "Current strategies for site-directed RNA editing using ADARs," Methods, 2018, 156:16-24.
Filipovska et al., "A universal code for RNA recognition by PUF proteins," Nature chemical biology, Jul. 2011, 7(7): 4 Pages.
Fouts et al., "Functional recognition of fragmented operator sites by R17/MS2 coat protein, a translational repressor," Nucleic acids research, Nov. 1, 1997, 25(22):4464-4473.
Freitas et al., "Mechanisms and signals for the nuclear import of proteins," Current genomics, Dec. 2009, 10(8):550-557.
Fu et al., "Improving CRISPR-Cas nuclease specificity using truncated guide RNAs," Nature biotechnology, Mar. 2014, 32(3): 8 Pages.
Fukuda et al., "Construction of a guide-RNA for site-directed RNA mutagenesis utilising intracellular A-to-I RNA editing," Sci Rep, 2017, 7:41478.
Fusco et al., Single mRNA molecules demonstrate probabilistic movement in living mammalian cells, Current Biology, Jan. 21, 2003, 13(2):161-167.
Garcia et al., "MS2 coat proteins bound to yeast mRNAs block 5' to 3' degradation and trap mRNA decay products: implications for the localization of mRNAs by MS2-MCP system," Rna, Aug. 1, 2015, 21(8): 4 Pages.
Gebeyehu et al., "Novel biotinylated nucleotide-analogs for labeling and colorimetric detection of DNA," Nucleic acids research, Jun. 11, 1987, 15(11):4513-4534.
Geisler et al., "RNA in unexpected places: long non-coding RNA functions in diverse cellular contexts," Nature reviews Molecular cell biology, Nov. 2013, 14(11): 14 Pages.
GenBank Accession No. FJ209302, "*Homo sapiens* MALAT1-associated small cytoplasmic RNA, complete sequence," Dec. 2, 2008, 1 page.
GenBank Accession No. NM_019852.4, "*Homo sapiens* methyltransferase like 3 (METTL3), mRNA," Oct. 21, 2018, 6 pages.
Gentz et al., "Bioassay for trans-activation using purified human immunodeficiency virus tat-encoded protein: trans-activation requires mRNA synthesis," Proc. Natl. Acad. Sci., 1989, 86:821-824.
German-Retana et al., "Mutational analysis of plant cap-binding protein eIF4E reveals key amino acids involved in biochemical functions and potyvirus infection," Journal of virology, Aug. 1, 2008, 82(15):7601-7612.
Gerstberger et al., "Evolutionary conservation and expression of human RNA-binding proteins and their role in human genetic disease," InSystems biology of RNA binding proteins, 2014 pp. 1-55.
Gilbert et al., "CRISPR-mediated modular RNA-guided regulation of transcription in eukaryotes," Cell, Jul. 18, 2013, 154(2):442-451.
Graham et al., "Resources for the design of CRISPR gene editing experiments," Genome Biol., 2015, 16(1):260.

(56) References Cited

OTHER PUBLICATIONS

Graveley et al., "Arginine/serine-rich domains of SR proteins can function as activators of pre-mRNA splicing," Molecular cell, Apr. 1, 1998, 1(5):765-771.
Gritsenko et al., "Sequence features of viral and human Internal Ribosome Entry Sites predictive of their activity," PLoS computational biology, Sep. 18, 2017, 13(9):e1005734, 23 Pages.
Guss et al., "Structure of the IgG-binding regions of streptococcal protein G," EMBO J., 1986, 5:1567-1575.
Guzzi et al., "Pseudouridylation of tRNA-derived fragments steers translational control in stem cells," Cell, May 17, 2018, 173(5): 40 pages.
Hale et al., "RNA-guided RNA cleavage by a CRISPR RNA-Cas protein complex," Cell, Nov. 25, 2009, 139(5):945-956.
Halo et al., "NanoFlares for the detection, isolation, and culture of live tumor cells from human blood," PNAS, 2014, 111(48):17104-17109.
Hamajima et al., "Intranasal administration of HIV-DNA vaccine formulated with a polymer, carboxymethylcellulose, augments mucosal antibody production and cell-mediated immune response," Clinical immunology and immunopathology, Aug. 1, 1998, 88(2):205-210.
Hanswillemenke et al., "Site-Directed RNA Editing in Vivo Can Be Triggered by the Light-Driven Assembly of an Artificial Riboprotein," J Am Chem Soc, 2015, 137(50):15875-81.
Heasman, "Morpholino oligos: making sense of antisense?" Developmental biology, Mar. 15, 2002, 243(2):209-214.
Hendel et al., "Chemically modified guide RNAs enhance CRISPR-Cas genome editing in human primary cells," Nature biotechnology, Jun. 29, 2015, 33(9):985-989.
Hermonat & Muzyczka, "Use of adeno-associated virus as a mammalian DNA cloning vector: transduction of neomycin resistance into mammalian tissue culture cells," Proc. Natl. Acad. Sci. USA, 1984, 81:6466-6470.
Higuchi et al., "RNA editing of AMPA receptor subunit GluR-B: a base-paired intron-exon structure determines position and efficiency," Cell, 1993, 75(7):1361-70.
Hinnebusch, "Molecular Mechanism of Scanning and Start Codon Selection in Eukaryotes," Microbiology and Molecular Biology Reviews, Sep. 2011, 75(3):434-467.
Hjelm et al., "Immunologically active and structurally similar fragments of protein A from *Staphylococcus aureus*," Eur. J. Biochem., 1975, 57:395-403.
Ho et al., "Colocalization of muscleblind with RNA foci is separable from mis-regulation of alternative splicing in myotonic dystrophy," Journal of cell science, Jul. 1, 2005, 118(13):2923-2933.
Hsu et al., "Development and applications of CRISPR-Cas9 for genome engineering," Cell, 2014, 156(6):1262-1278.
Hua et al., "Antisense correction of SMN2 splicing in the CNS rescues necrosis in a type III SMA mouse model," Genes & development, Aug. 1, 2010, 24(15):1634-1644.
Hua et al., "Antisense masking of an hnRNP A1/A2 intronic splicing silencer corrects SMN2 splicing in transgenic mice," The American Journal of Human Genetics, Apr. 11, 2008, 82(4):834-848.
Hua et al., Peripheral SMN restoration is essential for long-term rescue of a severe spinal muscular atrophy mouse model, Nature, Oct. 2011, 478(7367):123-126.
Huang et al., "Inducing nonsense suppression by targeted pseudouridylation," nature protocols, Apr. 2012, 7(4):789-800.
Hwang et al., "Efficient genome editing in zebrafish using a CRISPR-Cas system," Nature biotechnology, Mar. 2013, 31(3):227-229.
Hwang et al., "Efficient in vivo genome editing using RNA-guided nucleases," Nature biotechnology, Mar. 2013, 31(3): 12 Pages.
International Preliminary Report on Patentability in International Appln. No. PCT/US2016/063429, dated May 29, 2018, 12 pages.
International Preliminary Report on Patentability in International Appln. No. PCT/US2018/031913, dated Nov. 12, 2019, 10 pages.
International Preliminary Report on Patentability in International Appln. No. PCT/US2019/028580, dated Oct. 29, 2020, 9 pages.
International Preliminary Report on Patentability in International Appln. No. PCT/US2019/049182, dated Mar. 11, 2021, 7 pages.
International Preliminary Report on Patentability in International Appln. No. PCT/US2019/049197, dated Mar. 11, 2021, 9 pages.
International Preliminary Report on Patentability in International Appln. PCT/US2020/028501, dated Oct. 28, 2021, 10 pages.
International Preliminary Report on Patentability in International Appln. PCT/US2020/028546, dated Oct. 28, 2021, 11 pages.
International Search Report and Written Opinion in International Appln. No. PCT/US2018/031913, dated Aug. 2, 2018, 4 pages.
International Search Report and Written Opinion in International Appln. No. PCT/US2016/063429, dated Nov. 22, 2016, 21 pages.
International Search Report and Written Opinion in International Appln. No. PCT/US2019/028580, dated Aug. 27, 2019, 14 pages.
International Search Report and Written Opinion in International Appln. No. PCT/US2019/049182, dated Dec. 6, 2019, 11 pages.
International Search Report and Written Opinion in International Appln. No. PCT/US2019/049197, dated Dec. 12, 2019, 12 pages.
International Search Report and Written Opinion in International Appln. No. PCT/US2020/028501, dated Sep. 25, 2020, 12 pages.
International Search Report and Written Opinion in International Appln. No. PCT/US2020/028546, dated Jul. 14, 2020, 13 pages.
Jia et al., "N 6-methyladenosine in nuclear RNA is a major substrate of the obesity-associated FTO," Nature chemical biology, Dec. 2011, 7(12):885-887.
Jiang F, "Structures of a CRISPR-Cas9 R-loop complex primed for DNA cleavage," Science, 2016, 351(6275): 9 Pages.
Jinek et al., "A programmable dual RNA-guided DNA endonuclease in adaptive bacterial immunity," Science, 2012, 337(6096): 14 Pages.
Jinek et al., "RNA-programmed genome editing in human cells," elife, Jan. 29, 2013, 2:e00471, 9 Pages.
Kadokura et al., "Solid-phase synthesis of a 5'-terminal TMG-capped trinucleotide block of U1 snRNA," Tetrahedron Letters, Dec. 10, 2001, 42(50):8853-8856.
Kanadia et al., "A muscleblind knockout model for myotonic dystrophy," Science, Dec. 12, 2003, 302(5652):1978-1980.
Karijolich et al., "Converting nonsense codons into sense codons by targeted pseudouridylation," Nature, Jun. 2011, 474(7351):395-398.
Karijolich et al., "Transcriptome-wide dynamics of RNA pseudouridylation," Nature reviews Molecular cell biology, Oct. 2015, 16(10): 5 pages.
Kedersha et al., "Mammalian stress granules and processing bodies," Methods in enzymology, Jan. 1, 2007, 431:61-81.
Kelley et al., "Versatility of chemically synthesized guide RNAs for CRISPR-Cas9 genome editing," J. of Biotechnology, 2016, 233:25 Pages.
Khani et al., "AAV-mediated expression targeting of rod and cone photoreceptors with a human rhodopsin kinase promoter," Investigative ophthalmology & visual science, Sep. 1, 2007, 48(9):3954-3961.
Kirsebom, "RNase P RNA mediated cleavage: substrate recognition and catalysis," Biochimie, Oct. 1, 2007, 89(10):1183-1194.
Kislauskis et al., "Sequences responsible for intracellular localization of beta-actin messenger RNA also affect cell phenotype," The Journal of cell biology, Oct. 15, 1994, 127(2):441-451.
Kodama et al., "An improved bimolecular fluorescence complementation assay with a high signal-to-noise ratio," Biotechniques, 2010, 49(5):793-805.
Konermann et al., "Genome-scale transcriptional activation by an engineered CRISPR-Cas9 complex," Nature, 2015, 517(7356):583-588.
Konermann et al., "Transcriptome engineering with RNA-targeting type VI-D CRISPR effectors," Cell, Apr. 19, 2018, 173(3): 27 Pages.
Koren et al., "Cell-penetrating peptides: breaking through to the other side," Trends in molecular medicine, Jul. 1, 2012, 18(7):385-393.
Kormann et al., "Expression of therapeutic proteins after delivery of chemically modified mRNA in mice," Nature biotechnology, Feb. 2011, 29(2):154-157.
Koshkin et al., "LNA (Locked Nucleic Acids): Synthesis of the adenine, cytosine, guanine, 5-methylcytosine, thymine and uracil

(56) References Cited

OTHER PUBLICATIONS bicyclonucleoside monomers, oligomerisation, and unprecedented nucleic acid recognition," Tetrahedron, Apr. 2, 1998, 54(14):3607-3630.
Kotterman et al., "Viral Vectors for Gene Therapy: Translational and Clinical Outlook," Annual Review of Biomedical Engineering, 2015, 17:63-89.
Kuscu et al., "Genome-wide analysis reveals characteristics of off-target sites bound by the Cas9 endonuclease," Nature biotechnology, Jul. 2014, 32(7): 9 Pages.
Kuttan & Bass, "Mechanistic insights into editing-site specificity of ADARs," PNAS, 2012, 109(48):E3295-E3304.
Lacerra et al., "Restoration of hemoglobin A synthesis in erythroid cells from peripheral blood of thalassemic patients," Proceedings of the National Academy of Sciences, Aug. 15, 2000, 97(17):9591-9596.
Lai et al., "Unexpected diversity of RNase P, an ancient tRNA processing enzyme: challenges and prospects," FEBS letters, Jan. 21, 2010, 584(2):287-296.
Laird-Offringa et al., "Analysis of RNA-binding proteins by in vitro genetic selection: identification of an amino acid residue important for locking U1A onto its RNA target," Proceedings of the National Academy of Sciences, Dec. 5, 1995, 92(25):11859-11863.
Lebkowski et al., "Adeno-associated virus: a vector system for efficient introduction and integration of DNA into a variety of mammalian cell types," Mol. Cell. Biol., 1988, 8:3988-3996.
Li et al., "Heritable gene targeting in the mouse and rat using a CRISPR-Cas system," Nature biotechnology, Aug. 2013, 31(8):681-683.
Li et al., "Stress granules as crucibles of ALS pathogenesis," Journal of cell biology, Apr. 29, 2013, 201(3):361-372.
Li et al., "Targeted mRNA demethylation using an engineered dCas13b-ALKBH5 fusion protein," Nucleic acids research, Jun. 4, 2020, 48(10):5684-5694.
Lionnet et al., "A transgenic mouse for in vivo detection of endogenous labeled mRNA," Nature methods, Feb. 2011, 8(2): 9 Pages.
Long et al., "Postnatal genome editing partially restores dystrophin expression in a mouse model of muscular dystrophy," Science, Jan. 22, 2016, 351(6271):400-403.
Lovci et al., "Rbfox proteins regulate alternative mRNA splicing through evolutionarily conserved RNA bridges," Nature structural & molecular biology, Dec. 2013, 20(12): 11 Pages.
Lu et al., "MicroRNA expression profiles classify human cancers," nature, Jun. 2005, 435(7043):834-838.
MacKenzie et al., "Stromal expression of miR-21 identifies high-risk group in triple-negative breast cancer," The American journal of pathology, Dec. 1, 2014, 184(12):3217-3225.
Maddalo et al., "In vivo engineering of oncogenic chromosomal rearrangements with the CRISPR/Cas9 system," Nature, Dec. 2014, 516(7531): 15 Pages.
Maity et al., "N6-methyladenosine modification in mRNA: machinery, function and implications for health and diseases," The FEBS journal, May 2016, 283(9):1607-1630.
Mali et al., "CAS9 transcriptional activators for target specificity screening and paired nickases for cooperative genome engineering," Nature biotechnology, Sep. 2013, 31(9): 8 Pages.
Mali et al., "RNA-guided human genome engineering via Cas9," Science, Feb. 15, 2013, 339(6121): 5 Pages.
Manders et al., "Dynamics of three-dimensional replication patterns during the S-phase, analysed by double labelling of DNA and confocal microscopy," Journal of cell science, Nov. 1, 1992, 103(3):857-862.
Martin, "Ein neuer Zugang zu 2'-O-Alkylribonucleosiden und Eigenschaften deren Oligonucleotide," Helvetica Chimica Acta, Mar. 22, 1995, 78(2):486-504.
Massie et al., "Inducible overexpression of a toxic protein by an adenovirus vector with a tetracycline-regulatable expression cassette," Journal of Virology, Mar. 1, 1998, 72(3):2289-2296.
Matthews et al., "Structures of human ADAR2 bound to dsRNA reveal base-flipping mechanism and basis for site selectivity," Nature structural & molecular biology, May 2016, 23(5): 23 Pages.
McMahon et al., "TRIBE: Hijacking an RNA-Editing Enzyme to Identify Cell-Specific Targets of RNA-Binding Proteins," Cell, 2016, 165(3):742-53.
Meng et al., "Towards a therapy for Angelman syndrome by targeting a long non-coding RNA," Nature, Feb. 2015, 518(7539): 16 Pages.
Mingozzi et al., "Therapeutic in vivo gene transfer for genetic disease using AAV: progress and challenges," Nature reviews genetics, May 2011, 12(5):341-355.
Miyanohara et al., "Potent spinal parenchymal AAV9-mediated gene delivery by subpial injection in adult rats and pigs," Molecular Therapy—Methods & Clinical Development, Jan. 1, 2016, 3:16046, 10 pages.
Mohr et al., "CRISPR guide RNA design for research applications," FEBS Journal, 2016, 283(17):3232-3238.
Montiel-Gonzalez et al "An efficient system for selectively altering genetic information within mRNAs." Nucleic Acids Res., 2016, 44:e157.
Montiel-Gonzalez et al., "Correction of mutations within the cystic fibrosis transmembrane conductance regulator by site-directed RNA editing." PNAS, 2013, 110(45):18285-90.
Mouisel et al., "Outcome of acetylcholinesterase deficiency for neuromuscular functioning," Neuroscience research, Aug. 1, 2006, 55(4):389-396.
Muddashetty et al., "Reversible inhibition of PSD-95 mRNA translation by miR-125a, FMRP phosphorylation, and mGluR signaling," Molecular cell, Jun. 10, 2011, 42(5):673-688.
Mukhopadhyay et al., "C→ U editing of neurofibromatosis 1 mRNA occurs in tumors that express both the type II transcript and apobec-1, the catalytic subunit of the apolipoprotein B mRNA-editing enzyme," The American Journal of Human Genetics, Jan. 1, 2002, 70(1):38-50.
Muzyczka, "Use of adeno-associated virus as a general transduction vector for mammalian cells," Viral expression vectors, 1992, 97-129.
Nakayama et al., "Simple and efficient CRISPR/Cas9-mediated targeted mutagenesis in Xenopus tropicalis," genesis, Dec. 2013, 51(12):835-843.
Nasevicius et al., "Effective targeted gene 'knockdown' in zebrafish," Nature genetics, Oct. 2000, 26(2):216-220.
Nelles et al., "Applications of Cas9 as an RNA-programmed RNA-binding protein," BioEssays, Jul. 2015, 37(7): 8 Pages.
Nelles et al., "Programmable RNA tracking in live cells with CRISPR/Cas9," Cell, Apr. 7, 2016, 165(2): 10 Pages.
Nielsen "Sequence-selective recognition of DNA by strand displacement with a thymine-substituted polyamide," Science, Dec. 6, 1991, 254(5037):1497-1500.
Nishikura, "A-to-I editing of coding and non-coding RNAs by ADARs," Nat Rev Mol Cell Biol, 2016, 17(2):83-96.
Nishimasu, et al. "Crystal structure of Cas9 in complex with guide RNA and target DNA," Cell, Feb. 27, 2014, 156(5):935-949.
Nissim-Rafinia et al., "Splicing regulation as a potential genetic modifier," Trends in Genetics, Mar. 1, 2002, 18(3):123-127.
O'Connell et al., "Programmable RNA recognition and cleavage by CRISPR/Cas9," Nature., 2014, 516(7530): 23 Pages.
Ohkubo et al., "Efficient solid-phase synthesis of oligodeoxynucleotides having a 5'-terminal 2, 2, 7 trimethylguanosine pyrophosphate linkage," Bioorganic & medicinal chemistry, Jul. 1, 2009, 17(13):4819-4824.
O'Keefe et al., "Scaleable manufacture of HIV-1 entry inhibitor griffithsin and validation of its safety and efficacy as a topical microbicide component," Proc. Nat. Acad. Sci. USA, 2009, 106(15):6099-6104.
Orengo et al., "Expanded CTG repeats within the DMPK 3' UTR causes severe skeletal muscle wasting in an inducible mouse model for myotonic dystrophy," Proceedings of the National Academy of Sciences, Feb. 19, 2008, 105(7):2646-2651.
Ozawa et al., "Imaging dynamics of endogenous mitochondrial RNA in single living cells," Nature methods, May 2007, 4(5):413-419.

(56) References Cited

OTHER PUBLICATIONS

Paige et al., "RNA mimics of green fluorescent protein," Science, Jul. 29, 2011, 333(6042): 35 Pages.
Pang et al., "Comparative analysis of in vivo and in vitro AAV vector transduction in the neonatal mouse retina: effects of serotype and site of administration," Vision research, Feb. 1, 2008, 48(3):377-385.
Park et al., "Visualization of dynamics of single endogenous mRNA labeled in live mouse," Science, Jan. 24, 2014, 343(6169):422-424.
Partial International Search Report dated Feb. 28, 2017 for corresponding Application No. PCT/US2016/063429, 11 pages.
Pasca et al. "Using iPSC-derived neurons to uncover cellular phenotypes associated with Timothy syndrome," Nat Med, 2011, 17(12):18 Pages.
Passini et al., "Antisense oligonucleotides delivered to the mouse CNS ameliorate symptoms of severe spinal muscular atrophy," Science translational medicine, Mar. 2, 2011, 3(72):72ra18, 11 Pages.
Phelps et al., "Recognition of duplex RNA by the deaminase domain of the RNA editing enzyme ADAR2," Nuc. Acid Res., 2015, 43(2):1123-1132.
Price et al., "Cas9-mediated targeting of viral RNA in eukaryotic cells," Proceedings of the National Academy of Sciences, May 12, 2015, 112(19): 14 Pages.
Qi et al., "Repurposing CRISPR as an RNA-guided platform for sequence-specific control of gene expression," Cell, Feb. 28, 2013, 152(5):1173-1183.
Rackham et al., "Visualization of RNA-protein interactions in living cells: FMRP and IMP1 interact on mRNAs, The EMBO journal," Aug. 18, 2004, 23(16):3346-3355.
Rahdar et al., "Synthetic CRISPR RNA-Cas9-guided genome editing in human cells," Proceedings of the National Academy of Sciences, Dec. 22, 2015, 112(51):E7110-7117.
Rath et al., "Genetically encoded tools for RNA imaging in living cells," Current opinion in biotechnology, Feb. 1, 2015, 31:42-49.
Renton et al., "A hexanucleotide repeat expansion in C9ORF72 is the cause of chromosome 9p21-linked ALS-FTD," Neuron., Oct. 20, 2011, 72(2):257-268.
Sachdeva et al., "In vivo co-localization of enzymes on RNA scaffolds increases metabolic production in a geometrically dependent manner," Nucleic acids research, Aug. 18, 2014, 42(14):9493-9503.
Sampson et al., "A CRISPR/Cas system mediates bacterial innate immune evasion and virulence," Nature, May 2013, 497(7448): 5 Pages.
Sander et al., "CRISPR-Cas systems for editing, regulating and targeting genomes," Nature biotechnology, Apr. 2014, 32(4):347-355.
Schellenberger et al., "A recombinant polypeptide extends the in vivo half-life of peptides and proteins in a tunable manner," Nat Biotechnol., 2009, 27(12):1186-1190.
Schindelin et al., "Fiji: an open-source platform for biological-image analysis," Nature methods, Jul. 2012, 9(7):676-682.
Schlesinger & Dubensky, "Alphavirus vectors for gene expression and vaccines," Curr. Opin. Biotechnol., 1999, 10(5):434-439.
Schneider et al "Optimal guideRNAs for re-directing deaminase activity of hADARI and hADAR2 in trans." Nucleic Acids Res., 2014, 42:e87.
Shestakova et al., "The physiological significance of β-actin mRNA localization in determining cell polarity and directional motility," Proceedings of the National Academy of Sciences, Jun. 19, 2001, 98(13):7045-7050.
Shi et al., "YTHDF3 facilitates translation and decay of N 6-methyladenosine-modified RNA," Cell research, Mar. 2017, 27(3):315-328.
Shin et al., "Live-cell imaging of Pol II promoter activity to monitor gene expression with RNA IMAGEtag reporters," Nucleic acids research, Jun. 17, 2014, 42(11):e90, 9 Pages.
Sikkema, "An Fc-binding protein," Amer. Biotech. Lab., Apr. 1, 1989, 7:42, 1 page.
Singh et al., "LNA (locked nucleic acids): synthesis and high-affinity nucleic acid recognition," Chemical communications, 1998, (4):455-456.
Sjoquist et al., "Protein A isolated from *Staphylococcus aureus* after digestion with lysostaphin," Eur. J. Biochem., 1972, 29:572-578.
Skuse et al., "The neurofibromatosis type I messenger RNA undergoes base-modification RNA editing," Nucleic acids research, Feb. 1, 1996, 24(3):478-486.
Soukarieh et al., "Design of nucleotide-mimetic and non-nucleotide inhibitors of the translation initiation factor eIF4E: Synthesis, structural and functional characterisation," European journal of medicinal chemistry, Nov. 29, 2016, 124:200-217.
Staals et al., "RNA targeting by the type III-A CRISPR-Cas Csm complex of Thermus thermophilus," Molecular cell, Nov. 20, 2014, 56(4):518-530.
Stepto et al., "Modelling C9ORF72 hexanucleotide repeat expansion in amyotrophic lateral sclerosis and frontotemporal dementia," Acta Neuropathol., 2014, 127(3):377-89.
Sternberg et al., "DNA interrogation by the CRISPR RNA-guided endonuclease Cas9," Nature, Mar. 2014, 507(7490): 17 Pages.
Strack et al., "A superfolding Spinach2 reveals the dynamic nature of trinucleotide repeat-containing RNA," Nature methods, Dec. 2013, 10(12): 9 Pages.
Strenkowska et al., "Cap analogs modified with 1, 2-dithiodiphosphate moiety protect mRNA from decapping and enhance its translational potential. Nucleic acids research," Nov. 16, 2016, 44(20):9578-9590.
Sunbul et al., "Contact-Mediated Quenching for RNA Imaging in Bacteria with a Fluorophore-Binding Aptamer," Angewandte Chemie International Edition, Dec. 9, 2013, 52(50), 13401-13404.
Supplementary Partial European Search Report in European Appln. No. 19788702.9, dated Jun. 11, 2021, 12 pages.
Swiech et al., "In vivo interrogation of gene function in the mammalian brain using CRISPR-Cas9," Nature biotechnology, Jan. 2015, 33(1): 9 Pages.
Tourriere et al., "The RasGAP-associated endoribonuclease G3BP assembles stress granules," The Journal of cell biology, Mar. 17, 2003, 160(6):823-831.
TransIT-LT1 Transfection Reagent Data Sheet, Mirus Bio, 2017, 6 pages.
Tyagi et al., "Molecular beacons: probes that fluoresce upon hybridization," Nature biotechnology, Mar. 1996, 14(3):303-308.
Unsworth et al., "mRNA escape from stress granule sequestration is dictated by localization to the endoplasmic reticulum," The FASEB journal, Sep. 2010, 24(9):3370-3380.
Urnov et al., "Genome editing with engineered zinc finger nucleases," Nature Reviews Genetics, Sep. 2010, 11(9):636-646.
Vu et al., "C-to-U editing and site-directed RNA editing for the correction of genetic mutations," Bioscience trends, Jun. 30, 2017, 11(3):243-253.
Wahlestedt et al., "Potent and nontoxic antisense oligonucleotides containing locked nucleic acids," Proceedings of the National Academy of Sciences, May 9, 2000, 97(10):5633-5638.
Walczak et al., "A novel route for preparing 5' cap mimics and capped RNAs: phosphate-modified cap analogues obtained via click chemistry," Chemical science, 2017, 8(1):260-267.
Wang et al., "Crystal structure of a Pumilio homology domain," Molecular cell, Apr. 1, 2001, 7(4):855-865.
Wang et al., "Cyclohexene nucleic acids (CeNA): serum stable oligonucleotides that activate RNase H and increase duplex stability with complementary RNA," Journal of the American Chemical Society, Sep. 13, 2000, 122(36):8595-8602.
Wang et al., "Engineering splicing factors with designed specificities," Nat Methods, Nov. 2009, 6(11):825-830.
Wang et al., "Modular recognition of RNA by a human pumilio-homology domain," Cell, Aug. 23, 2002, 110(4):501-512.
Wang et al., "Probing RNA recognition by human ADAR2 using a high-throughput mutagenesis method," Nucleic acids research, Nov. 2016, 44(20):9872-9880.
Wang et al., "Unbiased detection of off-target cleavage by CRISPR-Cas9 and TALENs using integrase-defective lentiviral vectors," Nature biotechnology, Feb. 2015, 33(2): 5 Pages.

(56) References Cited

OTHER PUBLICATIONS

Warda et al., "Human METTL16 is a N6-methyladenosine (m6A) methyltransferase that targets pre-mRNAs and various non-coding RNAs, " EMBO reports, Nov. 2017, 18(11):2004-2014.
Warren et al., "Highly efficient reprogramming to pluripotency and directed differentiation of human cells with synthetic modified mRNA," Cell stem cell, Nov. 5, 2010, 7(5):618-630.
Wernersson et al., "OligoWiz 2.0—integrating sequence feature annotation into the design of microarray probes," Nucleic acids research, Jul. 1, 2005, 33(suppl_2):W611-615.
Weyn-Van Hentenryci et al., "HITS-CLIP and integrative modeling define the Rbfox splicing-regulatory network linked to brain development and autism," Cell Rep., Mar. 27, 2014, 6(6): 1139-1152.
Wheeler et al., "Correction of CIC-1 splicing eliminates chloride channelopathy and myotonia in mouse models of myotonic dystrophy," The Journal of clinical investigation, Dec. 3, 2007, 117(12):3952-3957.
Wiedenheft et al., "RNA-guided genetic silencing systems in bacteria and archaea," Nature, Feb. 2012, 482(7385):331-338.
Wilson et al., "The structure of an antigenic determinant in a protein," Cell, 1984, 37:767-778.
Wojciechowska et al., "Cellular toxicity of expanded RNA repeats: focus on RNA foci," Human Molecular Genetics, 2011, 20:3811-3821.
Wold and Toth, "Adenovirus Vectors for Gene Therapy, Vaccination and Cancer Gene Therapy," Curr. Gene. Ther., 2013, 13(6):421-433.
Wright et al., "Biology and Applications of CRISPR Systems: Harnessing Nature's Toolbox for Genome Engineering," Cell, 2016, 164(1-2):29-44.
Wright et al., "Rational design of a split-Cas9 enzyme complex," Proceedings of the National Academy of Sciences, Mar. 10, 2015, 112(10):2984-2989.
Wu et al., "Target specificity of the CRISPRCas9 system," Quant Biol. 2014, 2(2):59-70.
Xiao et al., "Functionality and substrate specificity of human box H/ACA guide RNAs," Rna, Janaury 1, 2009, 15(1):176-186.
Xiao et al., "Nuclear m6A reader YTHDC1 regulates mRNA splicing," Molecular cell, Feb. 18, 2016, 61(4):507-519.
Xu et al., "A CRISPR-dCas toolbox for genetic engineering and synthetic biology," Journal of molecular biology, Jan. 4, 2019, 431(1):34-47.
Yamanaka et al., "A novel translational repressor mRNA is edited extensively in livers containing tumors caused by the transgene expression of the apoB mRNA-editing enzyme," Genes & development, Feb. 1, 1997, 11(3):321-333.
Yan et al., "Cas13d is a compact RNA-targeting type VI CRISPR effector positively modulated by a WYL-domain-containing accessory protein," Molecular cell, Apr. 19, 2018 70(2):327-339.
Yang et al., "A dual AAV system enables the Cas9-mediated correction of a metabolic liver disease in newborn mice," Nature biotechnology, Mar. 2016, 34(3):334-338.
Yang et al., "Effective gene targeting in rabbits using RNA-guided Cas9 nucleases," Journal of molecular cell biology, Feb. 1, 2014, 6(1):97-99.
Yeo et al., "An RNA code for the FOX2 splicing regulator revealed by mapping RNA-protein interactions in stem cells," Nature structural & molecular biology, Feb. 2009, 16(2): 130-137.
Ying et al., "Cancer therapy using a self-replicating RNA vaccine," Nat. Med., 1999, 5(7):823-827.
Zaganelli et al., "The pseudouridine synthase RPUSD4 is an essential component of mitochondrial RNA granules," Journal of Biological Chemistry, Mar. 17, 2017, 292(11):4519-4532.
Zambrowicz et al., "Disruption of overlapping transcripts in the ROSA beta geo 26 gene trap strain leads to widespread expression of beta-galactosidase in mouse embryos and hematopoietic cells," Proc. Natl. Acad. Sci., 1997, 94:3789-3794.
Zetche et al., "A split-Cas9 architecture for inducible genome editing and transcription modulation," Nat Biotechnol., 2015, 33(2): 6 Pages.
Zetsche et al., "A split-Cas9 architecture for inducible genome editing and transcription modulation," Nature biotechnology, Feb. 2015, 33(2): 3 Pages.
Zhang et al., "Treatment of type 1 myotonic dystrophy by engineering site-specific RNA endonuleases that target (CUG)(n)," Molecular Therapy, Feb. 1, 2014, 22(2):312-320.
Zuris et al., "Cationic lipid-mediated delivery of proteins enables efficient protein-based genome editing in vitro and in vivo," Nature biotechnology, Jan. 2015, 33(1):73-80.
Zuris et al., "Efficient Delivery of Genome-Editing Proteins in vitro and in vivo," Nature Biotechnol., Jan. 2015, 33(1): 26 Pages.
Extended European Search Report in EP Appln. No. 22195456.3, dated Mar. 14, 2023, 11 pages.
Glavan et al., "Structures of the PIN domains of SMG6 and SMG5 reveal a nuclease within the mRNA surveillance complex," The EMBO Journal, Nov. 1, 2006, 25(21):5117-5125.
Koeppen, "The pathogenesis of spinocerebellar ataxia," The Cerebellum, Mar. 2005, 4:62-73.
Nishimasu, "Crystal Structure of Cas9," Journal of the Crystallographic Society of Japan, Apr. 30, 2015, 57(2):96-103 (with English abstract).
Raz et al., "191st ENMC international workshop: recent advances in oculopharyngeal muscular dystrophy research: from bench to bedside Jun. 8-10, 2012, Naarden, The Netherlands," Neuromuscular Disorders, Jun. 2013, 23(6):516-523.
Wee et al., "The genetics of spinal muscular atrophies," Current Opinion in Neurology, Oct. 2010, 23(5):450-458.

* cited by examiner

FIG. 1A
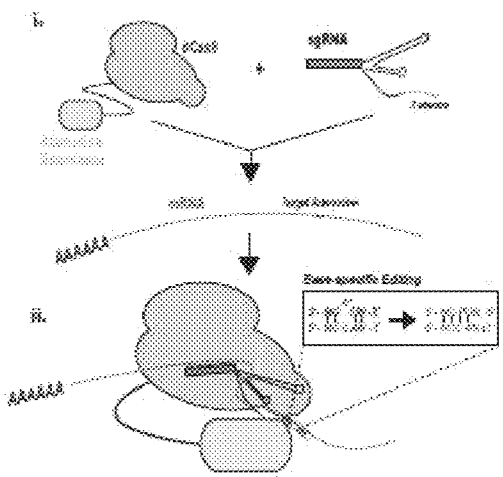
FIG. 1B
AXC
AX
AXC E488Q
AX E488Q
sgRNA
3' extension
FIG. 1C
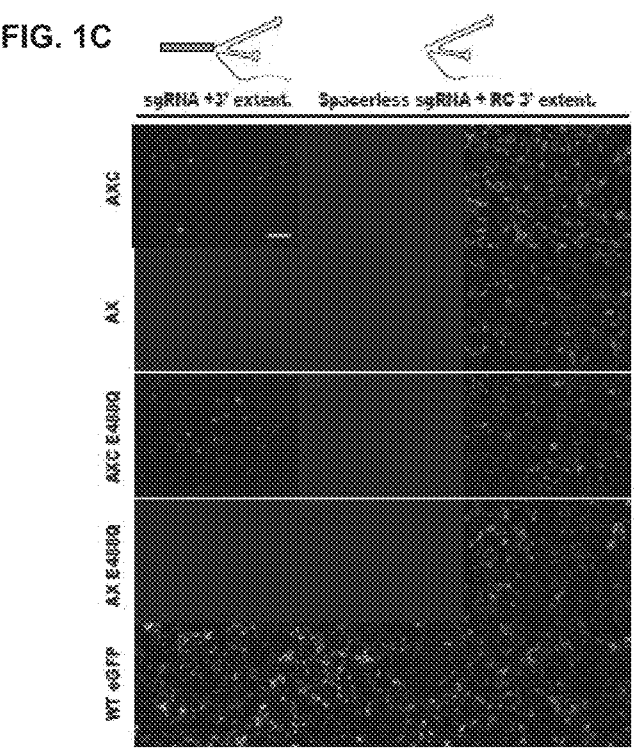
FIG. 1D
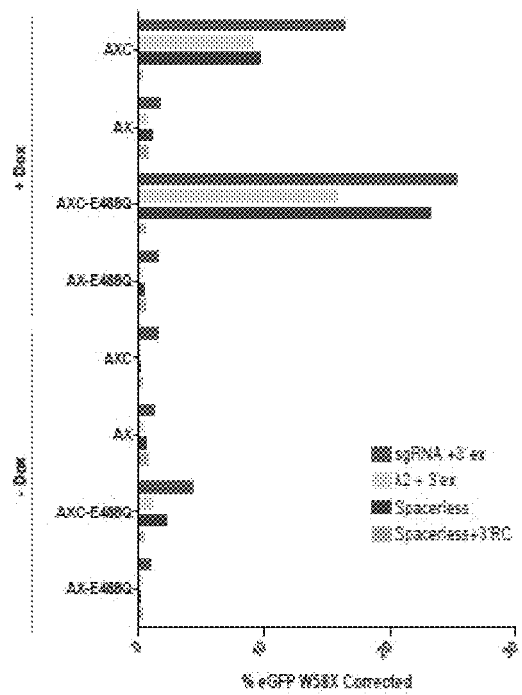

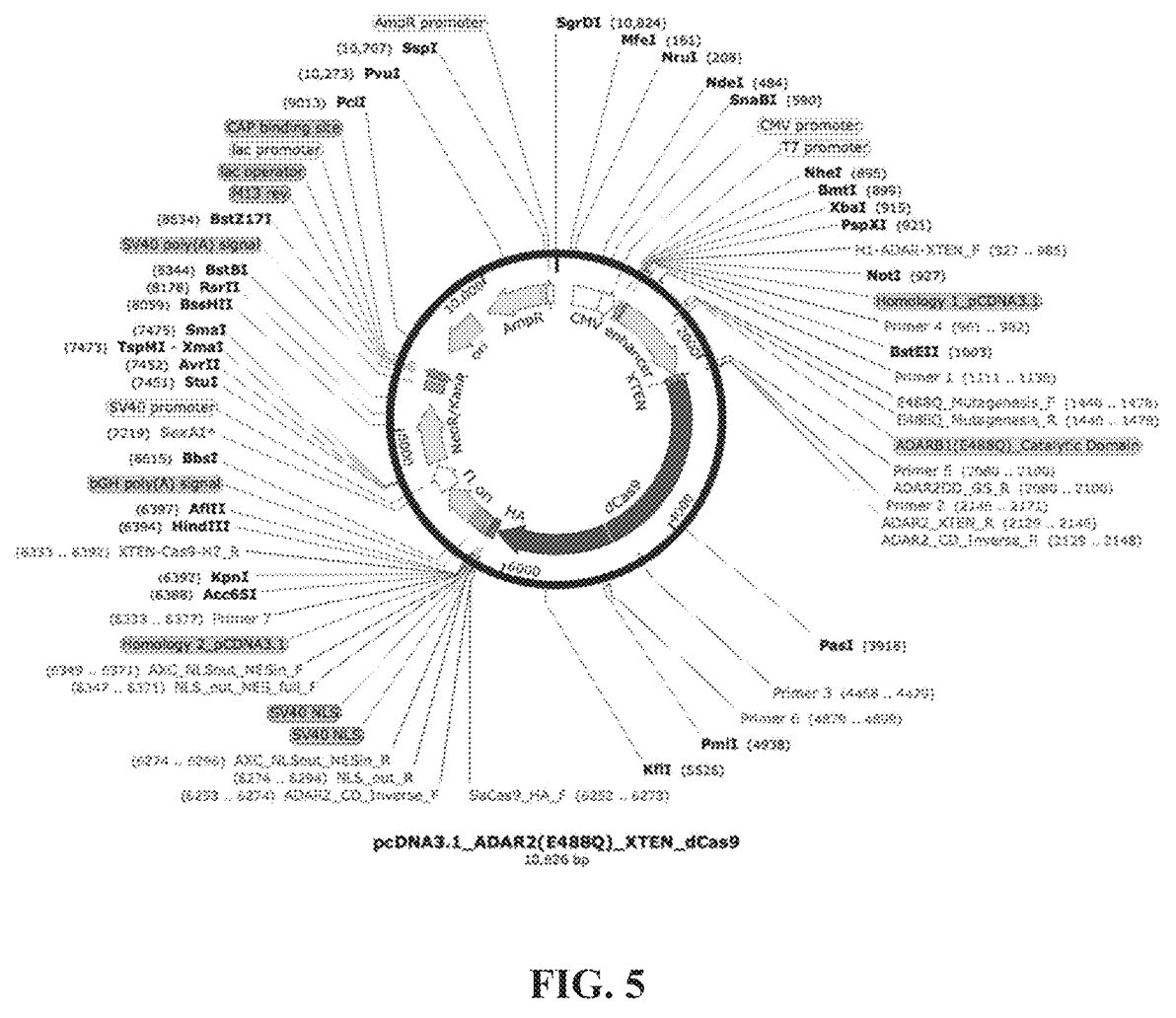

AmpR promoter
(10,707) SspI
(10,273) PvuI
(9013) PciI
CAP binding site
lac promoter
lac operator
M13 rev
(8634) BstZ17I
SV40 poly(A) signal
(8344) BstBI
(8178) RsrII
(8059) BssHII
(7475) SmaI
(7473) TspMI - XmaI
(7452) AvrII
(7451) StuI
SV40 promoter
(7219) SexAI*
(6615) BbsI
bGH poly(A) signal
(6397) AflII
(6394) HindIII
XTEN-Cas9-H7_R
(6392) KpnI
(6388) Acc65I
Primer 7
Homology 2_pcDNA3.1
AXC_NLSout_NESin_F
NLS_out_NES_full_F
SV40 NLS
SV40 NLS
AXC_NLSout_NESin_R
NLS_out_R
ADAR2_CD_Inverse_F
SaCas9_HA_F (6252 .. 6273)

SgrDI (10,824)
MfeI (161)
NruI (208)
NdeI (494)
SnaBI (590)
CMV promoter
T7 promoter
NheI (895)
BmtI (899)
XbaI (915)
PspXI (921)
R1-ADAR-XTEN_F (927 .. 986)
NotI (937)
Homology 1_pcDNA3.1
Primer 4 (961 .. 982)
BstEII (1003)
Primer 1 (1111 .. 1130)
E488Q_Mutagenesis_F (1440 .. 1478)
E488Q_Mutagenesis_R (1440 .. 1478)
ADAR2(E488Q) Catalytic Domain
Primer 5 (2080 .. 2100)
ADAR2DD_GS_R (2080 .. 2100)
Primer 2 (2146 .. 2171)
ADAR2_XTEN_R (2129 .. 2146)
ADAR2_CD_Inverse_R (2129 .. 2148)
PasI (3918)
Primer 3 (4458 .. 4479)
Primer 6 (4879 .. 4898)
PmlI (4938)
KflI (5526)

AmpR
ori
NeoR/KanR
f1 ori
HA
dCas9
XTEN
CMV enhancer
10,000 pcDNA3.1_ADAR2(E488Q)_XTEN_dCas9
10,836 bp

FIG. 5

Sp-CREDITv1

HA NLS
XTEN
CMV
dSpCas9(D10A, H840A)

Sa-CREDITv1

* < 0.05 p-value one-way ANOVA

DIRECTED EDITING OF CELLULAR RNA VIA NUCLEAR DELIVERY OF CRISPR/CAS9

CROSS-REFERENCE TO RELATED APPLICATION

This application is a divisional to U.S. application Ser. No. 15/975,728, filed on May 9, 2018, which claims benefit to U.S. Provisional Application No. 62/504,497 filed May 10, 2017, the contents of each application is incorporated herein by reference in its entirety.

STATEMENT OF GOVERNMENT SUPPORT

This invention was made with government support under Grant Nos. HG004659 and NS075449 awarded by the National Institutes of Health. The government has certain rights in the invention.

SEQUENCE LISTING

This application contains a Sequence Listing that has been submitted electronically as an XML file named 15670-0307002.xml. The XML file, created on Jul. 7, 2022, is 188000 bytes in size. The material in the XML file is hereby incorporated by reference in its entirety.

BACKGROUND

Present strategies aimed to target and manipulate RNA in living cells mainly rely on the use of antisense oligonucleotides (ASO) or engineered RNA binding proteins (RBP). Although ASO therapies have shown great promise in eliminating pathogenic transcripts or modulating RBP binding, they are synthetic in construction and thus cannot be encoded within DNA. This complicates potential gene therapy strategies, which would rely on regular administration of ASOs throughout the lifetime of the patient. Furthermore, they are incapable of modulating the genetic sequence of RNA. Although RBPs such as the Pumilio and FBF homology family (PUF) of proteins can be designed to recognize target transcripts and fuse to RNA modifying effectors to allow for specific recognition and manipulation, platforms based on these types of constructs require extensive protein engineering for each target and may prove to be difficult and costly.

Current systems used to directly edit RNA rely either on non encodable components, such as chemical fusion of guide RNAs to an editase moiety (e.g., SNAP tag), or relatively low affinity tethering by fusion of encodable aptamer binding moieties (e.g., BoxB protein).

Current CRISPR/Cas RNA targeting systems typically use a single guide RNA and optionally an oligonucleotide of alternating 2' OMe RNA and DNA bases (PAMmer) to provide a simple and rapidly programmable system for targeting of specific RNA molecules in live cells. However, improvements and/or alternatives to these systems can help address issues relating to efficiency, specificity and/or off-target editing events. The present disclosure addresses these needs and provides related advantages.

SUMMARY OF THE DISCLOSURE

Accordingly, provided herein are fully encodable and highly specific CRISPR/Cas systems, compositions, and methods to achieve efficient and reversible manipulation and modulation of target RNA with simplicity, reliability and versatility.

In some aspects, provided herein are recombinant expression systems for CRISPR/Cas-directed RNA editing of a target RNA comprising, consisting of, or consisting essentially of: (A) a nucleic acid sequence encoding a CRISPR/Cas RNA editing fusion protein comprising a nuclease-dead CRISPR associated endonuclease (dCas) fused to a catalytically active deaminase domain of Adenosine Deaminase acting on RNA (ADAR); and (B) a nucleic acid sequence encoding an extended single guide RNA (esgRNA) comprising: (i) a short extension sequence of homology to the target RNA comprising a mismatch for a target adenosine, and (ii) a dCas scaffold binding sequence. In some embodiments, said expression system expresses a dCas-ADAR nucleoprotein complex capable of CRISPR/Cas RNA-RNA base-specific Adenosine to Inosine (A-I) editing of the target sequence.

In some embodiments of the recombinant expression systems, the esgRNA further comprises (iii) a spacer sequence comprising a region of homology to the target RNA.

In some embodiments of the recombinant expression systems, (A) and (B) are comprised within the same vector or comprised within different vectors. In some embodiments of the recombinant expression systems, the vector is a viral vector. In some embodiments of the recombinant expression systems, the viral vector is an adeno-associated viral vector (AAV), lentiviral vector, or an adenoviral vector.

In some embodiments of the recombinant expression systems, the ADAR is selected from the group consisting of ADAR1, ADAR2, and ADAR3. In some embodiments, the catalytically active deaminase domain of ADAR is the catalytically active deaminase domain of ADAR2. In some embodiments of the recombinant expression systems, the catalytically active deaminase domain of ADAR2 is (1) a wildtype catalytically active deaminase domain of human ADAR2 or (2) a mutant human catalytically active deaminase domain of ADAR2 with increased catalytic activity compared to the wildtype human ADAR2. In some embodiments of the recombinant expression systems, the mutant human catalytically active deaminase domain of ADAR2 comprises a E488Q mutation.

In some embodiments of the recombinant expression systems, the dCas is nuclease-dead Cas9 (dCas9). In some embodiments of the recombinant expression systems, the dCas9 N-terminal domain is fused to the C-terminus of the catalytically active deaminase domain of ADAR. In some embodiments of the recombinant expression systems, the dCas is fused to the catalytically active deaminase domain of ADAR via a linker. In some embodiments of the recombinant expression systems, the linker is a semi-flexible XTEN peptide linker. In some embodiments, the linker is a GSGS linker.

In some embodiments of the recombinant expression systems, the short extension sequence of the esgRNA is a 3' extension sequence. In some embodiments of the recombinant expression systems, the short extension sequence of the esgRNA comprises a region of homology capable of near-perfect RNA-RNA base pairing with the target sequence. In some embodiments of the recombinant expression systems, the short extension sequence of the esgRNA further comprises a second mismatch for an adenosine within the target RNA. In some embodiments of the recombinant expression systems, the short extension sequence of the esgRNA further comprises a third mismatch for an adenosine within the target RNA and optionally a fourth mismatch for an adenosine within the target RNA. In some embodiments of the recombinant expression systems, the short extension sequence of the esgRNA is about 15 nucleotides to about 60 nucleotides in length.

In some embodiments of the recombinant expression systems, the esgRNA further comprises a marker sequence.

In some embodiments of the recombinant expression systems, the esgRNA further comprises a RNA polymerase III promoter sequence. In some embodiments of the recombinant expression systems, the RNA polymerase III promoter sequence is a U6 promoter sequence.

In some embodiments of the recombinant expression systems, the esgRNA comprises a linker sequence between the spacer sequence and the scaffold sequence.

In some embodiments of the recombinant expression systems, the sequences of the esgRNA (i), (ii), and (iii) are situated 3' to 5' in the esgRNA.

In some embodiments of the recombinant expression systems, the expression system further comprises a nucleic acid encoding a PAM sequence.

In some aspects, provided herein are vectors comprising, consisting of, or consisting essentially of a nucleic acid encoding an extended single guide RNA (esgRNA) comprising (i) a short extension sequence of homology to a target RNA comprising a mismatch for a target adenosine, (ii) a dCas scaffold binding sequence, and (iii) a sequence complementary to the target sequence (spacer sequence), wherein (i), (ii) and (iii) are situated 3' to 5' in the esgRNA.

In some embodiments of the vectors, the vector is a viral vector. In some embodiments of the vectors, the viral vector is an adeno-associated viral vector (AAV), lentiviral vector, or an adenoviral vector. In some embodiments of the vectors, the vectors further comprise an expression control element.

In some aspects, provided herein are viral particles comprising a vector comprising, consisting of, or consisting essentially of a nucleic acid encoding an extended single guide RNA (esgRNA) comprising (i) a short extension sequence of homology to a target RNA comprising a mismatch for a target adenosine, (ii) a dCas scaffold binding sequence, and (iii) a sequence complementary to the target sequence (spacer sequence), wherein (i), (ii) and (iii) are situated 3' to 5' in the esgRNA. In some embodiments, provided herein are viral particles comprising one or more vectors comprising (A) a nucleic acid sequence encoding a CRISPR/Cas RNA editing fusion protein comprising a nuclease-dead CRISPR associated endonuclease (dCas) fused to a catalytically active deaminase domain of Adenosine Deaminase acting on RNA (ADAR); and (B) a nucleic acid sequence encoding an extended single guide RNA (esgRNA) comprising: (i) a short extension sequence of homology to the target RNA comprising a mismatch for a target adenosine, and (ii) a dCas scaffold binding sequence.

In some aspects, provided herein are cells comprising recombinant expression systems, viral particles, and/or vectors comprising, consisting of, or consisting essentially of a nucleic acid encoding an extended single guide RNA (esgRNA) comprising (i) a short extension sequence of homology to a target RNA comprising a mismatch for a target adenosine, (ii) a dCas scaffold binding sequence, and (iii) a sequence complementary to the target sequence (spacer sequence), wherein (i), (ii) and (iii) are situated 3' to 5' in the esgRNA. In some embodiments, provided herein are cells comprising one or more viral particles, recombinant expression systems, and/or vectors comprising (A) a nucleic acid sequence encoding a CRISPR/Cas RNA editing fusion protein comprising a nuclease-dead CRISPR associated endonuclease (dCas) fused to a catalytically active deaminase domain of Adenosine Deaminase acting on RNA (ADAR); and (B) a nucleic acid sequence encoding an extended single guide RNA (esgRNA) comprising: (i) a short extension sequence of homology to the target RNA comprising a mismatch for a target adenosine, and (ii) a dCas scaffold binding sequence.

Also provided herein are methods of selective RNA editing comprising, consisting of, or consisting essentially of administering any one of the recombinant expression systems, viral particles, and/or vectors comprising, consisting of, or consisting essentially of a nucleic acid encoding an extended single guide RNA (esgRNA) comprising (i) a short extension sequence of homology to a target RNA comprising a mismatch for a target adenosine, (ii) a dCas scaffold binding sequence, and (iii) a sequence complementary to the target sequence (spacer sequence), wherein (i), (ii) and (iii) are situated 3' to 5' in the esgRNA to a cell. In some embodiments, the methods further comprise administering an antisense synthetic oligonucleotide compound comprising alternating 2'OMe RNA and DNA bases (PAMmer). In some embodiments, the method is in vitro or in vivo. In some embodiments, provided herein are methods of selective RNA editing comprising, consisting of, or consisting essentially of administering any one of the recombinant expression systems, viral particles, and/or vectors comprising, consisting of, or consisting essentially of (A) a nucleic acid sequence encoding a CRISPR/Cas RNA editing fusion protein comprising a nuclease-dead CRISPR associated endonuclease (dCas) fused to a catalytically active deaminase domain of Adenosine Deaminase acting on RNA (ADAR); and (B) a nucleic acid sequence encoding an extended single guide RNA (esgRNA) comprising: (i) a short extension sequence of homology to the target RNA comprising a mismatch for a target adenosine, and (ii) a dCas scaffold binding sequence.

Also provided herein are methods of characterizing the effects of directed cellular RNA editing on processing and dynamics comprising administering any one of the recombinant expression systems, viral particles, and/or vectors comprising, consisting of, or consisting essentially of a nucleic acid encoding an extended single guide RNA (esgRNA) comprising (i) a short extension sequence of homology to a target RNA comprising a mismatch for a target adenosine, (ii) a dCas scaffold binding sequence, and (iii) a sequence complementary to the target sequence (spacer sequence), wherein (i), (ii) and (iii) are situated 3' to 5' in the esgRNA to a sample and determining its effects. In some embodiments, the sample is derived from a subject. In some embodiments, the method is in vitro or in vivo. In some embodiments, provided herein are methods of characterizing the effects of directed cellular RNA editing on processing and dynamics comprising administering any one of the recombinant expression systems, viral particles, and/or vectors comprising, consisting of, or consisting essentially of (A) a nucleic acid sequence encoding a CRISPR/Cas RNA editing fusion protein comprising a nuclease-dead CRISPR associated endonuclease (dCas) fused to a catalytically active deaminase domain of Adenosine Deaminase acting on RNA (ADAR); and (B) a nucleic acid sequence encoding an extended single guide RNA (esgRNA) comprising: (i) a short extension sequence of homology to the target RNA comprising a mismatch for a target adenosine, and (ii) a dCas scaffold binding sequence to a sample and determining its effects.

In other aspects, provided herein are methods of treating a disease or condition in a subject comprising administering any one of the recombinant expression systems, viral particles, and/or vectors comprising, consisting of, or consisting essentially of a nucleic acid encoding an extended single guide RNA (esgRNA) comprising (i) a short extension sequence of homology to a target RNA comprising a mismatch for a target adenosine, (ii) a dCas scaffold binding sequence, and (iii) a sequence complementary to the target sequence (spacer sequence), wherein (i), (ii) and (iii) are situated 3' to 5' in the esgRNA to a subject or a sample isolated from a subject. In some embodiments, provided herein are methods of treating a disease or condition in a subject comprising administering any one of the recombinant expression systems, viral particles, and/or vectors comprising, consisting of, or consisting essentially of (A) a nucleic acid sequence encoding a CRISPR/Cas RNA editing fusion protein comprising a nuclease-dead CRISPR associated endonuclease (dCas) fused to a catalytically active deaminase domain of Adenosine Deaminase acting on RNA (ADAR); and (B) a nucleic acid sequence encoding an extended single guide RNA (esgRNA) comprising: (i) a short extension sequence of homology to the target RNA comprising a mismatch for a target adenosine, and (ii) a dCas scaffold binding sequence to a subject or a sample isolated from a subject.

In some embodiments, the methods further correcting a G to A mutation in a target RNA. In some embodiments, the disease is selected from the group of Hurler's syndrome, Cystic fibrosis, Duchenne muscular dystrophy, spinal cord injury, stroke, traumatic brain injury, hearing loss (through noise overexposure or ototoxicity), multiple sclerosis, Alzheimer's disease, amyotrophic lateral sclerosis (ALS), Parkinson's disease, alcoholism, alcohol withdrawal, over-rapid benzodiazepine withdrawal, and Huntington's disease.

In other aspects, provided herein are kits comprising, consisting of, or consisting of one or more of: recombinant expression systems, viral particles, and/or vectors comprising, consisting of, or consisting essentially of (A) a nucleic acid sequence encoding a CRISPR/Cas RNA editing fusion protein comprising a nuclease-dead CRISPR associated endonuclease (dCas) fused to a catalytically active deaminase domain of Adenosine Deaminase acting on RNA (ADAR); and (B) a nucleic acid sequence encoding an extended single guide RNA (esgRNA) comprising: (i) a short extension sequence of homology to the target RNA comprising a mismatch for a target adenosine, and (ii) a dCas scaffold binding sequence and instructions for use. In some embodiments, the instructions are for use according to any one of the methods described herein.

BRIEF DESCRIPTION OF THE DRAWINGS

FIGS. 1A-1D illustrate, without limitation, embodiments of the recombinant expression system and data relating thereto. FIG. 1A shows (i) a conceptual concept of CREDIT in living cells for the editing of a variety of RNAs that can cause various diseases, such as cancer and neurodegeneration and (ii) that the binding of the dCas9-deaminase fusion to guide RNA directs the hybridization of guide-extension around target adenosines generating double-stranded RNA (dsRNA) A-I base-specific editing targets. In particular, FIG. 1B shows a CREDIT recombinant expression system comprised of the *Streptococcus pyogenes* Cas9 protein fused by an XTEN linker to the deaminase domain (DD) of human ADARB1 (ADAR2), and a single guide RNA (sgRNA) with a 3' short RNA extension (esgRNA). The fluorescent imaging data of FIG. 1C shows that the recombinant expression system of FIG. 1B requires targeted dual guide RNA with 3' extension directing deamination and allows reversal of premature termination codon (PTC) mediated silencing of expression from eGFP reporter transcripts. FIG. 1D shows FACS quantification of recombinant expression systems utilizing wild-type and hyper-active deaminase fusions to RCas9 directed by targeting and non-targeting guides.

FIG. 5 illustrates a map of pcDNA3.1_ADAR2(E488Q)_XTEN_dCas9 (SEQ ID NO: 29). A CMV enhancer is located at position 235 to 614 (380 bp) and drives constitutive expression of recombinant protein in mammalian cells. A CMV promoter is located at position 615 to 818 (204 bp) and drives constitutive expression of recombinant protein in mammalian cells. ADARB1(E488Q) Catalytic Domain is located at position 961 to 2100 (1140 bp) and encodes a catalytically-active deaminating domain of human ADAR2 (ADARB1) with hyperactive point mutation (E488Q). XTEN is located at position 2101 to 2148 (48 bp)

and encodes a peptide linker connecting recombinant protein domains. dCas9 is located at position 2149 to 6252 (4104 bp) and encodes a catalytically-inactive (D10A and H841A) CRISPR-Cas9 protein from *Streptococcus pyogenes*. HA is located at position 6256 to 6282 (27 bp) and encodes human influenza hemagglutinin (HA) epitope tag. 2×SV40 NLS is located at position 6301 to 6348 (48 bp) and encodes a nuclear localization signal (NLS) derived from Simian Virus 40 (SV40) large T-antigen bGH. poly(A) signal is located at position 6426 to 6650 (225 bp) and encodes bovine growth hormone (bGH) polyadenylation signal.

Figure 2:
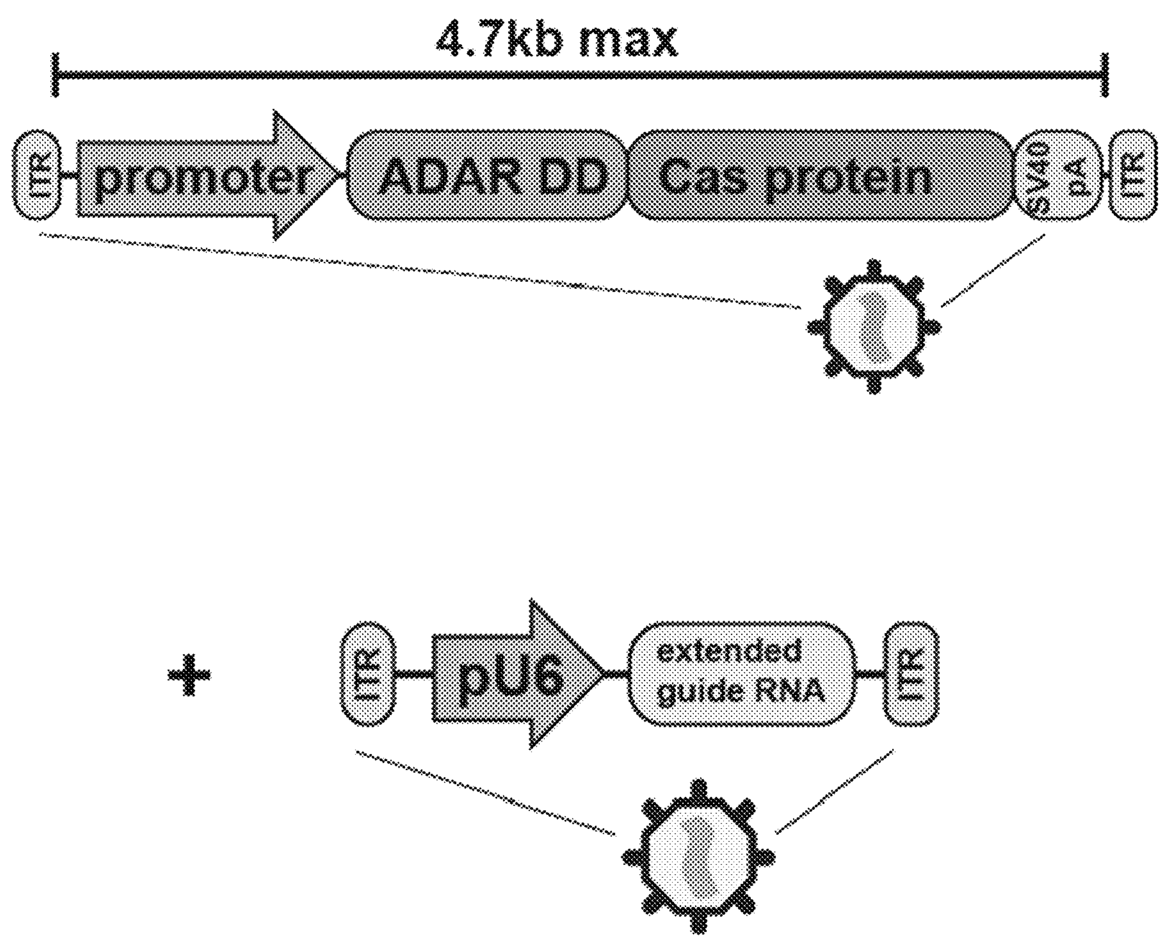
FIG. 2 illustrates, without limitation, an exemplary recombinant expression system as an AAV-based vector system. The AAV system comprises vectors carrying the nucleic acid sequence encoding the ADAR Deaminase domain/Cas endonuclease fusion protein and the extended single guide RNA (esgRNA) to be packaged as AAV virions.
Figure 3:
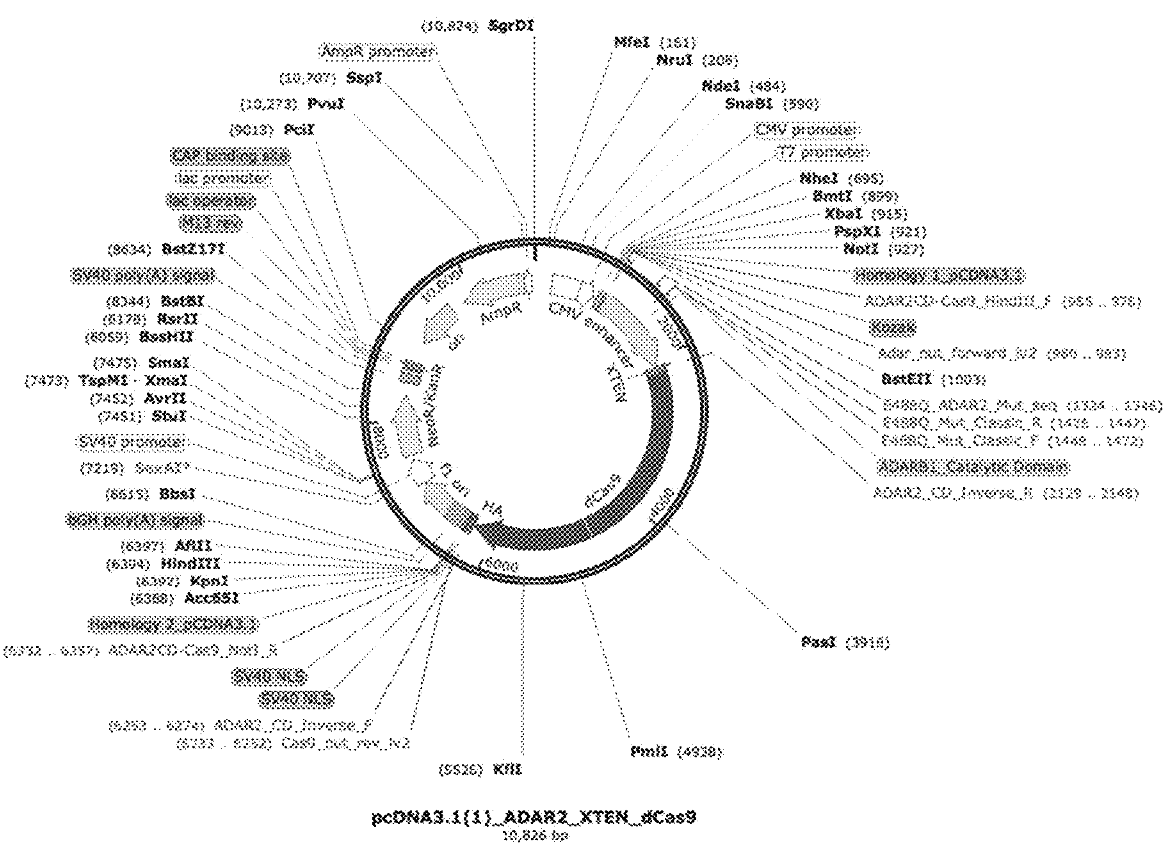
FIG. 3 illustrates a map of pcDNA3.1(1)_ADAR2_XTEN_dCas9 (SEQ ID NO: 27). The CMV enhancer is located at position 235 to 614 (380 bp in length) and drives constitutive expression of recombinant protein in mammalian cells. The CMV promoter is located at position 615 to 818 (204 bp in length) and drives constitutive expression of recombinant protein in mammalian cells. The ADARB1 Catalytic Domain is located at position 961 to 2100 (1140 bp in length) and encodes a catalytically-active deaminating domain of human ADAR2 (ADARB1). XTEN is located at position 2101 to 2148 (48 bp in length) and encodes a peptide linker connecting recombinant protein domains. dCas9 is located at position 2149 to 6252 (4104 bp in length) and encodes a catalytically-inactive (D10A and H841A) CRISPR-Cas9 protein from *Streptococcus pyogenes*. HA is located at position 6256 to 6282 (27 bp in length) and encodes human influenza hemagglutinin (HA) epitope tag. 2×SV40 NLS is located at position 6301 to 6348 (48 bp in length) and encodes a Nuclear localization signal (NLS) derived from Simian Virus 40 (SV40) large T-antigen. bGH poly(A) signal is located at position 6426 to 6650 (225 bp in length) and encodes a bovine growth hormone (bGH) polyadenylation signal.
Figure 4:
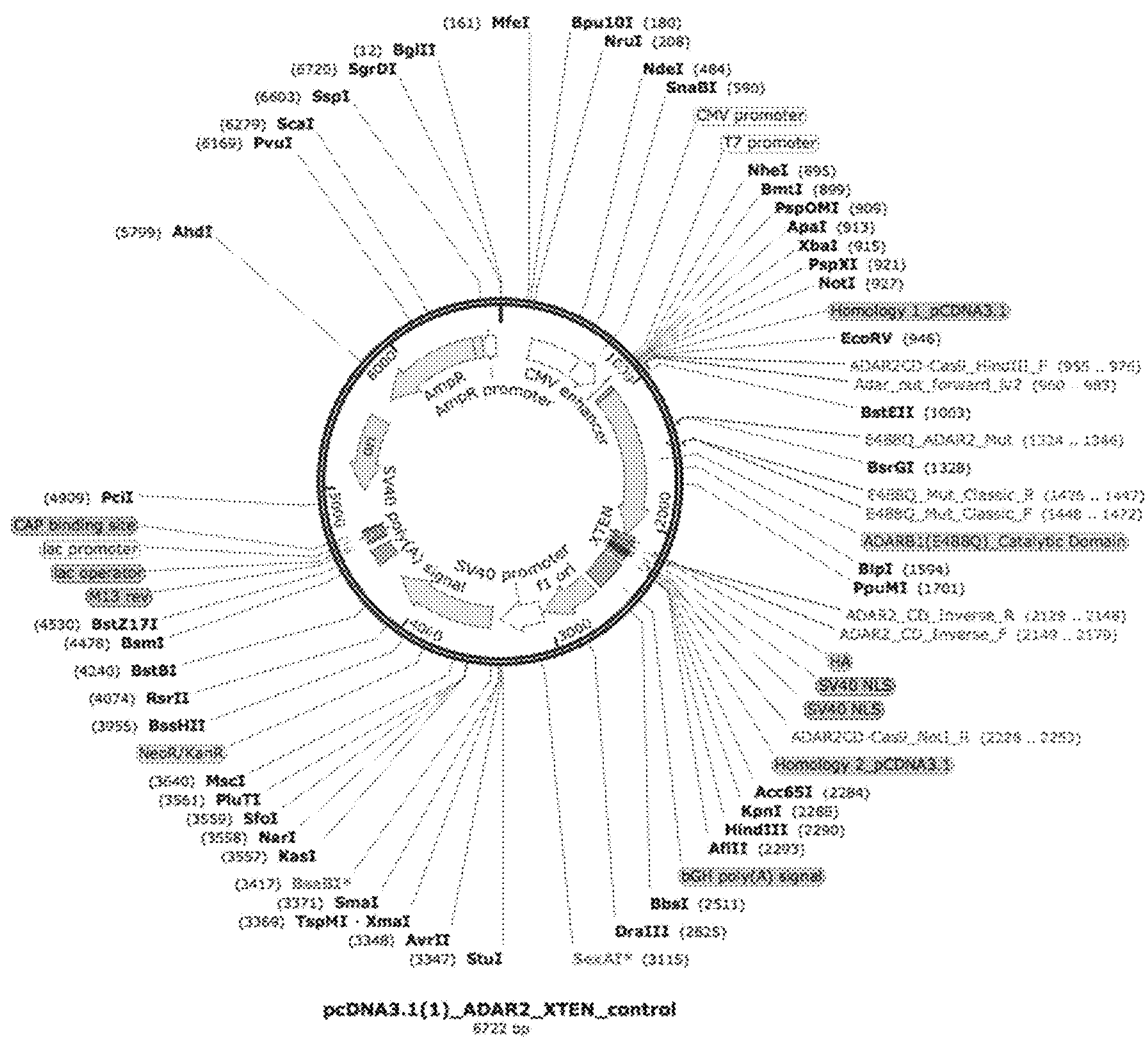
FIG. 4 illustrates a map of pcDNA3.1(1)_ADAR2_XTEN_control (SEQ ID NO: 28). A CMV enhancer is located at position 235 to 614 (380 bp in length) and drives constitutive expression of recombinant protein in mammalian cells. A CMV promoter is located at position 615 to 818 (204 bp in length) and drives constitutive expression of recombinant protein in mammalian cells. An ADARB1 Catalytic Domain is located at position 961 to 2100 (1140 bp in length) and encodes a catalytically-active deaminating domain of human ADAR2 (ADARB1). XTEN is located at position 2101 to 2148 (48 bp) and encodes a peptide linker connecting recombinant protein domains. HA is located at position 2152 to 2178 (27 bp) and encodes human influenza hemagglutinin (HA) epitope tag 2×SV40 NLS is located at position 2197 to 2244 (48 bp) nuclear localization signal (NLS) derived from Simian Virus 40 (SV40) large T-antigen. bGH poly(A) signal is located at position 2322 to 2546 (225 bp) and encodes bovine growth hormone (bGH) polyadenylation signal.
Figure 6:
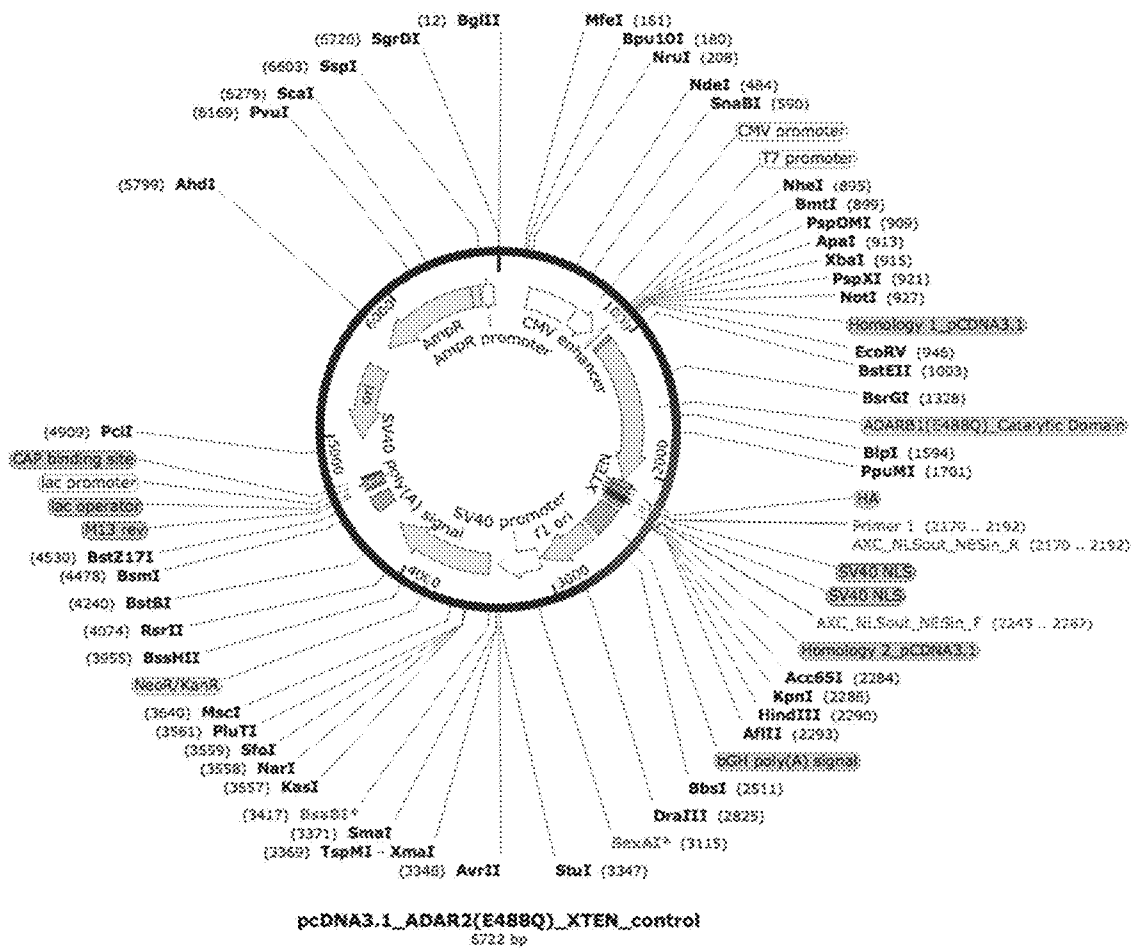

FIG. 6 illustrates a map of pcDNA3.1_ADAR2(E488Q)_XTEN_control (SEQ ID NO: 30). A CMV enhancer is located at position 235 to 614 (380 bp) and drives constitutive expression of recombinant protein in mammalian cells. A CMV promoter is located at position 615 to 818 (204 bp) and drives constitutive expression of recombinant protein in mammalian cells. ADARB1(E488Q) Catalytic Domain is located at position 961 to 2100 (1140 bp) and encodes a catalytically-active deaminating domain of human ADAR2 (ADARB1) with hyperactive point mutation (E488Q). XTEN is located at position 2101 to 2148 (48 bp) and encodes a peptide linker connecting recombinant protein domains. HA is located at position 2152 to 2178 (27 bp) and encodes a human influenza hemagglutinin (HA) epitope tag. 2×SV40 NLS is located at position 2197 to 2244 (48 bp) and encodes a nuclear localization signal (NLS) derived from Simian Virus 40 (SV40) large T-antigen. bGH poly(A) signal is located at position 2322 to 2546 (225 bp) and encodes bovine growth hormone (bGH) polyadenylation signal.

Figure 7:
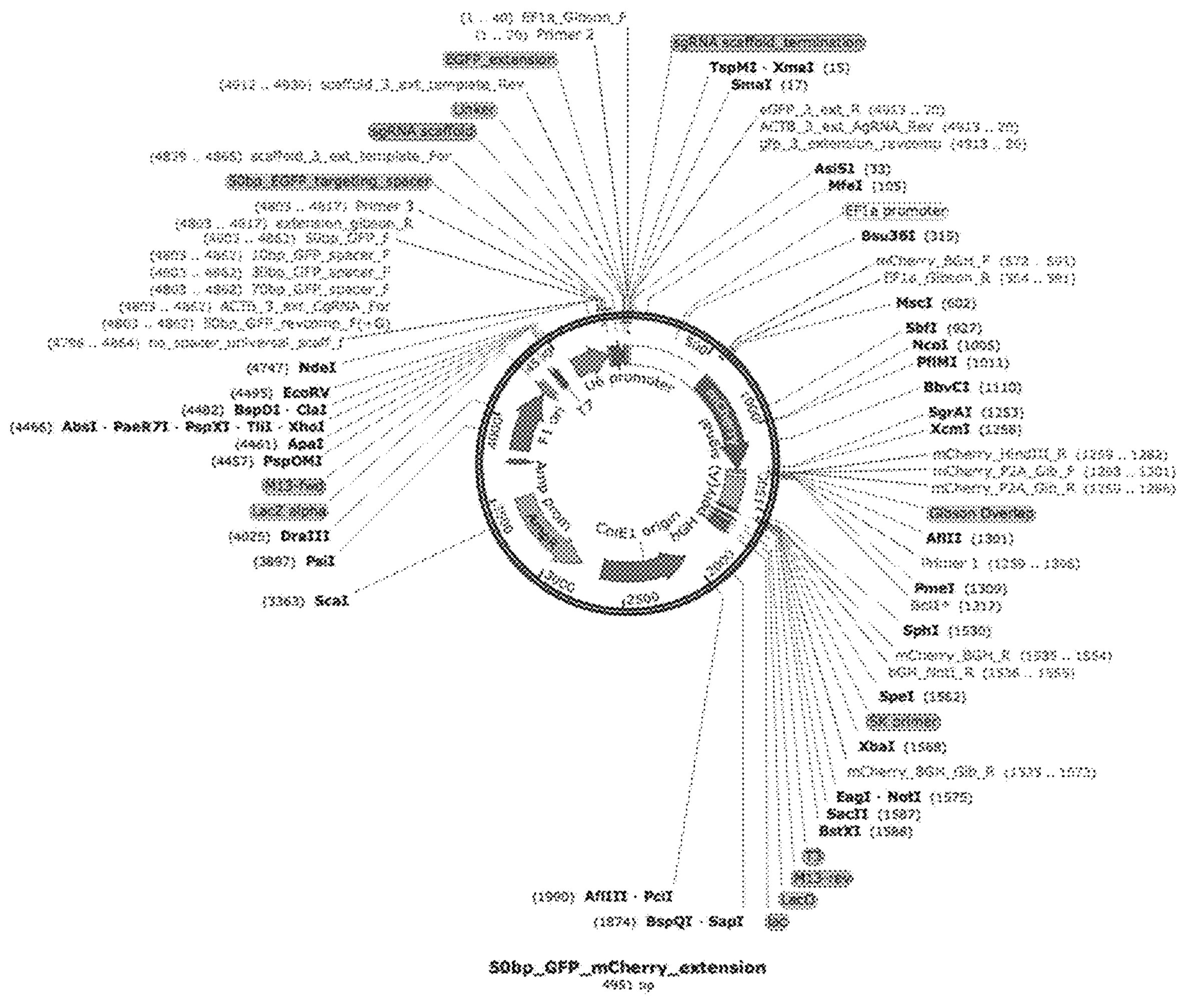

FIG. 7 illustrates a map of 50 bp_GFP_mCherry_extension (SEQ ID NO: 31). A U6 promoter is located at position 4555 to 4817 (263 bp) and is a Pol III promoter driving expression of sgRNA in mammalian cells. An EGFP targeting spacer is located at position 4818 to 4838 (21 bp) and encodes a spacer sequence of sgRNA that targets complementary EGFP reporter mRNA. An sgRNA scaffold is located at position 4839 to 4924 (86 bp) and encodes an sgRNA scaffold for *Streptococcus pyogenes* CRISPR-Cas9 system with (F+E) modification (Chen et al. 2014). Linker is located at position 4925 to 4930 (6 bp) encoding a linker sequence bridging the sgRNA scaffold with the extension sequence. And EGFP extension is located at position 4931 to 4951 (21 bp) encoding an RNA extension sequence that base pairs with target site and forces A-to-I editing using A-C mismatch. A sgRNA scaffold termination site is located at position 1 to 7 (7 bp) comprising a Poly(T) sequence that terminates Pol III RNA synthesis. An EF1a promoter is located at position 21 to 566 (546 bp) which is a constitutive promoter driving protein expression in mammalian cells. mCherry is located at position 572 to 1282 (711 bp) encoding a monomeric derivative of DsRed fluorescent protein. A bGH poly(A) signal is located at position 1330 to 1554 (225 bp) encoding a bovine growth hormone (bGH) polyadenylation signal.

Figure 8:
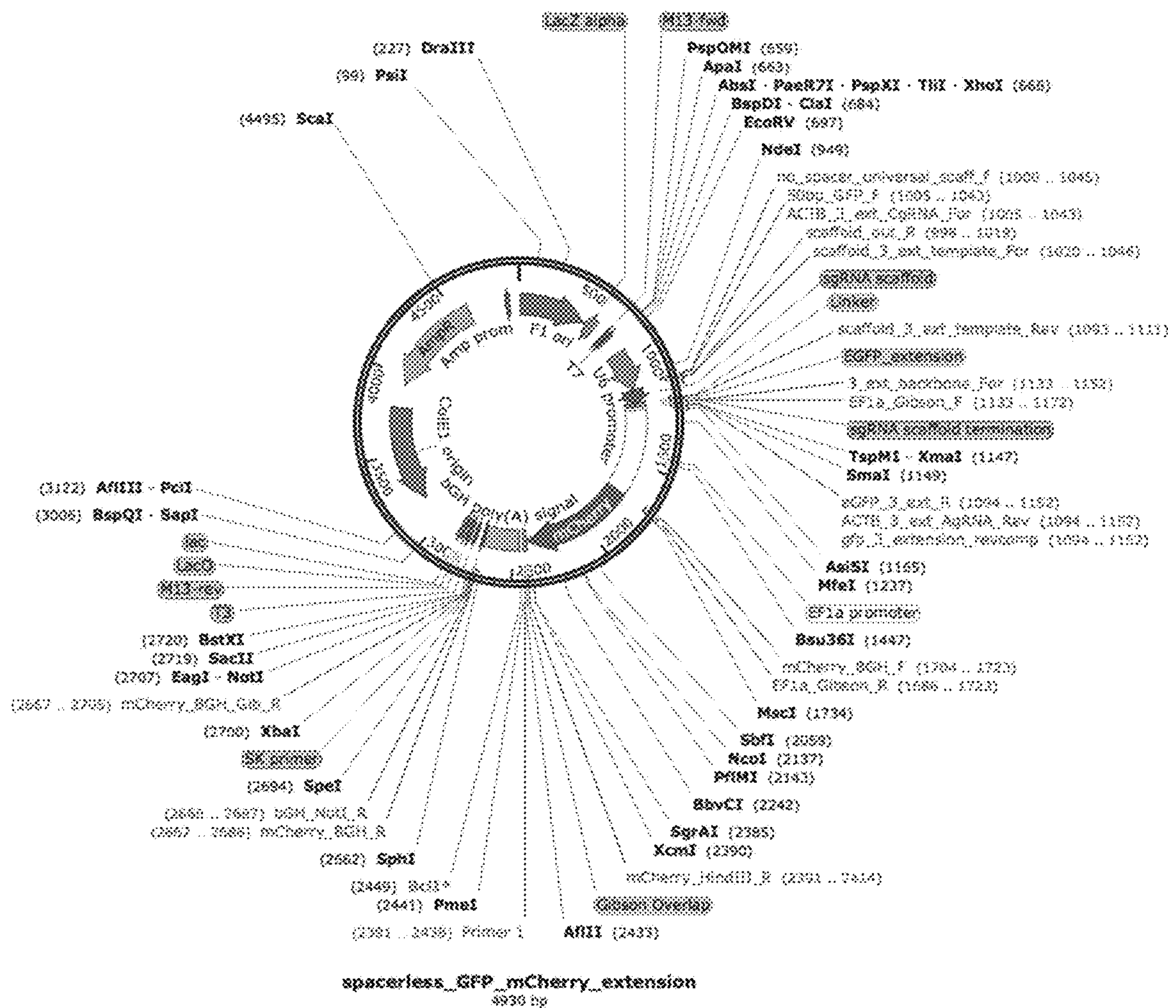

FIG. 8 illustrates a map of spacerless_GFP_mCherry_extension (SEQ ID NO: 32). A U6 promoter is located at position 757 to 1019 (263 bp) and is a Pol III promoter driving expression of sgRNA in mammalian cells. An sgRNA scaffold is located at position 1020 to 1105 (86 bp) encoding an sgRNA scaffold for *Streptococcus pyogenes* CRISPR-Cas9 system with (F+E) modification (Chen et al. 2014). A Linker is located at position 1106 to 1111 (6 bp) comprising a linker sequence bridging the sgRNA scaffold with the extension sequence. An EGFP extension is located at position 1112 to 1132 (21 bp) encoding an RNA extension sequence that base pairs with target site and forces A-to-I editing using A-C mismatch. An sgRNA scaffold termination is located at position 1133 to 1139 (7 bp) comprising a poly(T) sequence that terminates Pol III RNA synthesis. An EF1a promoter is located at position 1153 to 1698 (546 bp) and is a constitutive promoter driving protein expression in mammalian cells. mCherry is located at position 1704 to 2414 (711 bp) encoding a monomeric derivative of DsRed fluorescent protein. A bGH poly(A) signal is located at position 2462 to 2686 (225 bp) encoding bovine growth hormone (bGH) polyadenylation signal.

Figure 9:
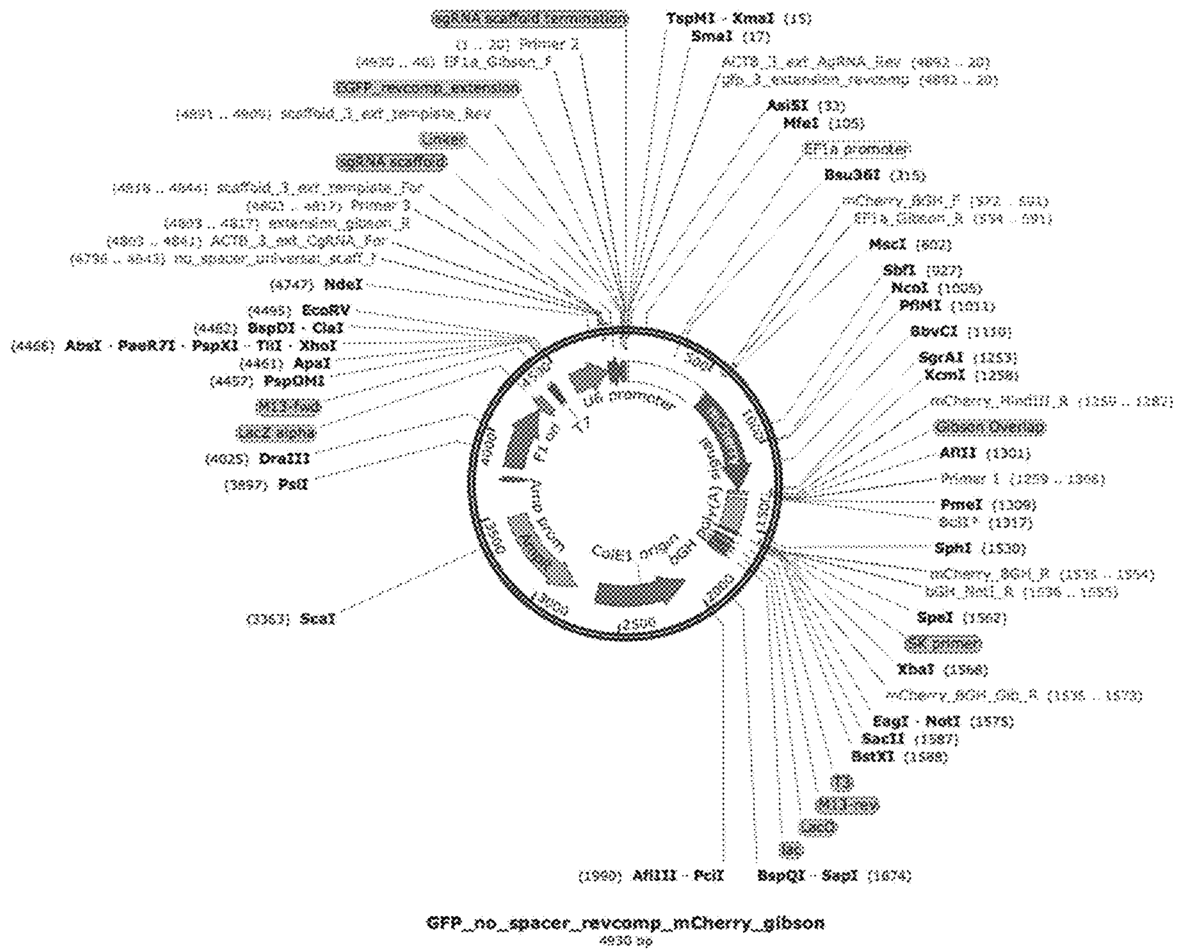

FIG. 9 illustrates a map of GFP_no_spacer_revcomp_mCherry_gibson (SEQ ID NO: 33). A U6 promoter is located at position 4555 to 4817 (263 bp) and is a Pol III promoter driving expression of sgRNA in mammalian cells. An sgRNA scaffold is located at position 4818 to 4903 (86 bp) and encodes a sgRNA scaffold for *Streptococcus pyogenes* CRISPR-Cas9 system with (F+E) modification (Chen et al. 2014). A linker is located at position 4904 to 4909 (6 bp) encoding a linker sequence bridging the sgRNA scaffold with the extension sequence. An EGFP revcomp extension is located at position 4910 to 4930 (21 bp) encoding an RNA reverse complement extension sequence that matches the sequence of the EGFP mRNA target site. An sgRNA scaffold termination site is located at position 1 to 7 (7 bp) comprising a poly(T) sequence that terminates Pol III RNA synthesis. An EF1a promoter is located at position 21 to 566 (546 bp) and is a constitutive promoter driving protein expression in mammalian cells. mCherry is located at position 572 to 1282 (711 bp) encoding a monomeric derivative of DsRed fluorescent protein. A bGH poly(A) signal is located at position 1330 to 1554 (225 bp) encoding a bovine growth hormone (bGH) polyadenylation signal.

Figure 10:
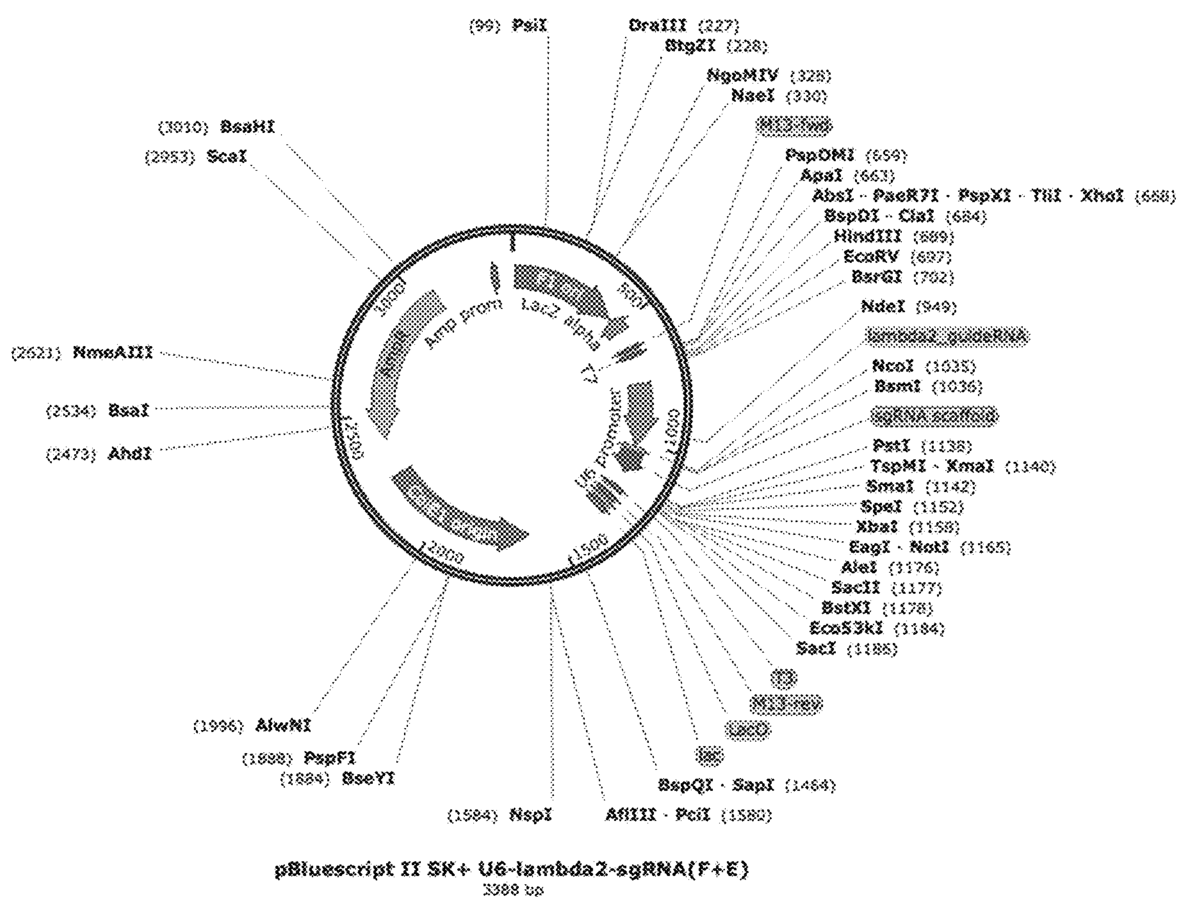

FIG. 10 illustrates a map of pBluescript II SK+U6-lambda2-sgRNA(F+E) (SEQ ID NO: 34). A U6 promoter is located at position 757 to 1019 (263 bp) and is a Pol III promoter driving expression of sgRNA in mammalian cells. A lambda2 guideRNA is located at position 1020 to 1039 (20 bp) encoding a non-targeting sgRNA sequence targeting lambda phage 2. An sgRNA scaffold is located at position 1041 to 1132 (92 bp) encoding a sgRNA scaffold for *Streptococcus pyogenes* CRISPR-Cas9 system with (F+E) modification (Chen et al. 2014).

Figure 11:
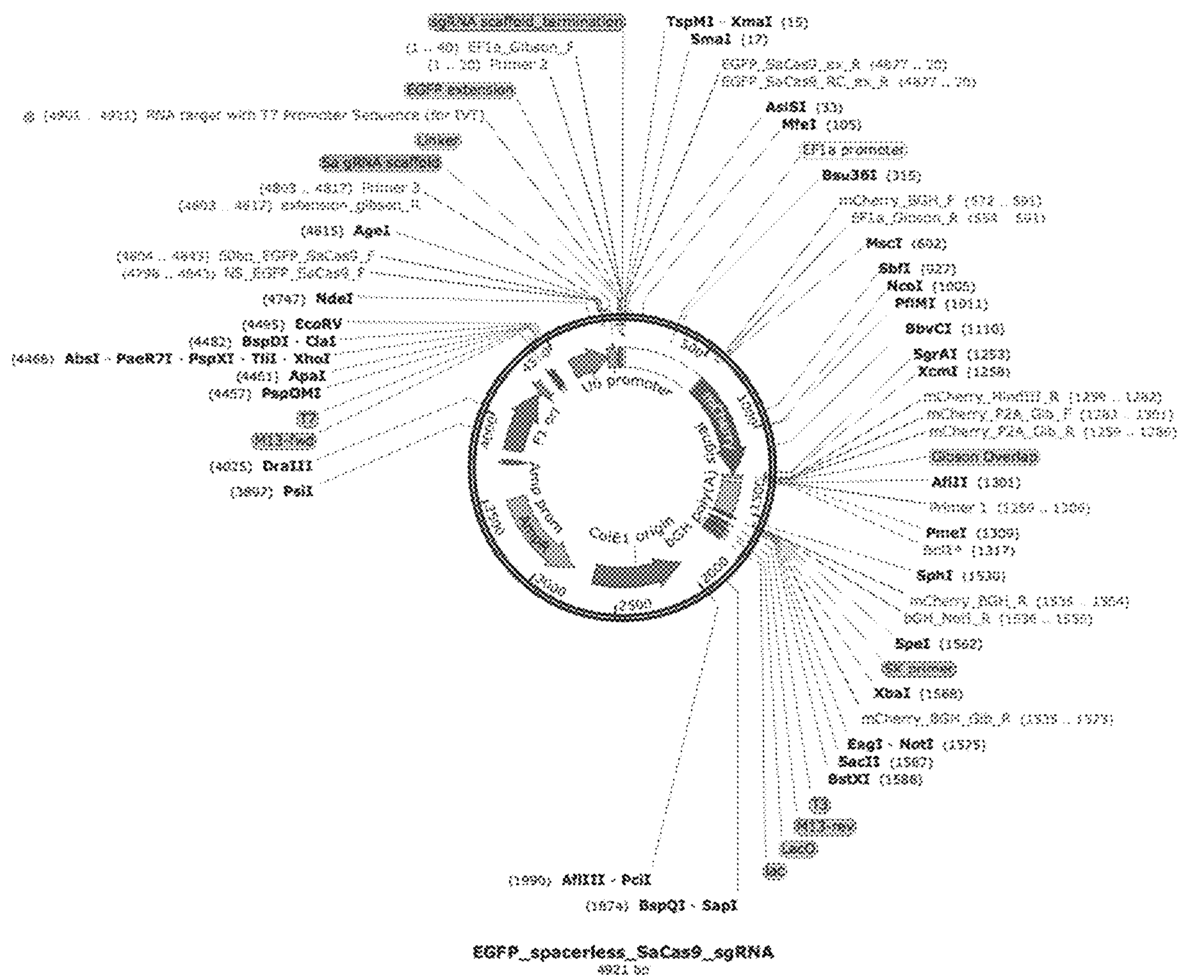

FIG. 11 illustrates a map of EGFP_spacerless_SaCas9_sgRNA (SEQ ID NO: 47). A U6 promoter is located at position 4555 to 4817 (263 bp) and is a Pol III promoter driving expression of sgRNA in mammalian cells. An Sa sgRNA scaffold is located at position 4819 to 4894 (76 bp) encoding an sgRNA scaffold for *Staphylococcus aureus* CRISPR-Cas9 system with A-U base flip (Chen et al. 2016). A linker is located at position 4895 to 4900 (6 bp) encoding a linker sequence bridging the sgRNA scaffold with the extension sequence. An EGFP extension is located at position 4901 to 4921 (21 bp) encoding an RNA extension sequence that base pairs with target site and forces A-to-I editing using A-C mismatch. An sgRNA scaffold termination site is located at position 1 to 7 (7 bp) comprising a poly(T) sequence that terminates pol III RNA synthesis. An EF1a promoter is located at position 21 to 566 (546 bp) which is a constitutive promoter driving protein expression in mammalian cells. mCherry is located at position 572 to 1282 (711 bp) encoding a monomeric derivative of DsRed fluorescent protein. A bGH poly(A) signal is located at position 1330 to 1554 (225 bp) encoding bovine growth hormone (bGH) polyadenylation signal.

Figure 12:
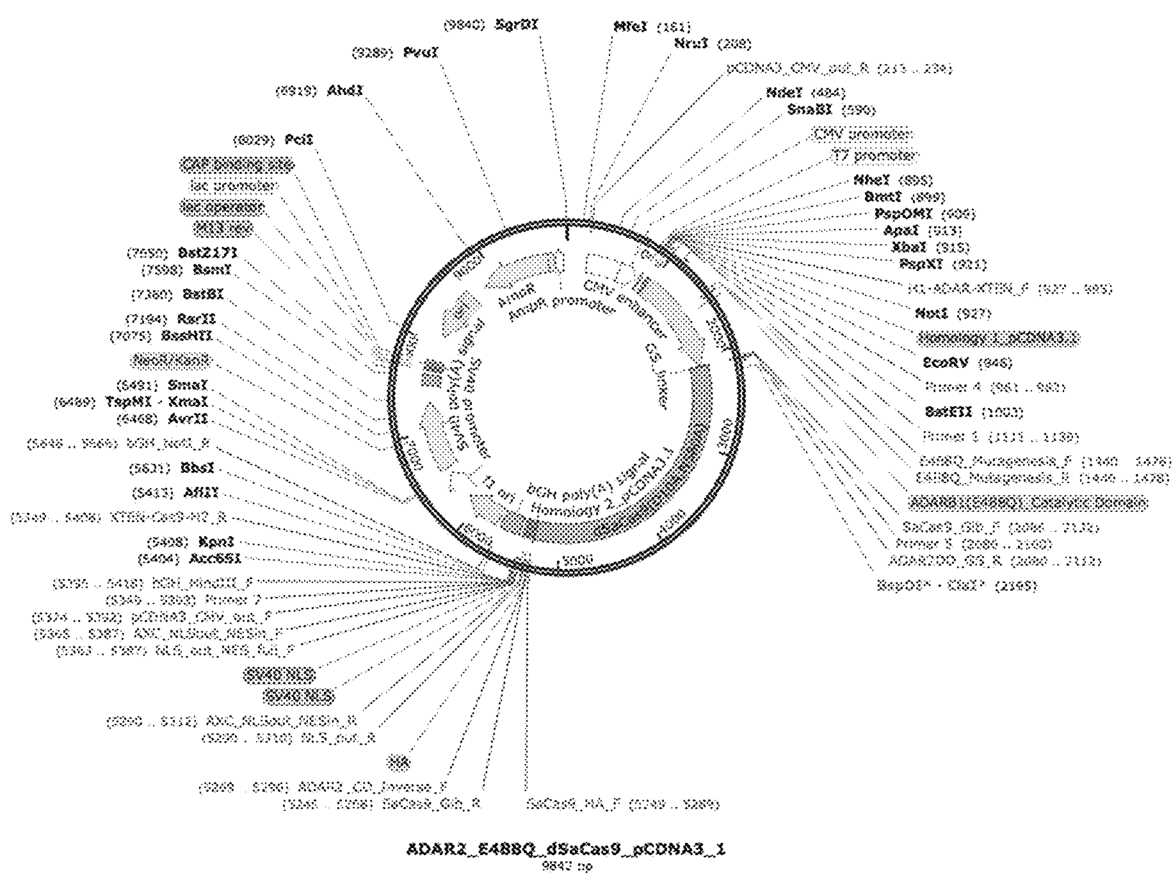

FIG. 12 illustrates a map of ADAR2_E488Q_dSaCas9_pCDNA3_1 (SEQ ID NO: 48).

A CMV enhancer is located at position 235 to 614 (380 bp) and drives constitutive expression of recombinant protein in mammalian cells. A CMV promoter is located at position 615 to 818 (204 bp) and drives constitutive expression of recombinant protein in mammalian cells. ADARB1 Catalytic Domain is located at position 961 to 2100 (1140 bp) and encodes a catalytically-active deaminating domain of human ADAR2 (ADARB1). A GS linker is located at position 2101 to 2112 (12 bp) and encodes a Glycine-Serine peptide linker to bridge protein domains. A dSaCas9 is located at position 2113 to 5268 (3156 bp) encoding a catalytically-inactive (with point mutations D10A and N580A) CRISPR-Cas9 protein from *Staphylococcus aureus*. HA is located at position 5272 to 5298 (27 bp) encoding human influenza hemagglutinin (HA) epitope tag. A 2×SV40 NLS is located at position 5317 to 5364 (48 bp) nuclear localization signal (NLS) derived from Simian Virus 40 (SV40) large T-antigen. A bGH poly(A) signal is located at position 5442 to 5666 (225 bp) encoding a bovine growth hormone (bGH) polyadenylation signal.

Figure 13A:
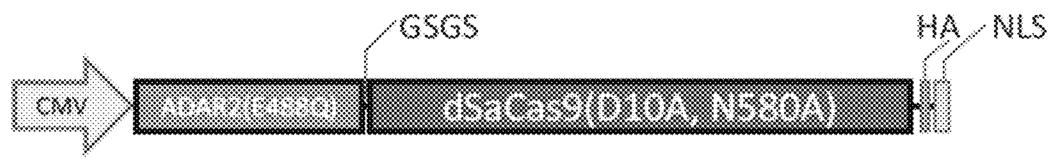
Figure 13B:
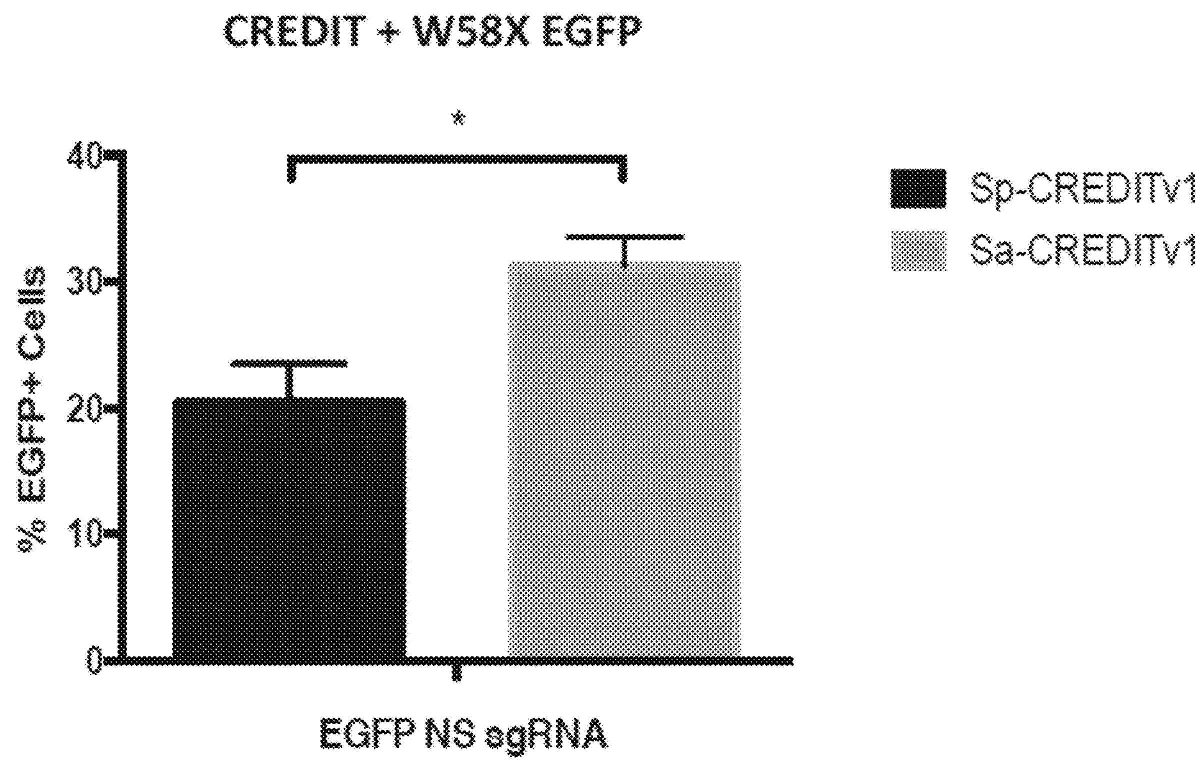

FIGS. 13A-13B illustrate a comparison between a recombinant expression system comprising a nuclease dead Cas9 derived from *S. pyogenes* (dSpCas9) and a nuclease dead Cas9 derived from *S. aureus* (dSaCas9). dSaCas9 is significantly smaller than dSpCas9, which provides efficiency in viral packaging. FIG. 13A shows an illustration of an ADAR2(E488Q)-dSpCas9 fusion construct with an XTEN linker (Sp-CREDITv1) and an illustration of an ADAR2 (E488Q)-dSaCas9 fusion construct with an GSGS linker (Sa-CREDITv1). FIG. 13B shows the results of an experiment wherein the efficiency of Sp-CREDITv1 is compared to the efficiency of Sa-CREDITv1. This data shows successful editing of the GFP reporter by both CREDIT systems, with Sa-CREDITv1 exhibiting the highest frequency of edited cells.

DETAILED DESCRIPTION

Embodiments according to the present disclosure will be described more fully hereinafter. Aspects of the disclosure may, however, be embodied in different forms and should not be construed as limited to the embodiments set forth herein. Rather, these embodiments are provided so that this disclosure will be thorough and complete, and will fully convey the scope of the invention to those skilled in the art. The terminology used in the description herein is for the purpose of describing particular embodiments only and is not intended to be limiting.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. While not explicitly defined below, such terms should be interpreted according to their common meaning.

The terminology used in the description herein is for the purpose of describing particular embodiments only and is not intended to be limiting of the invention. All publications, patent applications, patents and other references mentioned herein are incorporated by reference in their entirety.

The practice of the present technology will employ, unless otherwise indicated, conventional techniques of tissue culture, immunology, molecular biology, microbiology, cell biology, and recombinant DNA, which are within the skill of the art.

Unless the context indicates otherwise, it is specifically intended that the various features of the invention described herein can be used in any combination. Moreover, the disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless explicitly indicated otherwise, all specified embodiments, features, and terms intend to include both the recited embodiment, feature, or term and biological equivalents thereof.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

Definitions

As used in the description of the invention and the appended claims, the singular forms "a," "an" and "the" are intended to include the plural forms as well, unless the context clearly indicates otherwise.

The term "about," as used herein when referring to a measurable value such as an amount or concentration and the like, is meant to encompass variations of 20%, 10%, 5%, 1%, 0.5%, or even 0.1% of the specified amount.

The terms or "acceptable," "effective," or "sufficient" when used to describe the selection of any components, ranges, dose forms, etc. disclosed herein intend that said component, range, dose form, etc. is suitable for the disclosed purpose.

"Polynucleotide" or "nucleotide," as used interchangeably herein, refer to polymers of nucleotides of any length, and include DNA and RNA. A polynucleotide or nucleotide sequence could be either double-stranded or single-stranded. When a polynucleotide or nucleotide sequence is single stranded, it could refer to either of the two complementary strands. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (such as methyl phosphonates, phosphotriesters, phosphoamidates, cabamates, etc.) and with charged linkages (such as phosphorothioates, phosphorodithioates, etc.), those containing pendant moieties, such as, for example, proteins (such as nucleases, toxins, antibodies, signal peptides, ply-L-lysine, etc.), those with intercalators (such as acridine, psoralen, etc.), those containing chelators (such as metals, radioactive metals, boron, oxidative metals, etc.), those containing alkylators, those with modified linkages (such as alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR 2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Nucleic acids", "nucleic acid molecules," or "nucleic acid sequences" are used interchangeably herein to refer to polynucleotides and/or oligonucleotides. In some embodiments, nucleic acid is used interchangeably with polynucleotide and/or oligonucleotide.

As used herein, "substantially complementary or substantially matched" means that two nucleic acid sequences have at least 90% sequence identity. Preferably, the two nucleic acid sequences have at least 95%, 96%, 97%, 98%, 99% or 100% of sequence identity. Alternatively, "substantially complementary or substantially matched" means that two nucleic acid sequences can hybridize under high stringency condition(s).

As used herein, "improve" means a change of at least about 1%, 2%, 5%, 10%, 15%, 20%, 25%, 30%, 35%, 40%, 35%, 50%, 55%, 60%, 65%, 70%, 75%, 80%, 85%, 90%, 95%, 100%, 125%, 150%, 175%, 200%, 225%, 250%, 275%, 300%, 350%, 400%, 450%, 500%, 600%, 700%, 800%, 900%, 1000% or more or any value between any of the listed values. Alternatively, "improve" could mean a change of at least about 1-fold, 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, 60-fold, 70-fold, 80-fold, 90-fold, 100-fold, 500-fold, 1000-fold, 2000-fold or more or any value between any of the listed values.

As used herein, "nuclease null" or "nuclease dead" may refer to a polypeptide with reduced nuclease activity, reduced endo- or exo-DNAse activity or RNAse activity, reduced nickase activity, or reduced ability to cleave DNA and/or RNA. Non-limiting examples of Cas-associated endonucleases that are nuclease dead include endonucleases with mutations that render the RuvC and/or HNH nuclease domains inactive. For example, *S. pyogenes* Cas9 can be rendered inactive by point mutations D10A and H840A, resulting in a nuclease dead Cas9 molecule that cannot cleave target DNA or RNA. The dCas9 molecule retains the ability to bind to target RNA based on the gRNA targeting sequence.

As used herein, "reduced nuclease activity" means a decline in nuclease, nickase, DNAse, or RNAse activity of at least about 1%, 2%, 5%, 10%, 15%, 20%, 25%, 30%, 35%, 40%, 35%, 50%, 55%, 60%, 65%, 70%, 75%, 80%, 85%, 90%, 95%, 100% or more or any value between any of the listed values. Alternatively, "reduced nuclease activity" may refer to a decline of at least about 1-fold, 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, 60-fold, 70-fold, 80-fold, 90-fold, 100-fold, 500-fold, 1000-fold, 2000-fold or more or any value between any of the listed values.

As used herein, "increased catalytic activity" means an increase in catalytic activity of e.g. deaminase activity of at least about 1%, 2%, 5%, 10%, 15%, 20%, 25%, 30%, 35%, 40%, 35%, 50%, 55%, 60%, 65%, 70%, 75%, 80%, 85%, 90%, 95%, 100% or more or any value between any of the listed values as compared to the corresponding wild type catalytic activity (e.g., wild type deaminase activity). Alternatively, "increased catalytic activity" may refer to an increase of at least about 1-fold, 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, 60-fold, 70-fold, 80-fold, 90-fold, 100-fold, 500-fold, 1000-fold, 2000-fold or more or any value between any of the listed values as compared to the corresponding wild type catalytic activity (e.g., wild type deaminase activity).

As used herein, the term "ADAR" refers to a double-stranded RNA specific adenosine deaminase which catalyzes the hydrolytic deamination of adenosine to inosine in double-stranded RNA (dsRNA), referred to as A to I editing and also known as Adenosine Deaminase Acting on RNA. Non-limiting exemplary sequences of this protein and annotation of its domains is found under UniProt reference number P55265 (human) and Q99MU3 (mouse).

The term "adeno-associated virus" or "AAV" as used herein refers to a member of the class of viruses associated with this name and belonging to the genus dependoparvovirus, family Parvoviridae. Multiple serotypes of this virus are known to be suitable for gene delivery; all known serotypes can infect cells from various tissue types. At least 11, sequentially numbered, are disclosed in the prior art. Non-limiting exemplary serotypes useful in the methods disclosed herein include any of the 11 serotypes, e.g., AAV2 and AAV8.

Also as used herein, "and/or" refers to and encompasses any and all possible combinations of one or more of the associated listed items, as well as the lack of combinations when interpreted in the alternative ("or").

The term "aptamer" as used herein refers to single stranded DNA or RNA molecules that can bind to one or more selected targets with high affinity and specificity. Non-limiting exemplary targets include but are not limited to proteins or peptides.

The term "Cas-associated" refers to a CRISPR (Clustered Regularly Interspaced Short Palindromic Repeats) associated endonuclease. "Cas9" is a Cas-associated endonuclease referred to by this name (UniProtKB G3ECR1 (CAS9_STRTR)). DeadCas-9 or "dCas9" is a Cas9 endonuclease which lacks or substantially lacks endonuclease and/or cleavage activity. A non-limiting example of dCas9 is the dCas9 encoded in AddGene plasmid. #74710, which is commercially available through the AddGene database.

The term "cell" as used herein may refer to either a prokaryotic or eukaryotic cell, optionally obtained from a subject or a commercially available source.

The term "gRNA" or "guide RNA" as used herein refers to the guide RNA sequences used to target specific genes for correction employing the CRISPR technique. Techniques of designing gRNAs and donor therapeutic polynucleotides for target specificity are well known in the art. For example, Doench, J., et al. Nature biotechnology 2014; 32(12):1262-7 and Graham, D., et al. Genome Biol. 2015; 16: 260, incorporated by reference herein.

As used herein, the term "CRISPR" refers to a technique of sequence specific genetic manipulation relying on the clustered regularly interspaced short palindromic repeats pathway, which unlike RNA interference regulates gene expression at a transcriptional level. The term "gRNA" or "guide RNA" as used herein refers to the guide RNA sequences used to target specific genes for correction employing the CRISPR technique. Techniques of designing gRNAs and donor therapeutic polynucleotides for target specificity are well known in the art. For example, Doench, J., et al. Nature biotechnology 2014; 32(12):1262-7 and Graham, D., et al. Genome Biol. 2015; 16: 260. "Single guide RNA" or "sgRNA" is a specific type of gRNA that combines tracrRNA (transactivating RNA), which binds to Cas9 to activate the complex to create the necessary strand breaks, and crRNA (CRISPR RNA), comprising complimentary nucleotides to the tracrRNA, into a single RNA construct. As described herein, an "extended single guide RNA" or "esgRNA" is a specific type of sgRNA that includes an extension sequence of homology to the target RNA comprising a mismatch for a target adenosine of the target RNA to be edited in a manner such that a A-C mismatch is formed with a target transcript generating a 'pseudo-dsRNA' substrate to be edited at the bulged adenosine residue.

As used herein, the term "comprising" is intended to mean that the compositions and methods include the recited elements, but do not exclude others. As used herein, the transitional phrase "consisting essentially of" (and grammatical variants) is to be interpreted as encompassing the recited materials or steps "and those that do not materially affect the basic and novel characteristic(s)" of the recited embodiment. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising." "Consisting of" shall mean excluding more than trace elements of other ingredients and substantial method steps for administering the compositions disclosed herein. Aspects defined by each of these transition terms are within the scope of the present disclosure.

The term "encode" as it is applied to nucleic acid sequences refers to a polynucleotide which is said to "encode" a polypeptide if, in its native state or when manipulated by methods well known to those skilled in the art, can be transcribed and/or translated to produce the mRNA for the polypeptide and/or a fragment thereof. The antisense strand is the complement of such a nucleic acid, and the encoding sequence can be deduced therefrom.

The terms "equivalent" or "biological equivalent" are used interchangeably when referring to a particular molecule, biological, or cellular material and intend those having minimal homology while still maintaining desired structure or functionality.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell. The expression level of a gene may be determined by measuring the amount of mRNA or protein in a cell or tissue sample; further, the expression level of multiple genes can be determined to establish an expression profile for a particular sample.

As used herein, the term "sample" can refer to a composition comprising targets. Suitable samples for analysis by the disclosed methods, devices, and systems include cells, tissues, organs, or organisms or compositions obtained from cells, tissues or organisms. In some embodiments, samples are isolated from a subject.

As used herein, the term "functional" may be used to modify any molecule, biological, or cellular material to intend that it accomplishes a particular, specified effect.

A "gene delivery vehicle" is defined as any molecule that can carry inserted polynucleotides into a host cell. Examples of gene delivery vehicles are liposomes, micelles biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide disclosed herein can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extra-chromosomal replicon (e.g., a plasmid) or a nuclear or mitochondrial chromosome. A number of "vectors" are known to be capable of mediating transfer of genes to mammalian cells, as is known in the art and described herein.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmid vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacterium produces proteins to confer its antibiotic resistance, it can also be induced to produce large amounts of proteins from the inserted gene.

A "yeast artificial chromosome" or "YAC" refers to a vector used to clone large DNA fragments (larger than 100 kb and up to 3000 kb). It is an artificially constructed chromosome and contains the telomeric, centromeric, and replication origin sequences needed for replication and preservation in yeast cells. Built using an initial circular plasmid, they are linearized by using restriction enzymes, and then DNA ligase can add a sequence or gene of interest within the linear molecule by the use of cohesive ends. Yeast expression vectors, such as YACs, YIps (yeast integrating plasmid), and YEps (yeast episomal plasmid), are extremely useful as one can get eukaryotic protein products with posttranslational modifications as yeasts are themselves eukaryotic cells, however YACs have been found to be more unstable than BACs, producing chimeric effects.

A "viral vector" is defined as a recombinantly produced virus or viral particle that comprises a polynucleotide to be delivered into a host cell, either in vivo, ex vivo or in vitro.

Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffithsin in tobacco leaves (O'Keefe et al. (2009) Proc. Nat. Acad. Sci. USA 106(15):6099-6104). Alphavirus vectors, such as Semliki Forest virus-based vectors and Sindbis virus-based vectors, have also been developed for use in gene therapy and immunotherapy. See, Schlesinger & Dubensky (1999) Curr. Opin. Biotechnol. 5:434-439 and Ying et al. (1999) Nat. Med. 5(7):823-827. In aspects where gene transfer is mediated by a retroviral vector, a vector construct refers to the polynucleotide comprising the retroviral genome or part thereof, and a therapeutic gene. Further details as to modern methods of vectors for use in gene transfer may be found in, for example, Kotterman et al. (2015) Viral Vectors for Gene Therapy: Translational and Clinical Outlook Annual Review of Biomedical Engineering 17.

As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. Ads do not require integration into the host cell genome. Recombinant Ad derived vectors, particularly those that reduce the potential for recombination and generation of wild-type virus, have also been constructed. Such vectors are commercially available from sources such as Takara Bio USA (Mountain View, CA), Vector Biolabs (Philadelphia, PA), and Creative Biogene (Shirley, NY). Wild-type AAV has high infectivity and specificity integrating into the host cell's genome. See, Wold and Toth (2013) Curr. Gene. Ther. 13(6):421-433, Hermonat & Muzyczka (1984) Proc. Natl. Acad. Sci. USA 81:6466-6470, and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Agilent Technologies (Santa Clara, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods disclosed herein. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins disclosed herein are other non-limiting techniques.

"Homology" or "identity" or "similarity" refers to sequence similarity between two peptides or between two nucleic acid molecules. Homology can be determined by comparing a position in each sequence that may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure.

"Homology" or "identity" or "similarity" can also refer to two nucleic acid molecules that hybridize under stringent conditions.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

As used herein, the term "specifically binds" refers to the binding specificity of a specific binding pair. Hybridization by a target-specific nucleic acid sequence of a particular target polynucleotide sequence in the presence of other potential targets is one characteristic of such binding. Specific binding involves two different nucleic acid molecules wherein one of the nucleic acid molecules specifically hybridizes with the second nucleic acid molecule through chemical or physical means. The two nucleic acid molecules are related in the sense that their binding with each other is such that they are capable of distinguishing their binding partner from other assay constituents having similar characteristics. The members of the binding component pair are referred to as ligand and receptor (anti-ligand), specific binding pair (SBP) member and SBP partner, and the like.

The term "isolated" as used herein refers to molecules or biologicals or cellular materials being substantially free from other materials.

As used herein, the term "linker" refers to a short peptide sequence that may occur between two protein domains. Linkers may often comprise flexible amino acid residues, e.g. glycine or serine, to allow for free movement of adjacent but fused protein domains. "XTEN" refers to any one of the exemplary linkers provided in Schellenberger et al. (2009) Nat Biotechnol. 27:1186-1190. doi: 10.1038/nbt.1588 or equivalent variants thereof.

As used herein, the term "organ" is a structure which is a specific portion of an individual organism, where a certain function or functions of the individual organism is locally performed and which is morphologically separate. Non-limiting examples of organs include the skin, blood vessels, cornea, thymus, kidney, heart, liver, umbilical cord, intestine, nerve, lung, placenta, pancreas, thyroid and brain.

The term"photospacer adjacent motif" or "PAM" refers to a sequence that activates the nuclease domain of Cas9. A "PAMmer" refers to a PAM-presenting oligonucleotide. As used herein, the term PAMmer generally refers to an anti-sense synthetic oligonucleotide composed alternating 2'OMe RNA and DNA bases and/or other variations of a PAM presenting oligonucleotide that can optimize the CRISPR/Cas9 system and generate specific cleavage of RNA targets without cross reactivity between non-target RNA or against genomic DNA. See, e.g., O'Connell et al. (2014) Nature. 516(7530):263-266.

The term "promoter" as used herein refers to any sequence that regulates the expression of a coding sequence, such as a gene. Promoters may be constitutive, inducible, repressible, or tissue-specific, for example. A "promoter" is a control sequence that is a region of a polynucleotide sequence at which initiation and rate of transcription are controlled. It may contain genetic elements at which regulatory proteins and molecules may bind such as RNA polymerase and other transcription factors. Non-limiting exemplary promoters include CMV promoter and U6 promoter.

The term "protein", "peptide" and "polypeptide" are used interchangeably and in their broadest sense to refer to a compound of two or more subunits of amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. Proteins and peptides are known to have a C-terminus, referring to the end with an unbound carboxy group on the terminal amino acid, and an N-terminus, referring to the end with an unbound amine group on the terminal amino acid. As used herein the term "amino acid" refers to either natural and/or unnatural or synthetic amino acids, including glycine and both the D and L optical isomers, amino acid analogs and peptidomimetics. The term "fused" in context of a protein or polypeptide refers to the linkage between termini of two or more proteins or polypeptides (or domains thereof) to form a fusion protein.

As used herein, the term "recombinant expression system" refers to a genetic construct for the expression of certain genetic material or proteins formed by recombination.

As used herein, the term "subject" is used interchangeably with "patient" and is intended to mean any animal. In some embodiments, the subject may be a mammal. In some embodiments, the mammal is a non-human mammal. In some embodiments, the mammal is a bovine, equine, porcine, murine, feline, canine, simian, rat, or human.

The term "tissue" is used herein to refer to tissue of a living or deceased organism or any tissue derived from or designed to mimic a living or deceased organism. The tissue may be healthy, diseased, and/or have genetic mutations. The biological tissue may include any single tissue (e.g., a collection of cells that may be interconnected) or a group of tissues making up an organ or part or region of the body of an organism. The tissue may comprise a homogeneous cellular material or it may be a composite structure such as that found in regions of the body including the thorax which for instance can include lung tissue, skeletal tissue, and/or muscle tissue. Exemplary tissues include, but are not limited to those derived from liver, lung, thyroid, skin, pancreas, blood vessels, bladder, kidneys, brain, biliary tree, duodenum, abdominal aorta, iliac vein, heart and intestines, including any combination thereof.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

As used herein, the term "vector" intends a recombinant vector that retains the ability to infect and transduce non-dividing and/or slowly-dividing cells and integrate into the target cell's genome. The vector may be derived from or based on a wild-type virus. Aspects of this disclosure relate to an adeno-associated virus vector.

A number of other vector elements are disclosed herein; e.g., plasmids, promoters, linkers, signals, etc. The nature and function of these vector elements are commonly understood in the art and a number of these vector elements are commercially available. Non-limiting exemplary sequences thereof, e.g., SEQ ID NOS: 1-8 are disclosed herein and further description thereof is provided herein below and/or illustrated in FIGS. 3-10.

CRISPRICas Directed RNA-Editing (CREDIT)

Disclosed herein is an efficient, versatile and simplified platform technology for performing programmable RNA editing at single-nucleotide resolution using RNA-targeting CRISPR/Cas (RCas). This approach, which Applicants have termed "Cas-directed RNA editing" or "CREDIT," provides a means to reversibly alter genetic information in a temporal manner, unlike traditional CRISPR/Cas9 driven genomic engineering which relies on permanently altering DNA sequence. Recombinant expression systems are engineered to induce edits to specific RNA bases as determined by the guide RNA design. As such, in some embodiments, Applicants provide a fully encodeable recombinant expression system comprising a nuclease-dead version of *Streptococcus pyogenes* Cas9 (dCas9) fused to an ADAR deaminase domain and a corresponding extended single guide RNA (esgRNA). In some embodiments, the system generates recombinant proteins with effector deaminase enzyme complexes capable of performing ribonucleotide base modification to alter how the sequence of the RNA molecule is recognized by cellular machinery. In some embodiments, the CREDIT expression system comprises A) a nucleic acid sequence encoding a nuclease-dead CRISPR associated endonuclease (dCas) fused to a catalytically active deaminase domain of ADAR (Adenosine Deaminase acting on RNA) and B) an extended single guide RNA (esgRNA) sequence comprising i) a short extension sequence of homology to the target RNA comprising a mismatch for a target adenosine, ii) a dCas scaffold binding sequence, and optionally iii) a sequence complementary to the target RNA sequence (also known as a spacer sequence in a sgRNA context). Exemplary constructs that express CREDIT expression system components include, without limitation, dCas9 fused to catalytically active deaminase domains of human ADAR2 (hADAR2DD, E488QhADAR2DD) using an 'XTEN' linker peptide for spatial separation (FIG. 1B). With dCas9 as a surrogate RBD (RNA-Binding Domain), Applicants engineered and customized single guide RNAs (sgRNAs) with unique short extension sequences (esgRNA) to direct hADAR2DD to RNA sites for target specific A-I editing. For the purposes of the present disclosure, CRISPR/Cas associated endonucleases other than Cas9 or Cas9 orthologs (e.g., Cas13 (also known as C2c2), Cpf1, Cas6f/Csy4, CasX, CasY, and CasRx) are also provided herein for use in the CREDIT expression system. See also Wright et al., Biology and Applications of CRISPR Systems: Harnessing Nature's Toolbox for Genome Engineering, Cell, Vol. 164 (1-2): 29-44, 2016.

In some embodiments disclosed herein, dCas polypeptide has been engineered to recognize a target RNA, wherein the inactive Cas polypeptide is associated with an effector. In some embodiments, the dCas polypeptide is a *Streptococcus pyogenes* dCas9 polypeptide. In some embodiments, the dCas9 polypeptide comprises a mutation, such as D10A, H840A, or both, in the *Streptococcus pyogenes* Cas9 polypeptide. This repurposed or engineered dCas9 polypeptide-comprising nucleoprotein complex that binds to RNA is referred to herein as RdCas9. CRISPR has revolutionized genome engineering by allowing simply-programmed recognition of DNA in human cells and supported related technologies in imaging and gene expression modulation. In WO 2017/091630, incorporated by reference in its entirety herein, an analogous means to target RNA using an RCas9 was developed. In this earlier work, engineered nucleoprotein complexes comprise a Cas9 protein and a single guide RNA (sgRNA). Together, the Cas9 protein and sgRNA components were engineered to hypothetically recognize any target RNA sequence. Optionally, in such systems, an (chemically-modified or synthetic) antisense PAMmer oligonucleotide could be included in the RCas9 system to simulate a DNA substrate for recognition by Cas9 via hybridization to the target RNA. However, surprisingly highly effective RNA targeting without PAMmer was also shown. Now, herein is disclosed RdCas-ADAR RNA editing systems which do not require a PAMmer and as such are fully encodeable Cas9-mediated RNA targeting systems which provide a reversible platform for modification of target RNA.

For the purposes of the present disclosure, Cas9 endonucleases used herein include, without limitation, orthologs derived from archaeal or bacterial Cas9 polypeptides. Such polypeptides can be derived from, without limitations *Haloferax mediteranii*, Mycobacterium *tuberculosis, Francisella tularensis subsp. novicida, Pasteurella multocida, Neisseria meningitidis, Campylobacter jejune, Streptococcus thermophilus* CRISPR 3, *Campylobacter lari* CF89-12, *Mycoplasma gallisepticum* str. F, *Nitratifractor salsuginis* str DSM 1651 1, *Parvibaculum lavamentivorans, Roseburia intestinalis, Neisseria cinerea, Gluconacetobacter diazotrophicus, Azospirillum* B510, *Sphaerochaeta globus* str. Buddy, *Flavobacterium columnare, Fluviicola tafensis, Bacteroides coprophiles, Mycoplasma mobile, Lactobacillus farciminis, Streptococcus pasteurianus, Lactobacillus johnsonii, Staphylococcus pseudintermedius, Filifactor alocis, Treponema denticola, Legionella pneumophila* str. Paris, *Sutterella wadsworthensis, Corynebacter diphtheriae*, or *Streptococcus aureus; Francisella novicida* (e.g., *Francisella novicida* CPf1), or *Natronobacterium gregoryi* Argonaute. Each of these respective candidate Cas polypeptides are modified and/or repurposed to target RNA and fused to an ADAR deaminase domain for use in the systems disclosed herein, which system additionally comprises an extended sgRNA (esgRNA) which comprises a guide "scaffold sequence" which comprises all or part of, or is derived from, the wild type (WT) cognate guide nucleic acid of each of these respective bacteria or archaeal organisms. In some embodiments, Cas endonucleases for use herein include, without limitation, Cas13 (c2C2), Cpf1, CasX, CasY, and CasRx.

Further nonlimiting examples of orthologs and biological equivalents Cas9 are provided in the table below:

| Name | Protein Sequence |
| --- | --- |
| *S. pyogenes* Cas9<br>SEQ ID NO: 1 | MDKKYSIGLDIGTNSVGWAVITDEYKVPSKKFKVLGNTDRHSIKKNLIGALLFD<br>SGETAEATRLKRTARRRYTRRKNRICYLQEIFSNEMAKVDDSFFHRLEESFLVE<br>EDKKHERHPIFGNIVDEVAYHEKYPTIYHLRKKLVDSTDKADLRLIYLALAHMI<br>KFRGHFLIEGDLNPDNSDVDKLFIQLVQTYNQLFEENPINASGVDAKAILSARLS<br>KSRRLENLIAQLPGEKKNGLFGNLIALSLGLTPNFKSNFDLAEDAKLQLSKDTY<br>DDDLDNLLAQIGDQYADLFLAAKNLSDAILLSDILRVNTEITKAPLSASMIKRYD<br>EHHQDLTLLKALVRQQLPEKYKEIFFDQSKNGYAGYIDGGASQEEFYKFIKPILE<br>KMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQ<br>SFIERMTNFDKNLPNEKVLPKHSLLYEYFTVYNELTKVKYVTEGMRKPAFLSGE<br>QKKAIVDLLFKTNRKVTVKQLKEDYFKKIECFDSVEISGVEDRFNASLGTYHDL<br>LKIIKDKDFLDNEENEDILEDIVLTLTLFEDREMIEERLKTYAHLFDDKVMKQLK<br>RRRYTGWGRLSRKLINGIRDKQSGKTILDFLKSDGFANRNFMQLIHDDSLTFKE<br>DIQKAQVSGQGDSLHEHIANLAGSPAIKKGILQTVKVVDELVKVMGRHKPENIV<br>IEMARENQTTQKGQKNSRERMKRIEEGIKELGSQILKEHPVENTQLQNEKLYLY<br>YLQNGRDMYVDQELDINRLSDYDVDHIVPQSFLKDDSIDNKVLTRSDKNRGKS<br>DNVPSEEVVKKMKNYWRQLLNAKLITQRKFDNLTKAERGGLSELDKAGFIKR<br>QLVETRQITKHVAQILDSRMNTKYDENDKLIREVKVITLKSKLVSDFRKDFQFY<br>KVREINNYHHAHDAYLNAVVGTALIKKYPKLESEFVYGDYKVYDVRKMIAKS<br>EQEIGKATAKYFFYSNIMNFFKTEITLANGEIRKRPLIETNGETGEIVWDKGRDF<br>ATVRKVLSMPQVNIVKKTEVQTGGFSKESILPKRNSDKLIARKKDWDPKKYGG<br>FDSPTVAYSVLVVAKVEKGKSKKLKSVKELLGITIMERSSFEKNPIDFLEAKGY<br>KEVKKDLIIKLPKYSLFELENGRKRMLASAGELQKGNELALPSKYVNFLYLASH<br>YEKLKGSPEDNEQKQLFVEQHKHYLDEIIEQISEFSKRVILADANLDKVLSAYN<br>KHRDKPIREQAENIIHLFTLTNLGAPAAFKYFDTTIDRKRYTSTKEVLDATLIHQS<br>ITGLYETRIDLSQLGGD* |
| *Staphylococcus aureus* Cas9<br>SEQ ID NO: 2 | MKRNYILGLDIGITSVGYGIIDYETRDVIDAGVRLFKEANVENNEGRRSKRGAR<br>RLKRRRRHRIQRVKKLLFDYNLLTDHSELSGINPYEARVKGLSQKLSEEEFSAA<br>LLHLAKRRGVHNVNEVEEDTGNELSTKEQISRNSKALEEKYVAELQLERLKKD<br>GEVRGSINRFKTSDYVKEAKQLLKVQKAYHQLDQSFIDTYIDLLETRRTYYEGP<br>GEGSPFGWKDIKEWYEMLMGHCTYFPEELRSVKYAYNADLYNALNDLNNLVI<br>TRDENEKLEYYEKFQIIENVFKQKKKPTLKQIAKEILVNEEDIKGYRVTSTGKPE<br>FTNLKVYHDIKDITARKEIIENAELLDQIAKILTIYQSSEDIQEELTNLNSELTQEEI<br>EQISNLKGYTGTHNLSLKAINLILDELWHTNDNQIAIFNRLKLVPKKVDLSQQKE<br>IPTTLVDDFILSPVVKRSFIQSIKVINAIIKKYGLPNDIIIELAREKNSKDAQKMINE<br>MQKRNRQTNERIEEIIRTTGKENAKYLIEKIKLHDMQEGKCLYSLEAIPLEDLLN<br>NPFNYEVDHIIPRSVSFDNSFNNKVLVKQEENSKKGNRTPFQYLSSSDSKISYET<br>FKKHILNLAKGKGRISKTKKEYLLEERDINRFSVQKDFINRNLVDTRYATRGLM<br>NLLRSYFRVNNLDVKVKSINGGFTSFLRRKWKFKKERNKGYKHHAEDALIIAN<br>ADFIFKEWKKLDKAKKVMENQMFEEKQAESMPEIETEQEYKEIFITPHQIKHIK<br>DFKDYKYSHRVDKKPNRELINDTLYSTRKDDKGNTLIVNNLNGLYDKDNDKL<br>KKLINKSPEKLLMYHHDPQTYQKLKLIMEQYGDEKNPLYKYYEETGNYLTKYS<br>KKDNGPVIKKIKYYGNKLNAHLDITDDYPNSRNKVVKLSLKPYRFDVYLDNGV<br>YKFVTVKNLDVIKKENYYEVNSKCYEEAKKLKKISNQAEFIASFYNNDLIKING<br>ELYRVIGVNNDLLNRIEVNMIDITYREYLENMNDKRPPRIIKTIASKTQSIKKYST<br>DILGNLYEVKSKKHPQIIKKG* |
| *S. thermophilus* CRISPR 1 Cas9<br>SEQ ID NO: 3 | MSDLVLGLDIGIGSVGVGILNKVTGEIIHKNSRIFPAAQAENNLVRRTNRQGRRL<br>ARRKKHRRVRLNRLFEESGLITDFTKISINLNPYQLRVKGLTDELSNEELFIALKN<br>MVKHRGISYLDDASDDGNSSVGDYAQIVKENSKQLETKTPGQIQLERYQTYGQ<br>LRGDFTVEKDGKKHRLINVFPTSAYRSEALRILQTQQEFNPQITDEFINRYLEILT<br>GKRKYYHGPGNEKSRTDYGRYRTSGETLDNIFGILIGKCTFYPDEFRAAKASYT<br>AQEFNLLNDLNNLTVPTETKKLSKEQKNQIINYVKNEKAMGPAKLFKYIAKLLS<br>CDVADIKGYRIDKSGKAEIHTFEAYRKMKTLETLDIEQMDRETLDKLAYVLTLN<br>TEREGIQEALEHEFADGSFSQKQVDELVQFRKANSSIFGKGWHNFSVKLMMELI<br>PELYETSEEQMTILTRLGKQKTTSSSNKTKYIDEKLLTEEIYNPVVAKSVRQAIKI<br>VNAAIKEYGDFDNIVIEMARETNEDDEKKAIQKIQKANKDEKDAAMLK<br>AANQYNGKAELPHSVFHGHKQLATKIRLWHQQGERCLYTGKTISIHDLINNSN<br>QFEVDHILPLSITFDDSLANKVLVYATANQEKGQRTPYQALDSMDDAWSFREL<br>KAFVRESKTLSNKKKEYLLTEEDISKFDVRKKFIERNLVDTRYASRVVLNALQE<br>HFRAHKIDTKVSVVRGQFTSQLRRHWGIEKTRDTYHHHAVDALIIAASSQLNL<br>WKKQKNTLVSYSEDQLLDIETGELISDDEYKESVFKAPYQHFVDTLKSKEFEDSI<br>LFSYQVDSKFNRKISDATIYATRQAKVGKDKADETYVLGKIKDIYTQDGYDAF<br>MKIYKKDKSKFLMYRHDPQTFEKVIEPILENYPNKQINDKGKEVPCNPFLKYKE<br>EHGYIRKYSKKGNGPEIKSLKYYDSKLGNHIDITPKDSNNKVVLQSVSPWRADV<br>YFNKTTGKYEILGLKYADLQFDKGTGTYKISQEKYNDIKKKEGVDSDSEFKFTL<br>YKNDLLLVKDTETKEQQLFRFLSRTMPKQKHYVELKPYDKQKFEGGEALIKVL<br>GNVANSGQCKKGLGKSNISIYKVRTDVLGNQHIIKNEGDKPKLDF* |

-continued

| Name | Protein Sequence |
|---|---|
| *N. meningitidis* Cas9<br>SEQ ID NO: 4 | MAAFKPNPINYILGLDIGIASVGWAMVEIDEDENPICLIDLGVRVFERAEVPKTG<br>DSLAMARRLARSVRRLTRRRAHRLLRARRLLKREGVLQAADFDENGLIKSLPN<br>TPWQLRAAALDRKLTPLEWSAVLLHLIKHRGYLSQRKNEGETADKELGALLKG<br>VADNAHALQTGDFRTPAELALNKFEKESGHIRNQRGDYSHTFSRKDLQAELILL<br>FEKQKEFGNPHVSGGLKEGIETLLMTQRPALSGDAVQKMLGHCTFEPAEPKAA<br>KNTYTAERFIWLTKLNNLRILEQGSERPLTDTERATLMDEPYRKSKLTYAQARK<br>LLGLEDTAFFKGLRYGKDNAEASTLMEMKAYHAISRALEKEGLKDKKSPLNLS<br>PELQDEIGTAFSLFKTDEDITGRLKDRIQPEILEALLKHISFDKFVQISLKALRRIV<br>PLMEQGKRYDEACAEIYGDHYGKKNTEEKIYLPPIPADEIRNPVVLRALSQARK<br>VINGVVRRYGSPARIHIETAREVGKSFKDRKEIEKRQEENRKDREKAAAKFREY<br>FPNFVGEPKSKDILKLRLYEQQHGKCLYSGKEINLGRLNEKGYVEIDHALPFSRT<br>WDDSFNNKVLVLGSENQNKGNQTPYEYFNGKDNSREWQEFKARVETSRFPRS<br>KKQRILLQKFDEDGFKERNLNDTRYVNRFLCQFVADRMRLTGKGKKRVFASN<br>GQITNLLRGFWGLRKVRAENDRHHALDAVVVACSTVAMQQKITRFVRYKEMN<br>AFDGKTIDKETGEVLHQKTHFPQPWEFFAQEVMIRVFGKPDGKPEFEEADTPEK<br>LRTLLAEKLSSRPEAVHEYVTPLFVSRAPNRKMSGQGHMETVKSAKRLDEGVS<br>VLRVPLTQLKLKDLEKMVNREREPKLYEALKARLEAHKDDPAKAFAEPFYKY<br>DKAGNRTQQVKAVRVEQVQKTGVWVRNHNGIADNATMVRVDVFEKGDKYY<br>LVPIYSWQVAKGILPDRAVVQGKDEEDWQLIDDSFNFKFSLHPNDLVEVITKKA<br>RMFGYFASCHRGTGNINIRIHDLDHKIGKNGILEGIGVKTALSFQKYQIDELGKEI<br>RPCRLKKRPPVR* |
| *Parvibaculum lavamentivorans* Cas9<br>SEQ ID NO: 5 | MERIFGFDIGTTSIGFSVIDYSSTQSAGNIQRLGVRIFPEARDPDGTPLNQQRRQK<br>RMMRRQLRRRRIRRKALNETLHEAGFLPAYGSADWPVVMADEPYELRRRGLE<br>EGLSAYEFGRAIYHLAQHRHFKGRELEESDTPDPDVDDEKEAANERAATLKAL<br>KNEQTTLGAWLARRPPSDRKRGIHAHRNVVAEEFERLWEVQSKFHPALKSEEM<br>RARISDTIFAQRPVFWRKNTLGECRFMPGEPLCPKGSWLSQQRRMLEKLNNLAI<br>AGGNARPLDAEERDAILSKLQQQASMSWPGVRSALKALYKQRGEPGAEKSLK<br>FNLELGGESKLLGNALEAKLADMFGPDWPAHPRKQEIRHAVHERLWAADYGE<br>TPDKKRVIILSEKDRKAHREAAANSFVADFGITGEQAAQLQALKLPTGWEPYSI<br>PALNLFLAELEKGERFGALVNGPDWEGWRRTNFPHRNQPTGEILDKLPSPASKE<br>ERERISQLRNPTVVRTQNELRKVVNNLIGLYGKPDRIRIEVGRDVGKSKREREEI<br>QSGIRRNEKQRKKATEDLIKNGIANPSRDDVEKWILWKEGQERCPYTGDQIGFN<br>ALFREGRYEVEHIWPRSRSFDNSPRNKTLCRKDVNIEKGNRMPFEAFGHDEDR<br>WSAIQIRLQGMVSAKGGTGMSPGKVKRFLAKTMPEDFAARQLNDTRYAAKQI<br>LAQLKRLWPDMGPEAPVKVEAVTGQVTAQLRKLWTLNNILADDGEKTRADH<br>RHHAIDALTVACTHPGMTNKLSRYWQLRDDPRAEKPALTPPWDTIRADAEKA<br>VSEIVVSHRVRKKVSGPLHKETTYGDTGTDIKTKSGTYRQFVTRKKIESLSKGEL<br>DEIRDPRIKEIVAAHVAGRGGDPKKAFPPYPCVSPGGPEIRKVRLTSKQQLNLM<br>AQTGNGYADLGSNHHIAIYRLPDGKADFEIVSLFDASRRLAQRNPIVQRTRADG<br>ASFVMSLAAGEAIMIPEGSKKGIWIVQGVWASGQVVLERDTDADHSTTTRPMP<br>NPILKDDAKKVSIDPIGRVRPSND* |
| *Corynebacter diphtheria* Cas9<br>SEQ ID NO: 6 | MKYHVGIDVGTFSVGLAAIEVDDAGMPIKTLSLVSHIHDSGLDPDEIKSAVTRL<br>ASSGIARRTRRLYRRKRRRLQQLDKFIQRQGWPVIELEDYSDPLYPWKVRAELA<br>ASYIADEKERGEKLSVALRHIARHRGWRNPYAKVSSLYLPDGPSDAFKAIREEI<br>KRASGQPVPETATVGQMVTLCELGTLKLRGEGGVLSARLQQSDYAREIQEICR<br>MQEIGQELYRKIIDVVFAAESPKGSASSRVGKDPLQPGKNRALKASDAFQRYRI<br>AALIGNLRVRVDGEKRILSVEEKNLVFDHLVNLTPKKEPEWVTIAEILGIDRGQL<br>IGTATMTDDGERAGARPPTHDTNRSIVNSRIAPLVDWWKTASALEQHAMVKAL<br>SNAEVDDFDSPEGAKVQAFFADLDDDVHAKLDSLHLPVGRAAYSEDTLVRLTR<br>RMLSDGVDLYTARLQEFGIEPSWTPPTPRIGEPVGNPAVDRVLKTVSRWLESAT<br>KTWGAPERVIIEHVREGFVTEKRAREMDGDMRRRAARNAKLFQEMQEKLNVQ<br>GKPSRADLWRYQSVQRQNCQCAYCGSPITFSNSEMDHIVPRAGQGSTNTRENL<br>VAVCHRCNQSKGNTPFAIWAKNTSIEGVSVKEAVERTRHWVTDTGMRSTDFK<br>KFTKAVVERFQRATMDEEIDARSMESVAWMANELRSRVAQHFASHGTTVRVY<br>RGSLTAEARRASGISGKLKFFDGVGKSRLDRRHHAIDAAVIAFTSDYVAETLAV<br>RSNLKQSQAHRQEAPQWREFTGKDAEHRAAWRVWCQKMEKLSALLTEDLRD<br>DRVVVMSNVRLRLGNGSAHKETIGKLSKVKLSSQLSVSDIDKASSEALWCALT<br>REPGFDPKEGLPANPERHIRVNGTHVYAGDNIGLFPVSAGSIALRGGYAELGSSF<br>HHARVYKITSGKKPAFAMLRVYTIDLLPYRNQDLFSVELKPQTMSMRQAEKKL<br>RDALATGNAEYLGWLVVDDELVVDTSKIATDQVKAVEAELGTIRRWRVDGFF<br>SPSKLRLRPLQMSKEGIKKESAPELSKIIDRPGWLPAVNKLFSDGNVTVVRRDSL<br>GRVRLESTAHLPVTWKVQ* |
| *Streptococcus pasteurianus* Cas9<br>SEQ ID NO: 7 | MTNGKILGLDIGIASVGVGIIEAKTGKVVHANSRLFSAANAENNAERRGFRGSR<br>RLNRRKKHRVKRVRDLFEKYGIVTDFRNLNLNPYELRVKGLTEQLKNEELFAA<br>LRTISKRRGISYLDDAEDDSTGSTDYAKSIDENRRLLKNKTPGQIQLERLEKYGQ<br>LRGNFTVYDENGEAHRLINVFSTSDYEKEARKILETQADYNKKITAEFIDDYVEI<br>LTQKRKYYHGPGNEKSRTDYGRFRTDGTTLENIFGILIGKCNFYPDEYRASKAS<br>YTAQEYNFLNDLNNLKVSTETGKLSTEQKESLVEFAKNTATLGPAKLLKEIAKI<br>LDCKVDEIKGYREDDKGKPDLHTFEPYRKLKFNLESINIDDLSREVIDKLADILT<br>LNTEREGIEDAIKRNLPNQFTEEQISEIIKVRKSQSTAFNKGWHSFSAKLMNELIP<br>ELYATSDEQMTILTRLEKFKVNKKSSKNTKTIDEKEVTDEIYNPVVAKSVRQTIK<br>IINAAVKKYGDFDKIVIEMPRDKNADDEKKFIDKRNKENKKEKDDALKRAAYL<br>YNSSDKLPDEVFHGNKQLETKIRLWYQQGERCLYSGKPISIQELVHNSNNFEID |

-continued

| Name | Protein Sequence |
|---|---|
| | HILPLSLSFDDSLANKVLVYAWTNQEKGQKTPYQVIDSMDAAWSFREMKDYV<br>LKQKGLGKKKRDYLLTTENIDKIEVKKKFIERNLVDTRYASRVVLNSLQSALRE<br>LGKDTKVSVVRGQFTSQLRRKWKIDKSRETYHHHAVDALIIAASSQLKLWEKQ<br>DNPMFVDYGKNQVVDKQTGEILSVSDDEYKELVFQPPYQGFVNTISSKGFEDEI<br>LFSYQVDSKYNRKVSDATIYSTRKAKIGKDKKEETYVLGKIKDIYSQNGFDTFIK<br>KYNKDKTQFLMYQKDSLTWENVIEVILRDYPTTKKSEDGKNDVKCNPFEEYRR<br>ENGLICKYSKKGKGTPIKSLKYYDKKLGNCIDITPEESRNKVILQSINPWRADVY<br>FNPETLKYELMGLKYSDLSFEKGTGNYHISQEKYDAIKEKEGIGKKSEFKFTLY<br>RNDLILIKDIASGEQEIYRFLSRTMPNVNHYVELKPYDKEKFDNVQELVEALGE<br>ADKVGRCIKGLNKPNISIYKVRTDVLGNKYFVKKKGDKPKLDFKNNKK* |
| *Neisseria cinerea*<br>Cas9<br>SEQ ID NO: 8 | MAAFKPNPMNYILGLDIGIASVGWAIVEIDEEENPIRLIDLGVRVFERAEVPKTG<br>DSLAAARRLARSVRRLTRRRAHRLLRARRLLKREGVLQAADFDENGLIKSLPN<br>TPWQLRAAALDRKLTPLEWSAVLLHLIKHRGYLSQRKNEGETADKELGALLKG<br>VADNTHALQTGDFRTPAELALNKFEKESGHIRNQRGDYSHTFNRKDLQAELNL<br>LFEKQKEFGNPHVSDGLKEGIETLLMTQRPALSGDAVQKMLGHCTFEPTEPKA<br>AKNTYTAERFVWLTKLNNLRILEQGSERPLTDTERATLMDEPYRKSKLTYAQA<br>RKLLDLDDTAFFKGLRYGKDNAEASTLMEMKAYHAISRALEKEGLKDKKSPL<br>NLSPELQDEIGTAFSLFKTDEDITGRLKDRVQPEILEALLKHISFDKFVQISLKAL<br>RRIVPLMEQGNRYDEACTEIYGDHYGKKNTEEKIYLPPIPADEIRNPVVLRALSQ<br>ARKVINGVVRRYGSPARIHIETAREVGKSFKDRKEIEKRQEENRKDREKSAAKF<br>REYFPNFVGEPKSKDILKLRLYEQQHGKCLYSGKEINLGRLNEKGYVEIDHALP<br>FSRTWDDSFNNKVLALGSENQNKGNQTPYEYFNGKDNSREWQEFKARVETSR<br>FPRSKKQRILLQKFDEDGFKERNLNDTRYINRFLCQFVADHMLLTGKGKRRVF<br>ASNGQITNLLRGFWGLRKVRAENDRHHALDAVVVACSTIAMQQKITRFVRYKE<br>MNAFDGKTIDKETGEVLHQKAHFPQPWEFFAQEVMIRVFGKPDGKPEFEEADT<br>PEKLRTLLAEKLSSRPEAVHKYVTPLFISRAPNRKMSGQGHMETVKSAKRLDE<br>GISVLRVPLTQLKLKDLEKMVNREREPKLYEALKARLEAHKDDPAKAFAEPFY<br>KYDKAGNRTQQVKAVRVEQVQKTGVWVHNHNGIADNATIVRVDVFEKGGKY<br>YLVPIYSWQVAKGILPDRAVVQGKDEEDWTVMDDSFEFKFVLYANDLIKLTAK<br>KNEFLGYFVSLNRATGAIDIRTHDTDSTKGKNGIFQSVGVKTALSFQKYQIDEL<br>GKEIRPCRLKKRPPVR* |
| *Campylobacter lari*<br>Cas9<br>SEQ ID NO: 9 | MRILGFDIGINSIGWAFVENDELKDCGVRIFTKAENPKNKESLALPRRNARSSRR<br>RLKRRKARLIAIKRILAKELKLNYKDYVAADGELPKAYEGSLASVYELRYKALT<br>QNLETKDLARVILHIAKHRGYMNKNEKKSNDAKKGKILSALKNNALKLENYQS<br>VGEYFYKEFFQKYKKNTKNFIKIRNTKDNYNNCVLSSDLEKELKLILEKQKEFG<br>YNYSEDFINEILKVAFFQRPLKDFSHLVGACTFFEEEKRACKNSYSAWEFVALT<br>KIINEIKSLEKISGEIVPTQTINEVLNLILDKGSITYKKFRSCINLHESISFKSLKYDK<br>ENAENAKLIDFRKLVEFKKALGVHSLSRQELDQISTHITLIKDNVKLKTVLEKYN<br>LSNEQINNLLEIEFNDYINLSFKALGMILPLMREGKRYDEACEIANLKPKTVDEK<br>KDFLPAFCDSIFAHELSNPVVNRAISEYRKVLNALLKKYGKVHKIHLELARDVG<br>LSKKAREKIEKEQKENQAVNAWALKECENIGLKASAKNILKLKLWKEQKEICIY<br>SGNKISIEHLKDEKALEVDHIYPYSRSFDDSFINKVLVFTKENQEKLNKTPFEAF<br>GKNIEKWSKIQTLAQNLPYKKKNKILDENFKDKQQEDFISRNLNDTRYIATLIAK<br>YTKEYLNFLLLSENENANLKSGEKGSKIHVQTISGMLTSVLRHTWGFDKKDRN<br>NHLHHALDAIIVAYSTNSIIKAFSDFRKNQELLKARFYAKELTSDNYKHQVKFFE<br>PFKSFREKILSKIDEIFVSKPPRKRARRALHKDTFHSENKIIDKCSYNSKEGLQIAL<br>SCGRVRKIGTKYVENDTIVRVDIFKKQNKFYAIPIYAMDFALGILPNKIVITGKD<br>KNNNPKQWQTIDESYEFCFSLYKNDLILLQKKNMQEPEFAYYNDFSISTSSICVE<br>KHDNKFENLTSNQKLLFSNAKEGSVKVESLGIQNLKVFEKYIITPLGDKIKADFQ<br>PRENISLKTSKKYGLR* |
| *T. denticola* Cas9<br>SEQ ID NO: 10 | MKKEIKDYFLGLDVGTGSVGWAVTDTDYKLLKANRKDLWGMRCFETAETAE<br>VRRLHRGARRRIERRKKRIKLLQELFSQEIAKTDEGFFQRMKESPFYAEDKTILQ<br>ENTLFNDKDFADKTYHKAYPTINHLIKAWIENKVKPDPRLLYLACHNIIKKRGH<br>FLFEGDFDSENQFDTSIQALFEYLREDMEVDIDADSQKVKEILKDSSLKNSEKQS<br>RLNKILGLKPSDKQKKAITNLISGNKINFADLYDNPDLKDAEKNSISFSKDDFDA<br>LSDDLASILGDSFELLLKAKAVYNCSVLSKVIGDEQYLSFAKVKIYEKHKTDLT<br>KLKNVIKKHFPKDYKKVFGYNKNEKNNNNYSGYVGVCKTKSKKLIINNSVNQ<br>EDFYKFLKTILSAKSEIKEVNDILTEIETGTFLPKQISKSNAEIPYQLRKMELEKIL<br>SNAEKHFSFLKQKDEKGLSHSEKIIMLLTFKIPYYIGPINDNHKKFFPDRCWVVK<br>KEKSPSGKTTPWNFFDHIDKEKTAEAFITSRTNFCTYLVGESVLPKSSLLYSEYT<br>VLNEINNLQIIIDGKNICDIKLKQKIYEDLFKKYKKITQKQISTFIKHEGICNKTDE<br>VIILGIDKECTSSLKSYIELKNIFGKQVDEISTKNMLEEIIRWATIYDEGEGKTILK<br>TKIKAEYGKYCSDEQIKKILNLKFSGWGRLSRKFLETVTSEMPGFSEPVNIITAM<br>RETQNNLMELLSSEFTFTENIKKINSGFEDAEKQFSYDGLVKPLFLSPSVKKML<br>WQTLKLVKEISHITQAPPKKIFIEMAKGAELEPARTKTRLKILQDLYNNCKNDA<br>DAFSSEIKDLSGKIENEDNLRLRSDKLYLYYTQLGKCMYCGKPIEIGHVFDTSNY<br>DIDHIYPQSKIKDDSISNRVLVCSSCNKNKEDKYPLKSEIQSKQRGFWNFLQRNN<br>FISLEKLNRLTRATPISDDETAKFIARQLVETRQATKVAAKVLEKMFPETKIVYS<br>KAETVSMFRNKFDIVKCREINDFHHAHDAYLNIVVGNVYNTKFTNNPWNFIKE<br>KRDNPKIADTYNYYKVFDYDVKRNNITAWEKGKTIITVKDMLKRNTPIYTRQA<br>ACKKGELFNQTIMKKGLGQHPLKKEGPFSNISKYGGYNKVSAAYYTLIEYEEK<br>GNKIRSLETIPLYLVKDIQKDQDVLKSYLTDLLGKKEFKILVPKIKINSLLKINGF<br>PCHITGKTNDSFLLRPAVQFCCSNNEVLYFKKIIRFSEIRSQREKIGKTISPYEDLS<br>FRSYIKENLWKKTKNDEIGEKEFYDLLQKKNLEIYDMLLTKHKDTIYKKRPNSA |

-continued

| Name | Protein Sequence |
|---|---|
| | TIDILVKGKEKFKSLIIENQFEVILEILKLFSATRNVSDLQHIGGSKYSGVAKIGNK<br>ISSLDNCILIYQSITGIFEKRIDLLKV* |
| *S. mutans* Cas9<br>SEQ ID NO: 11 | MKKPYSIGLDIGTNSVGWAVVTDDYKVPAKKMKVLGNTDKSHIEKNLLGALL<br>FDSGNTAEDRRLKRTARRRYTRRRNRILYLQEIFSEEMGKVDDSFFHRLEDSFL<br>VTEDKRGERHPIFGNLEEEVKYHENFPTIYHLRQYLADNPEKVDLRLVYLALAH<br>IIKFRGHFLIEGKFDTRNNDVQRLFQEFLAVYDNTFENSSLQEQNVQVEEILTDKI<br>SKSAKKDRVLKLFPNEKSNGRFAEFLKLIVGNQADFKKHFELEEKAPLQFSKDT<br>YEEELEVLLAQIGDNYAELFLSAKKLYDSILLSGILTVTDVGTKAPLSASMIQRY<br>NEHQMDLAQLKQFIRQKLSDKYNEVFSDVSKDGYAGYIDGKTNQEAFYKYLK<br>GLLNKIEGSGYFLDKIEREDFLRKQRTFDNGSIPHQIHLQEMRAIIRRQAEFYPFL<br>ADNQDRIEKLLTFRIPYYVGPLARGKSDFAWLSRKSADKITPWNFDEIVDKESS<br>AEAFINRMTNYDLYLPNQKVLPKHSLLYEKFTVYNELTKVKYKTEQGKTAFFD<br>ANMKQEIFDGVFKVYRKVTKDKLMDFLEKEFDEFRIVDLTGLDKENKVFNASY<br>GTYHDLCKILDKDFLDNSKNEKILEDIVLTLTLFEDREMIRKRLENYSDLLTKEQ<br>VKKLERRHYTGWGRLSAELIHGIRNKESRKTILDYLIDDGNSNRNFMQLINDDA<br>LSFKEEIAKAQVIGETDNLNQVVSDIAGSPAIKKGILQSLKIVDELVKIMGHQPE<br>NIVVEMARENQFTNQGRRNSQQRLKGLTDSIKEFGSQILKEHPVENSQLQNDRL<br>FLYYLQNGRDMYTGEELDIDYLSQYDIDHIIPQAFIKDNSIDNRVLTSSKENRGK<br>SDDVPSKDVVRKMKSYWSKLLSAKLITQRKFDNLTKAERGGLTDDDKAGFIKR<br>QLVETRQITKHVARILDERFNTETDENNKKIRQVKIVTLKSNLVSNFRKEFELYK<br>VREINDYHHAHDAYLNAVIGKALLGVYPQLEPEFVYGDYPHFHGHKENKATA<br>KKFFYSNIMNFFKKDDVRTDKNGEIIWKKDEHISNIKKVLSYPQVNIVKKVEEQ<br>TGGFSKESILPKGNSDKLIPRKTKKFYWDTKKYGGFDSPIVAYSILVIADIEKGKS<br>KKLKTVKALVGVTIMEKMTFERDPVAFLERKGYRNVQEENIIKLPKYSLFKLEN<br>GRKRLLASARELQKGNEIVLPNHLGTLLYHAKNIHKVDEPKHLDYVDKHKDEF<br>KELLDVVSNFSKKYTLAEGNLEKIKELYAQNNGEDLKELASSFINLLTFTAIGAP<br>ATFKFFDKNIDRKRYTSTTEILNATLIHQSITGLYETRIDLNKLGGD |
| *S. thermophilus*<br>CRISPR 3 Cas9<br>SEQ ID NO: 12 | MTKPYSIGLDIGTNSVGWAVTTDNYKVPSKKMKVLGNTSKKYIKKNLLGVLLF<br>DSGITAEGRRLKRTARRRYTRRRNRILYLQEIFSTEMATLDDAFFQRLDDSFLVP<br>DDKRDSKYPIFGNLVEEKAYHDEFPTIYHLRKYLADSTKKADLRLVYLALAHM<br>IKYRGHFLIEGEFNSKNNDIQKNFQDFLDTYNAIFESDLSLENSKQLEEIVKDKIS<br>KLEKKDRILKLFPGEKNSGIFSEFLKLIVGNQADFRKCFNLDEKASLHFSKESYD<br>EDLETLLGYIGDDYSDVFLKAKKLYDAILLSGFLTVTDNETEAPLSSAMIKRYN<br>EHKEDLALLKEYIRNISLKTYNEVFKDDTKNGYAGYIDGKTNQEDFYVYLKKL<br>LAEFEGADYFLEKIDREDFLRKQRTFDNGSIPYQIHLQEMRAILDKQAKFYPFLA<br>KNKERIEKILTFRIPYYVGPLARGNSDFAWSIRKRNEKITPWNFEDVIDKESSAE<br>AFINRMTSFDLYLPEEKVLPKHSLLYETFNVYNELTKVRFIAESMRDYQFLDSK<br>QKKDIVRLYFKDKRKVTDKDIIEYLHAIYGYDGIELKGIEKQFNSSLSTYHDLLN<br>IINDKEFLDDSSNEAIIEEIIHTLTIFEDREMIKQRLSKFENIFDKSVLKKLSRRHYT<br>GWGKLSAKLINGIRDEKSGNTILDYLIDDGISNRNFMQLIHDDALSFKKKIQKAQ<br>IIGDEDKGNIKEVVKSLPGSPAIKKGILQSIKIVDELVKVMGGRKPESIVVEMARE<br>NQYTNQGKSNSQQRLKRLEKSLKELGSKILKENIPAKLSKIDNNALQNDRLYLY<br>YLQNGKDMYTGDDLDIDRLSNYDIDHIIPQAFLKDNSIDNKVLVSSASNRGKSD<br>DVPSLEVVKKRKTFWYQLLKSKLISQRKFDNLTKAERGGLSPEDKAGFIQRQLV<br>ETRQITKHVARLLDEKFNNKKDENNRAVRTVKIITLKSTLVSQFRKDFELYKVR<br>EINDFHHAHDAYLNAVVASALLKKYPKLEPEFVYGDYPKYNSFRERKSATEKV<br>YFYSNIMNIFKKSISLADGRVIERPLIEVNEETGESVWNKESDLATVRRVLSYPQ<br>VNVVKKVEEQNHGLDRGKPKGLFNANLSSKPKPNSNENLVGAKEYLDPKKYG<br>GYAGISNSFTVLVKGTIEKGAKKKITNVLEFQGISILDRINYRKDKLNFLLEKGY<br>KDIELIIELPKYSLFELSDGSRRMLASILSTNNKRGEIHKGNQIFLSQKFVKLLYH<br>AKRISNTINENHRKYVENHKKEFEELFYYILEFNENYVGAKKNGKLLNSAFQSW<br>QNHSIDELCSSFIGPTGSERKGLFELTSRGSAADFEFLGVKIPRYRDYTPSSLLKD<br>ATLIHQSVTGLYETRIDLAKLGEG |
| *C. jejuni* Cas9<br>SEQ ID NO: 13 | MARILAFDIGISSIGWAFSENDELKDCGVRIFTKVENPKTGESLALPRRLARSAR<br>KRLARRKARLNHLKHLIANEFKLNYEDYQSFDESLAKAYKGSLISPYELRFRAL<br>NELLSKQDFARVILHIAKRRGYDDIKNSDDKEKGAILKAIKQNEEKLANYQSVG<br>EYLYKEYFQKFKENSKEFTNVRNKKESYERCIAQSFLKDELKLIFKKQREFGFSF<br>SKKFEEEVLSVAFYKRALKDFSHLVGNCSFFTDEKRAPKNSPLAFMFVALTRIIN<br>LLNNLKNTEGILYTKDDLNALLNEVLKNGTLTYKQTKKLLGLSDDYEFKGEKG<br>TYFIEFKKYKEFIKALGEHNLSQDDLNEIAKDITLIKDEIKLKKALAKYDLNQNQ<br>IDSLSKLEFKDHLNISFKALKLVTPLMLEGKKYDEACNELNLKVAINEDKKDFL<br>PAFNETYYKDEVTNPVVLRAIKEYRKVLNALLKKYGKVHKINIELAREVGKNH<br>SQRAKIEKEQNENYKAKKDAELECEKLGLKINSKNILKLRLFKEQKEFCAYSGE<br>KIKISDLQDEKMLEIDHIYPYSRSFDDSYMNKVLVFTKQNQEKLNQTPFEAFGN<br>DSAKWQKIEVLAKNLPTKKQKRILDKNYKDKEQKNFKDRNLNDTRYIARLVL<br>NYTKDYLDFLPLSDDENTKLNDTQKGSKVHVEAKSGMLTSALRHTWGFSAKD<br>RNNHLHHAIDAVIIAYANNSIVKAFSDFKKEQESNSAELYAKKISELDYKNKRK<br>FFEPFSGFRQKVLDKIDEIFVSKPERKKPSGALHEETFRKEEEFYQSYGGKEGVL<br>KALELGKIRKVNGKIVKNGDMFRVDIFKHKKTNKFYAVPIYTMDFALKVLPNK<br>AVARSKKGEIKDWILMDENYEFCFSLYKDSLILIQTKDMQEPEFVYYNAFTSST<br>VSLIVSKHDNKFETLSKNQKILFKNANEKEVIAKSIGIQNLKVFEKYIVSALGEVT<br>KAEFRQREDFKK |

-continued

| Name | Protein Sequence |
|---|---|
| *P. multocida* Cas9<br>SEQ ID NO: 14 | MQTTNLSYILGLDLGIASVGWAVVEINENEDPIGLIDVGVRIFERAEVPKTGESL<br>ALSRRLARSTRRLIRRRAHRLLLAKRFLKREGILSTIDLEKGLPNQAWELRVAGL<br>ERRLSAIEWGAVLLHLIKHRGYLSKRKNESQTNNKELGALLSGVAQNHQLLQS<br>DDYRTPAELALKKFAKEEGHIRNQRGAYTHTFNRLDLLAELNLLFAQQHQFGN<br>PHCKEHIQQYMTELLMWQKPALSGEAILKMLGKCTHEKNEFKAAKHTYSAER<br>FVWLTKLNNLRILEDGAERALNEEERQLLINHPYEKSKLTYAQVRKLLGLSEQA<br>IFKHLRYSKENAESATFMELKAWHAIRKALENQGLKDTWQDLAKKPDLLDEIG<br>TAFSLYKTDEDIQQYLTNKVPNSVINALLVSLNFDKFIELSLKSLRKILPLMEQG<br>KRYDQACREIYGHHYGEANQKTSQLLPAIPAQEIRNPVVLRTLSQARKVINAIIR<br>QYGSPARVHIETGRELGKSFKERREIQKQQEDNRTKRESAVQKFKELFSDFSSEP<br>KSKDILKFRLYEQQHGKCLYSGKEINIHRLNEKGYVEIDHALPFSRTWDDSFNN<br>KVLVLASENQNKGNQTPYEWLQGKINSERWKNFVALVLGSQCSAAKKQRLLT<br>QVIDDNKFIDRNLNDTRYIARFLSNYIQENLLLVGKNKKNVFTPNGQITALLRSR<br>WGLIKARENNNRHHALDAIVVACATPSMQQKITRFIRFKEVHPYKIENRYEMV<br>DQESGEIISPHFPEPWAYFRQEVNIRVFDNHPDTVLKEMLPDRPQANHQFVQPL<br>FVSRAPTRKMSGQGHMETIKSAKRLAEGISVLRIPLTQLKPNLLENMVNKEREP<br>ALYAGLKARLAEFNQDPAKAFATPFYKQGGQQVKAIRVEQVQKSGVLVRENN<br>GVADNASIVRTDVFIKNNKFFLVPIYTWQVAKGILPNKAIVAHKNEDEWEEMD<br>EGAKFKFSLFPNDLVELKTKKEYFFGYYIGLDRATGNISLKEHDGEISKGKDGV<br>YRVGVKLALSFEKYQVDELGKNRQICRPQQRQPVR |
| *F. novicida* Cas9<br>SEQ ID NO: 15 | MNFKILPIAIDLGVKNTGVFSAFYQKGTSLERLDNKNGKVYELSKDSYTLLMNN<br>RTARRHQRRGIDRKQLVKRLFKLIWTEQLNLEWDKDTQQAISFLFNRRGFSFIT<br>DGYSPEYLNIVPEQVKAILMDIFDDYNGEDDLDSYLKLATEQESKISEIYNKLM<br>QKILEFKLMKLCTDIKDDKVSTKTLKEITSYEFELLADYLANYSESLKTQKFSYT<br>DKQGNLKELSYYHHDKYNIQEFLKRHATINDRILDTLLTDDLDIWNFNFEKFDF<br>DKNEEKLQNQEDKDHIQAHLHHFVFAVNKIKSEMASGGRHRSQYFQEITNVLD<br>ENNHQEGYLKNFCENLHNKKYSNLSVKNLVNLIGNLSNLELKPLRKYFNDKIH<br>AKADHWDEQKFTETYCHWILGEWRVGVKDQDKKDGAKYSYKDLCNELKQK<br>VTKAGLVDFLLELDPCRTIPPYLDNNNRKPPKCQSLILNPKFLDNQYPNWQQYL<br>QELKKLQSIQNYLDSFETDLKVLKSSKDQPYFVEYKSSNQQIASGQRDYKDLDA<br>RILQFIFDRVKASDELLLNEIYFQAKKLKQKASSELEKLESSKKLDEVIANSQLSQ<br>ILKSQHTNGIFEQGTFLHLVCKYYKQRQRARDSRLYIMPEYRYDKKLHKYNNT<br>GRFDDDNQLLTYCNHKPRQKRYQLLNDLAGVLQVSPNFLKDKIGSDDDLFISK<br>WLVEHIRGFKKACEDSLKIQKDNRGLLNHKINIARNTKGKCEKEIFNLICKIEGS<br>EDKKGNYKHGLAYELGVLLFGEPNEASKPEFDRKIKKFNSIYSFAQIQQIAFAER<br>KGNANTCAVCSADNAHRMQQIKITEPVEDNKDKIILSAKAQRLPAIPTRIVDGA<br>VKKMATILAKNIVDDNWQNIKQVLSAKHQLHIPIITESNAFEFEPALADVKGKS<br>LKDRRKKALERISPENIFKDKNNRIKEFAKGISAYSGANLTDGDFDGAKEELDHI<br>IPRSHKKYGTLNDEANLICVTRGDNKNKGNRIFCLRDLADNYKLKQFETTDDLE<br>IEKKIADTIWDANKKDFKFGNYRSFINLTPQEQKAFRHALFLADENPIKQAVIRA<br>INNRNRTFVNGTQRYFAEVLANNIYLRAKKENLNTDKISFDYFGIPTIGNGRGIA<br>EIRQLYEKVDSDIQAYAKGDKPQASYSHLIDAMLAFCIAADEHRNDGSIGLEID<br>KNYSLYPLDKNTGEVFTKDIFSQIKITDNEFSDKKLVRKKAIEGFNTHRQMTRD<br>GIYAENYLPILIHKELNEVRKGYTWKNSEEIKIFKGKKYDIQQLNNLVYCLKFV<br>DKPISIDIQISTLEELRNILTTNNIAATAEYYYINLKTQKLHEYYIENYNTALGYK<br>KYSKEMEFLRSLAYRSERVKIKSIDDVKQVLDKDSNFIIGKITLPFKKEWQRLYR<br>EWQNTTIKDDYEFLKSFFNVKSITKLHKKVRKDFSLPISTNEGKFLVKRKTWDN<br>NFIYQILNDSDSRADGTKPFIPAFDISKNEIVEAIIDSFTSKNIFWLPKNIELQKVD<br>NKNIFAIDTSKWFEVETPSDLRDIGIATIQYKIDNNSRPKVRVKLDYVIDDDSKIN<br>YFMNHSLLKSRYPDKVLEILKQSTIIEFESSGFNKTIKEMLGMKLAGIYNETSNN |
| *Lactobacillus buchneri* Cas9<br>SEQ ID NO: 16 | MKVNNYHIGLDIGTSSIGWVAIGKDGKPLRVKGKTAIGARLFQEGNPAADRRM<br>FRTTRRRLSRRKWRLKLLEEIFDPYITPVDSTFFARLKQSNLSPKDSRKEFKGSM<br>LFPDLTDMQYHKNYPTIYHLRHALMTQDKKFDIRMVYLAIHHIVKYRGNFLNS<br>TPVDSFKASKVDFVDQFKKLNELYAAINPEESFKINLANSEDIGHQFLDPSIRKF<br>DKKKQIPKIVPVMMNDKVTDRLNGKIASEIIHAILGYKAKLDVVLQCTPVDSKP<br>WALKFDDEDIDAKLEKILPEMDENQQSIVAILQNLYSQVTLNQIVPNGMSLSES<br>MIEKYNDHHDHLKLYKKLIDQLADPKKKAVLKKAYSQYVGDDGKVIEQAEFW<br>SSVKKNLDDSELSKQIMDLIDAEKFMPKQRTSQNGVIPHQLHQRELDEIIEHQSK<br>YYPWLVEINPNKHDLHLAKYKIEQLVAFRVPYYVGPMITPKDQAESAETVFSW<br>MERKGTETGQITPWNFDEKVDRKASANRFIKRMTTKDTYLIGEDVLPDESLLYE<br>KFKVLNELNMVRVNGKLLKVADKQAIFQDLFENYKHVSVKKLQNYIKAKTGL<br>PSDPEISGLSDPEHFNNSLGTYNDFKKLFGSKVDEPDLQDDFEKIVEWSTVFEDK<br>KILREKLNEITWLSDQQKDVLESSRYQGWGRLSKKLLTGIVNDQGERIIDKLWN<br>TNKNFMQIQSDDDFAKRIHEANADQMQAVDVEDVLADAYTSPQNKKAIRQVV<br>KVVDDIQKAMGGVAPKYISIEFTRSEDRNPRRTISRQRQLENTLKDTAKSLAKSI<br>NPELLSELDNAAKSKKGLTDRLYLYFTQLGKDIYTGEPINIDELNKYDIDHILPQ<br>AFIKDNSLDNRVLVLTAVNNGKSDNVPLRMFGAKMGHFWKQLAEAGLISKRK<br>LKNLQTDPDTISKYAMHGFIRRQLVETSQVIKLVANILGDKYRNDDTKIIEITAR<br>MNHQMRDEFGFIKNREINDYHHAFDAYLTAFLGRYLYHRYIKLRPYFVYGDFK<br>KFREDKVTMRNFNFLHDLTDDTQEKIADAETGEVIWDRENSIQQLKDVYHYKF<br>MLISHEVYTLRGAMFNQTVYPASDAGKRKLIPVKADRPVNVYGGYSGSADAY<br>MAIVRIHNKKGDKYRVVGVPMRALDRLDAAKNVSDADFDRALKDVLAPQLT<br>KTKKSRKTGEITQVIEDFEIVLGKVMYRQLMIDGDKKFMLGSSTYQYNAKQLV<br>LSDQSVKTLASKGRLDPLQESMDYNNVYTEILDKVNQYFSLYDMNKFRHKLN |

-continued

| Name | Protein Sequence |
|---|---|
| | LGFSKFISFPNHNVLDGNTKVSSGKREILQEILNGLHANPTFGNLKDVGITTPFG<br>QLQQPNGILLSDETKIRYQSPTGLFERTVSLKDL |
| *Listeria innocua*<br>Cas9<br>SEQ ID NO: 17 | MKKPYTIGLDIGTNSVGWAVLTDQYDLVKRKMKIAGDSEKKQIKKNFWGVRL<br>FDEGQTAADRRMARTARRRIERRRNRISYLQGIFAEEMSKTDANFFCRLSDSFY<br>VDNEKRNSRHPFFATIEEEVEYHKNYPTIYHLREELVNSSEKADLRLVYLALAHI<br>IKYRGNFLIEGALDTQNTSVDGIYKQFIQTYNQVFASGIEDGSLKKLEDNKDVA<br>KILVEKVTRKEKLERILKLYPGEKSAGMFAQFISLIVGSKGNFQKPFDLIEKSDIE<br>CAKDSYEEDLESLLALIGDEYAELFVAAKNAYSAVVLSSIITVAETETNAKLSAS<br>MIERFDTHEEDLGELKAFIKLHLPKHYEEIFSNTEKHGYAGYIDGKTKQADFYK<br>YMKMTLENIEGADYFIAKIEKENFLRKQRTFDNGAIPHQLHLEELEAILHQQAK<br>YYPFLKENYDKIKSLVTFRIPYFVGPLANGQSEFAWLTRKADGEIRPWNIEEKV<br>DFGKSAVDFIEKMTNKDTYLPKENVLPKHSLCYQKYLVYNELTKVRYINDQGK<br>TSYFSGQEKEQIFNDLFKQKRKVKKKDLELFLRNMSHVESPTIEGLEDSFNSSYS<br>TYHDLLKVGIKQEILDNPVNTEMLENIVKILTVFEDKRMIKEQLQQFSDVLDGV<br>VLKKLERRHYTGWGRLSAKLLMGIRDKQSHLTILDYLMNDDGLNRNLMQLIN<br>DSNLSFKSIIEKEQVTTADKDIQSIVADLAGSPAIKKGILQSLKIVDELVSVMGYP<br>PQTIVVEMARENQTTGKGKNNSRPRYKSLEKAIKEFGSQILKEHPTDNQELRNN<br>RLYLYYLQNGKDMYTGQDLDIHNLSNYDIDHIVPQSFITDNSIDNLVLTSSAGN<br>REKGDDVPPLEIVRKRKVFWEKLYQGNLMSKRKFDYLTKAERGGLTEADKAR<br>FIHRQLVETRQITKNVANILHQRFNYEKDDHGNTMKQVRIVTLKSALVSQFRKQ<br>FQLYKVRDVNDYHHAHDAYLNGVVANTLLKVYPQLEPEFVYGDYHQFDWFK<br>ANKATAKKQFYTNIMLFFAQKDRIIDENGEILWDKKYLDTVKKVMSYRQMNIV<br>KKTEIQKGEFSKATIKPKGNSSKLIPRKTNWDPMKYGGLDSPNMAYAVVIEYA<br>KGKNKLVFEKKIIRVTIMERKAFEKDEKAFLEEQGYRQPKVLAKLPKYTLYECE<br>EGRRRMLASANEAQKGNQQVLPNHLVTLLHHAANCEVSDGKSLDYIESNREM<br>FAELLAHVSEFAKRYTLAEANLNKINQLFEQNKEGDIKAIAQSFVDLMAFNAM<br>GAPASFKFFETTIERKRYNNLKELLNSTIIYQSITGLYESRKRLDD |
| *L. pneumophilia*<br>Cas9<br>SEQ ID NO: 18 | MESSQILSPIGIDLGGKFTGVCLSHLEAFAELPNHANTKYSVILIDHNNFQLSQA<br>QRRATRHRVRNKKRNQFVKRVALQLFQHILSRDLNAKEETALCHYLNNRGYT<br>YVDTDLDEYIKDETTINLLKELLPSESEHNFIDWFLQKMQSSEFRKILVSKVEEK<br>KDDKELKNAVKNIKNFITGFEKNSVEGHRHRKVYFENIKSDITKDNQLDSIKKKI<br>PSVCLSNLLGHLSNLQWKNLHRYLAKNPKQFDEQTFGNEFLRMLKNFRHLKGS<br>QESLAVRNLIQQLEQSQDYISILEKTPPEITIPPYEARTNTGMEKDQSLLLNPEKL<br>NNLYPNWRNLIPGIIDAHPFLEKDLEHTKLRDRKRIISPSKQDEKRDSYILQRYLD<br>LNKKIDKFKIKKQLSFLGQGKQLPANLIETQKEMETHFNSSLVSVLIQIASAYNK<br>EREDAAQGIWFDNAFSLCELSNINPPRKQKILPLLVGAILSEDFINNKDKWAKFK<br>IFWNTHKIGRTSLKSKCKEIEEARKNSGNAFKIDYEEALNHPEHSNNKALIKIIQT<br>IPDIIQAIQSHLGHNDSQALIYHNPFSLSQLYTILETKRDGFHKNCVAVTCENYW<br>RSQKTEIDPEISYASRLPADSVRPFDGVLARMMQRLAYEIAMAKWEQIKHIPDN<br>SSLLIPIYLEQNRFEFEESFKKIKGSSSDKTLEQAIEKQNIQWEEKFQRIINASMNI<br>CPYKGASIGGQGEIDHIYPRSLSKKHFGVIFNSEVNLIYCSSQGNREKKEEHYLL<br>EHLSPLYLKHQFGTDNVSDIKNFISQNVANIKKYISFHLLTPEQQKAARHALFLD<br>YDDEAFKTITKFLMSQQKARVNGTQKFLGKQIMEFLSTLADSKQLQLEFSIKQIT<br>AEEVHDHRELLSKQEPKLVKSRQQSFPSHAIDATLTMSIGLKEFPQFSQELDNS<br>WFINHLMPDEVHLNPVRSKEKYNKPNISSTPLFKDSLYAERFIPVWVKGETFAIG<br>FSEKDLFEIKPSNKEKLFTLLKTYSTKNPGESLQELQAKSKAKWLYFPINKTLAL<br>EFLHHYFHKEIVTPDDTTVCHFINSLRYYTKKESITVKILKEPMPVLSVKFESSKK<br>NVLGSFKHTIALPATKDWERLFNHPNFLALKANPAPNPKEFNEFIRKYFLSDNN<br>PNSDIPNNGHNIKPQKHKAVRKVFSLPVIPGNAGTMMRIRRKDNKGQPLYQLQ<br>TIDDTPSMGIQINEDRLVKQEVLMDAYKTRNLSTIDGINNSEGQAYATFDNWLT<br>LPVSTFKPEIIKLEMKPHSKTRRYIRITQSLADFIKTIDEALMIKPSDSIDDPLNMP<br>NEIVCKNKLFGNELKPRDGKMKIVSTGKIVTYEFESDSTPQWIQTLYVTQLKKQ<br>P |
| *N. lactamica* Cas9<br>SEQ ID NO: 19 | MAAFKPNPMNYILGLDIGIASVGWAMVEVDEEENPIRLIDLGVRVFERAEVPKT<br>GDSLAMARRLARSVRRLTRRRAHRLLRARRLLKREGVLQDADFDENGLVKSL<br>PNTPWQLRAAALDRKLTCLEWSAVLLHLVKHRGYLSQRKNEGETADKELGAL<br>LKGVADNAHALQTGDFRTPAELALNKFEKESGHIRNQRGDYSHTFSRKDLQAE<br>LNLLFEKQKEFGNPHVSDGLKEDIETLLMAQRPALSGDAVQKMLGHCTFEPAE<br>PKAAKNTYTAERFIWLTKLNNLRILEQGSERPLTDTERATLMDEPYRKSKLTYA<br>QARKLLGLEDTAFFKGLRYGKDNAEASTLMEMKAYHAISRALEKEGLKDKKS<br>PLNLSTELQDEIGTAFSLFKTDKDITGRLKDRVQPEILEALLKHISFDKFVQISLK<br>ALRRIVPLMEQGKRYDEACAEIYGDHYCKKNAEEKIYLPPIPADEIRNPVVLRA<br>LSQARKVINCVVRRYGSPARIHIETAREVGKSFKDRKEIEKRQEENRKDREKAA<br>AKFREYFPNFVGEPKSKDILKLRLYEQQHGKCLYSGKEINLVRLNEKGYVEIDH<br>ALPFSRTWDDSFNNKVLVLGSENQNKGNQTPYEYFNGKDNSREWQEFKARVE<br>TSRFPRSKKQRILLQKFDEEGFKERNLNDTRYVNRFLCQFVADHILLTGKGKRR<br>VFASNGQITNLLRGFWGLRKVRTENDRHHALDAVVVACSTVAMQQKITRFVR<br>YKEMNAFDGKTIDKETGEVLHQKAHFPQPWEFFAQEVMIRVFGKPDGKPEFEE<br>ADTPEKLRTLLAEKLSSRPEAVHEYVTPLFVSRAPNRKMSGQGHMETVKSAKR<br>LDEGISVLRVPLTQLKLKGLEKMVNREREPKLYDALKAQLETHKDDPAKAFAE<br>PFYKYDKAGSRTQQVKAVRIEQVQKTGVWVRNHNGIADNATMVRVDVFEKG<br>GKYYLVPIYSWQVAKGILPDRAVVAFKDEEDWTVMDDSFEFRFVLYANDLIKL<br>TAKKNEFLGYFVSLNRATGAIDIRTHDTDSTKGKNGIFQSVGVKTALSFQKNQI<br>DELGKEIRPCRLKKRPPVR |

-continued

| Name | Protein Sequence |
|---|---|
| *N. meningitides*<br>Cas9<br>SEQ ID NO: 20 | MAAFKPNPINYILGLDIGIASVGWAMVEIDEDENPICLIDLGVRVFERAEVPKTG<br>DSLAMARRLARSVRRLTRRRAHRLLRARRLLKREGVLQAADFDENGLIKSLPN<br>TPWQLRAAALDRKLTPLEWSAVLLHLIKHRGYLSQRKNEGETADKELGALLKG<br>VADNAHALQTGDFRTPAELALNKFEKESGHIRNQRGDYSHTFSRKDLQAELILL<br>FEKQKEFGNPHVSGGLKEGIETLLMTQRPALSGDAVQKMLGHCTFEPAEPKAA<br>KNTYTAERFIWLTKLNNLRILEQGSERPLTDTERATLMDEPYRKSKLTYAQARK<br>LLGLEDTAFFKGLRYGKDNAEASTLMEMKAYHAISRALEKEGLKDKKSPLNLS<br>PELQDEIGTAFSLFKTDEDITGRLKDRIQPEILEALLKHISFDKFVQISLKALRRIV<br>PLMEQGKRYDEACAEIYGDHYGKKNTEEKIYLPPIPADEIRNPVVLRALSQARK<br>VINGVVRRYGSPARIHIETAREVGKSFKDRKEIEKRQEENRKDREKAAAKFREY<br>FPNFVGEPKSKDILKLRLYEQQHGKCLYSGKEINLGRLNEKGYVEIDHALPFSRT<br>WDDSFNNKVLVLGSENQNKGNQTPYEYFNGKDNSREWQEFKARVETSRFPRS<br>KKQRILLQKFDEDGFKERNLNDTRYVNRFLCQFVADRMRLTGKGKKRVFASN<br>GQITNLLRGFWGLRKVRAENDRHHALDAVVVACSTVAMQQKITRFVRYKEMN<br>AFDGKTIDKETGEVLHQKTHFPQPWEFFAQEVMIRVFGKPDGKPEFEEADTPEK<br>LRTLLAEKLSSRPEAVHEYVTPLFVSRAPNRKMSGQGHMETVKSAKRLDEGVS<br>VLRVPLTQLKLKDLEKMVNREREPKLYEALKARLEAHKDDPAKAFAEPFYKY<br>DKAGNRTQQVKAVRVEQVQKTGVWVRNHNGIADNATMVRVDVFEKGDKYY<br>LVPIYSWQVAKGILPDRAVVQGKDEEDWQLIDDSFNFKFSLHPNDLVEVITKKA<br>RMFGYFASCHRGTGNINIRIHDLDHKIGKNGILEGIGVKTALSFQKYQIDELGKEI<br>RPCRLKKRPPVR |
| *B. longum* Cas9<br>SEQ ID NO: 21 | MLSRQLLGASHLARPVSYSYNVQDNDVHCSYGERCFMRGKRYRIGIDVGLNSV<br>GLAAVEVSDENSPVRLLNAQSVIHDGGVDPQKNKEAITRKNMSGVARRTRRM<br>RRRKRERLHKLDMLLGKFGYPVIEPESLDKPFEEWHVRAELATRYIEDDELRRE<br>SISIALRHMARHRGWRNPYRQVDSLISDNPYSKQYGELKEKAKAYNDDATAAE<br>EESTPAQLVVAMLDAGYAEAPRLRWRTGSKKPDAEGYLPVRLMQEDNANELK<br>QIFRVQRVPADEWKPLFRSVFYAVSPKGSAEQRVGQDPLAPEQARALKASLAF<br>QEYRIANVITNLRIKDASAELRKLTVDEKQSIYDQLVSPSSEDITWSDLCDFLGF<br>KRSQLKGVGSLTEDGEERISSRPPRLTSVQRIYESDNKIRKPLVAWWKSASDNE<br>HEAMIRLLSNTVDIDKVREDVAYASAIEFIDGLDDDALTKLDSVDLPSGRAAYS<br>VETLQKLTRQMLTTDDDLHEARKTLFNVTDSWRPPADPIGEPLGNPSVDRVLK<br>NVNRYLMNCQQRWGNPVSVNIEHVRSSFSSVAFARKDKREYEKNNEKRSIFRS<br>SLSEQLRADEQMEKVRESDLRRLEAIQRQNGQCLYCGRTITFRTCEMDHIVPRK<br>GVGSTNTRTNFAAVCAECNRMKSNTPFAIWARSEDAQTRGVSLAEAKKRVTM<br>FTFNPKSYAPREVKAFKQAVIARLQQTEDDAAIDNRSIESVAWMADELHRRID<br>WYFNAKQYVNSASIDDAEAETMKTTVSVFQGRVTASARRAAGIEGKIHFIGQQ<br>SKTRLDRRHHAVDASVIAMMNTAAAQTLMERESLRESQRLIGLMPGERSWKE<br>YPYEGTSRYESFHLWLDNMDVLLELLNDALDNDRIAVMQSQRYVLGNSIAHD<br>ATIHPLEKVPLGSAMSADLIRRASTPALWCALTRLPDYDEKEGLPEDSHREIRV<br>HDTRYSADDEMGFFASQAAQIAVQEGSADIGSAIHHARVYRCWKTNAKGVRK<br>YFYGMIRVFQTDLLRACHDDLFTVPLPPQSISMRYGEPRVVQALQSGNAQYLG<br>SLVVGDEIEMDFSSLDVDGQIGEYLQFFSQFSGGNLAWKHWVVDGFFNQTQLR<br>IRPRYLAAEGLAKAFSDDVVPDGVQKIVTKQGWLPPVNTASKTAVRIVRRNAF<br>GEPRLSSAHHMPCSWQWRHE |
| *A. muciniphila* Cas9<br>SEQ ID NO: 22 | MSRSLTFSFDIGYASIGWAVIASASHDDADPSVCGCGTVLFPKDDCQAFKRREY<br>RRLRRNIRSRRVRIERIGRLLVQAQIITPEMKETSGHPAPFYLASEALKGHRTLAP<br>IELWHVLRWYAHNRGYDNNASWSNSLSEDGGNGEDTERVKHAQDLMDKHGT<br>ATMAETICRELKLEEGKADAPMEVSTPAYKNLNTAFPRLIVEKEVRRILELSAPL<br>IPGLTAEIIELIAQHHPLTTEQRGVLLQHGIKLARRYRGSLLFGQLIPRFDNRIISR<br>CPVTWAQVYEAELKKGNSEQSARERAEKLSKVPTANCPEFYEYRMARILCNIR<br>ADGEPLSAEIRRELMNQARQEGKLTKASLEKAISSRLGKETETNVSNYFTLHPD<br>SEEALYLNPAVEVLQRSGIGQILSPSVYRIAANRLRRGKSVTPNYLLNLLKSRGE<br>SGEALEKKIEKESKKKEADYADTPLKPKYATGRAPYARTVLKKVVEEILDGEDP<br>TRPARGEAHPDGELKAHDGCLYCLLDTDSSVNQHQKERRLDTMTNNHLVRHR<br>MLILDRLLKDLIQDFADGQKDRISRVCVEVGKELTTFSAMDSKKIQRELTLRQK<br>SHTDAVNRLKRKLPGKALSANLIRKCRIAMDMNWTCPFTGATYGDHELENLEL<br>EHIVPHSFRQSNALSSLVLTWPGVNRMKGQRTGYDFVEQEQENPVPDKPNLHI<br>CSLNNYRELVEKLDDKKGHEDDRRRKKKRKALLMVRGLSHKHQSQNHEAMK<br>EIGMTEGMMTQSSHLMKLACKSIKTSLPDAHIDMIPGAVTAEVRKAWDVFGVF<br>KELCPEAADPDSGKILKENLRSLTHLHHALDACVLGLIPYIIPAHHNGLLRRVLA<br>MRRIPEKLIPQVRPVANQRHYVLNDDGRMMLRDLSASLKENIREQLMEQRVIQ<br>HVPADMGGALLKETMQRVLSVDGSGEDAMVSLSKKKDGKKEKNQVKASKLV<br>GVFPEGPSKLKALKAAIEIDGNYGVALDPKPVVIRHIKVFKRIMALKEQNGGKP<br>VRILKKGMLIHLTSSKDPKHAGVWRIESIQDSKGGVKLDLQRAHCAVPKNKTH<br>ECNWREVDLISLLKKYQMKRYPTSYTGTPR |
| *O. laneus* Cas9<br>SEQ ID NO: 23 | METTLGIDLGTNSIGLALVDQEEHQILYSGVRIFPEGINKDTIGLGEKEESRNATR<br>RAKRQMRRQYFRKKLRKAKLLELLIAYDMCPLKPEDVRRWKNWDKQQKSTV<br>RQFPDTPAFREWLKQNPYELRKQAVTEDVTRPELGRILYQMIQRRGFLSSRKGK<br>EEGKIFTGKDRMVGIDETRKNLQKQTLGAYLYDIAPKNGEKYRFRTERVRARY<br>TLRDMYIREFEIIWQRQAGHLGLAHEQATRKKNIFLEGSATNVRNSKLITHLQA<br>KYGRGHVLIEDTRITVTFQLPLKEVLGGKIEIEEEQLKFKSNESVLFWQRPLRSQ<br>KSLLSKCVFEGRNFYDPVHQKWIIAGPTPAPLSHPEFEEFRAYQFINNIIYGKNEH<br>LTAIQREAVFELMCTESKDFNFEKIPKHLKLFEKFNFDDTTKVPACTTISQLRKL |

-continued

| Name | Protein Sequence |
|---|---|
| | FPHPVWEEKREEIWHCFYFYDDNTLLFEKLQKDYALQTNDLEKIKKIRLSESYG<br>NVSLKAIRRINPYLKKGYAYSTAVLLGGIRNSFGKRFEYFKEYEPEIEKAVCRIL<br>KEKNAEGEVIRKIKDYLVHNRFGFAKNDRAFQKLYHHSQAITTQAQKERLPET<br>GNLRNPIVQQGLNELRRTVNKLLATCREKYGPSFKFDHIHVEMGRELRSSKTER<br>EKQSRQIRENEKKNEAAKVKLAEYGLKAYRDNIQKYLLYKEIEEKGGTVCCPY<br>TGKTLNISHTLGSDNSVQIEHIIPYSISLDDSLANKTLCDATFNREKGELTPYDFY<br>QKDPSPEKWGASSWEEIEDRAFRLLPYAKAQRFIRRKPQESNEFISRQLNDTRYI<br>SKKAVEYLSAICSDVKAFPGQLTAELRHLWGLNNILQSAPDITFPLPVSATENHR<br>EYYVITNEQNEVIRLFPKQGETPRTEKGELLLTGEVERKVFRCKGMQEFQTDVS<br>DGKYWRRIKLSSSVTWSPLFAPKPISADGQIVLKGRIEKGVFVCNQLKQKLKTG<br>LPDGSYWISLPVISQTFKEGESVNNSKLTSQQVQLFGRVREGIFRCHNYQCPASG<br>ADGNFWCTLDTDTAQPAFTPIKNAPPGVGGGQIILTGDVDDKGIFHADDDLHYE<br>LPASLPKGKYYGIFTVESCDPTLIPIELSAPKTSKGENLIEGNIWVDEHTGEVRFD<br>PKKNREDQRHHAIDAIVIALSSQSLFQRLSTYNARRENKKRGLDSTEHFPSPWP<br>GFAQDVRQSVVPLLVSYKQNPKTLCKISKTLYKDGKKIHSCGNAVRGQLHKET<br>VYGQRTAPGATEKSYHIRKDIRELKTSKHIGKVVDITIRQMLLKHLQENYHIDIT<br>QEFNIPSNAFFKEGVYRIFLPNKHGEPVPIKKIRMKEELGNAERLKDNINQYVNP<br>RNNHHVMIYQDADGNLKEEIVSFWSVIERQNQGQPIYQLPREGRNIVSILQINDT<br>FLIGLKEEEPEVYRNDLSTLSKHLYRVQKLSGMYYTFRHHLASTLNNEREEFRI<br>QSLEAWKRANPVKVQIDEIGRITFLNGPLC |

In some embodiments, a nucleic acid sequence encoding a dCas endonuclease is a codon optimized dCas. An example of a codon optimized sequence, is in this instance, a sequence optimized for expression in, without limitation, a eukaryote, animal, and/or mammal e.g., a human (i.e. being optimized for expression in humans); see, e.g., SaCas9 human codon optimized sequence in WO 2014/093622, incorporated by reference herein in its entirety.

In some embodiments, a dCas endonuclease for use in the system provided herein is a variant Cas endonuclease comprising mutations which cause the endonuclease to lack cleavage activity or substantially lack cleavage activity as compared to its corresponding wild type Cas endonuclease. For example, with reference to WO 2017/091630, incorporated herein by reference in its entirety, in one embodiment disclosed herein, the Cas9 active sites (10 and 840) can be mutated to Alanine (D10A and H840A) to eliminate the cleavage activity of *Streptococcus pyogenes* Cas9, producing nuclease-deficient or dead Cas9 (i.e., dCas9). The RuvC domain is distributed among 3 non-contiguous portions of the dCas9 primary structure (residues 1-60, 719-775, and 910-1099). The Rec lobe is composed of residues 61-718. The HNH domain is composed of residues 776-909. The PAM-ID domain is composed of residues 1100-1368. The REC lobe can be considered the structural scaffold for recognition of the sgRNA and target DNA/RNA. The NUC lobe contains the two nuclease domains (HNH and RuvC), plus the PAM-interaction domain (PAM-ID), which recognizes an optional PAM sequence. In this prior work, for example and without limitation, an about 98-nucleotide sgRNA, is typically divided into two major structural components: the first contains the target-specific guide or "spacer" segment (nucleotides 1-20) plus the repeat-tetraloop-anti-repeat and stem-loop 1 (SL1) regions; the second contains stem-loops 2 and 3 (SL2, SL3). Accordingly, the guide-through-SL1 RNA segment is bound mainly by the Cas9 REC lobe and the SL2-SL3 segment is bound mainly by the NUC lobe.

In some embodiments of the dCas9 used in the system disclosed herein, a minimal (i.e., with as few nucleotide base pairs as possible) construct of Cas9 is engineered that will recognize a target RNA sequence with high affinity. In some embodiments, the smallest construct encoding dCas9 will be a REC-only construct. In some embodiments, the constructs will comprise less minimized constructs lacking the HNH, PAM-ID, parts of each domain, lacking both of each domain, or combinations thereof. In some embodiments, the HNH domain will be excised by inserting a five-residue flexible linker between residues 775 and 909 (ΔHNH). In some embodiments, all or part of the PAM-ID are removed. In some embodiments, truncating Cas9 at residue 1098 (ΔPAM-ID #1), fusing residues 1138 and 1345 with an 8-residue linker (ΔPAM-ID #2), or fusing residues 1138 with 1200 and 1218 with 1339 (with 5-residue and 2-residue linkers, respectively: ΔPAM-ID #3) are used to remove all or part of the PAM-ID. The ΔPAM-ID #2 and 3 constructs will retain elements of the PAM-ID that contribute to binding of the sgRNA repeat-anti-repeat (residues 1099-1138) and SL2-SL3 (residues 1200-1218 and 1339-1368) segments. In some embodiments, the HNH deletion will be combined with the three PAM-ID deletions. In some embodiments, Cas9 variants which lack or substantially lack nuclease and/or cleavage activity according to WO 2016/19655, incorporated herein by reference in its entirety, are examples of dCas9 used in the recombinant expression systems disclosed herein.

Accordingly for use in the recombinant expression systems disclosed herein are nucleic acid sequences encoding dCas—ADAR deaminase domain fusion proteins. In one embodiment, dCas9 is fused to a catalytically active ADAR deaminase domain. In the context of such systems a corresponding extended single guide RNA (esgRNA) is used to target and edit adenosines of the target RNA. The system generates recombinant proteins with effector deaminase enzymes capable of performing ribonucleotide base modification to alter how sequence of the RNA molecule is recognized by cellular machinery. In one embodiment the dCas and the ADAR deaminase domain are separated by a linker. In another embodiment, the linker is, without limitation, an XTEN linker which is a flexible linker used to isolate adjacent proteins domains. XTEN linkers are known in the art and can be found for example in WO 2013/130684, incorporated herein by reference in its entirety herein.

RNA editing is a natural process whereby the diversity of gene products of a given sequence is increased by minor modification in the RNA. Typically, the modification involves the conversion of adenosine (A) to inosine (I), resulting in an RNA sequence which is different from that encoded by the genome. RNA modification is generally ensured by the ADAR enzyme, whereby the pre-RNA target forms an imperfect duplex RNA by base-pairing between the exon that contains the adenosine to be edited and an intronic non-coding element. A classic example of A-I editing is the glutamate receptor GluR-B mRNA, whereby the change results in modified conductance properties of the channel (Higuchi M, et al. Cell. 1993; 75: 1361-70). For the purposes of the present disclosure, ADAR (Adenosine deaminase acting on RNA) deaminase domains can be ADAR 1, ADAR 2, or ADAR 3 deaminase domains. See Nishikura, K. A-to-I editing of coding and non-coding RNAs by ADARs. Nat Rev Mol Cell Biol 17, 83-96, doi:10.1038/nrm.2015.4 (2016).

In some embodiments, the ADAR deaminase domain is derived from all or part of ADAR1 (Uniprot P55265). A non-limiting exemplary sequence of ADAR1 is provided below (SEQ ID NO: 24):

```
MAEIKEKICDYLFNVSDSSALNLAKNIGLTKARDINAVLIDMERQGDVY
RQGTTPPIWHLTDKKRERMQIKRNTNSVPETAPAAIPETKRNAEFLTCN
IPTSNASNNMVTTEKVENGQEPVIKLENRQEARPEPARLKPPVHYNGPS
KAGYVDFENGQWATDDIPDDLNSIRAAPGEFRAIMEMPSFYSHGLPRCS
PYKKLTECQLKNPISGLLEYAQFASQTCEFNMIEQSGPPHEPRFKFQVV
INGREFPPAEAGSKKVAKQDAAMKAMTILLEEAKAKDSGKSEESSHYST
EKESEKTAESQTPTPSATSFFSGKSPVTTLLECMHKLGNSCEFRLLSKE
GPAHEPKFQYCVAVGAQTFPSVSAPSKKVAKQMAAEEAMKALHGEATNS
MASDNQPEGMISESLDNLESMMPNKVRKIGELVRYLNTNPVGGLLEYAR
SHGFAAEFKLVDQSGPPHEPKFVYQAKVGGRWFPAVCAHSKKQGKQEAA
DAALRVLIGENEKAERMGFTEVTPVTGASLRRTMLLLSRSPEAQPKTLP
LTGSTFHDQIAMLSHRCFNTLTNSFQPSLLGRKILAAIIMKKDSEDMGV
VVSLGTGNRCVKGDSLSLKGETVNDCHAEIISRRGFIRFLYSELMKYNS
QTAKDSIFEPAKGGEKLQIKKTVSFHLYISTAPCGDGALFDKSCSDRAM
ESTESRHYPVFENPKQGKLRTKVENGEGTIPVESSDIVPTWDGIRLGER
LRTMSCSDKILRWNVLGLQGALLTHFLQPIYLKSVTLGYLFSQGHLTRA
ICCRVTRDGSAFEDGLRHPFIVNHPKVGRVSIYDSKRQSGKTKETSVNW
CLADGYDLEILDGTRGTVDGPRNELSRVSKKNIFLLFKKLCSFRYRRDL
LRLSYGEAKKAARDYETAKNYFKKGLKDMGYGNWISKPQEEKNFYLCPV
```

In some embodiments, the ADAR deaminase domain is derived from all or part of ADAR2 (Uniprot P78563). A non-limiting exemplary sequence of ADAR2 is provided below (SEQ ID NO: 25):

```
MDIEDEENMSSSSTDVKENRNLDNVSPKDGSTPGPGEGSQLSNGGGGGP
GRKRPLEEGSNGHSKYRLKKRRKTPGPVLPKNALMQLNEIKPGLQYTLL
SQTGPVHAPLFVMSVEVNGQVFEGSGPTKKKAKLHAAEKALRSFVQFPN
ASEAHLAMGRTLSVNTDFTSDQADFPDTLFNGFETPDKAEPPFYVGSNG
DDSFSSSGDLSLSASPVPASLAQPPLPVLPPFPPPSGKNPVMILNELRP
GLKYDFLSESGESHAKSFVMSVVVDGQFFEGSGRNKKLAKARAAQSALA
AIFNLHLDQTPSRQPIPSEGLQLHLPQVLADAVSRLVLGKFGDLTDNFS
```

-continued

```
SPHARRKVLAGVVMTTGTDVKDAKVISVSTGTKCINGEYMSDRGLALND
CHAEIISRRSLLRFLYTQLELYLNNKDDQKRSIFQKSERGGFRLKENVQ
FHLYISTSPCGDARIFSPHEPILEEPADRHPNRKARGQLRTKIESGEGT
IPVRSNASIQTWDGVLQGERLLTMSCSDKIARWNVVGIQGSLLSIFVEP
IYFSSIILGSLYHGDHLSRAMYQRISNIEDLPPLYTLNKPLLSGISNAE
ARQPGKAPNFSVNWTVGDSAIEVINATTGKDELGRASRLCKHALYCRWM
RVHGKVPSHLLRSKITKPNVYHESKLAAKEYQAAKARLFTAFIKAGLGA
WVEKPTEQDQFSLTP
```

In some embodiments, the ADAR deaminase domain is derived from all or part of ADAR3 (Uniprot Q9NS39): A non-limiting exemplary sequence of ADAR2 is provided below (SEQ ID NO: 26):

```
MASVLGSGRGSGGLSSQLKCKSKRRRRRRSKRKDKVSILSTFLAPFKHL
SPGITNTEDDDTLSTSSAEVKENRNVGNLAARPPPSGDRARGGAPGAKR
KRPLEEGNGGHLCKLQLVWKKLSWSVAPKNALVQLHELRPGLQYRTVSQ
TGPVHAPVFAVAVEVNGLTFEGTGPTKKKAKMRAAELALRSFVQFPNAC
QAHLAMGGGPGPGTDFTSDQADFPDTLFQEFEPPAPRPGLAGGRPGDAA
LLSAAYGRRRLLCRALDLVGPTPATPAAPGERNPVVLLNRLRAGLRYVC
LAEPAERRARSFVMAVSVDGRTFEGSGRSKKLARGQAAQAALQELFDIQ
MPGHAPGRARRTPMPQEFADSISQLVTQKFREVTTDLTPMHARHKALAG
IVMTKGLDARQAQVVALSSGTKCISGEHLSDQGLVVNDCHAEVVARRAF
LHFLYTQLELHLSKRREDSERSIFVRLKEGGYRLRENILFHLYVSTSPC
GDARLHSPYEITTDLHSSKHLVRKFRGHLRTKIESGEGTVPVRGPSAVQ
TWDGVLLGEQLITMSCTDKIARWNVLGLQGALLSHFVEPVYLQSIVVGS
LHHTGHLARVMSHRMEGVGQLPASYRHNRPLLSGVSDAEARQPGKSPPF
SMNWVVGSADLEIINATTGRRSCGGPSRLCKHVLSARWARLYGRLSTRT
PSPGDTPSMYCEAKLGAHTYQSVKQQLFKAFQKAGLGTWVRKPPEQQQF
LLTL
```

In some embodiments, ADAR domains can include mutations which result in increased catalytic activity compared to wild type ADAR domains. In some embodiments, the catalytically active deaminase domain (DD) is derived from a wildtype human ADAR2 or a human ADAR2 DD bearing a mutation (E488Q) that increases enzymatic activity and affinity for RNA substrate (Phelps et al., January 2015, Nuc. Acid Res., 43(2): 1123-1132; Kuttan & Bass, November 2012, PNAS 109(48): E3295-E3304).

Because the catalytic domain of ADAR2, independent of its RNA recognition motif, preferably deaminates unpaired adenosine residues in dsRNA regions, Applicants modified the structure of the single guide RNA (sgRNA) component of the system disclosed herein to improve substrate specificity to single-nucleotide resolution. It has been reported that gRNAs engineered with supplementary 3' terminal cassettes maintain their targeting capacity in live cells (Konermann et al. January 2015, Nature, 517: 583-588).

Applicants developed a CRISPR/Cas-mediated RNA editing (CREDIT) platform based on the strategic modification of the system's sgRNA structure comprising an additional region of homology capable of base pairing with target RNA over the desired site of editing. Such a modification to the sgRNA structure generates the disclosed system's extended sgRNA (i.e., esgRNA), and results in an A-to-C mismatch with a target transcript generating a 'pseudo-dsRNA' substrate to be edited at the bulged adenosine (see FIG. 1A). The CREDIT platform and the systems disclosed herein thus provides the ability to target virtually any adenosine in the transcriptome to direct conversion to inosine (i.e., A-I RNA editing), which is ultimately read by translational and splicing machinery as guanosine.

Due to its overall design simplicity as well as its fully encodable nature, the recombinant expression systems disclosed herein provide high utility and engineering versatility when compared to other similar RNA modifying systems and methods. Because dCas9 binds with picomolar affinity to the sgRNA scaffold sequence, and because this improved system uses dual guide architecture as per the extended single guide RNA i.e., esgRNA, structure, to increase both target affinity and specificity, direct RNA editing with minimal potential off-target editing events is efficiently achieved. In some embodiments, the esgRNA can be designed with a i) scaffold sequence and ii) a short extension sequence but without a spacer sequence.

In one embodiment, the esgRNA is composed of at least two regions, i) a region of homology capable of near-perfect RNA-RNA base pairing (i.e., a short extension sequence of homology to the target RNA) and ii) a dCas9-binding region (i.e., scaffold sequence). In one embodiment, the short extension sequence comprises a mismatch which forms an A-C mismatch with a target transcriptome and generates a 'pseudo-RNA' substrate to be edited at the bulged adenosine residue. As such, the homology region of the short extension sequence determines the specificity of the recombinant expression system disclosed herein, and in particular it determines specifically which RNA base in the cellular transcriptome is edited. The RNA base that is edited is distinguished by a mismatched adenosine residue among the homology region and the target RNA duplex. See FIG. 1A. The orientation of the homology region of the short extension sequence and the scaffold is flexible. In one embodiment, the scaffold sequence is located at the 5' end of the esgRNA. In another embodiment, the short extension sequence carrying the homology region capable of near-perfect RNA-RNA base pairing is located at the 3' end of the esgRNA. In another embodiment, the short extension sequence is located at the 5' end of the esgRNA. For the purposes of the present disclosure, the "3' end" or "5' end" refers in either scenario of the esgRNA to an end terminus of the esgRNA. In another embodiment, the esgRNA additionally comprises a third region, iii) a spacer sequence which comprises a second homology region to the target RNA. In one embodiment, the spacer sequence is located at the 5' end of the scaffold sequence. The spacer sequence is complementary to the target RNA but does not require a mismatch to effect the A-I editing of the target RNA. In one embodiment, the spacer sequence is located on the 5' end of the scaffold sequence. In another embodiment, the short extension sequence is located on the 3' end of the scaffold sequence or on the 5' end of the spacer sequence. In another embodiment, the short extension sequence is located on an end terminus of the esgRNA. In another embodiment, the short extension sequence is continuous to the spacer sequence. In another embodiment, the short extension sequence is discontinuous to the spacer sequence. In another embodiment, the esgRNA comprising i-iii) in a 3' to 5' orientation.

In some embodiments, nucleoprotein complexes are complexed with a single guide RNA (sgRNA) or as disclosed herein an extended single guide RNA (esgRNA). In some embodiments, the single guide RNA or esgRNA carries extensions (other than and in addition to the short extension sequence of homology in the esgRNA capable of editing target adenosines) of secondary structures in the single guide RNA or esgRNA scaffold sequence. In some embodiments, the single guide RNA or esgRNA comprises one or more point mutations that improve expression levels of the single guide RNAs (or esgRNAs) via removal of partial or full transcription termination sequences or sequences that destabilize single guide RNAs (or esgRNAs) after transcription via action of trans-acting nucleases. In some embodiments, the single guide RNA (or esgRNA) comprises an alteration at the 5' end which stabilizes said single guide RNA or esgRNA against degradation. In some embodiments, the single guide RNA or esgRNA comprises an alteration at the 5' end which improves RNA targeting. In some embodiments, the alteration at the 5' end of said single guide RNA or esgRNA is selected from the group consisting of 2'O-methyl, phosphorothioates, and thiophosphonoacetate linkages and bases. In some embodiments, the single guide RNA or esgRNA comprises 2'-fluorine, 2'O-methyl, and/or 2'-methoxyethyl base modifications in the spacer or scaffold region of the sgRNA or esgRNA to improve target recognition or reduce nuclease activity on the single guide RNA or esgRNA. In some embodiments, the single guide RNA comprises one or more methylphosphonate, thiophosponoaceteate, or phosphorothioate linkages that reduce nuclease activity on the target RNA.

In some embodiments, the single guide RNA or esgRNA can recognize the target RNA, for example, by hybridizing to the target RNA. In some embodiments, the single guide RNA or esgRNA comprises a sequence that is complementary to the target RNA. In some embodiments, the single guide RNA or esgRNA has a length that is, is about, is less than, or is more than, 10 nt, 20 nt, 30 nt, 40 nt, 50 nt, 60 nt, 70 nt, 80 nt, 90 nt, 100 nt, 110 nt, 120 nt, 130 nt, 140 nt, 150 nt, 160 nt, 170 nt, 180 nt, 190 nt, 200 nt, 300 nt, 400 nt, 500 nt, 1,000 nt, 2,000 nt, or a range between any two of the above values. In some embodiments, the single guide RNA or esgRNA can comprise one or more modified nucleotides.

In additional embodiments, a variety of RNA targets can be recognized by the single guide RNA or esgRNA. For example, a target RNA can be messenger RNA (mRNA), ribosomal RNA (rRNA), signal recognition particle RNA (SRP RNA), transfer RNA (tRNA), small nuclear RNA (snRNA), small nucleolar RNA (snoRNA), antisense RNA (aRNA), long noncoding RNA (lncRNA), microRNA (miRNA), piwi-interacting RNA (piRNA), small interfering RNA (siRNA), short hairpin RNA (shRNA), retrotransposon RNA, viral genome RNA, viral noncoding RNA, or the like. In some embodiments, a target RNA can be an RNA involved in pathogenesis or a therapeutic target for conditions such as cancers, neurodegeneration, cutaneous conditions, endocrine conditions, intestinal diseases, infectious conditions, neurological disorders, liver diseases, heart disorders, autoimmune diseases, or the like.

In further embodiments, exemplary G to A mutation target RNA and corresponding diseases, conditions and/or syndromes to be treated are, without limitation:

SDHB (Succinate Dehydrogenase Complex Iron Sulfure Subunit B) for treating Paraganglioma, gastric stromal sarcoma, Paragangliomas 4, Pheochromocytoma, Paragangliomas 1, and/or Hereditary cancer-predisposing syndrome;

DPYD (Dihydropyrimidine Dehydrogenase) for treating Dihydropyrimidine dehydrogenase deficiency, Hirschsprung disease 1, Fluorouracil response, Pyrimidine analogues response—Toxicity/ADR, capecitabine response—Toxicity/ADR, fluorouracil response—Toxicity/ADR, and/or tegafur response—Toxicity/ADR;

MSH2 (mutS Homolog 2) for treating Lynch syndrome, tumor predisposition syndrome, and/or Turcot syndrome;

MSH6 (mutS Homolog 6) for treating Lynch syndrome;

DYSF (Dysferlin) for treating Miyoshi muscular dystrophy 1, and/or Limb-girdle muscular dystrophy-type 2B;

SCN1A (Sodium Voltage-Gated Channel Alpha Subunit 1) for treating Severe myoclonic epilepsy in infancy;

TTN (Titin)/TTN-AS1 for treating Primary dilated cardiomyopathy;

VHL (von Hippel-Lindau Tumor Suppressor) for treating Von Hippel-Lindau syndrome; and/or Hereditary cancer-predisposing syndrome;

MLH1 (mutL homolog 1) for treating Lynch syndrome, Hereditary cancer-predisposing syndrome, and/or tumor predisposition syndrome;

PDE6B (Phosphodiesterase 6B) for treating Retinitis pigmentosa and/or Retinitis pigmentosa 40;

CC2D2A (Coiled-coil and C2 Domain Containing 2A) for treating Familial aplasia of the vermis and/or Joubert syndrome 9;

FRAS1 (Fraser extracellular matrix complex subunit 1) for treating Cryptophthalmos syndrome;

DSP (Desmoplakin) for treating Arrhythmogenic right ventricular cardiomyopathy—type 8 and/or Cardiomyopathy;

PMS2 (PMS1 homolog 2, mismatch repair system component) for treating Lynch syndrome and/or tumor predisposition syndrome;

ASL (Argininosuccinate lyase) for treating Argininosuccinic aciduria;

ELN (Elastin) for treating Supravalvar aortic stenosis;

SLC26A4 (Solute Carrier Family 26 Member 4) for treating Enlarged vestibular aqueduct syndrome and/or Pendred's syndrome;

CFTR (Cystic Fibrosis Transmembrane Conductance Regulator) for treating Cystic Fibrosis;

CNGB3 (Cyclic Nucleotide Gated Channel Beta 3) for treating Achromatopsia 3;

FANCC (Fanconi Anemia Complementation Group C)—C9orf3 for treating Fanconi anemia and/or Hereditary cancer-predisposing syndrome;

PTEN (Phosphatase and Tensin homolog) for treating Hereditary cancer-predisposing syndrome, Bannayan-Riley-Ruvalcaba syndrome, Cowden syndrome, Breast cancer, Autism spectrum disorder, Head and neck squamous cell carcinoma, lung cancer, and/or prostate cancer;

ANO5 (Anoctamin 5) for treating Limb-girdle muscular dystrophy—type 2L, Gnathodiaphyseal dysplasmia, Miyoshi myopathy, and/or Miyoshi muscular dystrophy 3;

MYBPC3 (Myosin Binding Protein C, Cardiac) for treating Primary familial hypertrophic cardiomyopathy;

MEN1 (Menin 1) for treating Familial isolated hyperparathyroidism, multiple endocrine neoplasia, primary macronodular adrenal hyperplasia, and/or tumors;

ATM (ATM serine/threonine kinase) and/or ATM-C11orf65 for treating Ataxia-telangiectasia syndrome, and/or Hereditary cancer-predisposing syndrome;

PKP2 (Plakophilin 2) for treating Arrhythmogenic right ventricular cardiomyopathy—type 9 and/or Arrhythmogenic right ventricular cardiomyopathy;

PAH (Phenylalanine Hydroxylase) for treating Phenylketonuria;

GJB2 (Gap Junction Protein Beta 2) for treating Deafness, autosomal recessive 1A, Non-syndromic genetic deafness and/or Hearing impairment;

B3GLCT (beta 3-glucosyltransferase) for treating Peters plus syndrome;

BRCA2 (BRCA2, DNA repair associated) for treating Familial cancer of breast, Breast-ovarian cancer—familial 2, Hereditary cancer-predisposing syndrome, Fanconi anemia, complementation group D1, Hereditary breast and ovarian cancer syndrome, Hereditary cancer-predisposing syndrome, Breast-ovarian cancer—familial 1, and/or Hereditary breast and ovarian cancer syndrome;

MYH7 (Myosin Heavy Chain 7) for treating Primary dilated cardiomyopathy, Cardiomyopathy, and/or Cardiomyopathy—left ventricular noncompaction;

FBN1 (Fibrillin 1) for treating Marfan syndrome;

HEXA (Hexosaminidase Subunit Alpha) for treating Tay-Sachs disease;

TSC2 (TSC Complex Subunit 2) for treating Tuberous sclerosis 2, and/or Tuberous sclerosis syndrome;

CREBBP (CREB binding protein) for treating Rubinstein-Taybi syndrome;

CDH1 (Cadherin 1) for treating Hereditary diffuse gastric cancer, Tumor predisposition syndrome, and/or Hereditary cancer-predisposing syndrome;

SPG7 (SPG7, paraplegin matrix AAA peptidase subunit) for treating Spastic paraplegia 7;

BRCA1 (BRCA1, DNA repair associated) for treating Breast-ovarian cancer—familial 1, Hereditary breast and ovarian cancer syndrome, and/or Hereditary cancer-predisposing syndrome;

BRIP1 (BRCA1 Interacting Protein C-Terminal Helicase 1) for treating Familial cancer of breast and/or Tumor predisposition syndrome;

LDLR (Low Density Lipoprotein Receptor) and/or LDLR—MIR6886 for treating Familial hypercholesterolemia and/or Hypercholesterolaemia;

BCKDHA (Branced Chain Keto acid dehydrogenase E1, alpha polypeptide) for treating Maple syrup urine disease;

CHEK2 (Checkpoint Kinase 2) for treating Familial cancer of breast, Breast and colorectal cancer—susceptibility to, and/or Hereditary cancer-predisposing syndrome;

DMD (Dystrophin) for treating Becker muscular dystrophy, Duchenne muscular dystrophy, and/or Dilated cardiomyopathy 3B; and/or IDUA (Iduronidase, alpha-L) for treating Hurler syndrome, Dysostosis multiplex, Mucopolysaccharidosis, MPS-I-H/S, and/or Mucopolysaccharidosis type I.

In some embodiments, the esgRNA comprises a short extension sequence of homology to the target RNA which is about 10-100 nucleotides in length, or about 10, 15-60, 20-50, or 25-40, or any range therebetween nucleotides in length. In some embodiments, the short extension sequence of the esgRNA, without limitation, comprising about 1 mismatch or 2, 3, 4, or 5 mismatches.

In some embodiments, the single guide RNA or esgRNA includes, but is not limited to including, sequences which bind or hybridize to target RNA, such as spacer sequences comprising additional regions of homology (in addition to the short extension sequence of homology disclosed herein) to the target RNA such that RNA recognition is supported with specificity and provides uniquely flexible and accessible manipulation of the genome. See WO 2017/091630 incorporated by reference in its entirety herein.

Non-limiting exemplary spacer sequences and extension sequences designed for esgRNA targeting the CFTR mRNA (cystic fibrosis transmembrane conductance regulator, Ref Seq: NM_000492) and the IDUA mRNA (iduronidase, Ref Seq: NM_000203) are provided in the table below:

| Target | spacer sequence | ADAR extension sequence |
|---|---|---|
| CFTR | gttcatagggatccaagtttt (SEQ ID NO: 43) | tttcctccactgttgcaaag (SEQ ID NO: 44) |
| IDUA | ccagcgcccaccgcccccag (SEQ ID NO: 45) | acttcggcccagagctgctcc (SEQ ID NO: 46) |

In one embodiment, the system disclosed herein comprises nucleic acid sequences which are minimalized to a nucleotide length which fits in a single vector. In some embodiments, the vector is an AAV vector. AAV vectors are capable of packaging transgenes which are about 4.5 kbs in size. In some instances, AAV vectors are capable of packaging larger transgenes such as about 4.6 kb, 4.7 kb, 4.8 kb, 4.9 kb, 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb, 7.5 kb, 8.0 kb, 9.0 kb, 10.0 kb, 11.0 kb, 12.0 kb, 13.0 kb, 14.0 kb, 15.0 kb, or larger are used.

In another embodiment, the system disclosed herein comprises, without limitation, one or more promoter sequences for driving expression of the system components. Exemplary promoters for expressing small RNAs, without limitation, are polymerase III promoters such as U6 and H1. Other promoters for driving expression of system components are, without limitation, EF1alpha (or its short, intronless form, EFS), CAG (CMV enhancer, chicken beta-Actin promoter and rabbit beta-Globin splice acceptor site fusion), mini CMV (cytomegalovirus), CMV, MCK (muscle creatin kinase), MCK/SV40, desmin, and/or c512 (Glutamate carboxypeptidase II).

In one embodiment, the recombinant expression system is encoded in DNA carried by a vector, e.g., adeno-associated virus (AAV), and can be delivered to appropriate tissues via one of the following methods: use of specific AAV serotypes that display specific tissue tropism (such as AAV-9 targeting neurons or muscle); injection of naked DNA encoding the RdCas9 system into tissue such as muscle or liver; use of nanoparticles composed of lipids, polymers, or other synthetic or natural materials that carry DNA or RNA encoding the therapeutic recombinant expression system; or any of the above where the system is split between two separate viruses or DNA molecules so that: one virus encodes the dCas9 protein-ADAR fusion and the other virus encodes the sgRNA; or one virus encodes the dCas9 protein and/or the sgRNA while the other virus encodes the ADAR protein and/or the sgRNA. In embodiments in which the portions of CREDIT are encoded on separate vectors, the encoded portions of dCas9 and ADAR can interact with one another so as to form a functional dCas9—ADAR nucleoprotein complex. Exemplary split systems can be seen in Wright et al., Rational design of a split-Cas9 enzyme complex. PNAS 112:2984-2989 (2015), the content of which is hereby incorporated by reference in its entirety).

To use exemplary recombinant expression systems as provided herein in treatment of a human subject or animal, the vector, e.g., the AAV, system can, for example, be injected by the following methods: (1) Skeletal muscle tissue (intramuscular) at multiple sites simultaneously (relevant indication: myotonic dystrophy)—injection of $10^{11}$-$10^{14}$ GC (genome copies) per injection into major muscle group such as the abdominal muscles, biceps, deltoids, erector spinae, gastrocnemius, soleus, gluteus, hamstrings, latissimus dorsi, rhomboids, obliques, pectoralis, quadriceps, trapezius and/or triceps; (2) Intravenous delivery of a targeted AAV serotype such as AAV-9 or AAV-6 for muscle targeting—injection of $10^{11}$-$10^{14}$ GC per injection for a total of $10^{12}$-$10^{17}$ GC delivered; 3. Subpial spinal injection of AAV-6, AAV-9 or another serotype displaying neuronal tropism—injection of $10^{11}$-$10^{14}$ GC in a single or multiple doses; 4. Intracranial injection of AAV-6, AAV-9 or another serotype displaying neuronal tropism—injection of $10^{11}$-$10^{17}$ GC in a single or multiple doses.

In other embodiments, recombinant expression systems disclosed herein may be formulated by methods known in the art. In addition, any route of administration may be envisioned such as, e.g., by any conventional route of administration including, but not limited to oral, pulmonary, intraperitoneal (ip), intravenous (iv), intramuscular (im), subcutaneous (sc), transdermal, buccal, nasal, sublingual, ocular, rectal and vaginal. In addition, administration directly to the nervous system may include, and are not limited to, intracerebral, intraventricular, intracerebroventricular, intrathecal, intracistemal, intraspinal or peri-spinal routes of administration by delivery via intracranial or intravertebral needles or catheters with or without pump devices. Any dose or frequency of administration that provides the therapeutic effect described herein is suitable for use in the present treatment. In a particular embodiment, the subject is administered a viral vector encoding the recombinant expression system according to the disclosure by the intramuscular route. In one embodiment, the vector is an AAV vector as defined above, is an AAV9 vector. In some embodiments, the human subject may receive a single injection of the vector. Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. In addition, the pharmaceutical composition may comprise nanoparticles that contain the recombinant expression system of the present disclosure.

Also provided by this invention is a composition comprising, consisting of, or consisting essentially of one or more of a recombinant expression system, vector, cell, or viral particle as described herein and a carrier. In some embodiments, the carrier is a pharmaceutically acceptable carrier.

In some embodiments, the recombinant expression systems as disclosed herein can optionally include the additional administration of a PAMmer oligonucleotide, i.e., co-administration with the disclosed systems simultaneously or sequentially of a corresponding PAMmer. Selection techniques for PAMmer oligonucleotide sequences are well known in the art and can be found for example, in WO 2015/089277, incorporated herein by reference in its entirety. Although a PAMmer may in some instances increase binding affinity of dCas9 to RNA in vivo as well as in vitro, Applicants' prior work WO 2017/091630, incorporated herein by reference in its entirety, surprisingly found that a PAMmer is not required to achieve RNA recognition and editing. To simplify Applicants' delivery strategy herein and to maintain the disclosed systems herein as fully encodeable systems, the experiments below were performed in the absence of a PAMmer. A schematic of this mechanism is outlined in FIG. 1A.

Disclosed herein are methods of using recombinant expression systems as disclosed herein as a research tool, e.g. to characterize the effects of directed cellular RNA editing on processing and dynamics.

Additionally disclosed herein are methods of using recombinant expression systems as disclosed herein as a therapeutic for diseases, e.g. by using viral (AAV) or other vector-based delivery approaches to deliver the recombinant expression systems for in vivo or ex vivo RNA editing to treat a disease in need of such editing.

Non-limiting examples of targets and related diseases include, but are not limited to, premature termination codon RNA diseases such as Hurler's syndrome, Cystic fibrosis, Duchenne muscular dystrophy, others, as well as diseases associated with deficiencies in RNA editing such as excitotoxic neuronal disorders affiliated with under-editing of the Q/R residue of AMPA subunit GluA2. Excitotoxicity may be involved in spinal cord injury, stroke, traumatic brain injury, hearing loss (through noise overexposure or ototoxicity), and in neurodegenerative diseases of the central nervous system (CNS) such as multiple sclerosis, Alzheimer's disease, amyotrophic lateral sclerosis (ALS), Parkinson's disease, alcoholism or alcohol withdrawal and especially over-rapid benzodiazepine withdrawal, and also Huntington's disease.

EXAMPLES

The following examples are non-limiting and illustrative of procedures which can be used in various instances in carrying the disclosure into effect. Additionally, all reference disclosed herein below are incorporated by reference in their entirety.

Described below are prototypes of the recombinant expression system generated by Applicant that 1) recognize and edit a reporter mRNA construct in living cells at a base specific level and 2) reverse premature termination codon (PTC) mediated silencing of expression from eGFP reporter transcripts in living cells (see FIGS. 1C and 1D).

Example 1

Directed Editing of Cellular RNA Via Nuclear Delivery of CRISPR/Cas9 Plasmid Construction The sequence encoding dCas9-2×NLS was cloned from pCDNA3.1-dCas9-2×NLS-EGFP (Addgene plasmid #74710). For the ADAR2-XTEN-dCas9 fusion product, the dCas9 sequence fused to an XTEN peptide linker and an ADAR2 catalytic domain (PCR amplified from human ADAR2 ORF) into a pCDNA3.1 (Invitrogen) backbone using Gibson assembly. The dCas9 moiety was removed by inverse PCR using primers flanking the dCas9-NLS sequence to generate the ADAR2-XTEN fusion. PCR-mediated site-directed mutagenesis was performed to generate the ADAR2-XTEN-dCas9 E488Q and ADAR2-XTEN E488Q mutant variants, using the ADAR2-XTEN-dCas9 and ADAR2-XTEN respectively as templates. All fusion sequences were cloned into pCDNA5/FRT/TO (Invitrogen) through PCR amplification and restriction digestion using FastDigest HindIII and NotI (Thermo Fisher).

To construct the esgRNA backbone, sequences for mammalian EF1a promoter, mCherry ORF, and BGH poly(A) signal were Gibson assembled into pBlueScript II SK (+) (Agilent) backbone bearing a modified sgRNA scaffold (Chen et al. 2013) driven by a U6 polymerase III promoter. Individual sgRNAs bearing a 3' extension sequences were generated by PCR amplifying the modified sgRNA scaffold using tailed primers bearing the spacer and extension sequences and Gibson assembling into the pBlueScript II SK(+)-mCherry vector downstream of the U6 promoter.

Cell lines and Transfections

Flp-In T-REX 293 were cultured in Dulbecco's modified eagle medium (DMEM) supplemented with 10% fetal bovine serum (Gibco). Cells were passaged every 3-4 days using TrypLE Express (Gibco) and maintained in a tissue culture incubator at 37° C. with 5% $CO_2$.

Stable, doxycycline-inducible lines were generated by seeding cells on 10 cm tissue culture dished and co-transfecting at 60-70% confluency with 1 ug pCDNA5/FRT/TO bearing the ADAR2 fusion constructs along with 9 ug pOG44 (Invitrogen), which encodes the Flp recombinase using polyethylenimine (PEI). Cells were subsequently passaged to 25% confluency and selected with 5 ug/ml blasticidin and 100 ug/ml hygromycin B (Gibco) after 48 hours. Cells remained under selection until individual hygromycin-resistant colonies identified, and 8-10 colonies were picked for expansion and validation.

Prior to transfection, $0.1\times10^6$ cells were seeded onto a 24-well plate 24 hours prior to the day of transfection and pre-incubated with doxycycline at a final concentration of 1 ug/ml for 24 hours. Cells were then co-transfected with 150 ug of respective sgRNA-mCherry constructs with 350 ug of W58X mutant or WT eGFP reporter construct (generous gifts from Stafforst lab) using Lipofectamine 3000 (Invitrogen). Cells were kept under doxycycline induction for 48 hours following transfection before imaging and FACS analysis. Images were captured using a Zeiss fluorescence microscope at 20× magnification.

Flow Cytometry Analysis

Cells were dissociated with TrypLE Express using standard protocol. Cells were then resuspended in 1× DPBS (Corning) supplemented with 5% FBS, passed through a 35 μm nylon cell strainer, and subjected to flow cytometry analysis using an LSRFortessa or Accuri instrument (BD). Cells were appropriately gated and analyzed for GFP (FITC) fluorescence. To normalize for transfection efficiency, individual values of percent eGFP corrected for each fusion-esgRNA pair was calculated by taking the fraction of GFP-positive cells from the W58X eGFP transfection population and dividing by the fraction of GFP-positive cells when instead transfected with the WT eGFP reporter. FACS analysis was analyzed using FlowJo software and compiled results were plotted using Graphpad Prism 6.

Discussion

In these experiments, and without limitation, the recombinant expression system described above comprises A) nucleic acid sequences encoding a nuclease-dead Cas9 (dCas9) protein fused to the catalytic deaminase domain of the human ADAR2 protein, and B) an extended single guide RNA (esgRNA) sequence driven by a U6 polymerase III promoter. The systems were delivered to the nuclei of mammalian cells with the appropriate transfection reagents and the sequences bind and edit target mRNA after forming an RCas9-RNA recognition complex. This allows for selective RNA editing in which targeted adenosine residues are deaminated to inosine to be recognized as guanosine by the cellular machinery.

The catalytically active deaminase domains (DD) described in the above systems were either wildtype human ADAR2 or human ADAR2 DD bearing a mutation (E488Q) that increases enzymatic activity and affinity for RNA substrate as compared to wildtype human ADAR2. The DD was fused to a semi-flexible XTEN peptide linker at its C-terminus, which was then fused to dCas9 at its N-terminus (FIG. 1B). To control for RNA-recognition independent background editing, fusion constructs lacking the dCas9 moiety were also generated (AX, AX-488Q).

The esgRNA construct was modified with a region of homology capable of near-perfect RNA-RNA base pairing with over the desired site of editing. The homology region comprises a mismatch of the targeted adenosine, forcing an A-C mispairing and the generation of a 'pseudo-dsRNA' substrate on the target transcript (FIG. 1A). This generates a means of programmable RNA substrate recognition as well as simultaneous base-specific deamination. Furthermore, these modified esgRNA constructs were cloned into a vector additionally comprising a marker gene, e.g., mCherry construct driven by a separate EF1a pol II promoter, as shown in the examples. This provided for the sorting of cells transfected with the esgRNA using flow-cytometry, and furthermore enrichment of cells with targeted RNA editing.

Example 2

Comparison of dSpCas9 and dSaCas9 CREDIT Systems dSaCas9 is significantly smaller than dSpCas9, which provides efficiency in viral packaging. A CREDIT system was prepared comprising (1) an ADAR2(E488Q)-dSaCas9 fusion with a GSGS linker (SEQ ID NO: 12) and (2) an esgRNA with a scaffold sequence specific to SaCas9 that targets an EGFP reporter (SEQ ID NO: 11). The efficiency of mRNA editing by this system was compared to a system comprising ADAR2(E488Q)-dSpCas9, as shown in FIG. 13B. ADAR2-dSaCas9 resulted in about 30% of target cells expressing successfully edited EGFP RNA, as compared to about 20% by ADAR2-dSpCas9. Overall, this data shows successful editing by both ADAR2-dSaCas9 and ADAR2-dSpCas9.

Example 3

Treatment of Limb-Girdle Muscular Dystrophy—Type 2B

Limb-girdle muscular dystrophy-type 2B is caused by a defect in the Dysferlin gene. By developing methods to accurately correct Dysferlin mRNA in a subject, a fully functional dysferlin protein can be expressed in patients with this disorder.

The recombinant expression systems of the present disclosure allow for simple correction of the mutant dysferlin mRNA. When combined with the disclosed AAV delivery system, these systems can be used to efficiently target every major muscle with a single intravenous administration, and provide a robust therapeutic strategy to treat muscular dystrophy. Because the AAV will ultimately be used to target skeletal muscle, an AAV with skeletal muscle tropism should be used such as AAV1, AAV6, AAV7, AAV8, or AAV9.

Viral particles are prepared as described herein. Briefly, Flp-In T-REX 293 cells are transfected vectors as described in Example 1. An esgRNA is designed to target the mutant locus within the subject's dysferlin mRNA. The esgRNA can be designed to target a mutation in one or more of the following dysferlin mRNAs: NM_001130455, NM_001130976, NM_001130977, NM_001130978, NM_001130979, NM_001130980, NM_001130981, NM_001130982, NM_001130983, NM_001130984, NM_001130985, NM_001130986, NM_001130987, or NM_003494). In some embodiments, the subject's dysferlin mRNA is sequenced prior to design of the esgRNA to confirm the presence of a correctable A point mutation. A nucleic acid encoding the esgRNA is cloned into a suitable vector. Following transfection of the packaging cells, assembled viral particles are harvested and tested for Cas9 protein expression, as well as expression of esgRNA. The packaged virus is also assayed for viral titer which should range from about 10^8 GC/mL to 10^17 GC/mL, with titer optimally of about 10^13 GC/mL. Viral titer can be assayed by western blot or by viral genome copy number by qPCR and compared to copy number standard samples.

Modified viral particles can be administered ex vivo or in vitro to muscle stem or progenitor cells from subjects with Limb-girdle muscular dystrophy—type 2B. Upon integration of the viral vectors, the modified cells are transplanted back into subject via intramuscular injection. Effectiveness of cell therapy with the cells treated with modified AAV is measured by improved muscle morphology, decreases in sarcolemmal localization of the multimeric dystrophin-glycoprotein complex and neuronal nitric-oxide synthase, as well as detection of dysferlin expression.

Alternatively, the viral particles can be administered in vivo to muscle tissue through, for example, localized or systemic delivery such as intramuscular injection, intraperitoneal injection, or intravenous injection. Effectiveness of viral gene therapy is measured by improved muscle morphology as well as detection of dysferlin expression.

Efficiency of CRISPR—mediated RNA editing is assayed by designing PCR primers that detect a reverse transcribed copy of the repaired dysferlin mRNA fragment. Expression of repaired gene product can also be detected by PCR, histological staining, or western blot of treated muscle tissue.

Example 4

Editing of CFTR mRNA

Cystic fibrosis is a genetic disorder that affects the lungs, pancreas, liver, kidneys, and intestine. Long-term symptoms include difficulty breathing and coughing up mucus as a result of frequent lung infections. Other signs and symptoms may include sinus infections, poor growth, fatty stool, clubbing of the fingers and toes, and infertility. Cystic fibrosis is caused by mutations in the cystic fibrosis transmembrane conductance regulator (CFTR) gene. By developing methods to accurately correct CFTR mRNA in a subject, a fully functional CFTR protein can be expressed in these patients.

The recombinant expression systems of the present disclosure allow for simple correction of CFTR mRNA. When combined with the a viral delivery system such as AAV or lentivirus, these systems can be used to efficiently target affected tissues and provide a robust therapeutic strategy to treat Cystic Fibrosis. AAV with lung tropism include but are not limited to AAV4, AAV5, AAV6, and AAV9.

An esgRNA is designed to target the mutant locus within the subject's CTFR mRNA. In some embodiments, the subject's CFTR mRNA is sequenced prior to design of the esgRNA to confirm the presence of a correctable A point mutation. A nucleic acid encoding the esgRNA is cloned into a suitable vector. A non-limiting example of a suitable CFTR targeting spacer sequence is SEQ ID NO: 43. A non-limiting example of a suitable CFTR extension sequence is SEQ ID NO: 44. A non-limiting example of a lentiviral plasmid comprising an esgRNA targeted to CFTR is LCV2_purpo_CFTR_51_1217_gibson (SEQ ID NO: 35).

Following transfection of the packaging cells, assembled viral particles are harvested and tested for Cas9 protein expression, as well as expression of esgRNA. The packaged virus is also assayed for viral titer which should range from about 10^8 GC/mL to 10^17 GC/mL, with titer optimally of about 10^13 GC/mL. Viral titer can be assayed by western blot or by viral genome copy number by qPCR and compared to copy number standard samples.

Viral particles can be administered in vivo to the subject through, for example, localized or systemic delivery such as intraperitoneal injection, organ-targeted injection, or intravenous injection. Effectiveness of viral gene therapy is measured by improved lung function, a reduction or amelioration of one or more symptoms of Cystic Fibrosis, and/or detection of corrected CFTR protein expression.

Efficiency of CRISPR—mediated RNA editing is assayed by designing PCR primers that detect a reverse transcribed copy of the repaired CFTR mRNA fragment. Expression of repaired gene product can also be detected by PCR, histological staining, or western blot of treated lung tissue.

Example 5

Editing of IDUA mRNA

Hurler syndrome is a genetic disorder that results in the buildup of glycosaminoglycans due to a deficiency of alpha-L iduronidase (IDUA), an enzyme responsible for the degradation of mucopolysaccharides in lysosomes. Without this enzyme, a buildup of dermatan sulfate and heparan sulphate occurs in the body. Symptoms include but are not limited to hepatosplenomegaly, dwarfism, unique facial features, progressive mental retardation, and early death due to organ damage.

The recombinant expression systems of the present disclosure allow for simple correction of IDUA mRNA. When combined with the a viral delivery system such as AAV or lentivirus, these systems can be used to provide a robust therapeutic strategy to treat Hurler syndrome.

An esgRNA is designed to target the mutant locus within the subject's IDUA mRNA. In some embodiments, the subject's IDUA mRNA is sequenced prior to design of the esgRNA to confirm the presence of a correctable A point mutation. A nucleic acid encoding the esgRNA is cloned into a suitable vector. A non-limiting example of a suitable IDUA targeting spacer sequence is SEQ ID NO: 45. A non-limiting example of a suitable IDUA extension sequence is SEQ ID NO: 46. A non-limiting example of a lentiviral plasmid comprising an esgRNA targeted to IDUA is AXCM_LCV2_puro_IDUA_No-spacer_gibson (SEQ ID NO: 39).

Following transfection of the packaging cells, assembled viral particles are harvested and tested for Cas9 protein expression, as well as expression of esgRNA. The packaged virus is also assayed for viral titer which should range from about 10^8 GC/mL to 10^17 GC/mL, with titer optimally of about 10^13 GC/mL. Viral titer can be assayed by western blot or by viral genome copy number by qPCR and compared to copy number standard samples.

Viral particles can be administered in vivo to the subject through, for example, systemic delivery such as intravenous injection. Effectiveness of viral gene therapy is measured by decrease in the amount of heparin sulphate in the subject, a reduction or amelioration of one or more symptoms of Hurler syndrome, and/or detection of corrected IDUA protein expression.

Efficiency of CRISPR—mediated RNA editing is assayed by designing PCR primers that detect a reverse transcribed copy of the repaired IDUA mRNA fragment. Expression of repaired gene product can also be detected by PCR, histological staining, or western blot of treated tissues.

EQUIVALENTS

It should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be with the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

REFERENCES

1. Fukuda, M., et al., Construction of a guide-RNA for site-directed RNA mutagenesis utilising intracellular A-to-I RNA editing. Sci Rep, 2017. 7: p. 41478.
2. Halo et al "NanoFlares for the detection, isolation, and culture of live tumor cells from human blood" PNAS doi: 10.1073/pnas.1418637111.
3. Hanswillemenke et al., Site-Directed RNA Editing in Vivo Can Be Triggered by the Light-Driven Assembly of an Artificial Riboprotein. J Am Chem Soc, 2015. 137(50): p. 15875-81.
4. Hua et al "Peripheral SMN restoration is essential for long-term rescue of a severe spinal muscular atrophy mouse model." Nature. 2011 Oct. 5; 478(7367):123-6. doi: 10.1038/nature10485.
5. McMahon et al., TRIBE: Hijacking an RNA-Editing Enzyme to Identify Cell-Specific Targets of RNA-Binding Proteins. Cell, 2016. 165(3): p. 742-53.
6. Montiel-Gonzalez et al "An efficient system for selectively altering genetic information within mRNAs." Nucleic Acids Res. 2016 44: e157. doi: 10.1093/nar/gkw738.
7. Montiel-Gonzalez et al "Correction of mutations within the cystic fibrosis transmembrane conductance regulator by site-directed RNA editing." PNAS. 2013 110: 18285-90.
8. Schneider et al "Optimal guideRNAs for re-directing deaminase activity of hADAR1 and hADAR2 in trans." Nucleic Acids Res. 2014 42: e87. doi: 10.1093/nar/gku272.
9. Wang et al "Engineering splicing factors with designed specificities" Nat Methods. 2009 November; 6(11): 825-830. 10.1038/nmeth.1379
10. WO 2015089277
11. WO 2016183402

SEQUENCES

Provided below are exemplary sequences of the constructs described herein.

```
pcDNA3.1(1)_ADAR2_XTEN_dCas9 (SEQ ID NO: 27)

LOCUS                  Exported 10826 bp ds-DNA circular

DEFINITION             synthetic circular DNA

SOURCE                 synthetic DNA construct

ORGANISM               recombinant plasmid

REFERENCE              1 (bases 1 to 10826)

FEATURES               Location/Qualifiers

source                 1 . . .  10826
                       /organism = "recombinant plasmid"
                       /mol_type = "other DNA"

enhancer               235 . . . 614
                       /label = CMV enhancer
                       /note = "human cytomegalovirus immediate early enhancer"

promoter               615 . . . 818
                       /label = CMV promoter
                       /note = "human cytomegalovirus (CMV) immediate early
                       promoter"

promoter               863 . . . 881
                       /label = T7 promoter
                       /note = "promoter for bacteriophage T7 RNA polymerase"

misc_feature           927 . . . 954
                       /label = Homology 1_pCDNA3.1

primer_bind            955 . . . 976
                       /label = ADAR2CD-Cas9_HindIII_F

misc_feature           955 . . . 960
                       /label = Kozak

primer_bind            960 . . . 983
                       /label = Adar_out_forward_1v2

CDS                    961 . . . 2100
                       /codon_start = 1
                       /label = ADARB 1_Catalytic Domain

/translation = "MLADAVSRLVLGKFGDLTDNFSSPHARRKVLAGVVMTTGTDVKDA
KVISVSTGTKCINGEYMSDRGLALNDCHAEIISRRSLLRFLYTQLELYLNNKDDQKRSI
FQKSERGGFRLKENVQFHLYISTSPCGDARIFSPHEPILEEPADRHPNRKARGQLRTKI
ESGEGTIPVRSNASIQTWDGVLQGERLLTMSCSDKIARWNVVGIQGSLLSIFVEPIYFS
SIILGSLYHGDHLSRAMYQRISNIEDLPPLYTLNKPLLSGISNAEARQPGKAPNFSVNW
TVGDSAIEVINATTGKDELGRASRLCKHALYCRWMRVHGKVPSHLLRSKITKPNVYHES
KLAAKEYQAAKARLFTAFIKAGLGAWVEKPTEQDQFSLTP"

primer_bind            1324 . . . 1346
                       /label = E488Q_ADAR2_Mut_seq

primer_bind            complement(1426 . . . 1447)
                       /label = E488Q_Mut_Classic_R

primer_bind            1448 . . . 1472
                       /label = E488Q_Mut_Classic_F

CDS                    2101 . . . 2148
                       /codon_start = 1
                       /label = XTEN
                       /translation = "SGSETPGTSESATPES"

primer_bind            complement(2129 . . . 2148)
                       /label = ADAR2_CD_Inverse_R

CDS                    2149 . . . 6252
                       /codon_start = 1
                       /product = "catalytically dead mutant of the Cas9
```

```
                    endonuclease from the Streptococcus pyogenes Type II
                    CRISPR/Cas system"
                    /label = dCas9
                    /note = "RNA-guided DNA-binding protein that lacks
                    endonuclease activity due to the D10A mutation in the RuvC
                    catalytic domain and the H840A mutation in the HNH
                    catalytic domain"

/translation = "MDKKYSIGLAIGTNSVGWAVITDEYKVPSKKFKVLGNTDRHSIKK
NLIGALLFDSGETAEATRLKRTARRRYTRRKNRICYLQEIFSNEMAKVDDSFFHRLEES
FLVEEDKKHERHPIFGNIVDEVAYHEKYPTIYHLRKKLVDSTDKADLRLIYLALAHMIK
FRGHFLIEGDLNPDNSDVDKLFIQLVQTYNQLFEENPINASGVDAKAILSARLSKSRRL
ENLIAQLPGEKKNGLFGNLIALSLGLTPNFKSNFDLAEDAKLQLSKDTYDDDLDNLLAQ
IGDQYADLFLAAKNLSDAILLSDILRVNTEITKAPLSASMIKRYDEHHQDLTLLKALVR
QQLPEKYKEIFFDQSKNGYAGYIDGGASQEEFYKFIKPILEKMDGTEELLVKLNREDLL
RKQRTFDNGSIPHQIHLGELHAILRRQEDFYPFLKDNREKIEKILTFRIPYYVGPLARG
NSRFAWMTRKSEETITPWNFEEVVDKGASAQSFIERMTNFDKNLPNEKVLPKHSLLYEY
FTVYNELTKVKYVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLTLFEDREMIEER
LKTYAHLFDDKVMKQLKRRRYTGWGRLSRKLINGIRDKQSGKTILDFLKSDGFANRNFM
QLIHDDSLTFKEDIQKAQVSGQGDSLHEHIANLAGSPAIKKGILQTVKVVDELVKVMGR
HKPENIVIEMARENQTTQKGQKNSRERMKRIEEGIKELGSQILKEHPVENTQLQNEKLY
LYYLQNGRDMYVDQELDINRLSDYDVDAIVPQSFLKDDSIDNKVLTRSDKNRGKSDNVP
SEEVVKKMKNYWRQLLNAKLITQRKFDNLTKAERGGLSELDKAGFIKRQLVETRQITKH
VAQILDSRMNTKYDENDKLIREVKVITLKSKLVSDFRKDFQFYKVREINNYHHAHDAYL
NAVVGTALIKKYPKLESEFVYGDYKVYDVRKMIAKSEQEIGKATAKYFFYSNIMNFFKT
EITLANGEIRKRPLIETNGETGEIVWDKGRDFATVRKVLSMPQVNIVKKTEVQTGGFSK
ESILPKRNSDKLIARKKDWDPKKYGGFDSPTVAYSVLVVAKVEKGKSKKLKSVKELLGI
TIMERSSFEKNPIDFLEAKGYKEVKKDLIIKLPKYSLEELENGRKRMLASAGELQKGNE
LALPSKYVNFLYLASHYEKLKGSPEDNEQKQLFVEQHKHYLDEIIEQISEFSKRVILAD
ANLDKVLSAYNKHRDKPIREQAENIIHLFTLTNLGAPAAFKYFDTTIDRKRYTSTKEVL
DATLIHQSITGLYETRIDLSQLGGD"

primer_bind         complement(6233 . . . 6252)
                    /label = Cas9_out_rev_1v2

primer_bind         6253 . . . 6274
                    /label = ADAR2_CD_Inverse_F

CDS                 6256-6282
                    /codon_start = 1
                    /product = "HA (human influenza hemagglutinin) epitope tag"
                    /label = HA
                    /translation = "YPYDVPDYA"

CDS                 6301 . . . 6321
                    /codon_start = 1
                    /product = "nuclear localization signal of SV40 large T
                    antigen"
                    /label = SV40 NLS
                    /translation = "PKKKRKV"

CDS                 6328-6348
                    /codon_start = 1
                    /product = "nuclear localization signal of SV40 large T
                    antigen"
                    /label = SV40 NLS
                    /translation = "PKKKRKV"

primer_bind         complement(6332 . . . 6357)
                    /label = ADAR2CD-Cas9_NotI_R

misc_feature        6358 . . . 6392
                    /label = Homology 2_pCDNA3.1

polyA_signal        6426 . . . 6650
                    /label = bGH poly(A) signal
                    /note = "bovine growth hormone polyadenylation signal"

rep_origin          6696 . . . 7124
                    /direction = RIGHT
                    /label = f1 ori
                    /note = "f1 bacteriophage origin of replication; arrow
                    indicates direction of (+) strand synthesis"

promoter            7138 . . . 7467
                    /label = SV40 promoter
                    /note = "SV40 enhancer and early promoter"
```

```
rep_origin            7318 . . . 7453
                      /label = SV40 ori
                      /note = "SV40 origin of replication"

CDS                   7534 . . . 8328
                      /codon_start = 1
                      /gene = "aph(3')-II (or nptII)"
                      /product = "aminoglycoside phosphotransferase from Tn5"
                      /label = NeoR/KanR
                      /note = "confers resistance to neomycin, kanamycin, and G418
                      (Geneticin(R))"

/translation = "MIEQDGLHAGSPAAWVERLFGYDWAQQTIGCSDAAVFRLSAQGRP
VLFVKTDLSGALNELQDEAARLSWLATTGVPCAAVLDVVTEAGRDWLLLGEVPGQDLLS
SHLAPAEKVSIMADAMRRLHTLDPATCPFDHQAKHRIERARTRMEAGLVDQDDLDEEHQ
GLAPAELFARLKARMPDGEDLVVTHGDACLPNIMVENGRFSGFIDCGRLGVADRYQDIA
LATRDIAEELGGEWADRFLVLYGIAAPDSQRIAFYRLLDEFF"

polyA_signal          8502 . . . 8623
                      /label = SV40 poly(A) signal
                      /note = "SV40 polyadenylation signal"

primer_bind           complement(8672 . . . 8688)
                      /label = M13 rev
                      /note = "common sequencing primer, one of multiple similar
                      variants"

protein_bind          8696 . . . 8712
                      /label = lac operator
                      /bound_moiety = "lac repressor encoded by lacI"
                      /note = "The lac repressor binds to the lac operator to
                      inhibit transcription in E. coli. This inhibition can be
                      relieved by adding lactose or
                      isopropyl-beta-D-thiogalactopyranoside (IPTG)."

promoter              complement(8720 . . . 8750)
                      /label = lac promoter
                      /note = "promoter for the E. coli lac operon"

protein_bind          8765 . . . 8786
                      /label = CAP binding site
                      /bound_moiety = "E. coli catabolite activator protein"
                      /note = "CAP binding activates transcription in the presence
                      of cAMP."

rep_origin            complement(9074 . . . 9659)
                      /direction = LEFT
                      /label = ori
                      /note = "high-copy-number ColE1/pMB1/pBR322/pUC origin of
                      replication"

CDS                   complement(9830 . . . 10690)
                      /codon_start = 1
                      /gene = "bla"
                      /product = "beta-lactamase"
                      /label = AmpR
                      /note = "confers resistance to ampicillin, carbenicillin, and
                      related antibiotics"

/translation = "MSIQHFRVALIPFFAAFCLPVFAHPETLVKVKDAEDQLGARVGYI
ELDLNSGKILESFRPEERFPMMSTFKVLLCGAVLSRIDAGQEQLGRRIHYSQNDLVEYS
PVTEKHLTDGMTVRELCSAAITMSDNTAANLLLTTIGGPKELTAFLHNMGDHVTRLDRW
EPELNEAIPNDERDTTMPVAMATTLRKLLTGELLTLASRQQLIDWMEADKVAGPLLRSA
LPAGWFIADKSGAGERGSRGIIAALGPDGKPSRIVVIYTTGSQATMDERNRQIAEIGAS
LIKHW"

promoter              complement(10691 . . . 10795)
                      /gene = "bla"
                      /label = AmpR promoter

ORIGIN
      1   gacggatcgg gagatctccc gatcccctat ggtgcactct cagtacaatc tgctctgatg

     61   ccgcatagtt aagccagtat ctgctccctg cttgtgtgtt ggaggtcgct gagtagtgcg

    121   cgagcaaaat ttaagctaca acaaggcaag gcttgaccga caattgcatg aagaatctgc

    181   ttagggttag gcgttttgcg ctgcttcgcg atgtacgggc cagatatacg cgttgacatt
```

-continued

```
241   gattattgac tagttattaa tagtaatcaa ttacggggtc attagttcat agcccatata
301   tggagttccg cgttacataa cttacggtaa atggcccgcc tggctgaccg cccaacgacc
361   cccgcccatt gacgtcaata atgacgtatg ttcccatagt aacgccaata gggactttcc
421   attgacgtca atgggtggag tatttacggt aaactgccca cttggcagta catcaagtgt
481   atcatatgcc aagtacgccc cctattgacg tcaatgacgg taaatggccc gcctggcatt
541   atgcccagta catgacctta tgggactttc ctacttggca gtacatctac gtattagtca
601   tcgctattac catggtgatg cggttttggc agtacatcaa tgggcgtgga tagcggtttg
661   actcacgggg atttccaagt ctccacccca ttgacgtcaa tgggagtttg ttttggcacc
721   aaaatcaacg ggactttcca aaatgtcgta acaactccgc cccattgacg caaatgggcg
781   gtaggcgtgt acggtgggag gtctatataa gcagagctct ctggctaact agagaaccca
841   ctgcttactg gcttatcgaa attaatacga ctcactatag ggagacccaa gctggctagc
901   gtttaaacgg gccctctaga ctcgagcggc cgccactgtg ctggatatct gcagagaacc
961   atgttagctg acgctgtctc acgcctggtc ctgggtaagt ttggtgacct gaccgacaac
1021  ttctcctccc ctcacgctcg cagaaaagtg ctggctggag tcgtcatgac aacaggcaca
1081  gatgttaaag atgccaaggt gataagtgtt tctacaggaa caaaatgtat taatggtgaa
1141  tacatgagtg atcgtggcct tgcattaaat gactgccatg cagaaataat atctcggaga
1201  tccttgctca gatttcttta tacacaactt gagctttact taaataacaa agatgatcaa
1261  aaaagatcca tctttcagaa atcagagcga gggggtttta ggctgaagga gaatgtccag
1321  tttcatctgt acatcagcac ctctccctgt ggagatgcca gaatcttctc accacatgag
1381  ccaatcctgg aagaaccagc agatagacac ccaaatcgta aagcaagagg acagctacgg
1441  accaaaatag agtctggtga ggggacgatt ccagtgcgct ccaatgcgag catccaaacg
1501  tgggacgggg tgctgcaagg ggagcggctg ctcaccatgt cctgcagtga caagattgca
1561  cgctggaacg tggtgggcat ccagggatcc ctgctcagca ttttcgtgga gcccatttac
1621  ttctcgagca tcatcctggg cagcctttac cacggggacc acctttccag ggccatgtac
1681  cagcggatct ccaacataga ggacctgcca cctctctaca ccctcaacaa gcctttgctc
1741  agtggcatca gcaatgcaga agcacggcag ccagggaagg cccccaactt cagtgtcaac
1801  tggacggtag gcgactccgc tattgaggtc atcaacgcca cgactgggaa ggatgagctg
1861  ggccgcgcgt cccgcctgtg taagcacgcg ttgtactgtc gctggatgcg tgtgcacggc
1921  aaggttccct cccacttact acgctccaag attaccaagc ccaacgtgta ccatgagtcc
1981  aagctggcgg caaaggagta ccaggccgcc aaggcgcgtc tgttcacagc cttcatcaag
2041  gcggggctgg gggcctgggt ggagaagccc accgagcagg accagttctc actcacgccc
2101  agtggaagtg agacaccggg aacctcagag agcgccacgc cagaaagcat ggacaagaag
2161  tacagcatcg gcctggccat cggcaccaac tctgtgggct gggccgtgat caccgacgag
2221  tacaaggtgc ccagcaagaa attcaaggtg ctgggcaaca ccgaccggca cagcatcaag
2281  aagaacctga tcggcgccct gctgttcgac agcggagaaa cagccgaggc cacccggctg
2341  aagagaaccg ccagaagaag atacaccaga cggaagaacc ggatctgcta tctgcaagag
2401  atcttcagca acgagatggc caaggtggac gacagcttct tccacagact ggaagagtcc
2461  ttcctggtgg aagaggataa gaagcacgag cggcacccca tcttcggcaa catcgtggac
2521  gaggtggcct accacgagaa gtaccccacc atctaccacc tgagaaagaa actggtggac
2581  agcaccgaca aggccgacct gcggctgatc tatctggccc tggcccacat gatcaagttc
```

```
2641  cggggccact tcctgatcga gggcgacctg aaccccgaca acagcgacgt ggacaagctg
2701  ttcatccagc tggtgcagac ctacaaccag ctgttcgagg aaaaccccat caacgccagc
2761  ggcgtggacg ccaaggccat cctgtctgcc agactgagca agagcagacg gctggaaaat
2821  ctgatcgccc agctgcccgg cgagaagaag aatggcctgt tcggcaacct gattgccctg
2881  agcctgggcc tgacccccaa cttcaagagc aacttcgacc tggccgagga tgccaaactg
2941  cagctgagca aggacaccta cgacgacgac ctggacaacc tgctggccca gatcggcgac
3001  cagtacgccg acctgtttct ggccgccaag aacctgtccg acgccatcct gctgagcgac
3061  atcctgagag tgaacaccga gatcaccaag gcccccctga gcgcctctat gatcaagaga
3121  tacgacgagc accaccagga cctgaccctg ctgaaagctc tcgtgcggca gcagctgcct
3181  gagaagtaca aagagatttt cttcgaccag agcaagaacg gctacgccgg ctacatcgat
3241  ggcggagcca gccaggaaga gttctacaag ttcatcaagc ccatcctgga aaagatggac
3301  ggcaccgagg aactgctcgt gaagctgaac agagaggacc tgctgcggaa gcagcggacc
3361  ttcgacaacg gcagcatccc ccaccagatc cacctgggag agctgcacgc cattctgcgg
3421  cggcaggaag atttttaccc attcctgaag gacaaccggg aaaagatcga gaagatcctg
3481  accttccgca tcccctacta cgtgggccct ctggccaggg gaaacagcag attcgcctgg
3541  atgaccagaa agagcgagga aaccatcacc ccctggaact tcgaggaagt ggtggacaag
3601  ggcgccagcg cccagagctt catcgagcgg atgaccaact tcgataagaa cctgcccaac
3661  gagaaggtgc tgcccaagca cagcctgctg tacgagtact tcaccgtgta caacgagctg
3721  accaaagtga aatacgtgac cgagggaatg agaaagcccg ccttcctgag cggcgagcag
3781  aaaaaagcca tcgtggacct gctgttcaag accaaccgga aagtgaccgt gaagcagctg
3841  aaagaggact acttcaagaa aatcgagtgc ttcgactccg tggaaatctc cggcgtggaa
3901  gatcggttca acgcctccct gggcacatac cacgatctgc tgaaaattat caaggacaag
3961  gacttcctgg acaatgagga aaacgaggac attctggaag atatcgtgct gaccctgaca
4021  ctgtttgagg acagagagat gatcgaggaa cggctgaaaa cctatgccca cctgttcgac
4081  gacaaagtga tgaagcagct gaagcggcgg agatacaccg gctggggcag gctgagccgg
4141  aagctgatca acggcatccg ggacaagcag tccggcaaga caatcctgga tttcctgaag
4201  tccgacggct tcgccaacag aaacttcatg cagctgatcc acgacgacag cctgaccttt
4261  aaagaggaca tccagaaagc ccaggtgtcc ggccagggcg atagcctgca cgagcacatt
4321  gccaatctgg ccggcagccc cgccattaag aagggcatcc tgcagacagt gaaggtggtg
4381  gacgagctcg tgaaagtgat gggccggcac aagcccgaga acatcgtgat cgaaatggcc
4441  agagagaacc agaccaccca gaagggacag aagaacagcc gcgagagaat gaagcggatc
4501  gaagagggca tcaaagagct gggcagccag atcctgaaag aacaccccgt ggaaaacacc
4561  cagctgcaga acgagaagct gtacctgtac tacctgcaga atgggcggga tatgtacgtg
4621  gaccaggaac tggacatcaa ccggctgtcc gactacgatg tggacgctat cgtgcctcag
4681  agctttctga aggacgactc catcgataac aaagtgctga ctcggagcga caagaaccgg
4741  ggcaagagcg acaacgtgcc ctccgaagag gtcgtgaaga agatgaagaa ctactggcgc
4801  cagctgctga atgccaagct gattacccag aggaagttcg acaatctgac caaggccgag
4861  agaggcggcc tgagcgaact ggataaggcc ggcttcatca agagacagct ggtggaaacc
4921  cggcagatca caaagcacgt ggcacagatc ctggactccc ggatgaacac taagtacgac
```

-continued

```
4981 gagaacgaca aactgatccg ggaagtgaaa gtgatcaccc tgaagtccaa gctggtgtcc
5041 gatttccgga aggatttcca gttttacaaa gtgcgcgaga tcaacaacta ccaccacgcc
5101 cacgacgcct acctgaacgc cgtcgtggga accgccctga tcaaaaagta ccctaagctg
5161 gaaagcgagt tcgtgtacgg cgactacaag gtgtacgacg tgcggaagat gatcgccaag
5221 agcgagcagg aaatcggcaa ggctaccgcc aagtacttct tctacagcaa catcatgaac
5281 tttttcaaga ccgagattac cctggccaac ggcgagatcc ggaagcggcc tctgatcgag
5341 acaaacggcg aaacaggcga gatcgtgtgg gataagggcc gggactttgc caccgtgcgg
5401 aaagtgctgt ctatgcccca agtgaatatc gtgaaaaaga ccgaggtgca gacaggcggc
5461 ttcagcaaag agtctatcct gcccaagagg aacagcgaca agctgatcgc cagaaagaag
5521 gactgggacc ctaagaagta cggcggcttc gacagcccca ccgtggccta ttctgtgctg
5581 gtggtggcca aagtggaaaa gggcaagtcc aagaaactga agagtgtgaa agagctgctg
5641 gggatcacca tcatggaaag aagcagcttc gagaagaatc ccatcgactt tctggaagcc
5701 aagggctaca aagaagtgaa aaaggacctg atcatcaagc tgcctaagta ctccctgttc
5761 gagctggaaa acggccggaa gagaatgctg gcctctgccg gcgaactgca gaagggaaac
5821 gaactggccc tgccctccaa atatgtgaac ttcctgtacc tggccagcca ctatgagaag
5881 ctgaagggct cccccgagga taatgagcag aaacagctgt ttgtggaaca gcacaaacac
5941 tacctggacg agatcatcga gcagatcagc gagttctcca agagagtgat cctggccgac
6001 gctaatctgg acaaggtgct gagcgcctac aacaagcaca gagacaagcc tatcagagag
6061 caggccgaga atatcatcca cctgtttacc ctgaccaatc tgggagcccc tgccgccttc
6121 aagtactttg acaccaccat cgaccggaag aggtacacca gcaccaaaga ggtgctggac
6181 gccaccctga tccaccagag catcaccggc ctgtacgaga cacggatcga cctgtctcag
6241 ctgggaggcg acgcctatcc ctatgacgtg cccgattatg ccagcctggg cagcggctcc
6301 cccaagaaaa aacgcaaggt ggaagatcct aagaaaaagc ggaaagtgga cgtgtaacca
6361 ccacactgga ctagtggatc cgagctcggt accaagctta agtttaaacc gctgatcagc
6421 ctcgactgtg ccttctagtt gccagccatc tgttgtttgc ccctcccccg tgccttcctt
6481 gaccctggaa ggtgccactc ccactgtcct ttcctaataa aatgaggaaa ttgcatcgca
6541 ttgtctgagt aggtgtcatt ctattctggg gggtggggtg gggcaggaca gcaaggggga
6601 ggattgggaa gacaatagca ggcatgctgg ggatgcggtg ggctctatgg cttctgaggc
6661 ggaaagaacc agctggggct ctagggggta tccccacgcg ccctgtagcg gcgcattaag
6721 cgcggcgggt gtggtggtta cgcgcagcgt gaccgctaca cttgccagcg ccctagcgcc
6781 cgctcctttc gctttcttcc cttcctttct cgccacgttc gccggctttc cccgtcaagc
6841 tctaaatcgg gggctccctt tagggttccg atttagtgct ttacggcacc tcgaccccaa
6901 aaaacttgat tagggtgatg gttcacgtag tgggccatcg ccctgataga cggtttttcg
6961 ccctttgacg ttggagtcca cgttctttaa tagtggactc ttgttccaaa ctggaacaac
7021 actcaaccct atctcggtct attcttttga tttataaggg attttgccga tttcggccta
7081 ttggttaaaa aatgagctga tttaacaaaa atttaacgcg aattaattct gtggaatgtg
7141 tgtcagttag ggtgtggaaa gtccccaggc tccccagcag gcagaagtat gcaaagcatg
7201 catctcaatt agtcagcaac caggtgtgga aagtccccag gctccccagc aggcagaagt
7261 atgcaaagca tgcatctcaa ttagtcagca accatagtcc cgcccctaac tccgcccatc
7321 ccgcccctaa ctccgcccag ttccgcccat tctccgcccc atggctgact aattttttt
```

-continued

```
7381  atttatgcag aggccgaggc cgcctctgcc tctgagctat tccagaagta gtgaggaggc
7441  ttttttggag gcctaggctt ttgcaaaaag ctcccgggag cttgtatatc cattttcgga
7501  tctgatcaag agacaggatg aggatcgttt cgcatgattg aacaagatgg attgcacgca
7561  ggttctccgg ccgcttgggt ggagaggcta ttcggctatg actgggcaca acagacaatc
7621  ggctgctctg atgccgccgt gttccggctg tcagcgcagg ggcgcccggt tctttttgtc
7681  aagaccgacc tgtccggtgc cctgaatgaa ctgcaggacg aggcagcgcg gctatcgtgg
7741  ctggccacga cgggcgttcc ttgcgcagct gtgctcgacg ttgtcactga agcgggaagg
7801  gactggctgc tattgggcga agtgccgggg caggatctcc tgtcatctca ccttgctcct
7861  gccgagaaag tatccatcat ggctgatgca atgcggcggc tgcatacgct tgatccggct
7921  acctgcccat tcgaccacca agcgaaacat cgcatcgagc gagcacgtac tcggatggaa
7981  gccggtcttg tcgatcagga tgatctggac gaagagcatc aggggctcgc gccagccgaa
8041  ctgttcgcca ggctcaaggc gcgcatgccc gacggcgagg atctcgtcgt gacccatggc
8101  gatgcctgct tgccgaatat catggtggaa aatggccgct tttctggatt catcgactgt
8161  ggccggctgg gtgtggcgga ccgctatcag gacatagcgt tggctacccg tgatattgct
8221  gaagagcttg gcggcgaatg ggctgaccgc ttcctcgtgc tttacggtat cgccgctccc
8281  gattcgcagc gcatcgcctt ctatcgcctt cttgacgagt tcttctgagc gggactctgg
8341  ggttcgaaat gaccgaccaa gcgacgccca acctgccatc acgagatttc gattccaccg
8401  ccgccttcta tgaaaggttg ggcttcggaa tcgttttccg ggacgccggc tggatgatcc
8461  tccagcgcgg ggatctcatg ctggagttct tcgcccaccc caacttgttt attgcagctt
8521  ataatggtta caaataaagc aatagcatca caaatttcac aaataaagca tttttttcac
8581  tgcattctag ttgtggtttg tccaaactca tcaatgtatc ttatcatgtc tgtataccgt
8641  cgacctctag ctagagcttg gcgtaatcat ggtcatagct gtttcctgtg tgaaattgtt
8701  atccgctcac aattccacac aacatacgag ccggaagcat aaagtgtaaa gcctggggtg
8761  cctaatgagt gagctaactc acattaattg cgttgcgctc actgcccgct ttccagtcgg
8821  gaaacctgtc gtgccagctg cattaatgaa tcggccaacg cgcggggaga ggcggtttgc
8881  gtattgggcg ctcttccgct tcctcgctca ctgactcgct gcgctcggtc gttcggctgc
8941  ggcgagcggt atcagctcac tcaaaggcgg taatacggtt atccacagaa tcaggggata
9001  acgcaggaaa gaacatgtga gcaaaaggcc agcaaaaggc caggaaccgt aaaaaggccg
9061  cgttgctggc gtttttccat aggctccgcc cccctgacga gcatcacaaa aatcgacgct
9121  caagtcagag gtggcgaaac ccgacaggac tataaagata ccaggcgttt ccccctggaa
9181  gctccctcgt gcgctctcct gttccgaccc tgccgcttac cggatacctg tccgcctttc
9241  tcccttcggg aagcgtggcg ctttctcata gctcacgctg taggtatctc agttcggtgt
9301  aggtcgttcg ctccaagctg ggctgtgtgc acgaaccccc cgttcagccc gaccgctgcg
9361  ccttatccgg taactatcgt cttgagtcca acccggtaag acacgactta tcgccactgg
9421  cagcagccac tggtaacagg attagcagag cgaggtatgt aggcggtgct acagagttct
9481  tgaagtggtg gcctaactac ggctacacta gaagaacagt atttggtatc tgcgctctgc
9541  tgaagccagt taccttcgga aaaagagttg gtagctcttg atccggcaaa caaaccaccg
9601  ctggtagcgg tttttttgtt tgcaagcagc agattacgcg cagaaaaaaa ggatctcaag
9661  aagatccttt gatcttttct acggggtctg acgctcagtg gaacgaaaac tcacgttaag
```

-continued

```
 9721   ggattttggt catgagatta tcaaaaagga tcttcaccta gatcctttta aattaaaaat
 9781   gaagttttaa atcaatctaa agtatatatg agtaaacttg gtctgacagt taccaatgct
 9841   taatcagtga ggcacctatc tcagcgatct gtctatttcg ttcatccata gttgcctgac
 9901   tccccgtcgt gtagataact acgatacggg agggcttacc atctggcccc agtgctgcaa
 9961   tgataccgcg agacccacgc tcaccggctc cagatttatc agcaataaac cagccagccg
10021   gaagggccga gcgcagaagt ggtcctgcaa ctttatccgc ctccatccag tctattaatt
10081   gttgccggga agctagagta agtagttcgc cagttaatag tttgcgcaac gttgttgcca
10141   ttgctacagg catcgtggtg tcacgctcgt cgtttggtat ggcttcattc agctccggtt
10201   cccaacgatc aaggcgagtt acatgatccc ccatgttgtg caaaaaagcg gttagctcct
10261   tcggtcctcc gatcgttgtc agaagtaagt tggccgcagt gttatcactc atggttatgg
10321   cagcactgca taattctctt actgtcatgc catccgtaag atgcttttct gtgactggtg
10381   agtactcaac caagtcattc tgagaatagt gtatgcggcg accgagttgc tcttgcccgg
10441   cgtcaatacg ggataatacc gcgccacata gcagaacttt aaaagtgctc atcattggaa
10501   aacgttcttc ggggcgaaaa ctctcaagga tcttaccgct gttgagatcc agttcgatgt
10561   aacccactcg tgcacccaac tgatcttcag catcttttac tttcaccagc gtttctgggt
10621   gagcaaaaac aggaaggcaa aatgccgcaa aaaagggaat aagggcgaca cggaaatgtt
10681   gaatactcat actcttcctt tttcaatatt attgaagcat ttatcagggt tattgtctca
10741   tgagcggata catatttgaa tgtatttaga aaaataaaca aataggggtt ccgcgcacat
10801   ttccccgaaa agtgccacct gacgtc
```

pcDNA3.1(1)_ADAR2_XTEN_control (SEQ ID NO: 28).

```
LOCUS                 Exported 6722 bp ds-DNA circular

DEFINITION            synthetic circular DNA

FEATURES              Location/Qualifiers

source                1 . . . 6722
                      /organism = "synthetic DNA construct"
                      /mol_type = "other DNA"

enhancer              235 . . . 614
                      /label = CMV enhancer
                      /note = "human cytomegalovirus immediate early enhancer"

promoter              615 . . . 818
                      /label = CMV promoter
                      /note = "human cytomegalovirus (CMV) immediate early
                      promoter"

promoter              863 . . . 881
                      /label = T7 promoter
                      /note = "promoter for bacteriophage T7 RNA polymerase"

misc_feature          927 . . . 954
                      /label = Homology 1_pCDNA3.1

primer_bind           955 . . . 976
                      /label = ADAR2CD-Cas9_HindIII_F

primer_bind           960 . . . 983
                      /label = Adar_out_forward_1v2

CDS                   961 . . . 2100
                      /codon_start = 1
                      /label = ADARB1(E488Q)_Catalytic Domain

/translation = "MLADAVSRLVLGKFGDLTDNFSSPHARRKVLAGWMTTGTDVKDA
KVISVSTGTKCINGEYMSDRGLALNDCHAEIISRRSLLRFLYTQLELYLNNKDDQKRSI
FQKSERGGFRLKENVQFHLYISTSPCGDARIFSPHEPILEEPADRHPNRKARGQLRTKI
```

```
ESGEGTIPVRSNASIQTWDGVLQGERLLTMSCSDKIARWNWGIQGSLLSIFVEPIYFS
SIILGSLYHGDHLSRAMYQRISNIEDLPPLYTLNKPLLSGISNAEARQPGKAPNFSVNW
TVGDSAIEVINATTGKDELGRASRLCKHALYCRWMRVHGKVPSHLLRSKITKPNVYHES
KLAAKEYQAAKARLFTAFIKAGLGAWVEKPTEQDQFSLTP"

primer_bind          1324 . . . 1346
                     /label = E488Q_ADAR2_Mut

primer_bind          complement(1426 . . . 1447)
                     /label = E488Q_Mut_Classic_R

primer_bind          1448 . . . 1472
                     /label = E488Q_Mut_Classic_F

CDS                  2101 . . . 2148
                     /codon_start = 1
                     /label = XTEN
                     /translation = "SGSETPGTSESATPES"

primer_bind          complement(2129 . . . 2148)
                     /label = ADAR2_CD_Inverse_R

primer_bind          2149 . . . 2170
                     /label = ADAR2_CD_Inverse_F

CDS                  2152 . . . 2178
                     /codon_start = 1
                     /product = "HA (human influenza hemagglutinin) epitope tag"
                     /label = HA
                     /translation = "YPYDVPDYA"

CDS                  2197 . . . 2217
                     /codon_start = 1
                     /product = "nuclear localization signal of SV40 large T
                     antigen"
                     /label = SV40 NLS
                     /translation = "PKKKRKV"

CDS                  2224 . . . 2244
                     /codon_start = 1
                     /product = "nuclear localization signal of SV40 large T
                     antigen"
                     /label = SV40 NLS
                     /translation = "PKKKRKV"

primer_bind          complement(2228 . . . 2253)
                     /label = ADAR2CD-Cas9_NotI_R

misc_feature         2254 . . . 2288
                     /label = Homology 2_pCDNA3.1
                     polyA_signal 2322 . . . 2546
                     /label = bGH poly(A) signal
                     /note = "bovine growth hormone polyadenylation signal"

rep_origin           2592 . . . 3020
                     /direction = RIGHT
                     /label = f1 ori
                     /note = "f1 bacteriophage origin of replication; arrow
                     indicates direction of (+) strand synthesis"

promoter             3034 . . . 3363
                     /label = SV40 promoter
                     /note = "SV40 enhancer and early promoter"

rep_origin           3214 . . . 3349
                     /label = SV40 ori
                     /note = "SV40 origin of replication"

CDS                  3430 . . . 4224
                     /codon_start = 1
                     /gene = "aph(3')-II (or nptII)"
                     /product = "aminoglycoside phosphotransferase from Tn5"
                     /label = NeoR/KanR
                     /note = "confers resistance to neomycin, kanamycin, and G418
                     (Geneticin(R))"

/translation = "MIEQDGLHAGSPAAWVERLFGYDWAQQTIGCSDAAVFRLSAQGRP
VLFVKTDLSGALNELQDEAARLSWLATTGVPCAAVLDVVTEAGRDWLLLGEVPGQDLLS
SHLAPAEKVSIMADAMRRLHTLDPATCPFDHQAKHRIERARTRMEAGLVDQDDLDEEHQ
```

```
GLAPAELFARLKARMPDGEDLVVTHGDACLPNIMVENGRFSGFIDCGRLGVADRYQDIA
LATRDIAEELGGEWADRFLVLYGIAAPDSQRIAFYRLLDEFF"

polyA_signal          4398 . . . 4519
                      /label = SV40 poly(A) signal
                      /note = "SV40 polyadenylation signal"

primer_bind           complement(4568 . . . 4584)
                      /label = M13 rev
                      /note = "common sequencing primer, one of multiple similar
                      variants"

protein_bind          4592 . . . 4608
                      /label = lac operator
                      /bound_moiety = "lac repressor encoded by lacI"
                      /note = "The lac repressor binds to the lac operator to
                      inhibit transcription in E. coli. This inhibition can be
                      relieved by adding lactose or
                      isopropyl-beta-D-thiogalactopyranoside (IPTG)."

promoter              complement(4616 . . . 4646)
                      /label = lac promoter
                      /note = "promoter for the E. coli lac operon"

protein_bind          4661 . . . 4682
                      /label = CAP binding site
                      /bound_moiety = "E. coli catabolite activator protein"
                      /note = "CAP binding activates transcription in the presence
                      of cAMP."

rep_origin            complement(4970 . . . 5555)
                      /direction = LEFT
                      /label = ori
                      /note = "high-copy-number ColE1/pMB1/pBR322/pUC origin of
                      replication"

CDS                   complement(5726 . . . 6586)
                      /codon_start = 1
                      /gene = "bla"
                      /product = "beta-lactamase"
                      /label = AmpR
                      /note = "confers resistance to ampicillin, carbenicillin, and
                      related antibiotics"

/translation = "MSIQHFRVALIPFFAAFCLPVFAHPETLVKVKDAEDQLGARVGYI
ELDLNSGKILESFRPEERFPMMSTFKVLLCGAVLSRIDAGQEQLGRRIHYSQNDLVEYS
PVTEKHLTDGMTVRELCSAAITMSDNTAANLLLTTIGGPKELTAFLHNMGDHVTRLDRW
EPELNEAIPNDERDTTMPVAMATTLRKLLTGELLTLASRQQLIDWMEADKVAGPLLRSA
LPAGWFIADKSGAGERGSRGIIAALGPDGKPSRIVVIYTTGSQATMDERNRQIAEIGAS
LIKHW"

promoter              complement(6587 . . . 6691)
                      /gene = "bla"
                      /label = AmpR promoter

ORIGIN
     1  gacggatcgg gagatctccc gatcccctat ggtgcactct cagtacaatc tgctctgatg

    61  ccgcatagtt aagccagtat ctgctccctg cttgtgtgtt ggaggtcgct gagtagtgcg

   121  cgagcaaaat ttaagctaca acaaggcaag gcttgaccga caattgcatg aagaatctgc

   181  ttagggttag gcgttttgcg ctgcttcgcg atgtacgggc cagatatacg cgttgacatt

   241  gattattgac tagttattaa tagtaatcaa ttacggggtc attagttcat agcccatata

   301  tggagttccg cgttacataa cttacggtaa atggcccgcc tggctgaccg cccaacgacc

   361  cccgcccatt gacgtcaata atgacgtatg ttcccatagt aacgccaata gggactttcc

   421  attgacgtca atgggtggag tatttacggt aaactgccca cttggcagta catcaagtgt

   481  atcatatgcc aagtacgccc cctattgacg tcaatgacgg taaatggccc gcctggcatt

   541  atgcccagta catgacctta tgggactttc ctacttggca gtacatctac gtattagtca

   601  tcgctattac catggtgatg cggttttggc agtacatcaa tgggcgtgga tagcggtttg

   661  actcacgggg atttccaagt ctccacccca ttgacgtcaa tgggagtttg ttttggcacc
```

-continued

```
 721  aaaatcaacg ggactttcca aaatgtcgta acaactccgc cccattgacg caaatgggcg
 781  gtaggcgtgt acggtgggag gtctatataa gcagagctct ctggctaact agagaaccca
 841  ctgcttactg gcttatcgaa attaatacga ctcactatag ggagacccaa gctggctagc
 901  gtttaaacgg gccctctaga ctcgagcggc cgccactgtg ctggatatct gcagagaacc
 961  atgttagctg acgctgtctc acgcctggtc ctgggtaagt ttggtgacct gaccgacaac
1021  ttctcctccc ctcacgctcg cagaaaagtg ctggctggag tcgtcatgac aacaggcaca
1081  gatgttaaag atgccaaggt gataagtgtt tctacaggaa caaaatgtat taatggtgaa
1141  tacatgagtg atcgtggcct tgcattaaat gactgccatg cagaaataat atctcggaga
1201  tccttgctca gatttcttta tacacaactt gagctttact taaataacaa agatgatcaa
1261  aaaagatcca tctttcagaa atcagagcga ggggggttta ggctgaagga gaatgtccag
1321  tttcatctgt acatcagcac ctctccctgt ggagatgcca gaatcttctc accacatgag
1381  ccaatcctgg aagaaccagc agatagacac ccaaatcgta aagcaagagg acagctacgg
1441  accaaaatag agtctggtga ggggacgatt ccagtgcgct ccaatgcgag catccaaacg
1501  tgggacgggg tgctgcaagg ggagcggctg ctcaccatgt cctgcagtga caagattgca
1561  cgctggaacg tggtgggcat ccagggatcc ctgctcagca ttttcgtgga gcccatttac
1621  ttctcgagca tcatcctggg cagcctttac cacggggacc acctttccag ggccatgtac
1681  cagcggatct ccaacataga ggacctgcca cctctctaca ccctcaacaa gcctttgctc
1741  agtggcatca gcaatgcaga agcacggcag ccagggaagg cccccaactt cagtgtcaac
1801  tggacggtag gcgactccgc tattgaggtc atcaacgcca cgactgggaa ggatgagctg
1861  ggccgcgcgt cccgcctgtg taagcacgcg ttgtactgtc gctggatgcg tgtgcacggc
1921  aaggttccct cccacttact acgctccaag attaccaagc ccaacgtgta ccatgagtcc
1981  aagctggcgg caaaggagta ccaggccgcc aaggcgcgtc tgttcacagc cttcatcaag
2041  gcggggctgg gggcctgggt ggagaagccc accgagcagg accagttctc actcacgccc
2101  agtggaagtg agacaccggg aacctcagag agcgccacgc cagaaagcgc ctatccctat
2161  gacgtgcccg attatgccag cctgggcagc ggctccccca agaaaaaacg caaggtggaa
2221  gatcctaaga aaaagcggaa agtggacgtg taaccaccac actggactag tggatccgag
2281  ctcggtacca agcttaagtt taaaccgctg atcagcctcg actgtgcctt ctagttgcca
2341  gccatctgtt gtttgcccct cccccgtgcc ttccttgacc ctggaaggtg ccactcccac
2401  tgtcctttcc taataaaatg aggaaattgc atcgcattgt ctgagtaggt gtcattctat
2461  tctggggggt ggggtggggc aggacagcaa gggggaggat tgggaagaca atagcaggca
2521  tgctggggat gcggtgggct ctatggcttc tgaggcggaa agaaccagct ggggctctag
2581  ggggtatccc cacgcgccct gtagcggcgc attaagcgcg gcgggtgtgg tggttacgcg
2641  cagcgtgacc gctacacttg ccagcgccct agcgcccgct cctttcgctt tcttcccttc
2701  ctttctcgcc acgttcgccg gctttccccg tcaagctcta aatcgggggc tccctttagg
2761  gttccgattt agtgctttac ggcacctcga ccccaaaaaa cttgattagg gtgatggttc
2821  acgtagtggg ccatcgccct gatagacggt ttttcgccct ttgacgttgg agtccacgtt
2881  ctttaatagt ggactcttgt tccaaactgg aacaacactc aaccctatct cggtctattc
2941  ttttgattta taagggattt tgccgatttc ggcctattgg ttaaaaaatg agctgattta
3001  acaaaaattt aacgcgaatt aattctgtgg aatgtgtgtc agttagggtg tggaaagtcc
```

-continued

```
3061  ccaggctccc cagcaggcag aagtatgcaa agcatgcatc tcaattagtc agcaaccagg
3121  tgtggaaagt ccccaggctc cccagcaggc agaagtatgc aaagcatgca tctcaattag
3181  tcagcaacca tagtcccgcc cctaactccg cccatcccgc ccctaactcc gcccagttcc
3241  gcccattctc cgccccatgg ctgactaatt ttttttattt atgcagaggc cgaggccgcc
3301  tctgcctctg agctattcca gaagtagtga ggaggctttt ttggaggcct aggcttttgc
3361  aaaaagctcc cgggagcttg tatatccatt ttcggatctg atcaagagac aggatgagga
3421  tcgtttcgca tgattgaaca agatggattg cacgcaggtt ctccggccgc ttgggtggag
3481  aggctattcg gctatgactg ggcacaacag acaatcggct gctctgatgc cgccgtgttc
3541  cggctgtcag cgcaggggcg cccggttctt tttgtcaaga ccgacctgtc cggtgccctg
3601  aatgaactgc aggacgaggc agcgcggcta tcgtggctgg ccacgacggg cgttccttgc
3661  gcagctgtgc tcgacgttgt cactgaagcg ggaagggact ggctgctatt gggcgaagtg
3721  ccggggcagg atctcctgtc atctcacctt gctcctgccg agaaagtatc catcatggct
3781  gatgcaatgc ggcggctgca tacgcttgat ccggctacct gcccattcga ccaccaagcg
3841  aaacatcgca tcgagcgagc acgtactcgg atggaagccg gtcttgtcga tcaggatgat
3901  ctggacgaag agcatcaggg gctcgcgcca gccgaactgt tcgccaggct caaggcgcgc
3961  atgcccgacg gcgaggatct cgtcgtgacc catggcgatg cctgcttgcc gaatatcatg
4021  gtggaaaatg gccgcttttc tggattcatc gactgtggcc ggctgggtgt ggcggaccgc
4081  tatcaggaca tagcgttggc tacccgtgat attgctgaag agcttggcgg cgaatgggct
4141  gaccgcttcc tcgtgcttta cggtatcgcc gctcccgatt cgcagcgcat cgccttctat
4201  cgccttcttg acgagttctt ctgagcggga ctctggggtt cgaaatgacc gaccaagcga
4261  cgcccaacct gccatcacga gatttcgatt ccaccgccgc cttctatgaa aggttgggct
4321  tcggaatcgt tttccgggac gccggctgga tgatcctcca gcgcggggat ctcatgctgg
4381  agttcttcgc ccaccccaac ttgtttattg cagcttataa tggttacaaa taaagcaata
4441  gcatcacaaa tttcacaaat aaagcatttt tttcactgca ttctagttgt ggtttgtcca
4501  aactcatcaa tgtatcttat catgtctgta taccgtcgac ctctagctag agcttggcgt
4561  aatcatggtc atagctgttt cctgtgtgaa attgttatcc gctcacaatt ccacacaaca
4621  tacgagccgg aagcataaag tgtaaagcct ggggtgccta atgagtgagc taactcacat
4681  taattgcgtt gcgctcactg cccgctttcc agtcgggaaa cctgtcgtgc cagctgcatt
4741  aatgaatcgg ccaacgcgcg gggagaggcg gtttgcgtat tgggcgctct tccgcttcct
4801  cgctcactga ctcgctgcgc tcggtcgttc ggctgcggcg agcggtatca gctcactcaa
4861  aggcggtaat acggttatcc acagaatcag gggataacgc aggaaagaac atgtgagcaa
4921  aaggccagca aaaggccagg aaccgtaaaa aggccgcgtt gctggcgttt ttccataggc
4981  tccgcccccc tgacgagcat cacaaaaatc gacgctcaag tcagaggtgg cgaaacccga
5041  caggactata aagataccag gcgtttcccc ctggaagctc cctcgtgcgc tctcctgttc
5101  cgaccctgcc gcttaccgga tacctgtccg cctttctccc ttcgggaagc gtggcgcttt
5161  ctcatagctc acgctgtagg tatctcagtt cggtgtaggt cgttcgctcc aagctgggct
5221  gtgtgcacga accccccgtt cagcccgacc gctgcgcctt atccggtaac tatcgtcttg
5281  agtccaaccc ggtaagacac gacttatcgc cactggcagc agccactggt aacaggatta
5341  gcagagcgag gtatgtaggc ggtgctacag agttcttgaa gtggtggcct aactacggct
5401  acactagaag aacagtattt ggtatctgcg ctctgctgaa gccagttacc ttcggaaaaa
```

-continued

```
5461  gagttggtag ctcttgatcc ggcaaacaaa ccaccgctgg tagcggtttt tttgtttgca
5521  agcagcagat tacgcgcaga aaaaaaggat ctcaagaaga tcctttgatc ttttctacgg
5581  ggtctgacgc tcagtggaac gaaaactcac gttaagggat tttggtcatg agattatcaa
5641  aaaggatctt cacctagatc cttttaaatt aaaaatgaag ttttaaatca atctaaagta
5701  tatatgagta aacttggtct gacagttacc aatgcttaat cagtgaggca cctatctcag
5761  cgatctgtct atttcgttca tccatagttg cctgactccc cgtcgtgtag ataactacga
5821  tacgggaggg cttaccatct ggccccagtg ctgcaatgat accgcgagac ccacgctcac
5881  cggctccaga tttatcagca ataaaccagc cagccggaag ggccgagcgc agaagtggtc
5941  ctgcaacttt atccgcctcc atccagtcta ttaattgttg ccgggaagct agagtaagta
6001  gttcgccagt taatagtttg cgcaacgttg ttgccattgc tacaggcatc gtggtgtcac
6061  gctcgtcgtt tggtatggct tcattcagct ccggttccca acgatcaagg cgagttacat
6121  gatcccccat gttgtgcaaa aaagcggtta gctccttcgg tcctccgatc gttgtcagaa
6181  gtaagttggc cgcagtgtta tcactcatgg ttatggcagc actgcataat tctcttactg
6241  tcatgccatc cgtaagatgc ttttctgtga ctggtgagta ctcaaccaag tcattctgag
6301  aatagtgtat gcggcgaccg agttgctctt gcccggcgtc aatacgggat aataccgcgc
6361  cacatagcag aactttaaaa gtgctcatca ttggaaaacg ttcttcgggg cgaaaactct
6421  caaggatctt accgctgttg agatccagtt cgatgtaacc cactcgtgca cccaactgat
6481  cttcagcatc ttttactttc accagcgttt ctgggtgagc aaaaacagga aggcaaaatg
6541  ccgcaaaaaa gggaataagg gcgacacgga aatgttgaat actcatactc ttcctttttc
6601  aatattattg aagcatttat cagggttatt gtctcatgag cggatacata tttgaatgta
6661  tttagaaaaa taaacaaata ggggttccgc gcacatttcc ccgaaaagtg ccacctgacg
6721  tc
```

pcDNA3.1 ADAR2(E488Q) XTEN dCas9 (SEQ ID NO: 29).

```
LOCUS          Exported 10826 bp ds-DNA circular
DEFINITION     synthetic circular DNA
SOURCE         synthetic DNA construct
ORGANISM       synthetic DNA construct
REFERENCE      1 (bases 1 to 10826)
FEATURES       Location/Qualifiers
source         1 . . . 10826
               /organism = "synthetic DNA construct"
               /mol_type = "other DNA"
enhancer       235 . . . 614
               /label = CMV enhancer
               /note = "human cytomegalovirus immediate early enhancer"
promoter       615 . . . 818
               /label = CMV promoter
               /note = "human cytomegalovirus (CMV) immediate early
               promoter"
promoter       863 . . . 881
               /label = T7 promoter
               /note = "promoter for bacteriophage T7 RNA polymerase"
primer_bind    927 . . . 985
               /label = H1-ADAR-XTEN_F
```

```
misc_feature            927 . . . 954
                        /label = Homology 1_pCDNA3.1

CDS                     961 . . . 2100
                        /codon_start = 1
                        /label = ADARB1(E488Q)_Catalytic Domain

/translation = "MLADAVSRLVLGKFGDLTDNFSSPHARRKVLAGVVMTTGTDVKDA
KVISVSTGTKCINGEYMSDRGLALNDCHAEIISRRSLLRFLYTQLELYLNNKDDQKRSI
FQKSERGGFRLKENVQFHLYISTSPCGDARIFSPHEPILEEPADRHPNRKARGQLRTKI
ESGQGTIPVRSNASIQTWDGVLQGERLLTMSCSDKIARWNVVGIQGSLLSIFVEPIYFS
SIILGSLYHGDHLSRAMYQRISNIEDLPPLYTLNKPLLSGISNAEARQPGKAPNFSVNW
TVGDSAIEVINATTGKDELGRASRLCKHALYCRWMRVHGKVPSHLLRSKITKPNVYHES
KLAAKEYQAAKARLFTAFIKAGLGAWVEKPTEQDQFSLTP"

primer_bind             961 . . . 982
                        /label = Primer 4

primer_bind             1111 . . . 1138
                        /label = Primer 1

primer_bind             1440 . . . 1478
                        /label = E488Q_Mutagenesis_F

primer_bind             complement 1440 . . . 1478)
                        /label = E488Q_Mutagenesis_R

primer_bind             complement(2080 . . . 2100)
                        /label = ADAR2DD_GS_R

primer_bind             complement(2080 . . . 2100)
                        /label = Primer 5

CDS                     2101 . . . 2148
                        /codon_start = 1
                        /label = XTEN
                        /translation = "SGSETPGTSESATPES"

primer_bind             complement(2129 . . . 2148)
                        /label = ADAR2_XTEN_R

primer_bind             complement(2129 . . . 2148)
                        /label = ADAR2_CD_Inverse_R

primer_bind             2148 . . . 2171
                        /label = Primer 2

CDS                     2149 . . . 6252
                        /codon_start = 1
                        /product = "catalytically dead mutant of the Cas9
                        endonuclease from the Streptococcus pyogenes Type II
                        CRISPR/Cas system"
                        /label = dCas9
                        /note = "RNA-guided DNA-binding protein that lacks
                        endonuclease activity due to the D10A mutation in the RuvC
                        catalytic domain and the H840A mutation in the HNH
                        catalytic domain"

/translation = "MDKKYSIGLAIGTNSVGWAVITDEYKVPSKKFKVLGNTDRHSIKK
NLIGALLFDSGETAEATRLKRTARRRYTRRKNRICYLQEIFSNEMAKVDDSFFHRLEES
FLVEEDKKHERHPIFGNIVDEVAYHEKYPTIYHLRKKLVDSTDKADLRLIYLALAHMIK
FRGHFLIEGDLNPDNSDVDKLFIQLVQTYNQLFEENPINASGVDAKAILSARLSKSRRL
ENLIAQLPGEKKNGLFGNLIALSLGLTPNFKSNFDLAEDAKLQLSKDTYDDDLDNLLAQ
IGDQYADLFLAAKNLSDAILLSDILRVNTEITKAPLSASMIKRYDEHHQDLTLLKALVR
QQLPEKYKEIFFDQSKNGYAGYIDGGASQEEFYKFIKPILEKMDGTEELLVKLNREDLL
RKQRTFDNGSIPHQIHLGELHAILRRQEDFYPFLKDNREKIEKILTFRIPYYVGPLARG
NSRFAWMTRKSEETITPWNFEEVVDKGASAQSFIERMTNFDKNLPNEKVLPKHSLLYEY
FTVYNELTKVKYVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLTLFEDREMIEER
LKTYAHLFDDKVMKQLKRRRYTGWGRLSRKLINGIRDKQSGKTILDFLKSDGFANRNFM
QLIHDDSLTFKEDIQKAQVSGQGDSLHEHIANLAGSPAIKKGILQTVKVVDELVKVMGR
HKPENIVIEMARENQTTQKGQKNSRERMKRIEEGIKELGSQILKEHPVENTQLQNEKLY
LYYLQNGRDMYVDQELDINRLSDYDVDAIVPQSFLKDDSIDNKVLTRSDKNRGKSDNVP
SEEVVKKMKNYWRQLLNAKLITQRKFDNLTKAERGGLSELDKAGFIKRQLVETRQITKH
VAQILDSRMNTKYDENDKLIREVKVITLKSKLVSDFRKDFQFYKVREINNYHHAHDAYL
NAVVGTALIKKYPKLESEFVYGDYKVYDVRKMIAKSEQEIGKATAKYFFYSNIMNFFKT
EITLANGEIRKRPLIETNGETGEIVWDKGRDFATVRKVLSMPQVNIVKKTEVQTGGFSK
ESILPKRNSDKLIARKKDWDPKKYGGFDSPTVAYSVLVVAKVEKGKSKKLKSVKELLGI
TIMERSSFEKNPIDFLEAKGYKEVKKDLIIKLPKYSLFELENGRKRMLASAGELQKGNE
```

```
LALPSKYVNFLYLASHYEKLKGSPEDNEQKQLFVEQHKHYLDEIIEQISEFSKRVILAD
ANLDKVLSAYNKHRDKPIREQAENIIHLFTLTNLGAPAAFKYFDTTIDRKRYTSTKEVL
DATLIHQSITGLYETRIDLSQLGGD"

primer_bind          complement(4458 . . . 4479)
                     /label = Primer 3

primer_bind          4879 . . . 4899
                     /label = Primer 6

primer_bind          6252 . . . 6273
                     /label = SaCas9_HA_F

primer_bind          6253 . . . 6274
                     /label = ADAR2_CD_Inverse_F

CDS                  6256-6282
                     /codon_start = 1
                     /product = "HA (human influenza hemagglutinin) epitope tag"
                     /label = HA
                     /translation = "YPYDVPDYA"

primer_bind          complement(6274 . . . 6296)
                     /label = AXC_NLSout_NESin_R

primer_bind          complement(6274 . . . 6294)
                     /label = NLS_out_R

CDS                  6301 . . . 6321
                     /codon_start = 1
                     /product = "nuclear localization signal of SV40 large T
                     antigen"
                     /label = SV40 NLS
                     /translation = "PKKKRKV"

CDS                  6328-6348
                     /codon_start = 1
                     /product = "nuclear localization signal of SV40 large T
                     antigen"
                     /label = SV40 NLS
                     /translation = "PKKKRKV"

primer_bind          complement(6333 . . . 6392)
                     /label = XTEN-Cas9-H2_R

primer_bind          complement(6333 . . . 6377)
                     /label = Primer 7

primer_bind          6347-6371
                     /label = NLS_out_NES_full_F

primer_bind          6349-6371
                     /label = AXC_NLSout_NESin_F

misc_feature         6358-6392
                     /label = Homology 2_pCDNA3.1

polyA_signal         6426-6650
                     /label = bGH poly(A) signal
                     /note = "bovine growth hormone polyadenylation signal"

rep_origin           6696-7124
                     /direction = RIGHT
                     /label = f1 ori
                     /note = "f1 bacteriophage origin of replication; arrow
                     indicates direction of (+) strand synthesis"

promoter             7138-7467
                     /label = SV40 promoter
                     /note = "SV40 enhancer and early promoter"

rep_origin           7318 . . . 7453
                     /label = SV40 ori
                     /note = "SV40 origin of replication"

CDS                  7534 . . . 8328
                     /codon_start = 1
                     /gene = "aph(3')-II (or nptII)"
                     /product = "aminoglycoside phosphotransferase from Tn5"
```

```
                         /label = NeoR/KanR
                         /note = "confers resistance to neomycin, kanamycin, and G418
                         (Geneticin(R))"

/translation = "MIEQDGLHAGSPAAWVERLFGYDWAQQTIGCSDAAVFRLSAQGRP
VLFVKTDLSGALNELQDEAARLSWLATTGVPCAAVLDVVTEAGRDWLLLGEVPGQDLLS
SHLAPAEKVSIMADAMRRLHTLDPATCPFDHQAKHRIERARTRMEAGLVDQDDLDEEHQ
GLAPAELFARLKARMPDGEDLVVTHGDACLPNIMVENGRFSGFIDCGRLGVADRYQDIA
LATRDIAEELGGEWADRFLVLYGIAAPDSQRIAFYRLLDEFF"

polyA_signal             8502 . . . 8623
                         /label = SV40 poly(A) signal
                         /note = "SV40 polyadenylation signal"

primer_bind              complement(8672 . . . 8688)
                         /label = M13 rev
                         /note = "common sequencing primer, one of multiple similar
                         variants"

protein_bind             8696 . . . 8712
                         /label = lac operator
                         /bound_moiety = "lac repressor encoded by lacI"
                         /note = "The lac repressor binds to the lac operator to
                         inhibit transcription in E. coli. This inhibition can be
                         relieved by adding lactose or
                         isopropyl-beta-D-thiogalactopyranoside (IPTG)."

promoter                 complement(8720 . . . 8750)
                         /label = lac promoter
                         /note = "promoter for the E. coli lac operon"

protein_bind             8765 . . . 8786
                         /label = CAP binding site
                         /bound_moiety = "E. coli catabolite activator protein"
                         /note = "CAP binding activates transcription in the presence
                         of cAMP."

rep_origin               complement(9074 . . . 9659)
                         /direction = LEFT
                         /label = ori
                         /note = "high-copy-number ColE1/pMB1/pBR322/pUC origin of
                         replication"

CDS                      complement(9830 . . . 10690)
                         /codon_start = 1
                         /gene = "bla"
                         /product = "beta-lactamase"
                         /label = AmpR
                         /note = "confers resistance to ampicillin, carbenicillin, and
                         related antibiotics"

/translation = "MSIQHFRVALIPFFAAFCLPVFAHPETLVKVKDAEDQLGARVGYI
ELDLNSGKILESFRPEERFPMMSTFKVLLCGAVLSRIDAGQEQLGRRIHYSQNDLVEYS
PVTEKHLTDGMTVRELCSAAITMSDNTAANLLLTTIGGPKELTAFLHNMGDHVTRLDRW
EPELNEAIPNDERDTTMPVAMATTLRKLLTGELLTLASRQQLIDWMEADKVAGPLLRSA
LPAGWFIADKSGAGERGSRGIIAALGPDGKPSRIVVIYTTGSQATMDERNRQIAEIGAS
LIKHW"

promoter                 complement(10691 . . . 10795)
                         /gene = "bla"
                         /label = AmpR promoter

ORIGIN
      1   gacggatcgg gagatctccc gatcccctat ggtgcactct cagtacaatc tgctctgatg

     61   ccgcatagtt aagccagtat ctgctccctg cttgtgtgtt ggaggtcgct gagtagtgcg

    121   cgagcaaaat ttaagctaca acaaggcaag gcttgaccga caattgcatg aagaatctgc

    181   ttagggttag gcgttttgcg ctgcttcgcg atgtacgggc cagatatacg cgttgacatt

    241   gattattgac tagttattaa tagtaatcaa ttacggggtc attagttcat agcccatata

    301   tggagttccg cgttacataa cttacggtaa atggcccgcc tggctgaccg cccaacgacc

    361   cccgcccatt gacgtcaata atgacgtatg ttcccatagt aacgccaata gggactttcc

    421   attgacgtca atgggtggag tatttacggt aaactgccca cttggcagta catcaagtgt
```

-continued

```
481   atcatatgcc aagtacgccc cctattgacg tcaatgacgg taaatggccc gcctggcatt
541   atgcccagta catgacctta tgggactttc ctacttggca gtacatctac gtattagtca
601   tcgctattac catggtgatg cggttttggc agtacatcaa tgggcgtgga tagcggtttg
661   actcacgggg atttccaagt ctccacccca ttgacgtcaa tgggagtttg ttttggcacc
721   aaaatcaacg ggactttcca aaatgtcgta acaactccgc cccattgacg caaatgggcg
781   gtaggcgtgt acggtgggag gtctatataa gcagagctct ctggctaact agagaaccca
841   ctgcttactg gcttatcgaa attaatacga ctcactatag ggagacccaa gctggctagc
901   gtttaaacgg gccctctaga ctcgagcggc cgccactgtg ctggatatct gcagagaacc
961   atgttagctg acgctgtctc acgcctggtc ctgggtaagt ttggtgacct gaccgacaac
1021  ttctcctccc ctcacgctcg cagaaaagtg ctggctggag tcgtcatgac aacaggcaca
1081  gatgttaaag atgccaaggt gataagtgtt tctacaggaa caaaatgtat taatggtgaa
1141  tacatgagtg atcgtggcct tgcattaaat gactgccatg cagaaataat atctcggaga
1201  tccttgctca gatttcttta tacacaactt gagctttact taaataacaa agatgatcaa
1261  aaaagatcca tctttcagaa atcagagcga gggggtttta ggctgaagga gaatgtccag
1321  tttcatctgt acatcagcac ctctccctgt ggagatgcca gaatcttctc accacatgag
1381  ccaatcctgg aagaaccagc agatagacac ccaaatcgta aagcaagagg acagctacgg
1441  accaaaatag agtctggtca ggggacgatt ccagtgcgct ccaatgcgag catccaaacg
1501  tgggacgggg tgctgcaagg ggagcggctg ctcaccatgt cctgcagtga caagattgca
1561  cgctggaacg tggtgggcat ccagggatcc ctgctcagca ttttcgtgga gcccatttac
1621  ttctcgagca tcatcctggg cagcctttac cacggggacc acctttccag ggccatgtac
1681  cagcggatct ccaacataga ggacctgcca cctctctaca ccctcaacaa gcctttgctc
1741  agtggcatca gcaatgcaga agcacggcag ccagggaagg cccccaactt cagtgtcaac
1801  tggacggtag gcgactccgc tattgaggtc atcaacgcca cgactgggaa ggatgagctg
1861  ggccgcgcgt cccgcctgtg taagcacgcg ttgtactgtc gctggatgcg tgtgcacggc
1921  aaggttccct cccacttact acgctccaag attaccaagc ccaacgtgta ccatgagtcc
1981  aagctggcgg caaaggagta ccaggccgcc aaggcgcgtc tgttcacagc cttcatcaag
2041  gcggggctgg gggcctgggt ggagaagccc accgagcagg accagttctc actcacgccc
2101  agtggaagtg agacaccggg aacctcagag agcgccacgc cagaaagcat ggacaagaag
2161  tacagcatcg gcctggccat cggcaccaac tctgtgggct gggccgtgat caccgacgag
2221  tacaaggtgc ccagcaagaa attcaaggtg ctgggcaaca ccgaccggca cagcatcaag
2281  aagaacctga tcggcgccct gctgttcgac agcggagaaa cagccgaggc cacccggctg
2341  aagagaaccg ccagaagaag atacaccaga cggaagaacc ggatctgcta tctgcaagag
2401  atcttcagca acgagatggc caaggtggac gacagcttct tccacagact ggaagagtcc
2461  ttcctggtgg aagaggataa gaagcacgag cggcacccca tcttcggcaa catcgtggac
2521  gaggtggcct accacgagaa gtaccccacc atctaccacc tgagaaagaa actggtggac
2581  agcaccgaca aggccgacct gcggctgatc tatctggccc tggcccacat gatcaagttc
2641  cggggccact tcctgatcga gggcgacctg aaccccgaca acagcgacgt ggacaagctg
2701  ttcatccagc tggtgcagac ctacaaccag ctgttcgagg aaaaccccat caacgccagc
2761  ggcgtggacg ccaaggccat cctgtctgcc agactgagca agagcagacg gctggaaaat
2821  ctgatcgccc agctgcccgg cgagaagaag aatggcctgt tcggcaacct gattgccctg
```

```
2881  agcctgggcc tgacccccaa cttcaagagc aacttcgacc tggccgagga tgccaaactg
2941  cagctgagca aggacaccta cgacgacgac ctggacaacc tgctggccca gatcggcgac
3001  cagtacgccg acctgtttct ggccgccaag aacctgtccg acgccatcct gctgagcgac
3061  atcctgagag tgaacaccga gatcaccaag gcccccctga gcgcctctat gatcaagaga
3121  tacgacgagc accaccagga cctgaccctg ctgaaagctc tcgtgcggca gcagctgcct
3181  gagaagtaca aagagatttt cttcgaccag agcaagaacg gctacgccgg ctacatcgat
3241  ggcggagcca gccaggaaga gttctacaag ttcatcaagc ccatcctgga aaagatggac
3301  ggcaccgagg aactgctcgt gaagctgaac agagaggacc tgctgcggaa gcagcggacc
3361  ttcgacaacg gcagcatccc ccaccagatc cacctgggag agctgcacgc cattctgcgg
3421  cggcaggaag atttttaccc attcctgaag gacaaccggg aaaagatcga gaagatcctg
3481  accttccgca tcccctacta cgtgggccct ctggccaggg gaaacagcag attcgcctgg
3541  atgaccagaa agagcgagga aaccatcacc ccctggaact tcgaggaagt ggtggacaag
3601  ggcgccagcg cccagagctt catcgagcgg atgaccaact tcgataagaa cctgcccaac
3661  gagaaggtgc tgcccaagca cagcctgctg tacgagtact tcaccgtgta caacgagctg
3721  accaaagtga aatacgtgac cgagggaatg agaaagcccg ccttcctgag cggcgagcag
3781  aaaaaagcca tcgtggacct gctgttcaag accaaccgga aagtgaccgt gaagcagctg
3841  aaagaggact acttcaagaa aatcgagtgc ttcgactccg tggaaatctc cggcgtggaa
3901  gatcggttca acgcctccct gggcacatac cacgatctgc tgaaaattat caaggacaag
3961  gacttcctgg acaatgagga aaacgaggac attctggaag atatcgtgct gaccctgaca
4021  ctgtttgagg acagagagat gatcgaggaa cggctgaaaa cctatgccca cctgttcgac
4081  gacaaagtga tgaagcagct gaagcggcgg agatacaccg gctggggcag gctgagccgg
4141  aagctgatca acggcatccg ggacaagcag tccggcaaga caatcctgga tttcctgaag
4201  tccgacggct tcgccaacag aaacttcatg cagctgatcc acgacgacag cctgaccttt
4261  aaagaggaca tccagaaagc ccaggtgtcc ggccagggcg atagcctgca cgagcacatt
4321  gccaatctgg ccggcagccc cgccattaag aagggcatcc tgcagacagt gaaggtggtg
4381  gacgagctcg tgaaagtgat gggccggcac aagcccgaga acatcgtgat cgaaatggcc
4441  agagagaacc agaccaccca gaagggacag aagaacagcc gcgagagaat gaagcggatc
4501  gaagagggca tcaaagagct gggcagccag atcctgaaag aacaccccgt ggaaaacacc
4561  cagctgcaga acgagaagct gtacctgtac tacctgcaga atgggcggga tatgtacgtg
4621  gaccaggaac tggacatcaa ccggctgtcc gactacgatg tggacgctat cgtgcctcag
4681  agctttctga aggacgactc catcgataac aaagtgctga ctcggagcga caagaaccgg
4741  ggcaagagcg acaacgtgcc ctccgaagag gtcgtgaaga agatgaagaa ctactggcgc
4801  cagctgctga atgccaagct gattacccag aggaagttcg acaatctgac caaggccgag
4861  agaggcggcc tgagcgaact ggataaggcc ggcttcatca agagacagct ggtggaaacc
4921  cggcagatca caaagcacgt ggcacagatc ctggactccc ggatgaacac taagtacgac
4981  gagaacgaca aactgatccg ggaagtgaaa gtgatcaccc tgaagtccaa gctggtgtcc
5041  gatttccgga aggatttcca gttttacaaa gtgcgcgaga tcaacaacta ccaccacgcc
5101  cacgacgcct acctgaacgc cgtcgtggga accgccctga tcaaaaagta ccctaagctg
5161  gaaagcgagt tcgtgtacgg cgactacaag gtgtacgacg tgcggaagat gatcgccaag
```

-continued

```
5221   agcgagcagg aaatcggcaa ggctaccgcc aagtacttct tctacagcaa catcatgaac

5281   tttttcaaga ccgagattac cctggccaac ggcgagatcc ggaagcggcc tctgatcgag

5341   acaaacggcg aaacaggcga gatcgtgtgg gataagggcc gggactttgc caccgtgcgg

5401   aaagtgctgt ctatgcccca agtgaatatc gtgaaaaaga ccgaggtgca gacaggcggc

5461   ttcagcaaag agtctatcct gcccaagagg aacagcgaca agctgatcgc cagaaagaag

5521   gactgggacc ctaagaagta cggcggcttc gacagcccca ccgtggccta ttctgtgctg

5581   gtggtggcca aagtggaaaa gggcaagtcc aagaaactga agagtgtgaa agagctgctg

5641   gggatcacca tcatggaaag aagcagcttc gagaagaatc ccatcgactt tctggaagcc

5701   aagggctaca aagaagtgaa aaaggacctg atcatcaagc tgcctaagta ctccctgttc

5761   gagctggaaa acggccggaa gagaatgctg gcctctgccg gcgaactgca gaagggaaac

5821   gaactggccc tgccctccaa atatgtgaac ttcctgtacc tggccagcca ctatgagaag

5881   ctgaagggct cccccgagga taatgagcag aaacagctgt ttgtggaaca gcacaaacac

5941   tacctggacg agatcatcga gcagatcagc gagttctcca agagagtgat cctggccgac

6001   gctaatctgg acaaggtgct gagcgcctac aacaagcaca gagacaagcc tatcagagag

6061   caggccgaga atatcatcca cctgtttacc ctgaccaatc tgggagcccc tgccgccttc

6121   aagtactttg acaccaccat cgaccggaag aggtacacca gcaccaaaga ggtgctggac

6181   gccaccctga tccaccagag catcaccggc ctgtacgaga cacggatcga cctgtctcag

6241   ctgggaggcg acgcctatcc ctatgacgtg cccgattatg ccagcctggg cagcggctcc

6301   cccaagaaaa aacgcaaggt ggaagatcct aagaaaaagc ggaaagtgga cgtgtaacca

6361   ccacactgga ctagtggatc cgagctcggt accaagctta agtttaaacc gctgatcagc

6421   ctcgactgtg ccttctagtt gccagccatc tgttgtttgc ccctcccccg tgccttcctt

6481   gaccctggaa ggtgccactc ccactgtcct ttcctaataa aatgaggaaa ttgcatcgca

6541   ttgtctgagt aggtgtcatt ctattctggg gggtggggtg gggcaggaca gcaaggggga

6601   ggattgggaa gacaatagca ggcatgctgg ggatgcggtg ggctctatgg cttctgaggc

6661   ggaaagaacc agctggggct ctagggggta tccccacgcg ccctgtagcg gcgcattaag

6721   cgcggcgggt gtggtggtta cgcgcagcgt gaccgctaca cttgccagcg ccctagcgcc

6781   cgctcctttc gctttcttcc cttcctttct cgccacgttc gccggctttc cccgtcaagc

6841   tctaaatcgg gggctccctt tagggttccg atttagtgct ttacggcacc tcgaccccaa

6901   aaaacttgat tagggtgatg gttcacgtag tgggccatcg ccctgataga cggtttttcg

6961   ccctttgacg ttggagtcca cgttctttaa tagtggactc ttgttccaaa ctggaacaac

7021   actcaaccct atctcggtct attcttttga tttataaggg attttgccga tttcggccta

7081   ttggttaaaa aatgagctga tttaacaaaa atttaacgcg aattaattct gtggaatgtg

7141   tgtcagttag ggtgtggaaa gtccccaggc tccccagcag gcagaagtat gcaaagcatg

7201   catctcaatt agtcagcaac caggtgtgga aagtccccag gctccccagc aggcagaagt

7261   atgcaaagca tgcatctcaa ttagtcagca accatagtcc cgcccctaac tccgcccatc

7321   ccgcccctaa ctccgcccag ttccgcccat tctccgcccc atggctgact aatttttttt

7381   atttatgcag aggccgaggc cgcctctgcc tctgagctat tccagaagta gtgaggaggc

7441   ttttttggag gcctaggctt ttgcaaaaag ctcccgggag cttgtatatc cattttcgga

7501   tctgatcaag agacaggatg aggatcgttt cgcatgattg aacaagatgg attgcacgca

7561   ggttctccgg ccgcttgggt ggagaggcta ttcggctatg actgggcaca acagacaatc
```

-continued

```
7621   ggctgctctg atgccgccgt gttccggctg tcagcgcagg ggcgcccggt tctttttgtc
7681   aagaccgacc tgtccggtgc cctgaatgaa ctgcaggacg aggcagcgcg gctatcgtgg
7741   ctggccacga cgggcgttcc ttgcgcagct gtgctcgacg ttgtcactga agcgggaagg
7801   gactggctgc tattgggcga agtgccgggg caggatctcc tgtcatctca ccttgctcct
7861   gccgagaaag tatccatcat ggctgatgca atgcggcggc tgcatacgct tgatccggct
7921   acctgcccat tcgaccacca agcgaaacat cgcatcgagc gagcacgtac tcggatggaa
7981   gccggtcttg tcgatcagga tgatctggac gaagagcatc aggggctcgc gccagccgaa
8041   ctgttcgcca ggctcaaggc gcgcatgccc gacggcgagg atctcgtcgt gacccatggc
8101   gatgcctgct tgccgaatat catggtggaa aatggccgct tttctggatt catcgactgt
8161   ggccggctgg gtgtggcgga ccgctatcag gacatagcgt tggctacccg tgatattgct
8221   gaagagcttg gcggcgaatg ggctgaccgc ttcctcgtgc tttacggtat cgccgctccc
8281   gattcgcagc gcatcgcctt ctatcgcctt cttgacgagt tcttctgagc gggactctgg
8341   ggttcgaaat gaccgaccaa gcgacgccca acctgccatc acgagatttc gattccaccg
8401   ccgccttcta tgaaaggttg ggcttcggaa tcgttttccg ggacgccggc tggatgatcc
8461   tccagcgcgg ggatctcatg ctggagttct tcgcccaccc caacttgttt attgcagctt
8521   ataatggtta caaataaagc aatagcatca caaatttcac aaataaagca tttttttcac
8581   tgcattctag ttgtggtttg tccaaactca tcaatgtatc ttatcatgtc tgtataccgt
8641   cgacctctag ctagagcttg gcgtaatcat ggtcatagct gtttcctgtg tgaaattgtt
8701   atccgctcac aattccacac aacatacgag ccggaagcat aaagtgtaaa gcctggggtg
8761   cctaatgagt gagctaactc acattaattg cgttgcgctc actgcccgct ttccagtcgg
8821   gaaacctgtc gtgccagctg cattaatgaa tcggccaacg cgcggggaga ggcggtttgc
8881   gtattgggcg ctcttccgct tcctcgctca ctgactcgct gcgctcggtc gttcggctgc
8941   ggcgagcggt atcagctcac tcaaaggcgg taatacggtt atccacagaa tcaggggata
9001   acgcaggaaa gaacatgtga gcaaaaggcc agcaaaaggc caggaaccgt aaaaaggccg
9061   cgttgctggc gtttttccat aggctccgcc cccctgacga gcatcacaaa aatcgacgct
9121   caagtcagag gtggcgaaac ccgacaggac tataaagata ccaggcgttt ccccctggaa
9181   gctccctcgt gcgctctcct gttccgaccc tgccgcttac cggatacctg tccgcctttc
9241   tcccttcggg aagcgtggcg ctttctcata gctcacgctg taggtatctc agttcggtgt
9301   aggtcgttcg ctccaagctg ggctgtgtgc acgaaccccc cgttcagccc gaccgctgcg
9361   ccttatccgg taactatcgt cttgagtcca acccggtaag acacgactta tcgccactgg
9421   cagcagccac tggtaacagg attagcagag cgaggtatgt aggcggtgct acagagttct
9481   tgaagtggtg gcctaactac ggctacacta gaagaacagt atttggtatc tgcgctctgc
9541   tgaagccagt taccttcgga aaaagagttg gtagctcttg atccggcaaa caaaccaccg
9601   ctggtagcgg tttttttgtt tgcaagcagc agattacgcg cagaaaaaaa ggatctcaag
9661   aagatccttt gatcttttct acggggtctg acgctcagtg gaacgaaaac tcacgttaag
9721   ggattttggt catgagatta tcaaaaagga tcttcaccta gatcctttta aattaaaaat
9781   gaagttttaa atcaatctaa agtatatatg agtaaacttg gtctgacagt taccaatgct
9841   taatcagtga ggcacctatc tcagcgatct gtctatttcg ttcatccata gttgcctgac
9901   tccccgtcgt gtagataact acgatacggg agggcttacc atctggcccc agtgctgcaa
```

-continued

```
 9961  tgataccgcg agacccacgc tcaccggctc cagatttatc agcaataaac cagccagccg
10021  gaagggccga gcgcagaagt ggtcctgcaa ctttatccgc ctccatccag tctattaatt
10081  gttgccggga agctagagta agtagttcgc cagttaatag tttgcgcaac gttgttgcca
10141  ttgctacagg catcgtggtg tcacgctcgt cgtttggtat ggcttcattc agctccggtt
10201  cccaacgatc aaggcgagtt acatgatccc ccatgttgtg caaaaaagcg gttagctcct
10261  tcggtcctcc gatcgttgtc agaagtaagt tggccgcagt gttatcactc atggttatgg
10321  cagcactgca taattctctt actgtcatgc catccgtaag atgcttttct gtgactggtg
10381  agtactcaac caagtcattc tgagaatagt gtatgcggcg accgagttgc tcttgcccgg
10441  cgtcaatacg ggataatacc gcgccacata gcagaacttt aaaagtgctc atcattggaa
10501  aacgttcttc ggggcgaaaa ctctcaagga tcttaccgct gttgagatcc agttcgatgt
10561  aacccactcg tgcacccaac tgatcttcag catcttttac tttcaccagc gtttctgggt
10621  gagcaaaaac aggaaggcaa aatgccgcaa aaaagggaat aagggcgaca cggaaatgtt
10681  gaatactcat actcttcctt tttcaatatt attgaagcat ttatcagggt tattgtctca
10741  tgagcggata catatttgaa tgtatttaga aaaataaaca aataggggtt ccgcgcacat
10801  ttccccgaaa agtgccacct gacgtc
```

pcDNA3.1_ADAR2(E488Q)_XTEN_control (SEQ ID NO: 30).

```
LOCUS             Exported 6722 bp ds-DNA circular
DEFINITION        synthetic circular DNA
SOURCE            synthetic DNA construct
ORGANISM          synthetic DNA construct
REFERENCE         1 (bases 1 to 6722)
FEATURES          Location/Qualifiers
source            1 . . . 6722
                  /organism = "synthetic DNA construct"
                  /mol_type = "other DNA"
enhancer          235 . . . 614
                  /label = CMV enhancer
                  /note = "human cytomegalovirus immediate early enhancer"
promoter          615 . . . 818
                  /label = CMV promoter
                  /note = "human cytomegalovirus (CMV) immediate early
                  promoter"
promoter          863 . . . 881
                  /label = T7 promoter
                  /note = "promoter for bacteriophage T7 RNA polymerase"
misc_feature      927 . . . 954
                  /label = Homology 1_pCDNA3.1
primer_bind       954 . . . 976
                  /label = ADARB1_1cv2_fw
primer_bind       955 . . . 976
                  /label = ADAR2CD-Cas9_HindIII_F
primer_bin        958 . . . 983
                  /label = AXC_1cv2_EFS-NS_fw
primer_bind       960 . . . 983
                  /label = Adar_out_forward_1v2
CDS               961 . . . 2100
                  /codon_start = 1
                  /label = ADARB1(E488Q)_Catalytic Domain
```

```
/translation = "MLADAVSRLVLGKFGDLTDNFSSPHARRKVLAGWMTTGTDVKDA
KVISVSTGTKCINGEYMSDRGLALNDCHAEIISRRSLLRFLYTQLELYLNNKDDQKRSI
FQKSERGGFRLKENVQFHLYISTSPCGDARIFSPHEPILEEPADRHPNRKARGQLRTKI
ESGQGTIPVRSNASIQTWDGVLQGERLLTMSCSDKIARWNVVGIQGSLLSIFVEPIYFS
SIILGSLYHGDHLSRAMYQRISNIEDLPPLYTLNKPLLSGISNAEARQPGKAPNFSVNW
TVGDSAIEVINATTGKDELGRASRLCKHALYCRWMRVHGKVPSHLLRSKITKPNVYHES
KLAAKEYQAAKARLFTAFIKAGLGAWVEKPTEQDQFSLTP"

primer_bind          1324 . . . 1346
                     /label = E488Q_ADAR2_Mut_seq

primer_bind          complement(1426 . . . 1447)
                     /label = E488Q_Mut_Classic_R

primer_bind          1440 . . . 1478
                     /label = E488Q_Mutagenesis_F

primer_bind          complement(1440 . . . 1478)
                     /label = E488Q_Mutagenesis_R

primer_bind          1448 . . . 1472
                     /label = E488Q_Mut_Classic_F

CDS                  2101 . . . 2148
                     /codon_start = 1
                     /label = XTEN
                     /translation = "SGSETPGTSESATPES"

primer_bind          complement(2129 . . . 2148)
                     /label = ADAR2_CD_Inverse_R

primer_bind          2149 . . . 2170
                     /label = ADAR2_CD_Inverse_F

CDS                  2152 . . . 2178
                     /codon_start = 1
                     /product = "HA (human influenza hemagglutinin) epitope tag"
                     /label = HA
                     /translation = "YPYDVPDYA"

primer_bind          complement(2170 . . . 2192)
                     /label = AXC_NLSout_NESin_R

primer_bind          complement(2170 . . . 2192)
                     /label = Primer 1

CDS                  2197 . . . 2217
                     /codon_start = 1
                     /product = "nuclear localization signal of SV40 large T
                     antigen"
                     /label = SV40 NLS
                     /translation = "PKKKRKV"

CDS                  2224 . . . 2244
                     /codon_start = 1
                     /product = "nuclear localization signal of SV40 large T
                     antigen"
                     /label = SV40 NLS
                     /translation = "PKKKRKV"

primer_bind          2245 . . . 2267
                     /label = AXC_NLSout_NESin_F

misc_feature         2254 . . . 2288
                     /label = Homology 2_pCDNA3.1

polyA_signal         2322 . . . 2546
                     /label = bGH poly(A) signal
                     /note = "bovine growth hormone polyadenylation signal"

rep_origin           2592 . . . 3020
                     /direction = RIGHT
                     /label = f1 ori
                     /note = "f1 bacteriophage origin of replication; arrow
                     indicates direction of (+) strand synthesis"

promoter             3034 . . . 3363
                     /label = SV40 promoter
```

```
                         /note = "SV40 enhancer and early promoter"

rep_origin               3214 . . . 3349
                         /label = SV40 ori
                         /note = "SV40 origin of replication"

CDS                      3430 . . . 4224
                         /codon_start = 1
                         /gene = "aph(3')-II (or nptII)"
                         /product = "aminoglycoside phosphotransferase from Tn5"
                         /label = NeoR/KanR
                         /note = "confers resistance to neomycin, kanamycin, and G418
                         (Geneticin(R))"

/translation = "MIEQDGLHAGSPAAWVERLFGYDWAQQTIGCSDAAVFRLSAQGRP
VLFVKTDLSGALNELQDEAARLSWLATTGVPCAAVLDVVTEAGRDWLLLGEVPGQDLLS
SHLAPAEKVSIMADAMRRLHTLDPATCPFDHQAKHRIERARTRMEAGLVDQDDLDEEHQ
GLAPAELFARLKARMPDGEDLVVTHGDACLPNIMVENGRFSGFIDCGRLGVADRYQDIA
LATRDIAEELGGEWADRFLVLYGIAAPDSQRIAFYRLLDEFF"

polyA_signal             4398 . . . 4519
                         /label = SV40 poly(A) signal
                         /note = "SV40 polyadenylation signal"

primer_bind              complement(4568 . . . 4584)
                         /label = M13 rev
                         /note = "common sequencing primer, one of multiple similar
                         variants"

protein_bind             4592 . . . 4608
                         /label = lac operator
                         /bound_moiety = "lac repressor encoded by lacI"
                         /note = "The lac repressor binds to the lac operator to
                         inhibit transcription in E. coli. This inhibition can be
                         relieved by adding lactose or
                         isopropyl-beta-D-thiogalactopyranoside (IPTG)."

promoter                 complement(4616 . . . 4646)
                         /label = lac promoter
                         /note = "promoter for the E. coli lac operon"

protein_bind             4661 . . . 4682
                         /label = CAP binding site
                         /bound_moiety = "E. coli catabolite activator protein"
                         /note = "CAP binding activates transcription in the presence
                         of cAMP."

rep_origin               complement(4970 . . . 5555)
                         /direction = LEFT
                         /label = ori
                         /note = "high-copy-number ColE1/pMB1/pBR322/pUC origin of
                         replication"

CDS                      complement(5726 . . . 6586)
                         /codon_start = 1
                         /gene = "bla"
                         /product = "beta-lactamase"
                         /label = AmpR
                         /note = "confers resistance to ampicillin, carbenicillin, and
                         related antibiotics"

/translation = "MSIQHFRVALIPFFAAFCLPVFAHPETLVKVKDAEDQLGARVGYI
ELDLNSGKILESFRPEERFPMMSTFKVLLCGAVLSRIDAGQEQLGRRIHYSQNDLVEYS
PVTEKHLTDGMTVRELCSAAITMSDNTAANLLLTTIGGPKELTAFLHNMGDHVTRLDRW
EPELNEAIPNDERDTTMPVAMATTLRKLLTGELLTLASRQQLIDWMEADKVAGPLLRSA
LPAGWFIADKSGAGERGSRGIIAALGPDGKPSRIVVIYTTGSQATMDERNRQIAEIGAS
LIKHW"

promoter                 complement(6587 . . . 6691)
                         /gene = "bla"
                         /label = AmpR promoter

ORIGIN
      1   gacggatcgg gagatctccc gatcccctat ggtgcactct cagtacaatc tgctctgatg

     61   ccgcatagtt aagccagtat ctgctccctg cttgtgtgtt ggaggtcgct gagtagtgcg

    121   cgagcaaaat ttaagctaca acaaggcaag gcttgaccga caattgcatg aagaatctgc
```

```
181   ttagggttag gcgttttgcg ctgcttcgcg atgtacgggc cagatatacg cgttgacatt
241   gattattgac tagttattaa tagtaatcaa ttacggggtc attagttcat agcccatata
301   tggagttccg cgttacataa cttacggtaa atggcccgcc tggctgaccg cccaacgacc
361   cccgcccatt gacgtcaata atgacgtatg ttcccatagt aacgccaata gggactttcc
421   attgacgtca atgggtggag tatttacggt aaactgccca cttggcagta catcaagtgt
481   atcatatgcc aagtacgccc cctattgacg tcaatgacgg taaatggccc gcctggcatt
541   atgcccagta catgacctta tgggactttc ctacttggca gtacatctac gtattagtca
601   tcgctattac catggtgatg cggttttggc agtacatcaa tgggcgtgga tagcggtttg
661   actcacgggg atttccaagt ctccacccca ttgacgtcaa tgggagtttg ttttggcacc
721   aaaatcaacg ggactttcca aaatgtcgta acaactccgc cccattgacg caaatgggcg
781   gtaggcgtgt acggtgggag gtctatataa gcagagctct ctggctaact agagaaccca
841   ctgcttactg gcttatcgaa attaatacga ctcactatag ggagacccaa gctggctagc
901   gtttaaacgg gccctctaga ctcgagcggc cgccactgtg ctggatatct gcagagaacc
961   atgttagctg acgctgtctc acgcctggtc ctgggtaagt ttggtgacct gaccgacaac
1021  ttctcctccc ctcacgctcg cagaaaagtg ctggctggag tcgtcatgac aacaggcaca
1081  gatgttaaag atgccaaggt gataagtgtt tctacaggaa caaaatgtat taatggtgaa
1141  tacatgagtg atcgtggcct tgcattaaat gactgccatg cagaaataat atctcggaga
1201  tccttgctca gatttcttta tacacaactt gagctttact taaataacaa agatgatcaa
1261  aaaagatcca tctttcagaa atcagagcga gggggggttta ggctgaagga gaatgtccag
1321  tttcatctgt acatcagcac ctctccctgt ggagatgcca gaatcttctc accacatgag
1381  ccaatcctgg aagaaccagc agatagacac ccaaatcgta aagcaagagg acagctacgg
1441  accaaaatag agtctggtca ggggacgatt ccagtgcgct ccaatgcgag catccaaacg
1501  tgggacgggg tgctgcaagg ggagcggctg ctcaccatgt cctgcagtga caagattgca
1561  cgctggaacg tggtgggcat ccagggatcc ctgctcagca ttttcgtgga gcccatttac
1621  ttctcgagca tcatcctggg cagcctttac cacggggacc acctttccag ggccatgtac
1681  cagcggatct ccaacataga ggacctgcca cctctctaca ccctcaacaa gcctttgctc
1741  agtggcatca gcaatgcaga agcacggcag ccagggaagg cccccaactt cagtgtcaac
1801  tggacggtag gcgactccgc tattgaggtc atcaacgcca cgactgggaa ggatgagctg
1861  ggccgcgcgt cccgcctgtg taagcacgcg ttgtactgtc gctggatgcg tgtgcacggc
1921  aaggttccct cccacttact acgctccaag attaccaagc ccaacgtgta ccatgagtcc
1981  aagctggcgg caaaggagta ccaggccgcc aaggcgcgtc tgttcacagc cttcatcaag
2041  gcggggctgg gggcctgggt ggagaagccc accgagcagg accagttctc actcacgccc
2101  agtggaagtg agacaccggg aacctcagag agcgccacgc cagaaagcgc ctatccctat
2161  gacgtgcccg attatgccag cctgggcagc ggctccccca agaaaaaacg caaggtggaa
2221  gatcctaaga aaaagcggaa agtggacgtg taaccaccac actggactag tggatccgag
2281  ctcggtacca agcttaagtt taaaccgctg atcagcctcg actgtgcctt ctagttgcca
2341  gccatctgtt gtttgcccct cccccgtgcc ttccttgacc ctggaaggtg ccactcccac
2401  tgtcctttcc taataaaatg aggaaattgc atcgcattgt ctgagtaggt gtcattctat
2461  tctggggggt ggggtggggc aggacagcaa gggggaggat tgggaagaca atagcaggca
2521  tgctggggat gcggtgggct ctatggcttc tgaggcggaa agaaccagct ggggctctag
```

```
2581  ggggtatccc cacgcgccct gtagcggcgc attaagcgcg gcgggtgtgg tggttacgcg
2641  cagcgtgacc gctacacttg ccagcgccct agcgcccgct cctttcgctt tcttcccttc
2701  ctttctcgcc acgttcgccg gctttccccg tcaagctcta aatcgggggc tccctttagg
2761  gttccgattt agtgctttac ggcacctcga ccccaaaaaa cttgattagg gtgatggttc
2821  acgtagtggg ccatcgccct gatagacggt ttttcgccct ttgacgttgg agtccacgtt
2881  ctttaatagt ggactcttgt tccaaactgg aacaacactc aaccctatct cggtctattc
2941  ttttgattta taagggattt tgccgatttc ggcctattgg ttaaaaaatg agctgattta
3001  acaaaaattt aacgcgaatt aattctgtgg aatgtgtgtc agttagggtg tggaaagtcc
3061  ccaggctccc cagcaggcag aagtatgcaa agcatgcatc tcaattagtc agcaaccagg
3121  tgtggaaagt ccccaggctc cccagcaggc agaagtatgc aaagcatgca tctcaattag
3181  tcagcaacca tagtcccgcc cctaactccg cccatcccgc ccctaactcc gcccagttcc
3241  gcccattctc cgccccatgg ctgactaatt ttttttattt atgcagaggc cgaggccgcc
3301  tctgcctctg agctattcca gaagtagtga ggaggctttt ttggaggcct aggcttttgc
3361  aaaaagctcc cgggagcttg tatatccatt ttcggatctg atcaagagac aggatgagga
3421  tcgtttcgca tgattgaaca agatggattg cacgcaggtt ctccggccgc ttgggtggag
3481  aggctattcg gctatgactg ggcacaacag acaatcggct gctctgatgc cgccgtgttc
3541  cggctgtcag cgcaggggcg cccggttctt tttgtcaaga ccgacctgtc cggtgccctg
3601  aatgaactgc aggacgaggc agcgcggcta tcgtggctgg ccacgacggg cgttccttgc
3661  gcagctgtgc tcgacgttgt cactgaagcg ggaagggact ggctgctatt gggcgaagtg
3721  ccggggcagg atctcctgtc atctcacctt gctcctgccg agaaagtatc catcatggct
3781  gatgcaatgc ggcggctgca tacgcttgat ccggctacct gcccattcga ccaccaagcg
3841  aaacatcgca tcgagcgagc acgtactcgg atggaagccg gtcttgtcga tcaggatgat
3901  ctggacgaag agcatcaggg gctcgcgcca gccgaactgt tcgccaggct caaggcgcgc
3961  atgcccgacg gcgaggatct cgtcgtgacc catggcgatg cctgcttgcc gaatatcatg
4021  gtggaaaatg gccgcttttc tggattcatc gactgtggcc ggctgggtgt ggcggaccgc
4081  tatcaggaca tagcgttggc tacccgtgat attgctgaag agcttggcgg cgaatgggct
4141  gaccgcttcc tcgtgcttta cggtatcgcc gctcccgatt cgcagcgcat cgccttctat
4201  cgccttcttg acgagttctt ctgagcggga ctctggggtt cgaaatgacc gaccaagcga
4261  cgcccaacct gccatcacga gatttcgatt ccaccgccgc cttctatgaa aggttgggct
4321  tcggaatcgt tttccgggac gccggctgga tgatcctcca gcgcggggat ctcatgctgg
4381  agttcttcgc ccaccccaac ttgtttattg cagcttataa tggttacaaa taaagcaata
4441  gcatcacaaa tttcacaaat aaagcatttt tttcactgca ttctagttgt ggtttgtcca
4501  aactcatcaa tgtatcttat catgtctgta taccgtcgac ctctagctag agcttggcgt
4561  aatcatggtc atagctgttt cctgtgtgaa attgttatcc gctcacaatt ccacacaaca
4621  tacgagccgg aagcataaag tgtaaagcct ggggtgccta atgagtgagc taactcacat
4681  taattgcgtt gcgctcactg cccgctttcc agtcgggaaa cctgtcgtgc cagctgcatt
4741  aatgaatcgg ccaacgcgcg gggagaggcg gtttgcgtat tgggcgctct tccgcttcct
4801  cgctcactga ctcgctgcgc tcggtcgttc ggctgcggcg agcggtatca gctcactcaa
4861  aggcggtaat acggttatcc acagaatcag gggataacgc aggaaagaac atgtgagcaa
```

-continued

```
4921    aaggccagca aaaggccagg aaccgtaaaa aggccgcgtt gctggcgttt ttccataggc
4981    tccgcccccc tgacgagcat cacaaaaatc gacgctcaag tcagaggtgg cgaaacccga
5041    caggactata aagataccag gcgtttcccc ctggaagctc cctcgtgcgc tctcctgttc
5101    cgaccctgcc gcttaccgga tacctgtccg cctttctccc ttcgggaagc gtggcgcttt
5161    ctcatagctc acgctgtagg tatctcagtt cggtgtaggt cgttcgctcc aagctgggct
5221    gtgtgcacga accccccgtt cagcccgacc gctgcgcctt atccggtaac tatcgtcttg
5281    agtccaaccc ggtaagacac gacttatcgc cactggcagc agccactggt aacaggatta
5341    gcagagcgag gtatgtaggc ggtgctacag agttcttgaa gtggtggcct aactacggct
5401    acactagaag aacagtattt ggtatctgcg ctctgctgaa gccagttacc ttcggaaaaa
5461    gagttggtag ctcttgatcc ggcaaacaaa ccaccgctgg tagcggtttt tttgtttgca
5521    agcagcagat tacgcgcaga aaaaaaggat ctcaagaaga tcctttgatc ttttctacgg
5581    ggtctgacgc tcagtggaac gaaaactcac gttaagggat tttggtcatg agattatcaa
5641    aaaggatctt cacctagatc cttttaaatt aaaaatgaag ttttaaatca atctaaagta
5701    tatatgagta aacttggtct gacagttacc aatgcttaat cagtgaggca cctatctcag
5761    cgatctgtct atttcgttca tccatagttg cctgactccc cgtcgtgtag ataactacga
5821    tacgggaggg cttaccatct ggccccagtg ctgcaatgat accgcgagac ccacgctcac
5881    cggctccaga tttatcagca ataaaccagc cagccggaag ggccgagcgc agaagtggtc
5941    ctgcaacttt atccgcctcc atccagtcta ttaattgttg ccgggaagct agagtaagta
6001    gttcgccagt taatagtttg cgcaacgttg ttgccattgc tacaggcatc gtggtgtcac
6061    gctcgtcgtt tggtatggct tcattcagct ccggttccca acgatcaagg cgagttacat
6121    gatcccccat gttgtgcaaa aaagcggtta gctccttcgg tcctccgatc gttgtcagaa
6181    gtaagttggc cgcagtgtta tcactcatgg ttatggcagc actgcataat tctcttactg
6241    tcatgccatc cgtaagatgc ttttctgtga ctggtgagta ctcaaccaag tcattctgag
6301    aatagtgtat gcggcgaccg agttgctctt gcccggcgtc aatacgggat aataccgcgc
6361    cacatagcag aactttaaaa gtgctcatca ttggaaaacg ttcttcgggg cgaaaactct
6421    caaggatctt accgctgttg agatccagtt cgatgtaacc cactcgtgca cccaactgat
6481    cttcagcatc ttttactttc accagcgttt ctgggtgagc aaaaacagga aggcaaaatg
6541    ccgcaaaaaa gggaataagg gcgacacgga aatgttgaat actcatactc ttcctttttc
6601    aatattattg aagcatttat cagggttatt gtctcatgag cggatacata tttgaatgta
6661    tttagaaaaa taaacaaata ggggttccgc gcacatttcc ccgaaaagtg ccacctgacg
6721    tc
```

50 bp GFP mCherry extension (SEQ ID NO: 31).

| | |
|---|---|
| LOCUS | Exported 4951 bp ds-DNA circular |
| DEFINITION | synthetic circular DNA |
| SOURCE | synthetic DNA construct |
| ORGANISM | recombinant plasmid |
| REFERENCE | 1 (bases 1 to 4951) |
| FEATURES | Location/Qualifiers |
| source | 1 . . . 4951<br>/organism = "recombinant plasmid"<br>/mol_type = "other DNA" |

```
primer_bind             1 . . . 40
                        /label = EF1a_Gibson_F

primer_bind             1 . . . 20
                        /label = Primer 2

misc_feature            1 . . . 7
                        /label = sgRNA scaffold_termination

promoter                21 . . . 566
                        /label = EF1a promoter

primer_bind             complement(554 . . . 591)
                        /label = EF1a_Gibson_R

CDS                     572 . . . 1282
                        /codon_start = 1
                        /product = "monomeric derivative of DsRed fluorescent protein
                        (Shaner et al., 2004)"
                        /label = mCherry
                        /note = "mammalian codon-optimized"

/translation = "MVSKGEEDNMAIIKEFMRFKVHMEGSVNGHEFEIEGEGEGRPYEG
TQTAKLKVTKGGPLPFAWDILSPQFMYGSKAYVKHPADIPDYLKLSFPEGFKWERVMNF
EDGGVVTVTQDSSLQDGEFIYKVKLRGTNFPSDGPVMQKKTMGWEASSERMYPEDGALK
GEIKQRLKLKDGGHYDAEVKTTYKAKKPVQLPGAYNVNIKLDITSHNEDYTIVEQYERA
EGRHSTGGMDELYK"

primer_bind             572 . . . 591
                        /label = mCherry_BGH_F

primer_bind             complement(1259 . . . 1306)
                        /label = Primer 1

primer_bind             complement(1259 . . . 1286)
                        /label = mCherry_P2A_Gib_R

primer_bind             complement(1259 . . . 1282)
                        /label = mCherry_HindIII_R

misc_feature            1283 . . . 1306
                        /label = Gibson Overlap

primer_bind             1283 . . . 1301
                        /label = mCherry_P2A_Gib_F

polyA_signal            1330 . . . 1554
                        /label = bGH poly(A) signal
                        /note = "bovine growth hormone polyadenylation signal"

primer_bind             complement(1535 . . . 1573)
                        /label = mCherry_BGH_Gib_R

primer_bind             complement(1535 . . . 1554)
                        /label = mCherry_BGH_R

primer_bind             complement(1536 . . . 1555)
                        /label = bGH_NotI_R

primer_bind             complement(1558 . . . 1573)
                        /label = SK primer
                        /note = "common sequencing primer, one of multiple similar
                        variants"

primer_bind             complement(1608 . . . 1627)
                        /label = T3

primer_bind             complement(1645 . . . 1665)
                        /label = M13-rev

misc_binding            complement(1671 . . . 1693)
                        /label = LacO

promoter                complement(1698 . . . 1727)
                        /label = lac

rep_origin              complement(2033 . . . 2661)
                        /direction = LEFT
```

```
                         /label = ColE1 origin

CDS                      complement(2813 . . . 3472)
                         /label = AmpR

promoter                 complement(3712 . . . 3740)
                         /label = Amp prom

rep_origin               3811 . . . 4251
                         /direction = RIGHT
                         /label = F1 ori

CDS                      complement(4258 . . . 4326)
                         /label = LacZ alpha

primer_bind              4397 . . . 4414
                         /label = M13-fwd

primer_bind              4424 . . . 4443
                         /label = T7

promoter                 4555 . . . 4817
                         /label = U6 promoter

primer_bind              4798 . . . 4864
                         /label = no_spacer_universal_scaff_f

primer_bind              4803 . . . 4862
                         /label = 50 bp_GFP_F

primer_bind              4803 . . . 4862
                         /label = 50 bp_GFP_revcomp_F(+G)

primer_bind              4803 . . . 4862
                         /label = 10 bp_GFP_spacer_F

primer_bind              4803 . . . 4862
                         /label = 30 bp_GFP_spacer_F

primer_bind              4803 . . . 4862
                         /label = 70 bp_GFP_spacer_F

primer_bind              4803 . . . 4862
                         /label = ACTB_3_ext_CgRNA_For

primer_bind              complement(4803 . . . 4817)
                         /label = Primer 3

primer_bind              complement(4803 . . . 4817)
                         /label = extension_gibson_R

misc_feature             4818 . . . 4838
                         /label = 50 bp_EGFP_targeting_spacer

misc_feature             4839 . . . 4924
                         /label = sgRNA scaffold

primer_bind              4839 . . . 4865
                         /label = scaffold_3_ext_template_For

primer_bind              complement(4912 . . . 4930)
                         /label = scaffold_3_ext_template_Rev

primer_bind              complement(join(4913 . . . 4951, 1 . . . 20))
                         /label = eGFP_3_ext_R

primer_bind              complement(join(4913 . . . 4951, 1 . . . 20))
                         /label = gfp_3_extension_revcomp

primer_bind              complement(join(4913 . . . 4951, 1 . . . 20))
                         /label = ACTB_3_ext_AgRNA_Rev

misc_feature             4925 . . . 4930
                         /label = Linker

misc_feature             4931 . . . 4951
                         /label = EGFP_extension

ORIGIN
```

-continued

```
1     tttttttcct gcagcccggg aaggatctgc gatcgctccg gtgcccgtca gtgggcagag
61    cgcacatcgc ccacagtccc cgagaagttg gggggagggg tcggcaattg aacgggtgcc
121   tagagaaggt ggcgcggggt aaactgggaa agtgatgtcg tgtactggct ccgccttttt
181   cccgagggtg ggggagaacc gtatataagt gcagtagtcg ccgtgaacgt tctttttcgc
241   aacgggtttg ccgccagaac acagctgaag cttcgagggg ctcgcatctc tccttcacgc
301   gcccgcccgcc ctacctgagg ccgccatcca cgccggttga gtcgcgttct gccgcctccc
361   gcctgtggtg cctcctgaac tgcgtccgcc gtctaggtaa gtttaaagct caggtcgaga
421   ccgggccttt gtccggcgct cccttggagc ctacctagac tcagccggct ctccacgctt
481   tgcctgaccc tgcttgctca actctacgtc tttgtttcgt tttctgttct gcgccgttac
541   agatccaagc tgtgaccggc gcctacgcta gatggtgagc aagggcgagg aggataacat
601   ggccatcatc aaggagttca tgcgcttcaa ggtgcacatg gagggctccg tgaacggcca
661   cgagttcgag atcgagggcg agggcgaggg ccgcccctac gagggcaccc agaccgccaa
721   gctgaaggtg accaagggtg gccccctgcc cttcgcctgg gacatcctgt cccctcagtt
781   catgtacggc tccaaggcct acgtgaagca ccccgccgac atccccgact acttgaagct
841   gtccttcccc gagggcttca agtgggagcg cgtgatgaac ttcgaggacg gcggcgtggt
901   gaccgtgacc caggactcct ccctgcagga cggcgagttc atctacaagg tgaagctgcg
961   cggcaccaac ttcccctccg acggccccgt aatgcagaag aagaccatgg gctgggaggc
1021  ctcctccgag cggatgtacc ccgaggacgg cgccctgaag ggcgagatca agcagaggct
1081  gaagctgaag gacggcggcc actacgacgc tgaggtcaag accacctaca aggccaagaa
1141  gcccgtgcag ctgcccggcg cctacaacgt caacatcaag ttggacatca cctcccacaa
1201  cgaggactac accatcgtgg aacagtacga acgcgccgag ggccgccact ccaccggcgg
1261  catggacgag ctgtacaagt aatccgagct cggtaccaag cttaagttta aaccgctgat
1321  cagcctcgac tgtgccttct agttgccagc catctgttgt ttgcccctcc cccgtgcctt
1381  ccttgaccct ggaaggtgcc actcccactg tcctttccta ataaaatgag gaaattgcat
1441  cgcattgtct gagtaggtgt cattctattc tggggggtgg ggtggggcag gacagcaagg
1501  gggaggattg ggaagacaat agcaggcatg ctggggatgc ggtgggctct atgggggatc
1561  cactagttct agagcggccg ccaccgcggt ggagctccag cttttgttcc ctttagtgag
1621  ggttaattgc gcgcttggcg taatcatggt catagctgtt tcctgtgtga aattgttatc
1681  cgctcacaat tccacacaac atacgagccg gaagcataaa gtgtaaagcc tggggtgcct
1741  aatgagtgag ctaactcaca ttaattgcgt tgcgctcact gcccgctttc cagtcgggaa
1801  acctgtcgtg ccagctgcat taatgaatcg gccaacgcgc ggggagaggc ggtttgcgta
1861  ttgggcgctc ttccgcttcc tcgctcactg actcgctgcg ctcggtcgtt cggctgcggc
1921  gagcggtatc agctcactca aaggcggtaa tacggttatc cacagaatca ggggataacg
1981  caggaaagaa catgtgagca aaaggccagc aaaaggccag gaaccgtaaa aaggccgcgt
2041  tgctggcgtt tttccatagg ctccgccccc ctgacgagca tcacaaaaat cgacgctcaa
2101  gtcagaggtg gcgaaacccg acaggactat aaagatacca ggcgtttccc cctggaagct
2161  ccctcgtgcg ctctcctgtt ccgaccctgc cgcttaccgg atacctgtcc gcctttctcc
2221  cttcgggaag cgtggcgctt tctcatagct cacgctgtag gtatctcagt tcggtgtagg
2281  tcgttcgctc caagctgggc tgtgtgcacg aaccccccgt tcagcccgac cgctgcgcct
2341  tatccggtaa ctatcgtctt gagtccaacc cggtaagaca cgacttatcg ccactggcag
```

```
2401   cagccactgg taacaggatt agcagagcga ggtatgtagg cggtgctaca gagttcttga
2461   agtggtggcc taactacggc tacactagaa ggacagtatt tggtatctgc gctctgctga
2521   agccagttac cttcggaaaa agagttggta gctcttgatc cggcaaacaa accaccgctg
2581   gtagcggtgg tttttttgtt tgcaagcagc agattacgcg cagaaaaaaa ggatctcaag
2641   aagatccttt gatcttttct acggggtctg acgctcagtg gaacgaaaac tcacgttaag
2701   ggattttggt catgagatta tcaaaaagga tcttcaccta gatcctttta aattaaaaat
2761   gaagttttaa atcaatctaa agtatatatg agtaaacttg gtctgacagt taccaatgct
2821   taatcagtga ggcacctatc tcagcgatct gtctatttcg ttcatccata gttgcctgac
2881   tccccgtcgt gtagataact acgatacggg agggcttacc atctggcccc agtgctgcaa
2941   tgataccgcg agacccacgc tcaccggctc cagatttatc agcaataaac cagccagccg
3001   gaagggccga gcgcagaagt ggtcctgcaa ctttatccgc ctccatccag tctattaatt
3061   gttgccggga agctagagta agtagttcgc cagttaatag tttgcgcaac gttgttgcca
3121   ttgctacagg catcgtggtg tcacgctcgt cgtttggtat ggcttcattc agctccggtt
3181   cccaacgatc aaggcgagtt acatgatccc ccatgttgtg caaaaaagcg gttagctcct
3241   tcggtcctcc gatcgttgtc agaagtaagt tggccgcagt gttatcactc atggttatgg
3301   cagcactgca taattctctt actgtcatgc catccgtaag atgcttttct gtgactggtg
3361   agtactcaac caagtcattc tgagaatagt gtatgcggcg accgagttgc tcttgcccgg
3421   cgtcaatacg ggataatacc gcgccacata gcagaacttt aaaagtgctc atcattggaa
3481   aacgttcttc ggggcgaaaa ctctcaagga tcttaccgct gttgagatcc agttcgatgt
3541   aacccactcg tgcacccaac tgatcttcag catcttttac tttcaccagc gtttctgggt
3601   gagcaaaaac aggaaggcaa aatgccgcaa aaaagggaat aagggcgaca cggaaatgtt
3661   gaatactcat actcttcctt tttcaatatt attgaagcat ttatcagggt tattgtctca
3721   tgagcggata catatttgaa tgtatttaga aaaataaaca aataggggtt ccgcgcacat
3781   ttccccgaaa agtgccacct aaattgtaag cgttaatatt ttgttaaaat tcgcgttaaa
3841   tttttgttaa atcagctcat tttttaacca ataggccgaa atcggcaaaa tcccttataa
3901   atcaaaagaa tagaccgaga tagggttgag tgttgttcca gtttggaaca agagtccact
3961   attaaagaac gtggactcca acgtcaaagg gcgaaaaacc gtctatcagg gcgatggccc
4021   actacgtgaa ccatcaccct aatcaagttt tttggggtcg aggtgccgta aagcactaaa
4081   tcggaaccct aaagggagcc cccgatttag agcttgacgg ggaaagccgg cgaacgtggc
4141   gagaaaggaa gggaagaaag cgaaaggagc gggcgctagg gcgctggcaa gtgtagcggt
4201   cacgctgcgc gtaaccacca cacccgccgc gcttaatgcg ccgctacagg gcgcgtccca
4261   ttcgccattc aggctgcgca actgttggga agggcgatcg gtgcgggcct cttcgctatt
4321   acgccagctg gcgaaagggg gatgtgctgc aaggcgatta agttgggtaa cgccagggtt
4381   ttcccagtca cgacgttgta aaacgacggc cagtgagcgc gcgtaatacg actcactata
4441   gggcgaattg ggtaccgggc ccccctcga ggtcgacggt atcgataagc ttgatatcgt
4501   gtacaaaaaa gcaggcttta aaggaaccaa ttcagtcgac tggatccggt accaaggtcg
4561   ggcaggaaga gggcctattt cccatgattc cttcatattt gcatatacga tacaaggctg
4621   ttagagagat aattagaatt aatttgactg taaacacaaa gatattagta caaaatacgt
4681   gacgtagaaa gtaataattt cttgggtagt ttgcagtttt aaaattatgt tttaaaatgg
```

-continued

```
4741    actatcatat gcttaccgta acttgaaagt atttcgattt cttggcttta tatatcttgt

4801    ggaaaggacg aaacaccgaa gtcatgccgt ttcatgtggt ttaagagcta tgctggaaac

4861    agcatagcaa gtttaaataa ggctagtccg ttatcaactt gaaaaagtgg caccgagtcg

4921    gtgcttcatt gtgtcggcca cggaacaggc a
```

spacerless_GFP_mCherry_extension (SEQ ID NO: 32).

```
LOCUS           Exported 4930 bp ds-DNA circular

DEFINITION      synthetic circular DNA

SOURCE          synthetic DNA construct

ORGANISM        recombinant plasmid

REFERENCE       1 (bases 1 to 4930)

FEATURES        Location/Qualifiers

source          1 . . . 4930
                /organism = "recombinant plasmid"
                /mol_type = "other DNA"

rep_origin      13 . . . 453
                /direction = RIGHT
                /label = F1 ori

CDS             complement(460 . . . 528)
                /label = LacZ alpha

primer_bind     599 . . . 616
                /label = M13-fwd

primer_bind     626 . . . 645
                /label = T7

promoter        757 . . . 1019
                /label = U6 promoter

primer_bind     complement(998 . . . 1019)
                /label = scaffold_out_R

primer_bind     1000 . . . 1045
                /label = no_spacer_universal_scaff_f

primer_bind     1005 . . . 1043
                /label = 50 bp_GFP_F

primer_bind     1005 . . . 1043
                /label = ACTB_3_ext_CgRNA_For

misc_feature    1020 . . . 1105
                /label = sgRNA scaffold

primer_bind     1020 . . . 1046
                /label = scaffold_3_ext_template_For

primer_bind     complement(1093 . . . 1111)
                /label = scaffold_3_ext_template_Rev

primer_bind     complement(1094 . . . 1152)
                /label = eGFP_3_ext_R

primer_bind     complement(1094 . . . 1152)
                /label = gfp_3_extension_revcomp

primer_bind     complement(1094 . . . 1152)
                /label = ACTB_3_ext_AgRNA_Rev

misc_feature    1106 . . . 1111
                /label = Linker

misc_feature    1112 . . . 1132
                /label = EGFP_extension
```

```
primer_bind                 1133 . . . 1172
                            /label = EF1a_Gibson_F

primer_bind                 1133 . . . 1152
                            /label = 3_ext_backbone_For

misc_feature                1133 . . . 1139
                            /label = sgRNA scaffold termination

promoter                    1153 . . . 1698
                            /label = EF1a promoter

primer_bind                 complement(1686 . . . 1723)
                            /label = EF1a_Gibson_R

CDS                         1704 . . . 2414
                            /codon_start = 1
                            /product = "monomeric derivative of DsRed fluorescent protein
                            (Shaner et al., 2004)"
                            /label = mCherry
                            /note = "mammalian codon-optimized"

/translation = "MVSKGEEDNMAIIKEFMRFKVHMEGSVNGHEFEIEGEGEGRPYEG
TQTAKLKVTKGGPLPFAWDILSPQFMYGSKAYVKHPADIPDYLKLSFPEGFKWERVMNF
EDGGVVTVTQDSSLQDGEFIYKVKLRGTNFPSDGPVMQKKTMGWEASSERMYPEDGALK
GEIKQRLKLKDGGHYDAEVKTTYKAKKPVQLPGAYNVNIKLDITSHNEDYTIVEQYERA
EGRHSTGGMDELYK"

primer_bind                 1704 . . . 1723
                            /label = mCherry_BGH_F

primer_bind                 complement(2391 . . . 2438)
                            /label = Primer 1

primer_bind                 complement(2391 . . . 2414)
                            /label = mCherry_HindIII_R

misc_feature                2415 . . . 2438
                            /label = Gibson Overlap

polyA_signal                2462 . . . 2686
                            /label = bGH poly(A) signal
                            /note = "bovine growth hormone polyadenylation signal"

primer_bind                 complement(2667 . . . 2705)
                            /label = mCherry_BGH_Gib_R

primer_bind                 complement(2667 . . . 2686)
                            /label = mCherry_BGH_R

primer_bind                 complement(2668 . . . 2687)
                            /label = bGH_NotI_R

primer_bind                 complement(2690 . . . 2705)
                            /label = SK primer
                            /note = "common sequencing primer, one of multiple similar
                            variants"

primer_bind                 complement(2740 . . . 2759)
                            /label = T3

primer_bind                 complement(2777 . . . 2797)
                            /label = M13-rev

misc_binding                complement(2803 . . . 2825)
                            /label = LacO

promoter                    complement(2830 . . . 2859)
                            /label = lac

rep_origin                  complement(3165 . . . 3793)
                            /direction = LEFT
                            /label = ColE1 origin

CDS                         complement(3945 . . . 4604)
                            /label = AmpR

promoter                    complement(4844 . . . 4872)
                            /label = Amp prom
```

```
ORIGIN
      1 ctaaattgta agcgttaata ttttgttaaa attcgcgtta aatttttgtt aaatcagctc
     61 atttttaac caataggccg aaatcggcaa aatcccttat aaatcaaaag aatagaccga
    121 gatagggttg agtgttgttc cagtttggaa caagagtcca ctattaaaga acgtggactc
    181 caacgtcaaa gggcgaaaaa ccgtctatca gggcgatggc ccactacgtg aaccatcacc
    241 ctaatcaagt tttttggggt cgaggtgccg taaagcacta aatcggaacc ctaaagggag
    301 cccccgattt agagcttgac ggggaaagcc ggcgaacgtg gcgagaaagg aagggaagaa
    361 agcgaaagga gcgggcgcta gggcgctggc aagtgtagcg gtcacgctgc gcgtaaccac
    421 cacacccgcc gcgcttaatg cgccgctaca gggcgcgtcc cattcgccat tcaggctgcg
    481 caactgttgg gaagggcgat cggtgcgggc ctcttcgcta ttacgccagc tggcgaaagg
    541 gggatgtgct gcaaggcgat taagttgggt aacgccaggg ttttcccagt cacgacgttg
    601 taaaacgacg gccagtgagc gcgcgtaata cgactcacta tagggcgaat tgggtaccgg
    661 gccccccctc gaggtcgacg gtatcgataa gcttgatatc gtgtacaaaa aagcaggctt
    721 taaaggaacc aattcagtcg actggatccg gtaccaaggt cgggcaggaa gagggcctat
    781 ttcccatgat tccttcatat ttgcatatac gatacaaggc tgttagagag ataattagaa
    841 ttaatttgac tgtaaacaca aagatattag tacaaaatac gtgacgtaga aagtaataat
    901 ttcttgggta gtttgcagtt ttaaaattat gttttaaaat ggactatcat atgcttaccg
    961 taacttgaaa gtatttcgat ttcttggctt tatatatctt gtggaaagga cgaaacaccg
   1021 tttaagagct atgctggaaa cagcatagca agtttaaata aggctagtcc gttatcaact
   1081 tgaaaaagtg gcaccgagtc ggtgcttcat tgtgtcggcc acggaacagg catttttttc
   1141 ctgcagcccg ggaaggatct gcgatcgctc cggtgcccgt cagtgggcag agcgcacatc
   1201 gcccacagtc cccgagaagt tggggggagg ggtcggcaat tgaacgggtg cctagagaag
   1261 gtggcgcggg gtaaactggg aaagtgatgt cgtgtactgg ctccgccttt ttcccgaggg
   1321 tgggggagaa ccgtatataa gtgcagtagt cgccgtgaac gttctttttc gcaacgggtt
   1381 tgccgccaga acacagctga agcttcgagg ggctcgcatc tctccttcac gcgcccgccg
   1441 ccctacctga ggccgccatc cacgccggtt gagtcgcgtt ctgccgcctc ccgcctgtgg
   1501 tgcctcctga actgcgtccg ccgtctaggt aagtttaaag ctcaggtcga gaccgggcct
   1561 ttgtccggcg ctcccttgga gcctacctag actcagccgg ctctccacgc tttgcctgac
   1621 cctgcttgct caactctacg tctttgtttc gttttctgtt ctgcgccgtt acagatccaa
   1681 gctgtgaccg gcgcctacgc tagatggtga gcaagggcga ggaggataac atggccatca
   1741 tcaaggagtt catgcgcttc aaggtgcaca tggagggctc cgtgaacggc cacgagttcg
   1801 agatcgaggg cgagggcgag ggccgcccct acgagggcac ccagaccgcc aagctgaagg
   1861 tgaccaaggg tggccccctg cccttcgcct gggacatcct gtcccctcag ttcatgtacg
   1921 gctccaaggc ctacgtgaag caccccgccg acatccccga ctacttgaag ctgtccttcc
   1981 ccgagggctt caagtgggag cgcgtgatga acttcgagga cggcggcgtg gtgaccgtga
   2041 cccaggactc ctccctgcag gacggcgagt tcatctacaa ggtgaagctg cgcggcacca
   2101 acttcccctc cgacggcccc gtaatgcaga agaagaccat gggctgggag gcctcctccg
   2161 agcggatgta ccccgaggac ggcgccctga agggcgagat caagcagagg ctgaagctga
   2221 aggacggcgg ccactacgac gctgaggtca agaccaccta caaggccaag aagcccgtgc
   2281 agctgcccgg cgcctacaac gtcaacatca agttggacat cacctcccac aacgaggact
```

-continued

```
2341  acaccatcgt ggaacagtac gaacgcgccg agggccgcca ctccaccggc ggcatggacg
2401  agctgtacaa gtaatccgag ctcggtacca agcttaagtt taaaccgctg atcagcctcg
2461  actgtgcctt ctagttgcca gccatctgtt gtttgcccct cccccgtgcc ttccttgacc
2521  ctggaaggtg ccactcccac tgtcctttcc taataaaatg aggaaattgc atcgcattgt
2581  ctgagtaggt gtcattctat tctggggggt ggggtggggc aggacagcaa gggggaggat
2641  tgggaagaca atagcaggca tgctggggat gcggtgggct ctatggggga tccactagtt
2701  ctagagcggc cgccaccgcg gtggagctcc agcttttgtt ccctttagtg agggttaatt
2761  gcgcgcttgg cgtaatcatg gtcatagctg tttcctgtgt gaaattgtta tccgctcaca
2821  attccacaca acatacgagc cggaagcata aagtgtaaag cctggggtgc ctaatgagtg
2881  agctaactca cattaattgc gttgcgctca ctgcccgctt tccagtcggg aaacctgtcg
2941  tgccagctgc attaatgaat cggccaacgc gcggggagag gcggtttgcg tattgggcgc
3001  tcttccgctt cctcgctcac tgactcgctg cgctcggtcg ttcggctgcg gcgagcggta
3061  tcagctcact caaaggcggt aatacggtta tccacagaat caggggataa cgcaggaaag
3121  aacatgtgag caaaaggcca gcaaaaggcc aggaaccgta aaaaggccgc gttgctggcg
3181  tttttccata ggctccgccc ccctgacgag catcacaaaa atcgacgctc aagtcagagg
3241  tggcgaaacc cgacaggact ataaagatac caggcgtttc cccctggaag ctccctcgtg
3301  cgctctcctg ttccgaccct gccgcttacc ggatacctgt ccgcctttct cccttcggga
3361  agcgtggcgc tttctcatag ctcacgctgt aggtatctca gttcggtgta ggtcgttcgc
3421  tccaagctgg gctgtgtgca cgaacccccc gttcagcccg accgctgcgc cttatccggt
3481  aactatcgtc ttgagtccaa cccggtaaga cacgacttat cgccactggc agcagccact
3541  ggtaacagga ttagcagagc gaggtatgta ggcggtgcta cagagttctt gaagtggtgg
3601  cctaactacg gctacactag aaggacagta tttggtatct gcgctctgct gaagccagtt
3661  accttcggaa aaagagttgg tagctcttga tccggcaaac aaaccaccgc tggtagcggt
3721  ggtttttttg tttgcaagca gcagattacg cgcagaaaaa aaggatctca agaagatcct
3781  ttgatctttt ctacggggtc tgacgctcag tggaacgaaa actcacgtta agggattttg
3841  gtcatgagat tatcaaaaag gatcttcacc tagatccttt taaattaaaa atgaagtttt
3901  aaatcaatct aaagtatata tgagtaaact tggtctgaca gttaccaatg cttaatcagt
3961  gaggcaccta tctcagcgat ctgtctattt cgttcatcca tagttgcctg actccccgtc
4021  gtgtagataa ctacgatacg ggagggctta ccatctggcc ccagtgctgc aatgataccg
4081  cgagacccac gctcaccggc tccagattta tcagcaataa accagccagc cggaagggcc
4141  gagcgcagaa gtggtcctgc aactttatcc gcctccatcc agtctattaa ttgttgccgg
4201  gaagctagag taagtagttc gccagttaat agtttgcgca acgttgttgc cattgctaca
4261  ggcatcgtgg tgtcacgctc gtcgtttggt atggcttcat tcagctccgg ttcccaacga
4321  tcaaggcgag ttacatgatc ccccatgttg tgcaaaaaag cggttagctc cttcggtcct
4381  ccgatcgttg tcagaagtaa gttggccgca gtgttatcac tcatggttat ggcagcactg
4441  cataattctc ttactgtcat gccatccgta agatgctttt ctgtgactgg tgagtactca
4501  accaagtcat tctgagaata gtgtatgcgg cgaccgagtt gctcttgccc ggcgtcaata
4561  cgggataata ccgcgccaca tagcagaact ttaaaagtgc tcatcattgg aaaacgttct
4621  tcggggcgaa aactctcaag gatcttaccg ctgttgagat ccagttcgat gtaacccact
4681  cgtgcaccca actgatcttc agcatctttt actttcacca gcgtttctgg gtgagcaaaa
```

```
4741   acaggaaggc aaaatgccgc aaaaaaggga ataagggcga cacggaaatg ttgaatactc
4801   atactcttcc tttttcaata ttattgaagc atttatcagg gttattgtct catgagcgga
4861   tacatatttg aatgtattta gaaaaataaa caaatagggg ttccgcgcac atttccccga
4921   aaagtgccac
```

GFP_no_spacer_revcomp_mCherry_gibson (SEQ ID NO: 33).

```
LOCUS                     Exported 4930 bp ds-DNA circular

DEFINITION                synthetic circular DNA

SOURCE                    synthetic DNA construct

ORGANISM                  recombinant plasmid

REFERENCE                 1 (bases 1 to 4930)

FEATURES                  Location/Qualifiers

source                    1 . . . 4930
                          /organism = "recombinant plasmid"
                          /mol_type = "other DNA"

primer_bind               1 . . . 20
                          /label = Primer 2

misc_feature              1 . . . 7
                          /label = sgRNA scaffold termination

promoter                  21 . . . 566
                          /label = EF1a promoter

primer_bind               complement(554 . . . 591)
                          /label = EF1a_Gibson_R

CDS                       572 . . . 1282
                          /codon_start = 1
                          /product = "monomeric derivative of DsRed fluorescent protein
                          (Shaner et al., 2004)"
                          /label = mCherry
                          /note = "mammalian codon-optimized"

/translation = "MVSKGEEDNMAIIKEFMRFKVHMEGSVNGHEFEIEGEGEGRPYEG
TQTAKLKVTKGGPLPFAWDILSPQFMYGSKAYVKHPADIPDYLKLSFPEGFKWERVMNF
EDGGVVTVTQDSSLQDGEFIYKVKLRGTNFPSDGPVMQKKTMGWEASSERMYPEDGALK
GEIKQRLKLKDGGHYDAEVKTTYKAKKPVQLPGAYNVNIKLDITSHNEDYTIVEQYERA
EGRHSTGGMDELYK"

primer_bind               572 . . . 591
                          /label = mCherry_BGH_F

primer_bind               complement(1259 . . . 1306)
                          /label = Primer 1

primer_bind               complement(1259 . . . 1282)
                          /label = mCherry_HindIII_R

misc_feature              1283 . . . 1306
                          /label = Gibson Overlap

polyA_signal              1330 . . . 1554
                          /label = bGH poly(A) signal
                          /note = "bovine growth hormone polyadenylation signal"

primer_bind               complement(1535 . . . 1573)
                          /label = mCherry_BGH_Gib_R

primer_bind               complement(1535 . . . 1554)
                          /label = mCherry_BGH_R

primer_bind               complement(1536 . . . 1555)
                          /label = bGH_NotI_R

primer_bind               complement(1558 . . . 1573)
                          /label = SK primer
```

```
                    /note = "common sequencing primer, one of multiple similar
                    variants"

primer_bind         complement(1608 . . . 1627)
                    /label = T3

primer_bind         complement(1645 . . . 1665)
                    /label = M13-rev

misc_binding        complement(1671 . . . 1693)
                    /label = LacO

promoter            complement(1698 . . . 1727)
                    /label = lac

rep_origin          complement(2033 . . . 2661)
                    /direction = LEFT
                    /label = ColE1 origin

CDS                 complement(2813 . . . 3472)
                    /label = AmpR

promoter            complement(3712 . . . 3740)
                    /label = Amp prom

rep_origin          3811 . . . 4251
                    /direction = RIGHT
                    /label = F1 ori

CDS                 complement(4258 . . . 4326)
                    /label = LacZ alpha

primer_bind         4397 . . . 4414
                    /label = M13-fwd

primer_bind         4424 . . . 4443
                    /label = T7

promoter            4555 . . . 4817
                    /label = U6 promoter

primer_bind         4798 . . . 4843
                    /label = no_spacer_universal_scaff_f

primer_bind         4803 . . . 4841
                    /label = ACTB_3_ext_CgRNA_For

primer_bind         complement(4803 . . . 4817)
                    /label = Primer 3

primer_bind         complement(4803 . . . 4817)
                    /label = extension_gibson_R

misc_feature        4818 . . . 4903
                    /label = sgRNA scaffold

primer_bind         4818 . . . 4844
                    /label = scaffold_3_ext_template_For

primer_bind         complement(4891 . . . 4909)
                    /label = scaffold_3_ext_template_Rev

primer_bind         complement(join(4892 . . . 4930, 1 . . . 20))
                    /label = gfp_3_extension_revcomp

primer_bind         complement(join(4892 . . . 4930, 1 . . . 20))
                    /label = ACTB_3_ext_AgRNA_Rev

misc_feature        4904 . . . 4909
                    /label = Linker

misc_feature        4910 . . . 4930
                    /label = EGFP_revcomp_extension

primer_bind         join(4930, 1 . . . 40)
                    /label = EF1a_Gibson_F
```

```
ORIGIN
      1  tttttttcct gcagcccggg aaggatctgc gatcgctccg gtgcccgtca gtgggcagag
     61  cgcacatcgc ccacagtccc cgagaagttg gggggagggg tcggcaattg aacgggtgcc
    121  tagagaaggt ggcgcggggt aaactgggaa agtgatgtcg tgtactggct ccgccttttt
    181  cccgagggtg ggggagaacc gtatataagt gcagtagtcg ccgtgaacgt tctttttcgc
    241  aacgggtttg ccgccagaac acagctgaag cttcgagggg ctcgcatctc tccttcacgc
    301  gcccgccgcc ctacctgagg ccgccatcca cgccggttga gtcgcgttct gccgcctccc
    361  gcctgtggtg cctcctgaac tgcgtccgcc gtctaggtaa gtttaaagct caggtcgaga
    421  ccgggccttt gtccggcgct cccttggagc ctacctagac tcagccggct ctccacgctt
    481  tgcctgaccc tgcttgctca actctacgtc tttgtttcgt tttctgttct gcgccgttac
    541  agatccaagc tgtgaccggc gcctacgcta gatggtgagc aagggcgagg aggataacat
    601  ggccatcatc aaggagttca tgcgcttcaa ggtgcacatg gagggctccg tgaacggcca
    661  cgagttcgag atcgagggcg agggcgaggg ccgcccctac gagggcaccc agaccgccaa
    721  gctgaaggtg accaagggtg gccccctgcc cttcgcctgg gacatcctgt cccctcagtt
    781  catgtacggc tccaaggcct acgtgaagca ccccgccgac atccccgact acttgaagct
    841  gtccttcccc gagggcttca agtgggagcg cgtgatgaac ttcgaggacg gcggcgtggt
    901  gaccgtgacc caggactcct ccctgcagga cggcgagttc atctacaagg tgaagctgcg
    961  cggcaccaac ttcccctccg acggccccgt aatgcagaag aagaccatgg gctgggaggc
   1021  ctcctccgag cggatgtacc ccgaggacgg cgccctgaag ggcgagatca agcagaggct
   1081  gaagctgaag gacggcggcc actacgacgc tgaggtcaag accacctaca aggccaagaa
   1141  gcccgtgcag ctgcccggcg cctacaacgt caacatcaag ttggacatca cctcccacaa
   1201  cgaggactac accatcgtgg aacagtacga acgcgccgag ggccgccact ccaccggcgg
   1261  catggacgag ctgtacaagt aatccgagct cggtaccaag cttaagttta aaccgctgat
   1321  cagcctcgac tgtgccttct agttgccagc catctgttgt ttgcccctcc cccgtgcctt
   1381  ccttgaccct ggaaggtgcc actcccactg tcctttccta ataaaatgag gaaattgcat
   1441  cgcattgtct gagtaggtgt cattctattc tggggggtgg ggtggggcag gacagcaagg
   1501  gggaggattg ggaagacaat agcaggcatg ctggggatgc ggtgggctct atgggggatc
   1561  cactagttct agagcggccg ccaccgcggt ggagctccag cttttgttcc ctttagtgag
   1621  ggttaattgc gcgcttggcg taatcatggt catagctgtt tcctgtgtga aattgttatc
   1681  cgctcacaat tccacacaac atacgagccg gaagcataaa gtgtaaagcc tggggtgcct
   1741  aatgagtgag ctaactcaca ttaattgcgt tgcgctcact gcccgctttc cagtcgggaa
   1801  acctgtcgtg ccagctgcat taatgaatcg gccaacgcgc ggggagaggc ggtttgcgta
   1861  ttgggcgctc ttccgcttcc tcgctcactg actcgctgcg ctcggtcgtt cggctgcggc
   1921  gagcggtatc agctcactca aaggcggtaa tacggttatc cacagaatca ggggataacg
   1981  caggaaagaa catgtgagca aaaggccagc aaaaggccag gaaccgtaaa aaggccgcgt
   2041  tgctggcgtt tttccatagg ctccgccccc ctgacgagca tcacaaaaat cgacgctcaa
   2101  gtcagaggtg gcgaaacccg acaggactat aaagatacca ggcgtttccc cctggaagct
   2161  ccctcgtgcg ctctcctgtt ccgaccctgc cgcttaccgg atacctgtcc gcctttctcc
   2221  cttcgggaag cgtggcgctt tctcatagct cacgctgtag gtatctcagt tcggtgtagg
   2281  tcgttcgctc caagctgggc tgtgtgcacg aaccccccgt tcagcccgac cgctgcgcct
```

```
2341    tatccggtaa ctatcgtctt gagtccaacc cggtaagaca cgacttatcg ccactggcag

2401    cagccactgg taacaggatt agcagagcga ggtatgtagg cggtgctaca gagttcttga

2461    agtggtggcc taactacggc tacactagaa ggacagtatt tggtatctgc gctctgctga

2521    agccagttac cttcggaaaa agagttggta gctcttgatc cggcaaacaa accaccgctg

2581    gtagcggtgg tttttttgtt tgcaagcagc agattacgcg cagaaaaaaa ggatctcaag

2641    aagatccttt gatcttttct acggggtctg acgctcagtg gaacgaaaac tcacgttaag

2701    ggattttggt catgagatta tcaaaaagga tcttcaccta gatcctttta aattaaaaat

2761    gaagttttaa atcaatctaa agtatatatg agtaaacttg gtctgacagt taccaatgct

2821    taatcagtga ggcacctatc tcagcgatct gtctatttcg ttcatccata gttgcctgac

2881    tccccgtcgt gtagataact acgatacggg agggcttacc atctggcccc agtgctgcaa

2941    tgataccgcg agacccacgc tcaccggctc cagatttatc agcaataaac cagccagccg

3001    gaagggccga gcgcagaagt ggtcctgcaa ctttatccgc ctccatccag tctattaatt

3061    gttgccggga agctagagta agtagttcgc cagttaatag tttgcgcaac gttgttgcca

3121    ttgctacagg catcgtggtg tcacgctcgt cgtttggtat ggcttcattc agctccggtt

3181    cccaacgatc aaggcgagtt acatgatccc ccatgttgtg caaaaaagcg gttagctcct

3241    tcggtcctcc gatcgttgtc agaagtaagt tggccgcagt gttatcactc atggttatgg

3301    cagcactgca taattctctt actgtcatgc catccgtaag atgcttttct gtgactggtg

3361    agtactcaac caagtcattc tgagaatagt gtatgcggcg accgagttgc tcttgcccgg

3421    cgtcaatacg ggataatacc gcgccacata gcagaacttt aaaagtgctc atcattggaa

3481    aacgttcttc ggggcgaaaa ctctcaagga tcttaccgct gttgagatcc agttcgatgt

3541    aacccactcg tgcacccaac tgatcttcag catcttttac tttcaccagc gtttctgggt

3601    gagcaaaaac aggaaggcaa aatgccgcaa aaaagggaat aagggcgaca cggaaatgtt

3661    gaatactcat actcttcctt tttcaatatt attgaagcat ttatcagggt tattgtctca

3721    tgagcggata catatttgaa tgtatttaga aaaataaaca aataggggtt ccgcgcacat

3781    ttccccgaaa agtgccacct aaattgtaag cgttaatatt ttgttaaaat tcgcgttaaa

3841    tttttgttaa atcagctcat tttttaacca ataggccgaa atcggcaaaa tcccttataa

3901    atcaaaagaa tagaccgaga tagggttgag tgttgttcca gtttggaaca agagtccact

3961    attaaagaac gtggactcca acgtcaaagg gcgaaaaacc gtctatcagg gcgatggccc

4021    actacgtgaa ccatcaccct aatcaagttt tttggggtcg aggtgccgta aagcactaaa

4081    tcggaaccct aaagggagcc cccgatttag agcttgacgg ggaaagccgg cgaacgtggc

4141    gagaaaggaa gggaagaaag cgaaaggagc gggcgctagg gcgctggcaa gtgtagcggt

4201    cacgctgcgc gtaaccacca cacccgccgc gcttaatgcg ccgctacagg gcgcgtccca

4261    ttcgccattc aggctgcgca actgttggga agggcgatcg gtgcgggcct cttcgctatt

4321    acgccagctg gcgaaagggg gatgtgctgc aaggcgatta agttgggtaa cgccagggtt

4381    ttcccagtca cgacgttgta aaacgacggc cagtgagcgc gcgtaatacg actcactata

4441    gggcgaattg ggtaccgggc cccccctcga ggtcgacggt atcgataagc ttgatatcgt

4501    gtacaaaaaa gcaggcttta aaggaaccaa ttcagtcgac tggatccggt accaaggtcg

4561    ggcaggaaga gggcctattt cccatgattc cttcatattt gcatatacga tacaaggctg

4621    ttagagagat aattagaatt aatttgactg taaacacaaa gatattagta caaaatacgt
```

-continued

```
4681    gacgtagaaa gtaataattt cttgggtagt ttgcagtttt aaaattatgt tttaaaatgg

4741    actatcatat gcttaccgta acttgaaagt atttcgattt cttggcttta tatatcttgt

4801    ggaaaggacg aaacaccgtt taagagctat gctggaaaca gcatagcaag tttaaataag

4861    gctagtccgt tatcaacttg aaaaagtggc accgagtcgg tgcttcattt gcctgttccg

4921    tggccgacac
```

pBluescript II SK + U6-lambda2-sgRNA(F + E) (SEQ ID NO: 34).

```
LOCUS                    Exported 3388 bp ds-DNA circular

DEFINITION               synthetic circular DNA

SOURCE                   synthetic DNA construct

ORGANISM                 synthetic DNA construct

REFERENCE                1 (bases 1 to 3388)

FEATURES                 Location/Qualifiers

source                   1 . . . 3388
                         /organism = "synthetic DNA construct"
                         /mol_type = "other DNA"

rep_origin               13 . . . 453
                         /direction = RIGHT
                         /label = F1 ori

CDS                      complement(460 . . . 528)
                         /label = LacZ alpha

primer_bind              599 . . . 616
                         /label = M13-fwd

primer_bind              626 . . . 645
                         /label = T7

promoter                 757 . . . 1019
                         /label = U6 promoter

misc_feature             1020 . . .  1039
                         /label = lambda2_guideRNA

misc_feature             1041 . . . 1132
                         /label = sgRNA scaffold

primer_bind              complement(1198 . . . 1217)
                         /label = T3

primer_bind              complement(1235 . . . 1255)
                         /label = M13-rev

misc_binding             complement(1261 . . . 1283)
                         /label = LacO

promoter                 complement(1288 . . . 1317)
                         /label = lac

rep_origin               complement(1623 . . . 2251)
                         /direction = LEFT
                         /label = ColE1 origin

CDS                      complement(2403 . . . 3062)
                         /label = AmpR

promoter                 complement(3302 . . . 3330)
                         /label = Amp prom

ORIGIN
      1   ctaaattgta agcgttaata ttttgttaaa attcgcgtta aatttttgtt aaatcagctc

     61   atttttaac caataggccg aaatcggcaa aatcccttat aaatcaaaag aatagaccga

    121   gatagggttg agtgttgttc cagtttggaa caagagtcca ctattaaaga acgtggactc
```

```
181   caacgtcaaa gggcgaaaaa ccgtctatca gggcgatggc ccactacgtg aaccatcacc
241   ctaatcaagt tttttggggt cgaggtgccg taaagcacta aatcggaacc ctaaagggag
301   cccccgattt agagcttgac ggggaaagcc ggcgaacgtg gcgagaaagg aagggaagaa
361   agcgaaagga gcgggcgcta gggcgctggc aagtgtagcg gtcacgctgc gcgtaaccac
421   cacacccgcc gcgcttaatg cgccgctaca gggcgcgtcc cattcgccat tcaggctgcg
481   caactgttgg gaagggcgat cggtgcgggc ctcttcgcta ttacgccagc tggcgaaagg
541   gggatgtgct gcaaggcgat taagttgggt aacgccaggg ttttcccagt cacgacgttg
601   taaaacgacg gccagtgagc gcgcgtaata cgactcacta tagggcgaat tgggtaccgg
661   gccccccctc gaggtcgacg gtatcgataa gcttgatatc gtgtacaaaa aagcaggctt
721   taaaggaacc aattcagtcg actggatccg gtaccaaggt cgggcaggaa gagggcctat
781   ttcccatgat tccttcatat ttgcatatac gatacaaggc tgttagagag ataattagaa
841   ttaatttgac tgtaaacaca aagatattag tacaaaatac gtgacgtaga aagtaataat
901   ttcttgggta gtttgcagtt ttaaaattat gttttaaaat ggactatcat atgcttaccg
961   taacttgaaa gtatttcgat ttcttggctt tatatatctt gtggaaagga cgaaacaccg
1021  tgataagtgg aatgccatgg tttaagagct atgctggaaa cagcatagca agtttaaata
1081  aggctagtcc gttatcaact tgaaaaagtg gcaccgagtc ggtgcttttt ttcctgcagc
1141  ccgggggatc cactagttct agagcggccg ccaccgcggt ggagctccag cttttgttcc
1201  ctttagtgag ggttaattgc gcgcttggcg taatcatggt catagctgtt tcctgtgtga
1261  aattgttatc cgctcacaat tccacacaac atacgagccg gaagcataaa gtgtaaagcc
1321  tggggtgcct aatgagtgag ctaactcaca ttaattgcgt tgcgctcact gcccgctttc
1381  cagtcgggaa acctgtcgtg ccagctgcat taatgaatcg gccaacgcgc ggggagaggc
1441  ggtttgcgta ttgggcgctc ttccgcttcc tcgctcactg actcgctgcg ctcggtcgtt
1501  cggctgcggc gagcggtatc agctcactca aaggcggtaa tacggttatc cacagaatca
1561  ggggataacg caggaaagaa catgtgagca aaaggccagc aaaaggccag gaaccgtaaa
1621  aaggccgcgt tgctggcgtt tttccatagg ctccgccccc ctgacgagca tcacaaaaat
1681  cgacgctcaa gtcagaggtg gcgaaacccg acaggactat aaagatacca ggcgtttccc
1741  cctggaagct ccctcgtgcg ctctcctgtt ccgaccctgc cgcttaccgg atacctgtcc
1801  gcctttctcc cttcgggaag cgtggcgctt tctcatagct cacgctgtag gtatctcagt
1861  tcggtgtagg tcgttcgctc caagctgggc tgtgtgcacg aaccccccgt tcagcccgac
1921  cgctgcgcct tatccggtaa ctatcgtctt gagtccaacc cggtaagaca cgacttatcg
1981  ccactggcag cagccactgg taacaggatt agcagagcga ggtatgtagg cggtgctaca
2041  gagttcttga agtggtggcc taactacggc tacactagaa ggacagtatt tggtatctgc
2101  gctctgctga agccagttac cttcggaaaa agagttggta gctcttgatc cggcaaacaa
2161  accaccgctg gtagcggtgg tttttttgtt tgcaagcagc agattacgcg cagaaaaaaa
2221  ggatctcaag aagatccttt gatcttttct acggggtctg acgctcagtg gaacgaaaac
2281  tcacgttaag ggattttggt catgagatta tcaaaaagga tcttcaccta gatcctttta
2341  aattaaaaat gaagttttaa atcaatctaa agtatatatg agtaaacttg gtctgacagt
2401  taccaatgct taatcagtga ggcacctatc tcagcgatct gtctatttcg ttcatccata
2461  gttgcctgac tccccgtcgt gtagataact acgatacggg agggcttacc atctggcccc
2521  agtgctgcaa tgataccgcg agacccacgc tcaccggctc cagatttatc agcaataaac
```

```
2581   cagccagccg gaagggccga gcgcagaagt ggtcctgcaa ctttatccgc ctccatccag
2641   tctattaatt gttgccggga agctagagta agtagttcgc cagttaatag tttgcgcaac
2701   gttgttgcca ttgctacagg catcgtggtg tcacgctcgt cgtttggtat ggcttcattc
2761   agctccggtt cccaacgatc aaggcgagtt acatgatccc ccatgttgtg caaaaaagcg
2821   gttagctcct tcggtcctcc gatcgttgtc agaagtaagt tggccgcagt gttatcactc
2881   atggttatgg cagcactgca taattctctt actgtcatgc catccgtaag atgcttttct
2941   gtgactggtg agtactcaac caagtcattc tgagaatagt gtatgcggcg accgagttgc
3001   tcttgcccgg cgtcaatacg ggataatacc gcgccacata gcagaacttt aaaagtgctc
3061   atcattggaa aacgttcttc ggggcgaaaa ctctcaagga tcttaccgct gttgagatcc
3121   agttcgatgt aacccactcg tgcacccaac tgatcttcag catcttttac tttcaccagc
3181   gtttctgggt gagcaaaaac aggaaggcaa aatgccgcaa aaaagggaat aagggcgaca
3241   cggaaatgtt gaatactcat actcttcctt tttcaatatt attgaagcat ttatcagggt
3301   tattgtctca tgagcggata catatttgaa tgtatttaga aaaataaaca aataggggtt
3361   ccgcgcacat ttccccgaaa agtgccac
```

EGFP_spacerless_SaCas9_sgRNA (SEQ ID NO: 47)

```
LOCUS                      Exported 4921 bp ds-DNA circular

DEFINITION                 synthetic circular DNA

SOURCE                     synthetic DNA construct

ORGANISM                   recombinant plasmid

REFERENCE                  1 (bases 1 to 4921)

FEATURES                   Location/Qualifiers

source                     1 . . . 4921
                           /organism = "recombinant plasmid"
                           /mol_type = "other DNA"

primer_bind                1 . . . 40
                           /label = EF1a_Gibson_F

primer_bind                1 . . . 20
                           /label = Primer 2

misc_feature               1 . . . 7
                           /label = sgRNA scaffold_termination

promoter                   21 . . . 566
                           /label = EF1a promoter

primer_bind                complement(554 . . . 591)
                           /label = EF1a_Gibson_R

CDS                        572 . . . 1282
                           /codon_start = 1
                           /product = "monomeric derivative of DsRed fluorescent protein
                           (Shaner et al., 2004)"
                           /label = mCherry
                           /note = "mammalian codon-optimized"

/translation = "MVSKGEEDNMAIIKEFMRFKVHMEGSVNGHEFEIEGEGEGRPYEG
TQTAKLKVTKGGPLPFAWDILSPQFMYGSKAYVKHPADIPDYLKLSFPEGFKWERVMNF
EDGGVVTVTQDSSLQDGEFIYKVKLRGTNFPSDGPVMQKKTMGWEASSERMYPEDGALK
GEIKQRLKLKDGGHYDAEVKTTYKAKKPVQLPGAYNVNIKLDITSHNEDYTIVEQYERA
EGRHSTGGMDELYK"

primer_bind                572 . . . 591
                           /label = mCherry_BGH_F
```

-continued

```
primer_bind          complement(1259 . . . 1306)
                     /label = Primer 1

primer_bind          complement(1259 . . . 1286)
                     /label = mCherry_P2A_Gib_R

primer_bind          complement(1259. 1282)
                     /label = mCherry_HindIII_R

misc_feature         1283 . . . 1306
                     /label = Gibson Overlap

primer_bind          1283 . . . 1301
                     /label = mCherry_P2A_Gib_F

polyA_signal         1330 . . . 1554
                     /label = bGH poly(A) signal
                     /note = "bovine growth hormone polyadenylation signal"

primer_bind          complement(1535 . . . 1573)
                     /label = mCherry_BGH_Gib_R

primer_bind          complement(1535 . . . 1554)
                     /label = mCherry_BGH_R

primer_bind          complement(1536 . . . 1555)
                     /label = bGH_NotI_R

primer_bind          complement(1558 . . . 1573)
                     /label = SK primer
                     /note = "common sequencing primer, one of multiple similar
                     variants"

primer_bind          complement(1608 . . . 1627)
                     /label = T3

primer_bind          complement(1645 . . . 1665)
                     /label = M13-rev

misc_binding         complement(1671 . . . 1693)
                     /label = LacO

promoter             complement(1698 . . . 1727)
                     /label = lac

rep_origin           complement(2033 . . . 2661)
                     /direction = LEFT
                     /label = ColE1 origin

CDS                  complement(2813 . . . 3472)
                     /label = AmpR

promoter             complement(3712 . . . 3740)
                     /label = Amp prom

rep_origin           3811 . . . 4251
                     /direction = RIGHT
                     /label = F1 ori

CDS                  complement(4258 . . . 4326)
                     /label = LacZ alpha

primer_bind          4397 . . . 4414
                     /label = M13-fwd

primer_bind          4424 . . . 4443
                     /label = T7

promoter             4555 . . . 4817
                     /label = U6 promoter

primer_bind          4798 . . . 4843
                     /label = NS_EGFP_SaCas9_F

primer_bind          complement(4803 . . . 4817)
                     /label = Primer 3
```

```
primer_bind                complement(4803 . . . 4817)
                           /label = extension_gibson_R

primer_bind                4804 . . . 4843
                           /label = 50 bp_EGFP_SaCas9_F

misc_RNA                   4819 . . . 4894
                           /label = Sa gRNA scaffold
                           /note = "guide RNA scaffold for the Staphylococcus aureus
                           CRISPR/Cas9 system"

primer_bind                complement(join(4877 . . . 4921, 1 . . . 20))
                           /label = EGFP_SaCas9_RC_ex_R

primer_bind                complement(join(4877 . . . 4921, 1 . . . 20))
                           /label = EGFP_SaCas9_ex_R

misc_feature               4895 . . . 4900
                           /label = Linker

misc_feature               4901 . . . 4921
                           /label = EGFP extension

primer_bind                4901 . . . 4921
                           /label = RNA target with T7 Promoter Sequence (for IVT)
ORIGIN
        1     tttttttcct gcagcccggg aaggatctgc gatcgctccg gtgcccgtca gtgggcagag

       61     cgcacatcgc ccacagtccc cgagaagttg gggggagggg tcggcaattg aacgggtgcc

      121     tagagaaggt ggcgcggggt aaactgggaa agtgatgtcg tgtactggct ccgccttttt

      181     cccgagggtg ggggagaacc gtatataagt gcagtagtcg ccgtgaacgt tctttttcgc

      241     aacgggtttg ccgccagaac acagctgaag cttcgagggg ctcgcatctc tccttcacgc

      301     gcccgccgcc ctacctgagg ccgccatcca cgccggttga gtcgcgttct gccgcctccc

      361     gcctgtggtg cctcctgaac tgcgtccgcc gtctaggtaa gtttaaagct caggtcgaga

      421     ccgggccttt gtccggcgct cccttggagc ctacctagac tcagccggct ctccacgctt

      481     tgcctgaccc tgcttgctca actctacgtc tttgtttcgt tttctgttct gcgccgttac

      541     agatccaagc tgtgaccggc gcctacgcta gatggtgagc aagggcgagg aggataacat

      601     ggccatcatc aaggagttca tgcgcttcaa ggtgcacatg gagggctccg tgaacggcca

      661     cgagttcgag atcgagggcg agggcgaggg ccgcccctac gagggcaccc agaccgccaa

      721     gctgaaggtg accaagggtg gccccctgcc cttcgcctgg gacatcctgt cccctcagtt

      781     catgtacggc tccaaggcct acgtgaagca ccccgccgac atccccgact acttgaagct

      841     gtccttcccc gagggcttca agtgggagcg cgtgatgaac ttcgaggacg gcggcgtggt

      901     gaccgtgacc caggactcct ccctgcagga cggcgagttc atctacaagg tgaagctgcg

      961     cggcaccaac ttcccctccg acggccccgt aatgcagaag aagaccatgg gctgggaggc

     1021     ctcctccgag cggatgtacc ccgaggacgg cgccctgaag ggcgagatca agcagaggct

     1081     gaagctgaag gacggcggcc actacgacgc tgaggtcaag accacctaca aggccaagaa

     1141     gcccgtgcag ctgcccggcg cctacaacgt caacatcaag ttggacatca cctcccacaa

     1201     cgaggactac accatcgtgg aacagtacga acgcgccgag ggccgccact ccaccggcgg

     1261     catggacgag ctgtacaagt aatccgagct cggtaccaag cttaagttta aaccgctgat

     1321     cagcctcgac tgtgccttct agttgccagc catctgttgt ttgcccctcc cccgtgcctt

     1381     ccttgaccct ggaaggtgcc actcccactg tcctttccta ataaaatgag gaaattgcat

     1441     cgcattgtct gagtaggtgt cattctattc tggggggtgg ggtggggcag gacagcaagg

     1501     gggaggattg ggaagacaat agcaggcatg ctggggatgc ggtgggctct atgggggatc

     1561     cactagttct agagcggccg ccaccgcggt ggagctccag cttttgttcc ctttagtgag
```

-continued 1621 ggttaattgc gcgcttggcg taatcatggt catagctgtt tcctgtgtga aattgttatc 1681 cgctcacaat tccacacaac atacgagccg gaagcataaa gtgtaaagcc tggggtgcct 1741 aatgagtgag ctaactcaca ttaattgcgt tgcgctcact gcccgctttc cagtcgggaa 1801 acctgtcgtg ccagctgcat taatgaatcg gccaacgcgc ggggagaggc ggtttgcgta 1861 ttgggcgctc ttccgcttcc tcgctcactg actcgctgcg ctcggtcgtt cggctgcggc 1921 gagcggtatc agctcactca aaggcggtaa tacggttatc cacagaatca ggggataacg 1981 caggaaagaa catgtgagca aaaggccagc aaaaggccag gaaccgtaaa aaggccgcgt 2041 tgctggcgtt tttccatagg ctccgccccc ctgacgagca tcacaaaaat cgacgctcaa 2101 gtcagaggtg gcgaaacccg acaggactat aaagatacca ggcgtttccc cctggaagct 2161 ccctcgtgcg ctctcctgtt ccgaccctgc cgcttaccgg atacctgtcc gcctttctcc 2221 cttcgggaag cgtggcgctt tctcatagct cacgctgtag gtatctcagt tcggtgtagg 2281 tcgttcgctc caagctgggc tgtgtgcacg aaccccccgt tcagcccgac cgctgcgcct 2341 tatccggtaa ctatcgtctt gagtccaacc cggtaagaca cgacttatcg ccactggcag 2401 cagccactgg taacaggatt agcagagcga ggtatgtagg cggtgctaca gagttcttga 2461 agtggtggcc taactacggc tacactagaa ggacagtatt tggtatctgc gctctgctga 2521 agccagttac cttcggaaaa agagttggta gctcttgatc cggcaaacaa accaccgctg 2581 gtagcggtgg tttttttgtt tgcaagcagc agattacgcg cagaaaaaaa ggatctcaag 2641 aagatccttt gatcttttct acggggtctg acgctcagtg gaacgaaaac tcacgttaag 2701 ggattttggt catgagatta tcaaaaagga tcttcaccta gatcctttta aattaaaaat 2761 gaagttttaa atcaatctaa agtatatatg agtaaacttg gtctgacagt taccaatgct 2821 taatcagtga ggcacctatc tcagcgatct gtctatttcg ttcatccata gttgcctgac 2881 tccccgtcgt gtagataact acgatacggg agggcttacc atctggcccc agtgctgcaa 2941 tgataccgcg agacccacgc tcaccggctc cagatttatc agcaataaac cagccagccg 3001 gaagggccga gcgcagaagt ggtcctgcaa ctttatccgc ctccatccag tctattaatt 3061 gttgccggga agctagagta agtagttcgc cagttaatag tttgcgcaac gttgttgcca 3121 ttgctacagg catcgtggtg tcacgctcgt cgtttggtat ggcttcattc agctccggtt 3181 cccaacgatc aaggcgagtt acatgatccc ccatgttgtg caaaaaagcg gttagctcct 3241 tcggtcctcc gatcgttgtc agaagtaagt tggccgcagt gttatcactc atggttatgg 3301 cagcactgca taattctctt actgtcatgc catccgtaag atgcttttct gtgactggtg 3361 agtactcaac caagtcattc tgagaatagt gtatgcggcg accgagttgc tcttgcccgg 3421 cgtcaatacg ggataatacc gcgccacata gcagaacttt aaaagtgctc atcattggaa 3481 aacgttcttc ggggcgaaaa ctctcaagga tcttaccgct gttgagatcc agttcgatgt 3541 aacccactcg tgcacccaac tgatcttcag catcttttac tttcaccagc gtttctgggt 3601 gagcaaaaac aggaaggcaa aatgccgcaa aaaagggaat aagggcgaca cggaaatgtt 3661 gaatactcat actcttcctt tttcaatatt attgaagcat ttatcagggt tattgtctca 3721 tgagcggata catatttgaa tgtatttaga aaaataaaca aataggggtt ccgcgcacat 3781 ttccccgaaa agtgccacct aaattgtaag cgttaatatt ttgttaaaat tcgcgttaaa 3841 tttttgttaa atcagctcat tttttaacca ataggccgaa atcggcaaaa tcccttataa 3901 atcaaaagaa tagaccgaga tagggttgag tgttgttcca gtttggaaca agagtccact 3961 attaaagaac gtggactcca acgtcaaagg gcgaaaaacc gtctatcagg gcgatggccc -continued

```
4021   actacgtgaa ccatcaccct aatcaagttt tttggggtcg aggtgccgta aagcactaaa
4081   tcggaaccct aaagggagcc cccgatttag agcttgacgg ggaaagccgg cgaacgtggc
4141   gagaaaggaa gggaagaaag cgaaaggagc gggcgctagg gcgctggcaa gtgtagcggt
4201   cacgctgcgc gtaaccacca cacccgccgc gcttaatgcg ccgctacagg gcgcgtccca
4261   ttcgccattc aggctgcgca actgttggga agggcgatcg gtgcgggcct cttcgctatt
4321   acgccagctg gcgaaagggg gatgtgctgc aaggcgatta agttgggtaa cgccagggtt
4381   ttcccagtca cgacgttgta aaacgacggc cagtgagcgc gcgtaatacg actcactata
4441   gggcgaattg ggtaccgggc ccccctcga ggtcgacggt atcgataagc ttgatatcgt
4501   gtacaaaaaa gcaggcttta aaggaaccaa ttcagtcgac tggatccggt accaaggtcg
4561   ggcaggaaga gggcctattt cccatgattc cttcatattt gcatatacga tacaaggctg
4621   ttagagagat aattagaatt aatttgactg taaacacaaa gatattagta caaaatacgt
4681   gacgtagaaa gtaataattt cttgggtagt ttgcagtttt aaaattatgt tttaaaatgg
4741   actatcatat gcttaccgta acttgaaagt atttcgattt cttggcttta tatatcttgt
4801   ggaaaggacg aaacaccggt tatagtactc tggaaacaga atctactata acaaggcaaa
4861   atgccgtgtt tatctcgtca acttgttggc gagattcatt gtgtcggcca cggaacaggc
4921   a
```

ADAR2_E488Q_dSaCas9_pCDNA3_1 (SEQ ID NO: 48)

```
LOCUS          Exported 9842 bp ds-DNA circular

DEFINITION     synthetic circular DNA

SOURCE         synthetic DNA construct

ORGANISM       recombinant plasmid

REFERENCE      1 (bases 1 to 9842)

FEATURES       Location/Qualifiers

source         1 . . . 9842
               /organism = "recombinant plasmid"
               /mol_type = "other DNA"

primer_bind    complement(213 . . . 234)
               /label = pCDNA3_CMV_out_R

enhancer       235 . . . 614
               /label = CMV enhancer
               /note = "human cytomegalovirus immediate early enhancer"

promoter       615 . . . 818
               /label = CMV promoter
               /note = "human cytomegalovirus (CMV) immediate early
               promoter"

promoter       863 . . . 881
               /label = T7 promoter
               /note = "promoter for bacteriophage T7 RNA polymerase"

primer_bind    927 . . . 985
               /label = H1-ADAR-XTEN_F

misc_feature   927 . . . 954
               /label = Homology 1_pCDNA3.1

CDS            961 . . . 2100
               /codon_start = 1
               /label = ADARB1(E488Q)_Catalytic Domain

/translation = "MLADAVSRLVLGKFGDLTDNFSSPHARRKVLAGWMTTGTDVKDA
KVISVSTGTKCINGEYMSDRGLALNDCHAEIISRRSLLRFLYTQLELYLNNKDDQKRSI
```

```
FQKSERGGFRLKENVQFHLYISTSPCGDARIFSPHEPILEEPADRHPNRKARGQLRTKI
ESGQGTIPVRSNASIQTWDGVLQGERLLTMSCSDKIARWNWGIQGSLLSIFVEPIYFS
SIILGSLYHGDHLSRAMYQRISNIEDLPPLYTLNKPLLSGISNAEARQPGKAPNFSVNW
TVGDSAIEVINATTGKDELGRASRLCKHALYCRWMRVHGKVPSHLLRSKITKPNVYHES
KLAAKEYQAAKARLFTAFIKAGLGAWVEKPTEQDQFSLTP"

primer_bind            961 . . . 982
                       /label = Primer 4

primer_bind            1111 . . . 1138
                       /label = Primer 1

primer_bind            1440 . . . 1478
                       /label = E488Q_Mutagenesis_F

primer_bind            complement(1440 . . . 1478)
                       /label = E488Q_Mutagenesis_R

primer_bind            complement(2080 . . . 2112)
                       /label = ADAR2DD_GS_R

primer_bind            complement(2080 . . . 2100)
                       /label = Primer 5

primer_bind            2086 . . . 2132
                       /label = SaCas9_Gib_F

misc_feature           2101 . . . 2112
                       /label = GS_linker

misc_feature           2113 . . . 5268
                       /label = dSaCas9(D10A, N580A)

primer_bind            complement(5245 . . . 5268)
                       /label = SaCas9_Gib_R

primer_bind            5249 . . . 5289
                       /label = SaCas9_HA_F

primer_bind            5269 . . . 5290
                       /label = ADAR2_CD_Inverse_F

CDS                    5272 . . . 5298
                       /codon_start = 1
                       /product = "HA (human influenza hemagglutinin) epitope tag"
                       /label = HA
                       /translation = "YPYDVPDYA"

primer_bind            complement(5290 . . . 5312)
                       /label = AXC_NLSout_NESin_R

primer_bind            complement(5290 . . . 5310)
                       /label = NLS_out_R

CDS                    5317 . . . 5337
                       /codon_start = 1
                       /product = "nuclear localization signal of SV40 large T
                       antigen"
                       /label = SV40 NLS
                       /translation = "PKKKRKV"

CDS                    5344 . . . 5364
                       /codon_start = 1
                       /product = "nuclear localization signal of SV40 large T
                       antigen"
                       /label = SV40 NLS
                       /translation = "PKKKRKV"

primer_bind            complement(5349 . . . 5408)
                       /label = XTEN-Cas9-H2_R

primer_bind            complement(5349 . . . 5393)
                       /label = Primer 7

primer_bind            5363 . . . 5387
                       /label = NLS_out_NES_full_F

primer_bind            5365 . . . 5387
                       /label = AXC_NLSout_NESin_F
```

```
misc_feature            5374 . . . 5408
                        /label = Homology 2_pCDNA3.1

primer_bind             5374 . . . 5392
                        /label = pCDNA3_CMV_out_F

primer_bind             5395 . . . 5418
                        /label = bGH_HindIII_F

polyA_signal            5442 . . . 5666
                        /label = bGH poly(A) signal
                        /note = "bovine growth hormone polyadenylation signal"

primer_bind             complement(5648 . . . 5666)
                        /label = bGH_NotI_R

rep_origin              5712 . . . 6140
                        /direction = RIGHT
                        /label = f1 ori
                        /note = "f1 bacteriophage origin of replication; arrow
                        indicates direction of (+) strand synthesis"

promoter                6154 . . . 6483
                        /label = SV40 promoter
                        /note = "SV40 enhancer and early promoter"

rep_origin              6334 . . . 6469
                        /label = SV40 ori
                        /note = "SV40 origin of replication"

CDS                     6550 . . . 7344
                        /codon_start = 1
                        /gene = "aph(3')-II (or nptII)"
                        /product = "aminoglycoside phosphotransferase from Tn5"
                        /label = NeoR/KanR
                        /note = "confers resistance to neomycin, kanamycin, and G418
                        (Geneticin(R))"

/translation = "MIEQDGLHAGSPAAWVERLFGYDWAQQTIGCSDAAVFRLSAQGRP
VLFVKTDLSGALNELQDEAARLSWLATTGVPCAAVLDVVTEAGRDWLLLGEVPGQDLLS
SHLAPAEKVSIMADAMRRLHTLDPATCPFDHQAKHRIERARTRMEAGLVDQDDLDEEHQ
GLAPAELFARLKARMPDGEDLVVTHGDACLPNIMVENGRFSGFIDCGRLGVADRYQDIA
LATRDIAEELGGEWADRFLVLYGIAAPDSQRIAFYRLLDEFF"

polyA_signal            7518 . . . 7639
                        /label = SV40 poly(A) signal
                        /note = "SV40 polyadenylation signal"

primer_bind             complement(7688 . . . 7704)
                        /label = M13 rev
                        /note = "common sequencing primer, one of multiple similar
                        variants"

protein_bind            7712 . . . 7728
                        /label = lac operator
                        /bound_moiety = "lac repressor encoded by lacI"
                        /note = "The lac repressor binds to the lac operator to
                        inhibit transcription in E. coli. This inhibition can be
                        relieved by adding lactose or
                        isopropyl-beta-D-thiogalactopyranoside (IPTG)."

promoter                complement(7736 . . . 7766)
                        /label = lac promoter
                        /note = "promoter for the E. coli lac operon"

protein_bind            7781 . . . 7802
                        /label = CAP binding site
                        /bound_moiety = "E. coli catabolite activator protein"
                        /note = "CAP binding activates transcription in the presence
                        of cAMP."

rep_origin              complement(8090 . . . 8675)
                        /direction = LEFT
                        /label = ori
                        /note = "high-copy-number ColE1/pMB1/pBR322/pUC origin of
                        replication"
```

```
CDS                       complement(8846 . . . 9706)
                          /codon_start = 1
                          /gene = "bla"
                          /product = "beta-lactamase"
                          /label = AmpR
                          /note = "confers resistance to ampicillin, carbenicillin, and
                          related antibiotics"

/translation = "MSIQHFRVALIPFFAAFCLPVFAHPETLVKVKDAEDQLGARVGYI
ELDLNSGKILESFRPEERFPMMSTFKVLLCGAVLSRIDAGQEQLGRRIHYSQNDLVEYS
PVTEKHLTDGMTVRELCSAAITMSDNTAANLLLTTIGGPKELTAFLHNMGDHVTRLDRW
EPELNEAIPNDERDTTMPVAMATTLRKLLTGELLTLASRQQLIDWMEADKVAGPLLRSA
LPAGWFIADKSGAGERGSRGIIAALGPDGKPSRIVVIYTTGSQATMDERNRQIAEIGAS
LIKHW"

promoter                  complement(9707 . . . 9811)
                          /gene = "bla"
                          /label = AmpR promoter

ORIGIN
        1     gacggatcgg gagatctccc gatcccctat ggtgcactct cagtacaatc tgctctgatg

       61     ccgcatagtt aagccagtat ctgctccctg cttgtgtgtt ggaggtcgct gagtagtgcg

      121     cgagcaaaat ttaagctaca acaaggcaag gcttgaccga caattgcatg aagaatctgc

      181     ttagggttag gcgttttgcg ctgcttcgcg atgtacgggc cagatatacg cgttgacatt

      241     gattattgac tagttattaa tagtaatcaa ttacggggtc attagttcat agcccatata

      301     tggagttccg cgttacataa cttacggtaa atggcccgcc tggctgaccg cccaacgacc

      361     cccgcccatt gacgtcaata atgacgtatg ttcccatagt aacgccaata gggactttcc

      421     attgacgtca atgggtggag tatttacggt aaactgccca cttggcagta catcaagtgt

      481     atcatatgcc aagtacgccc cctattgacg tcaatgacgg taaatggccc gcctggcatt

      541     atgcccagta catgacctta tgggactttc ctacttggca gtacatctac gtattagtca

      601     tcgctattac catggtgatg cggttttggc agtacatcaa tgggcgtgga tagcggtttg

      661     actcacgggg atttccaagt ctccacccca ttgacgtcaa tgggagtttg ttttggcacc

      721     aaaatcaacg ggactttcca aaatgtcgta acaactccgc cccattgacg caaatgggcg

      781     gtaggcgtgt acggtgggag gtctatataa gcagagctct ctggctaact agagaaccca

      841     ctgcttactg gcttatcgaa attaatacga ctcactatag ggagacccaa gctggctagc

      901     gtttaaacgg gccctctaga ctcgagcggc cgccactgtg ctggatatct gcagagaacc

      961     atgttagctg acgctgtctc acgcctggtc ctgggtaagt ttggtgacct gaccgacaac

     1021     ttctcctccc ctcacgctcg cagaaaagtg ctggctggag tcgtcatgac aacaggcaca

     1081     gatgttaaag atgccaaggt gataagtgtt tctacaggaa caaaatgtat taatggtgaa

     1141     tacatgagtg atcgtggcct tgcattaaat gactgccatg cagaaataat atctcggaga

     1201     tccttgctca gatttcttta tacacaactt gagctttact taaataacaa agatgatcaa

     1261     aaaagatcca tctttcagaa atcagagcga gggggtttta ggctgaagga gaatgtccag

     1321     tttcatctgt acatcagcac ctctccctgt ggagatgcca gaatcttctc accacatgag

     1381     ccaatcctgg aagaaccagc agatagacac ccaaatcgta aagcaagagg acagctacgg

     1441     accaaaatag agtctggtca ggggacgatt ccagtgcgct ccaatgcgag catccaaacg

     1501     tgggacgggg tgctgcaagg ggagcggctg ctcaccatgt cctgcagtga caagattgca

     1561     cgctggaacg tggtgggcat ccagggatcc ctgctcagca ttttcgtgga gcccatttac

     1621     ttctcgagca tcatcctggg cagcctttac cacggggacc acctttccag ggccatgtac

     1681     cagcggatct ccaacataga ggacctgcca cctctctaca ccctcaacaa gcctttgctc
```

```
1741  agtggcatca gcaatgcaga agcacggcag ccagggaagg cccccaactt cagtgtcaac
1801  tggacggtag gcgactccgc tattgaggtc atcaacgcca cgactgggaa ggatgagctg
1861  ggccgcgcgt cccgcctgtg taagcacgcg ttgtactgtc gctggatgcg tgtgcacggc
1921  aaggttccct cccacttact acgctccaag attaccaagc ccaacgtgta ccatgagtcc
1981  aagctggcgg caaaggagta ccaggccgcc aaggcgcgtc tgttcacagc cttcatcaag
2041  gcggggctgg gggcctgggt ggagaagccc accgagcagg accagttctc actcacgccc
2101  ggatccggat ccaagcggaa ctacatcctg ggcctggcca tcggcatcac cagcgtgggc
2161  tacggcatca tcgactacga gacacgggac gtgatcgatg ccggcgtgcg gctgttcaaa
2221  gaggccaacg tggaaaacaa cgagggcagg cggagcaaga gaggcgccag aaggetgaag
2281  cggcggaggc ggcatagaat ccagagagtg aagaagctgc tgttcgacta caacctgctg
2341  accgaccaca gcgagctgag cggcatcaac ccctacgagg ccagagtgaa gggcctgagc
2401  cagaagctga gcgaggaaga gttctctgcc gccctgctgc acctggccaa gagaagaggc
2461  gtgcacaacg tgaacgaggt ggaagaggac accggcaacg agctgtccac caaagagcag
2521  atcagccgga acagcaaggc cctggaagag aaatacgtgg ccgaactgca gctggaacgg
2581  ctgaagaaag acggcgaagt gcggggcagc atcaacagat tcaagaccag cgactacgtg
2641  aaagaagcca aacagctgct gaaggtgcag aaggcctacc accagctgga ccagagcttc
2701  atcgacacct acatcgacct gctggaaacc cggcggacct actatgaggg acctggcgag
2761  ggcagcccct tcggctggaa ggacatcaaa gaatggtacg agatgctgat gggccactgc
2821  acctacttcc ccgaggaact gcggagcgtg aagtacgcct acaacgccga cctgtacaac
2881  gccctgaacg acctgaacaa tctcgtgatc accagggacg agaacgagaa gctggaatat
2941  tacgagaagt tccagatcat cgagaacgtg ttcaagcaga agaagaagcc caccctgaag
3001  cagatcgcca aagaaatcct cgtgaacgaa gaggatatta agggctacag agtgaccagc
3061  accggcaagc ccgagttcac caacctgaag gtgtaccacg acatcaagga cattaccgcc
3121  cggaaagaga ttattgagaa cgccgagctg ctggatcaga ttgccaagat cctgaccatc
3181  taccagagca gcgaggacat ccaggaagaa ctgaccaatc tgaactccga gctgacccag
3241  gaagagatcg agcagatctc taatctgaag ggctataccg gcacccacaa cctgagcctg
3301  aaggccatca acctgatcct ggacgagctg tggcacacca acgacaacca gatcgctatc
3361  ttcaaccggc tgaagctggt gcccaagaag gtggacctgt cccagcagaa agagatcccc
3421  accaccctgg tggacgactt catcctgagc cccgtcgtga agagaagctt catccagagc
3481  atcaaagtga tcaacgccat catcaagaag tacggcctgc ccaacgacat cattatcgag
3541  ctggcccgcg agaagaactc caaggacgcc cagaaaatga tcaacgagat gcagaagcgg
3601  aaccggcaga ccaacgagcg gatcgaggaa atcatccgga ccaccggcaa agagaacgcc
3661  aagtacctga tcgagaagat caagctgcac gacatgcagg aaggcaagtg cctgtacagc
3721  ctggaagcca tccctctgga agatctgctg aacaacccct tcaactatga ggtggaccac
3781  atcatcccca gaagcgtgtc cttcgacaac agcttcaaca acaaggtgct cgtgaagcag
3841  gaagaagcca gcaagaaggg caaccggacc ccattccagt acctgagcag cagcgacagc
3901  aagatcagct acgaaacctt caagaagcac atcctgaatc tggccaaggg caagggcaga
3961  atcagcaaga ccaagaaaga gtatctgctg gaagaacggg acatcaacag gttctccgtg
4021  cagaaagact tcatcaaccg gaacctggtg gataccagat acgccaccag aggcctgatg
4081  aacctgctgc ggagctactt cagagtgaac aacctggacg tgaaagtgaa gtccatcaat
```

-continued

```
4141      ggcggcttca ccagctttct gcggcggaag tggaagttta agaaagagcg gaacaagggg
4201      tacaagcacc acgccgagga cgccctgatc attgccaacg ccgatttcat cttcaaagag
4261      tggaagaaac tggacaaggc caaaaaagtg atggaaaacc agatgttcga ggaaaagcag
4321      gccgagagca tgcccgagat cgaaaccgag caggagtaca aagagatctt catcaccccc
4381      caccagatca agcacattaa ggacttcaag gactacaagt acagccaccg ggtggacaag
4441      aagcctaata gagagctgat taacgacacc ctgtactcca cccggaagga cgacaagggc
4501      aacaccctga tcgtgaacaa tctgaacggc ctgtacgaca aggacaatga caagctgaaa
4561      aagctgatca acaagagccc cgaaaagctg ctgatgtacc accacgaccc ccagacctac
4621      cagaaactga agctgattat ggaacagtac ggcgacgaga agaatcccct gtacaagtac
4681      tacgaggaaa ccgggaacta cctgaccaag tactccaaaa aggacaacgg ccccgtgatc
4741      aagaagatta agtattacgg caacaaactg aacgcccatc tggacatcac cgacgactac
4801      cccaacagca gaaacaaggt cgtgaagctg tccctgaagc cctacagatt cgacgtgtac
4861      ctggacaatg gcgtgtacaa gttcgtgacc gtgaagaatc tggatgtgat caaaaaagaa
4921      aactactacg aagtgaatag caagtgctat gaggaagcta agaagctgaa gaagatcagc
4981      aaccaggccg agtttatcgc ctccttctac aacaacgatc tgatcaagat caacggcgag
5041      ctgtatagag tgatcggcgt gaacaacgac ctgctgaacc ggatcgaagt gaacatgatc
5101      gacatcacct accgcgagta cctggaaaac atgaacgaca agaggccccc caggatcatt
5161      aagacaatcg cctccaagac ccagagcatt aagaagtaca gcacagacat tctgggcaac
5221      ctgtatgaag tgaaatctaa gaagcaccct cagatcatca aaaagggcgc ctatccctat
5281      gacgtgcccg attatgccag cctgggcagc ggctccccca agaaaaaacg caaggtggaa
5341      gatcctaaga aaaagcggaa agtggacgtg taaccaccac actggactag tggatccgag
5401      ctcggtacca agcttaagtt taaaccgctg atcagcctcg actgtgcctt ctagttgcca
5461      gccatctgtt gtttgcccct cccccgtgcc ttccttgacc ctggaaggtg ccactcccac
5521      tgtcctttcc taataaaatg aggaaattgc atcgcattgt ctgagtaggt gtcattctat
5581      tctggggggt ggggtggggc aggacagcaa gggggaggat tgggaagaca atagcaggca
5641      tgctggggat gcggtgggct ctatggcttc tgaggcggaa agaaccagct ggggctctag
5701      ggggtatccc cacgcgccct gtagcggcgc attaagcgcg gcgggtgtgg tggttacgcg
5761      cagcgtgacc gctacacttg ccagcgccct agcgcccgct cctttcgctt tcttcccttc
5821      ctttctcgcc acgttcgccg gctttccccg tcaagctcta aatcgggggc tccctttagg
5881      gttccgattt agtgctttac ggcacctcga ccccaaaaaa cttgattagg gtgatggttc
5941      acgtagtggg ccatcgccct gatagacggt ttttcgccct ttgacgttgg agtccacgtt
6001      ctttaatagt ggactcttgt tccaaactgg aacaacactc aaccctatct cggtctattc
6061      ttttgattta taagggattt tgccgatttc ggcctattgg ttaaaaaatg agctgattta
6121      acaaaaattt aacgcgaatt aattctgtgg aatgtgtgtc agttagggtg tggaaagtcc
6181      ccaggctccc cagcaggcag aagtatgcaa agcatgcatc tcaattagtc agcaaccagg
6241      tgtggaaagt ccccaggctc cccagcaggc agaagtatgc aaagcatgca tctcaattag
6301      tcagcaacca tagtcccgcc cctaactccg cccatcccgc ccctaactcc gcccagttcc
6361      gcccattctc cgccccatgg ctgactaatt ttttttattt atgcagaggc cgaggccgcc
6421      tctgcctctg agctattcca gaagtagtga ggaggctttt ttggaggcct aggcttttgc
```

```
6481  aaaaagctcc cgggagcttg tatatccatt ttcggatctg atcaagagac aggatgagga
6541  tcgtttcgca tgattgaaca agatggattg cacgcaggtt ctccggccgc ttgggtggag
6601  aggctattcg gctatgactg ggcacaacag acaatcggct gctctgatgc cgccgtgttc
6661  cggctgtcag cgcaggggcg cccggttctt tttgtcaaga ccgacctgtc cggtgccctg
6721  aatgaactgc aggacgaggc agcgcggcta tcgtggctgg ccacgacggg cgttccttgc
6781  gcagctgtgc tcgacgttgt cactgaagcg ggaagggact ggctgctatt gggcgaagtg
6841  ccggggcagg atctcctgtc atctcacctt gctcctgccg agaaagtatc catcatggct
6901  gatgcaatgc ggcggctgca tacgcttgat ccggctacct gcccattcga ccaccaagcg
6961  aaacatcgca tcgagcgagc acgtactcgg atggaagccg gtcttgtcga tcaggatgat
7021  ctggacgaag agcatcaggg gctcgcgcca gccgaactgt tcgccaggct caaggcgcgc
7081  atgcccgacg gcgaggatct cgtcgtgacc catggcgatg cctgcttgcc gaatatcatg
7141  gtggaaaatg gccgcttttc tggattcatc gactgtggcc ggctgggtgt ggcggaccgc
7201  tatcaggaca tagcgttggc tacccgtgat attgctgaag agcttggcgg cgaatgggct
7261  gaccgcttcc tcgtgcttta cggtatcgcc gctcccgatt cgcagcgcat cgccttctat
7321  cgccttcttg acgagttctt ctgagcggga ctctggggtt cgaaatgacc gaccaagcga
7381  cgcccaacct gccatcacga gatttcgatt ccaccgccgc cttctatgaa aggttgggct
7441  tcggaatcgt tttccgggac gccggctgga tgatcctcca gcgcggggat ctcatgctgg
7501  agttcttcgc ccaccccaac ttgtttattg cagcttataa tggttacaaa taaagcaata
7561  gcatcacaaa tttcacaaat aaagcatttt tttcactgca ttctagttgt ggtttgtcca
7621  aactcatcaa tgtatcttat catgtctgta taccgtcgac ctctagctag agcttggcgt
7681  aatcatggtc atagctgttt cctgtgtgaa attgttatcc gctcacaatt ccacacaaca
7741  tacgagccgg aagcataaag tgtaaagcct ggggtgccta atgagtgagc taactcacat
7801  taattgcgtt gcgctcactg cccgctttcc agtcgggaaa cctgtcgtgc cagctgcatt
7861  aatgaatcgg ccaacgcgcg gggagaggcg gtttgcgtat tgggcgctct tccgcttcct
7921  cgctcactga ctcgctgcgc tcggtcgttc ggctgcggcg agcggtatca gctcactcaa
7981  aggcggtaat acggttatcc acagaatcag gggataacgc aggaaagaac atgtgagcaa
8041  aaggccagca aaaggccagg aaccgtaaaa aggccgcgtt gctggcgttt ttccataggc
8101  tccgcccccc tgacgagcat cacaaaaatc gacgctcaag tcagaggtgg cgaaacccga
8161  caggactata aagataccag gcgtttcccc ctggaagctc cctcgtgcgc tctcctgttc
8221  cgaccctgcc gcttaccgga tacctgtccg cctttctccc ttcgggaagc gtggcgcttt
8281  ctcatagctc acgctgtagg tatctcagtt cggtgtaggt cgttcgctcc aagctgggct
8341  gtgtgcacga accccccgtt cagcccgacc gctgcgcctt atccggtaac tatcgtcttg
8401  agtccaaccc ggtaagacac gacttatcgc cactggcagc agccactggt aacaggatta
8461  gcagagcgag gtatgtaggc ggtgctacag agttcttgaa gtggtggcct aactacggct
8521  acactagaag aacagtattt ggtatctgcg ctctgctgaa gccagttacc ttcggaaaaa
8581  gagttggtag ctcttgatcc ggcaaacaaa ccaccgctgg tagcggtttt tttgtttgca
8641  agcagcagat tacgcgcaga aaaaaaggat ctcaagaaga tcctttgatc ttttctacgg
8701  ggtctgacgc tcagtggaac gaaaactcac gttaagggat tttggtcatg agattatcaa
8761  aaaggatctt cacctagatc cttttaaatt aaaaatgaag ttttaaatca atctaaagta
8821  tatatgagta aacttggtct gacagttacc aatgcttaat cagtgaggca cctatctcag
```

-continued

```
8881     cgatctgtct atttcgttca tccatagttg cctgactccc cgtcgtgtag ataactacga
8941     tacgggaggg cttaccatct ggccccagtg ctgcaatgat accgcgagac ccacgctcac
9001     cggctccaga tttatcagca ataaaccagc cagccggaag ggccgagcgc agaagtggtc
9061     ctgcaacttt atccgcctcc atccagtcta ttaattgttg ccgggaagct agagtaagta
9121     gttcgccagt taatagtttg cgcaacgttg ttgccattgc tacaggcatc gtggtgtcac
9181     gctcgtcgtt tggtatggct tcattcagct ccggttccca acgatcaagg cgagttacat
9241     gatcccccat gttgtgcaaa aaagcggtta gctccttcgg tcctccgatc gttgtcagaa
9301     gtaagttggc cgcagtgtta tcactcatgg ttatggcagc actgcataat tctcttactg
9361     tcatgccatc cgtaagatgc ttttctgtga ctggtgagta ctcaaccaag tcattctgag
9421     aatagtgtat gcggcgaccg agttgctctt gcccggcgtc aatacgggat aataccgcgc
9481     cacatagcag aactttaaaa gtgctcatca ttggaaaacg ttcttcgggg cgaaaactct
9541     caaggatctt accgctgttg agatccagtt cgatgtaacc cactcgtgca cccaactgat
9601     cttcagcatc ttttactttc accagcgttt ctgggtgagc aaaaacagga aggcaaaatg
9661     ccgcaaaaaa gggaataagg gcgacacgga aatgttgaat actcatactc ttcctttttc
9721     aatattattg aagcatttat cagggttatt gtctcatgag cggatacata tttgaatgta
9781     tttagaaaaa taaacaaata ggggttccgc gcacatttcc ccgaaaagtg ccacctgacg
9841     tc
```

LCV2 puro CFTR 51 1217 gibson (SEQ ID NO: 35)

| | |
|---|---|
| LOCUS | Exported 14250 bp ds-DNA circular |
| DEFINITION | synthetic circular DNA |
| KEYWORDS | LCV2_puro_CFTR_51_1217_gibson |
| SOURCE | synthetic DNA construct |
| ORGANISM | recombinant plasmid |
| REFERENCE | 1 (bases 1 to 14250) |
| FEATURES | Location/Qualifiers |
| source | 1 . . . 14250<br>/organism = "recombinant plasmid"<br>/mol_type = "other DNA" |
| misc_feature | 1 . . . 33<br>/note = "NLS" |
| misc_feature | 34 . . . 57<br>/note = "FLAG" |
| misc_feature | 58 . . . 123<br>/note = "P2A" |
| CDS | 124 . . . 720<br>/note = "Puro" |
| misc_binding | 736 . . . 1324<br>/note = "WPRE" |
| misc_feature | 736 . . . 755<br>/note = "mCherry_PCR_tail" |
| LTR | 1395 . . . 1630<br>/note = "3' LTR" |
| rep_origin | 4079 . . . 4304<br>/note = "ColE1" |

```
misc_feature            4516 . . . 5322
                        /note = "AmpR"

LTR                     6472 . . . 6660
                        /note = "5' LTR (R and U5 portions; U3 was replaced by the
                        CMV promoter)"

misc_feature            6711 . . . 6848
                        /note = "Psi"

misc_feature            6768 . . . 6771
                        /note = "SD; splice donor"

misc_feature            6815 . . . 7179
                        /note = "gag"

misc_feature            7325 . . . 7566
                        /note = "RRE"

misc_feature            8084 . . . 8201
                        /note = "CPPT; central polypurine tract"

promoter                8252 . . . 8500
                        /note = "Human U6"

misc_feature            8522 . . . 8607
                        /note = "sgRNA scaffold"

misc_feature            8608 . . . 8613
                        /note = "Linker"

promoter                8665 . . . 8920
                        /note = "EFS-NS"

CDS                     8944 . . .  10083
                        /codon_start = 1
                        /note = "ADARB1_Catalytic Domain" (SEQ ID NO: 36)

/translation = "MLADAVSRLVLGKFGDLTDNFSSPHARRKVLAGVVMTTGTDVKDAKVIS
VSTGTKCINGEYMSDRGLALNDCHAEIISRRSLLRFLYTQLELYLNNKDDQKRSIFQKSE
RGGFRLKENVQFHLYISTSPCGDARIFSPHEPILEEPADRHPNRKARGQLRTKIESGQGTIP
VRSNASIQTWDGVLQGERLLTMSCSDKIARWNVVGIQGSLLSIFVEPIYFSSIILGSLYHG
DHLSRAMYQRISNIEDLPPLYTLNKPLLSGISNAEARQPGKAPNFSVNWTVGDSAIEVIN
ATTGKDELGRASRLCKHALYCRWMRVHGKVPSHLLRSKITKPNVYHESKLAAKEYQA
AKARLFTAFIKAGLGAWVEKPTEQDQFSLTP"

misc_feature            8944 . . . 8946
                        /note = "hSpCas9"

CDS                     10084 . . . 10131
                        /codon_start = 1
                        /note = "XTEN"
                        /translation = "SGSETPGTSESATPES" (SEQ ID NO: 37)

CDS                     10132 . . . 14235
                        /codon_start = 1
                        /product = "catalytically dead mutant of the Cas9
                        endonuclease from the Streptococcus pyogenes Type II
                        CRISPR/Cas system"
                        /note = "dCas9"
                        /note = "RNA-guided DNA-binding protein that lacks
                        endonuclease activity due to the D10A mutation in the RuvC
                        catalytic domain and the H840A mutation in the HNH
                        catalytic domain" (SEQ ID NO: 38)

/translation = "MDKKYSIGLAIGTNSVGWAVITDEYKVPSKKFKVLGNTDRHSIKKNLIGAL
LFDSGETAEATRLKRTARRRYTRRKNRICYLQEIFSNEMAKVDDSFFHRLEESFLVEEDK
KHERHPIFGNIVDEVAYHEKYPTIYHLRKKLVDSTDKADLRLIYLALAHMIKFRGHFLIE
GDLNPDNSDVDKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQIGDQYADLF
LAAKNLSDAILLSDILRVNTEITKAPLSASMIKRYDEHHQDLTLLKALVRQQLPEKYKEIF
FDQSKNGYAGYIDGGASQEEFYKFIKPILEKMDGTEELLVKLNREDLLRKQRTFDNGSIP
HQIHLGELHAILRRQEDFYPFLKDNREKIEKILTFRIPYYVGPLARGNSRFAWMTRKSEET
ITPWNFEEVVDKGASAQSFIERMTNFDKNLPNEKVLPKHSLLYEYFTVYNELTKVKYVT
EGMRKPAFLSGEQKKAIVDLLFKTNRKVTVKQLKEDYFKKIECFDSVEISGVEDRFNAS
LGTYHDLLKIIKDKDFLDNEENEDILEDIVLTLTLFEDREMIEERLKTYAHLFDDKVMKQ
LKRRRYTGWGRLSRKLINGIRDKQSGKTILDFLKSDGFANRNFMQLIHDDSLTFKEDIQK
AQVSGQGDSLHEHIANLAGSPAIKKGILQTVKVVDELVKVMGRHKPENIVIEMARENQT
TQKGQKNSRERMKRIEEGIKELGSQILKEHPVENTQLQNEKLYLYYLQNGRDMYVDQE
```

-continued

```
LDINRLSDYDVDAIVPQSFLKDDSIDNKVLTRSDKNRGKSDNVPSEEVVKKMKNYWRQ
LLNAKLITQRKFDNLTKAERGGLSELDKAGFIKRQLVETRQITKHVAQILDSRMNTKYD
ENDKLIREVKVITLKSKLVSDFRKDFQFYKVREINNYHHAHDAYLNAVVGTALIKKYPK
LESEFVYGDYKVYDVRKMIAKSEQEIGKATAKYFFYSNIMNFFKTEITLANGEIRKRPLIE
TNGETGEIVWDKGRDFATVRKVLSMPQVNIVKKTEVQTGGFSKESILPKRNSDKLIARK
KDWDPKKYGGFDSPTVAYSVLVVAKVEKGKSKKLKSVKELLGITIMERSSFEKNPIDFL
EAKGYKEVKKDLIIKLPKYSLFELENGRKRMLASAGELQKGNELALPSKYVNFLYLASH
YEKLKGSPEDNEQKQLFVEQHKHYLDEIIEQISEFSKRVILADANLDKVLSAYNKHRDKP
IREQAENIIHLFTLTNLGAPAAFKYFDTTIDRKRYTSTKEVLDATLIHQSITGLYETRIDLS
QLGGD"

ORIGIN (SEQ ID NO: 35)
     1  acaaagaagg ctggacaggc taagaagaag aaagattaca aagacgatga cgataaggga

    61  tccggcgcaa caaacttctc tctgctgaaa caagccggag atgtcgaaga gaatcctgga

   121  ccgaccgagt acaagcccac ggtgcgcctc gccacccgcg acgacgtccc cagggccgta

   181  cgcaccctcg ccgccgcgtt cgccgactac cccgccacgc gccacaccgt cgatccggac

   241  cgccacatcg agcgggtcac cgagctgcaa gaactcttcc tcacgcgcgt cgggctcgac

   301  atcggcaagg tgtgggtcgc ggacgacggc gccgcggtgg cggtctggac cacgccggag

   361  agcgtcgaag cgggggcggt gttcgccgag atcggcccgc gcatggccga gttgagcggt

   421  tcccggctgg ccgcgcagca acagatggaa ggcctcctgg cgccgcaccg gcccaaggag

   481  cccgcgtggt tcctggccac cgtcggagtc tcgcccgacc accagggcaa gggtctgggc

   541  agcgccgtcg tgctccccgg agtggaggcg gccgagcgcg ccggggtgcc cgccttcctg

   601  gagacctccg cgccccgcaa cctccccttc tacgagcggc tcggcttcac cgtcaccgcc

   661  gacgtcgagg tgcccgaagg accgcgcacc tggtgcatga cccgcaagcc cggtgcctga

   721  acgcgttaag tcgacaatca acctctggat tacaaaattt gtgaaagatt gactggtatt

   781  cttaactatg ttgctccttt tacgctatgt ggatacgctg ctttaatgcc tttgtatcat

   841  gctattgctt cccgtatggc tttcattttc tcctccttgt ataaatcctg gttgctgtct

   901  ctttatgagg agttgtggcc cgttgtcagg caacgtggcg tggtgtgcac tgtgtttgct

   961  gacgcaaccc ccactggttg gggcattgcc accacctgtc agctcctttc cgggactttc

  1021  gctttccccc tccctattgc cacggcggaa ctcatcgccg cctgccttgc ccgctgctgg

  1081  acaggggctc ggctgttggg cactgacaat tccgtggtgt tgtcggggaa atcatcgtcc

  1141  tttccttggc tgctcgcctg tgttgccacc tggattctgc gcgggacgtc cttctgctac

  1201  gtcccttcgg ccctcaatcc agcggacctt ccttcccgcg gcctgctgcc ggctctgcgg

  1261  cctcttccgc gtcttcgcct tcgccctcag acgagtcgga tctccctttg ggccgcctcc

  1321  ccgcgtcgac tttaagacca atgacttaca aggcagctgt agatcttagc cactttttaa

  1381  aagaaaaggg gggactggaa gggctaattc actcccaacg aagacaagat ctgctttttg

  1441  cttgtactgg gtctctctgg ttagaccaga tctgagcctg ggagctctct ggctaactag

  1501  ggaacccact gcttaagcct caataaagct tgccttgagt gcttcaagta gtgtgtgccc

  1561  gtctgttgtg tgactctggt aactagagat ccctcagacc cttttagtca gtgtggaaaa

  1621  tctctagcag ggcccgttta aacccgctga tcagcctcga ctgtgccttc tagttgccag

  1681  ccatctgttg tttgcccctc ccccgtgcct tccttgaccc tggaaggtgc cactcccact

  1741  gtcctttcct aataaaatga ggaaattgca tcgcattgtc tgagtaggtg tcattctatt

  1801  ctggggggtg gggtggggca ggacagcaag ggggaggatt gggaagacaa tagcaggcat

  1861  gctggggatg cggtgggctc tatggcttct gaggcggaaa gaaccagctg gggctctagg

  1921  gggtatcccc acgcgccctg tagcggcgca ttaagcgcgg cgggtgtggt ggttacgcgc

  1981  agcgtgaccg ctacacttgc cagcgcccta gcgcccgctc ctttcgcttt cttcccttcc
```

-continued

```
2041  tttctcgcca cgttcgccgg ctttccccgt caagctctaa atcgggggct ccctttaggg
2101  ttccgattta gtgctttacg gcacctcgac cccaaaaaac ttgattaggg tgatggttca
2161  cgtagtgggc catcgccctg atagacggtt tttcgccctt tgacgttgga gtccacgttc
2221  tttaatagtg gactcttgtt ccaaactgga acaacactca accctatctc ggtctattct
2281  tttgatttat aagggatttt gccgatttcg gcctattggt taaaaaatga gctgatttaa
2341  caaaaattta acgcgaatta attctgtgga atgtgtgtca gttagggtgt ggaaagtccc
2401  caggctcccc agcaggcaga agtatgcaaa gcatgcatct caattagtca gcaaccaggt
2461  gtggaaagtc cccaggctcc ccagcaggca gaagtatgca aagcatgcat ctcaattagt
2521  cagcaaccat agtcccgccc ctaactccgc ccatcccgcc cctaactccg cccagttccg
2581  cccattctcc gccccatggc tgactaattt tttttattta tgcagaggcc gaggccgcct
2641  ctgcctctga gctattccag aagtagtgag gaggcttttt tggaggccta ggcttttgca
2701  aaaagctccc gggagcttgt atatccattt tcggatctga tcagcacgtg ttgacaatta
2761  atcatcggca tagtatatcg gcatagtata atacgacaag gtgaggaact aaaccatggc
2821  caagttgacc agtgccgttc cggtgctcac cgcgcgcgac gtcgccggag cggtcgagtt
2881  ctggaccgac cggctcgggt tctcccggga cttcgtggag gacgacttcg ccggtgtggt
2941  ccgggacgac gtgaccctgt tcatcagcgc ggtccaggac caggtggtgc cggacaacac
3001  cctggcctgg gtgtgggtgc gcggcctgga cgagctgtac gccgagtggt cggaggtcgt
3061  gtccacgaac ttccgggacg cctccgggcc ggccatgacc gagatcggcg agcagccgtg
3121  ggggcgggag ttcgccctgc gcgacccggc cggcaactgc gtgcacttcg tggccgagga
3181  gcaggactga cacgtgctac gagatttcga ttccaccgcc gccttctatg aaaggttggg
3241  cttcggaatc gttttccggg acgccggctg gatgatcctc cagcgcgggg atctcatgct
3301  ggagttcttc gcccacccca acttgtttat tgcagcttat aatggttaca aataaagcaa
3361  tagcatcaca aatttcacaa ataaagcatt tttttcactg cattctagtt gtggtttgtc
3421  caaactcatc aatgtatctt atcatgtctg tataccgtcg acctctagct agagcttggc
3481  gtaatcatgg tcatagctgt ttcctgtgtg aaattgttat ccgctcacaa ttccacacaa
3541  catacgagcc ggaagcataa agtgtaaagc ctggggtgcc taatgagtga gctaactcac
3601  attaattgcg ttgcgctcac tgcccgcttt ccagtcggga aacctgtcgt gccagctgca
3661  ttaatgaatc ggccaacgcg cggggagagg cggtttgcgt attgggcgct cttccgcttc
3721  ctcgctcact gactcgctgc gctcggtcgt tcggctgcgg cgagcggtat cagctcactc
3781  aaaggcggta atacggttat ccacagaatc aggggataac gcaggaaaga acatgtgagc
3841  aaaaggccag caaaaggcca ggaaccgtaa aaaggccgcg ttgctggcgt ttttccatag
3901  gctccgcccc cctgacgagc atcacaaaaa tcgacgctca agtcagaggt ggcgaaaccc
3961  gacaggacta taaagatacc aggcgtttcc ccctggaagc tccctcgtgc gctctcctgt
4021  tccgaccctg ccgcttaccg gatacctgtc cgcctttctc ccttcgggaa gcgtggcgct
4081  ttctcatagc tcacgctgta ggtatctcag ttcggtgtag gtcgttcgct ccaagctggg
4141  ctgtgtgcac gaaccccccg ttcagcccga ccgctgcgcc ttatccggta actatcgtct
4201  tgagtccaac ccggtaagac acgacttatc gccactggca gcagccactg gtaacaggat
4261  tagcagagcg aggtatgtag gcggtgctac agagttcttg aagtggtggc ctaactacgg
4321  ctacactaga agaacagtat ttggtatctg cgctctgctg aagccagtta ccttcggaaa
```

-continued

```
4381   aagagttggt agctcttgat ccggcaaaca aaccaccgct ggtagcggtg gtttttttgt
4441   ttgcaagcag cagattacgc gcagaaaaaa aggatctcaa gaagatcctt tgatcttttc
4501   tacggggtct gacgctcagt ggaacgaaaa ctcacgttaa gggattttgg tcatgagatt
4561   atcaaaaagg atcttcacct agatcctttt aaattaaaaa tgaagtttta aatcaatcta
4621   aagtatatat gagtaaactt ggtctgacag ttaccaatgc ttaatcagtg aggcacctat
4681   ctcagcgatc tgtctatttc gttcatccat agttgcctga ctccccgtcg tgtagataac
4741   tacgatacgg gagggcttac catctggccc cagtgctgca atgataccgc gagacccacg
4801   ctcaccggct ccagatttat cagcaataaa ccagccagcc ggaagggccg agcgcagaag
4861   tggtcctgca actttatccg cctccatcca gtctattaat tgttgccggg aagctagagt
4921   aagtagttcg ccagttaata gtttgcgcaa cgttgttgcc attgctacag gcatcgtggt
4981   gtcacgctcg tcgtttggta tggcttcatt cagctccggt tcccaacgat caaggcgagt
5041   tacatgatcc cccatgttgt gcaaaaaagc ggttagctcc ttcggtcctc cgatcgttgt
5101   cagaagtaag ttggccgcag tgttatcact catggttatg gcagcactgc ataattctct
5161   tactgtcatg ccatccgtaa gatgcttttc tgtgactggt gagtactcaa ccaagtcatt
5221   ctgagaatag tgtatgcggc gaccgagttg ctcttgcccg gcgtcaatac gggataatac
5281   cgcgccacat agcagaactt taaaagtgct catcattgga aaacgttctt cggggcgaaa
5341   actctcaagg atcttaccgc tgttgagatc cagttcgatg taacccactc gtgcacccaa
5401   ctgatcttca gcatctttta ctttcaccag cgtttctggg tgagcaaaaa caggaaggca
5461   aaatgccgca aaaaagggaa taagggcgac acggaaatgt tgaatactca tactcttcct
5521   ttttcaatat tattgaagca tttatcaggg ttattgtctc atgagcggat acatatttga
5581   atgtatttag aaaaataaac aaataggggt tccgcgcaca tttccccgaa aagtgccacc
5641   tgacgtcgac ggatcgggag atctcccgat cccctatggt gcactctcag tacaatctgc
5701   tctgatgccg catagttaag ccagtatctg ctccctgctt gtgtgttgga ggtcgctgag
5761   tagtgcgcga gcaaaattta agctacaaca aggcaaggct tgaccgacaa ttgcatgaag
5821   aatctgctta gggttaggcg ttttgcgctg cttcgcgatg tacgggccag atatacgcgt
5881   tgacattgat tattgactag ttattaatag taatcaatta cggggtcatt agttcatagc
5941   ccatatatgg agttccgcgt tacataactt acggtaaatg gcccgcctgg ctgaccgccc
6001   aacgaccccc gcccattgac gtcaataatg acgtatgttc ccatagtaac gccaataggg
6061   actttccatt gacgtcaatg ggtggagtat ttacggtaaa ctgcccactt ggcagtacat
6121   caagtgtatc atatgccaag tacgccccct attgacgtca atgacggtaa atggcccgcc
6181   tggcattatg cccagtacat gaccttatgg gactttccta cttggcagta catctacgta
6241   ttagtcatcg ctattaccat ggtgatgcgg ttttggcagt acatcaatgg gcgtggatag
6301   cggtttgact cacggggatt tccaagtctc caccccattg acgtcaatgg gagtttgttt
6361   tggcaccaaa atcaacggga ctttccaaaa tgtcgtaaca actccgcccc attgacgcaa
6421   atgggcggta ggcgtgtacg gtgggaggtc tatataagca gcgcgttttg cctgtactgg
6481   gtctctctgg ttagaccaga tctgagcctg ggagctctct ggctaactag ggaacccact
6541   gcttaagcct caataaagct tgccttgagt gcttcaagta gtgtgtgccc gtctgttgtg
6601   tgactctggt aactagagat ccctcagacc cttttagtca gtgtggaaaa tctctagcag
6661   tggcgcccga acagggactt gaaagcgaaa gggaaaccag aggagctctc tcgacgcagg
6721   actcggcttg ctgaagcgcg cacggcaaga ggcgaggggc ggcgactggt gagtacgcca
```

-continued

```
6781    aaaattttga ctagcggagg ctagaaggag agagatgggt gcgagagcgt cagtattaag
6841    cgggggagaa ttagatcgcg atgggaaaaa attcggttaa ggccaggggg aaagaaaaaa
6901    tataaattaa aacatatagt atgggcaagc agggagctag aacgattcgc agttaatcct
6961    ggcctgttag aaacatcaga aggctgtaga caaatactgg gacagctaca accatccctt
7021    cagacaggat cagaagaact tagatcatta tataatacag tagcaaccct ctattgtgtg
7081    catcaaagga tagagataaa agacaccaag gaagctttag acaagataga ggaagagcaa
7141    aacaaaagta agaccaccgc acagcaagcg gccgctgatc ttcagacctg gaggaggaga
7201    tatgagggac aattggagaa gtgaattata taaatataaa gtagtaaaaa ttgaaccatt
7261    aggagtagca cccaccaagg caaagagaag agtggtgcag agagaaaaaa gagcagtggg
7321    aataggagct ttgttccttg ggttcttggg agcagcagga agcactatgg gcgcagcgtc
7381    aatgacgctg acggtacagg ccagacaatt attgtctggt atagtgcagc agcagaacaa
7441    tttgctgagg gctattgagg cgcaacagca tctgttgcaa ctcacagtct ggggcatcaa
7501    gcagctccag gcaagaatcc tggctgtgga aagataccta aaggatcaac agctcctggg
7561    gatttggggt tgctctggaa aactcatttg caccactgct gtgccttgga atgctagttg
7621    gagtaataaa tctctggaac agatttggaa tcacacgacc tggatggagt gggacagaga
7681    aattaacaat tacacaagct taatacactc cttaattgaa gaatcgcaaa accagcaaga
7741    aaagaatgaa caagaattat tggaattaga taaatgggca agtttgtgga attggtttaa
7801    cataacaaat tggctgtggt atataaaatt attcataatg atagtaggag gcttggtagg
7861    tttaagaata gtttttgctg tactttctat agtgaataga gttaggcagg gatattcacc
7921    attatcgttt cagacccacc tcccaacccc gaggggaccc gacaggcccg aaggaataga
7981    agaagaaggt ggagagagag acagagacag atccattcga ttagtgaacg gatcggcact
8041    gcgtgcgcca attctgcaga caaatggcag tattcatcca caattttaaa agaaaagggg
8101    ggattggggg gtacagtgca ggggaaagaa tagtagacat aatagcaaca gacatacaaa
8161    ctaaagaatt acaaaaacaa attacaaaaa ttcaaaattt tcgggtttat tacagggaca
8221    gcagagatcc agtttggtta attaaggtac cgagggccta tttcccatga ttccttcata
8281    tttgcatata cgatacaagg ctgttagaga gataattaga attaatttga ctgtaaacac
8341    aaagatatta gtacaaaata cgtgacgtag aaagtaataa tttcttgggt agtttgcagt
8401    tttaaaatta tgttttaaaa tggactatca tatgcttacc gtaacttgaa agtatttcga
8461    tttcttggct ttatatatct tgtggaaagg acgaaacacc gttcataggg atccaagttt
8521    tgtttaagag ctatgctgga aacagcatag caagtttaaa taaggctagt ccgttatcaa
8581    cttgaaaaag tggcaccgag tcggtgcttc atttttcctc cactgttgca aagttttttt
8641    cctgcagccc gggaattcgc tagctaggtc ttgaaaggag tgggaattgg ctccggtgcc
8701    cgtcagtggg cagagcgcac atcgcccaca gtccccgaga agttgggggg aggggtcggc
8761    aattgatccg gtgcctagag aaggtggcgc ggggtaaact gggaaagtga tgtcgtgtac
8821    tggctccgcc tttttcccga gggtggggga gaaccgtata taagtgcagt agtcgccgtg
8881    aacgttcttt ttcgcaacgg gtttgccgcc agaacacagg accggttcta gagcgctgcc
8941    accatgttag ctgacgctgt ctcacgcctg gtcctgggta agtttggtga cctgaccgac
9001    aacttctcct cccctcacgc tcgcagaaaa gtgctggctg gagtcgtcat gacaacaggc
9061    acagatgtta aagatgccaa ggtgataagt gtttctacag gaacaaaatg tattaatggt
```

-continued

```
9121   gaatacatga gtgatcgtgg ccttgcatta aatgactgcc atgcagaaat aatatctcgg
9181   agatccttgc tcagatttct ttatacacaa cttgagcttt acttaaataa caaagatgat
9241   caaaaaagat ccatctttca gaaatcagag cgagggggt ttaggctgaa ggagaatgtc
9301   cagtttcatc tgtacatcag cacctctccc tgtggagatg ccagaatctt ctcaccacat
9361   gagccaatcc tggaagaacc agcagataga cacccaaatc gtaaagcaag aggacagcta
9421   cggaccaaaa tagagtctgg tcaggggacg attccagtgc gctccaatgc gagcatccaa
9481   acgtgggacg gggtgctgca aggggagcgg ctgctcacca tgtcctgcag tgacaagatt
9541   gcacgctgga acgtggtggg catccaggga tccctgctca gcattttcgt ggagcccatt
9601   tacttctcga gcatcatcct gggcagcctt taccacgggg accacctttc cagggccatg
9661   taccagcgga tctccaacat agaggacctg ccacctctct acaccctcaa caagcctttg
9721   ctcagtggca tcagcaatgc agaagcacgg cagccaggga aggcccccaa cttcagtgtc
9781   aactggacgg taggcgactc cgctattgag gtcatcaacg ccacgactgg gaaggatgag
9841   ctgggccgcg cgtcccgcct gtgtaagcac gcgttgtact gtcgctggat gcgtgtgcac
9901   ggcaaggttc cctcccactt actacgctcc aagattacca agcccaacgt gtaccatgag
9961   tccaagctgg cggcaaagga gtaccaggcc gccaaggcgc gtctgttcac agccttcatc
10021  aaggcggggc tgggggcctg ggtggagaag cccaccgagc aggaccagtt ctcactcacg
10081  cccagtggaa gtgagacacc gggaacctca gagagcgcca cgccagaaag catggacaag
10141  aagtacagca tcggcctggc catcggcacc aactctgtgg gctgggccgt gatcaccgac
10201  gagtacaagg tgcccagcaa gaaattcaag gtgctgggca acaccgaccg gcacagcatc
10261  aagaagaacc tgatcggcgc cctgctgttc gacagcggag aaacagccga ggccacccgg
10321  ctgaagagaa ccgccagaag aagatacacc agacggaaga accggatctg ctatctgcaa
10381  gagatcttca gcaacgagat ggccaaggtg gacgacagct tcttccacag actggaagag
10441  tccttcctgg tggaagagga taagaagcac gagcggcacc ccatcttcgg caacatcgtg
10501  gacgaggtgg cctaccacga gaagtacccc accatctacc acctgagaaa gaaactggtg
10561  gacagcaccg acaaggccga cctgcggctg atctatctgg ccctggccca catgatcaag
10621  ttccggggcc acttcctgat cgagggcgac ctgaaccccg acaacagcga cgtggacaag
10681  ctgttcatcc agctggtgca gacctacaac cagctgttcg aggaaaaccc catcaacgcc
10741  agcggcgtgg acgccaaggc catcctgtct gccagactga gcaagagcag acggctggaa
10801  aatctgatcg cccagctgcc cggcgagaag aagaatggcc tgttcggcaa cctgattgcc
10861  ctgagcctgg gcctgacccc caacttcaag agcaacttcg acctggccga ggatgccaaa
10921  ctgcagctga gcaaggacac ctacgacgac gacctggaca acctgctggc ccagatcggc
10981  gaccagtacg ccgacctgtt tctggccgcc aagaacctgt ccgacgccat cctgctgagc
11041  gacatcctga gagtgaacac cgagatcacc aaggcccccc tgagcgcctc tatgatcaag
11101  agatacgacg agcaccacca ggacctgacc ctgctgaaag ctctcgtgcg gcagcagctg
11161  cctgagaagt acaaagagat tttcttcgac cagagcaaga acggctacgc cggctacatc
11221  gatggcggag ccagccagga agagttctac aagttcatca agcccatcct ggaaaagatg
11281  gacggcaccg aggaactgct cgtgaagctg aacagagagg acctgctgcg gaagcagcgg
11341  accttcgaca acggcagcat cccccaccag atccacctgg gagagctgca cgccattctg
11401  cggcggcagg aagatttta cccattcctg aaggacaacc gggaaaagat cgagaagatc
11461  ctgaccttcc gcatccccta ctacgtgggc cctctggcca ggggaaacag cagattcgcc
```

11521 tggatgacca gaaagagcga ggaaaccatc accccctgga acttcgagga agtggtggac 11581 aagggcgcca gcgcccagag cttcatcgag cggatgacca acttcgataa gaacctgccc 11641 aacgagaagg tgctgcccaa gcacagcctg ctgtacgagt acttcaccgt gtacaacgag 11701 ctgaccaaag tgaaatacgt gaccgaggga atgagaaagc ccgccttcct gagcggcgag 11761 cagaaaaaag ccatcgtgga cctgctgttc aagaccaacc ggaaagtgac cgtgaagcag 11821 ctgaaagagg actacttcaa gaaaatcgag tgcttcgact ccgtggaaat ctccggcgtg 11881 gaagatcggt tcaacgcctc cctgggcaca taccacgatc tgctgaaaat tatcaaggac 11941 aaggacttcc tggacaatga ggaaaacgag gacattctgg aagatatcgt gctgaccctg 12001 acactgtttg aggacagaga gatgatcgag gaacggctga aaacctatgc ccacctgttc 12061 gacgacaaag tgatgaagca gctgaagcgg cggagataca ccggctgggg caggctgagc 12121 cggaagctga tcaacggcat ccgggacaag cagtccggca agacaatcct ggatttcctg 12181 aagtccgacg gcttcgccaa cagaaacttc atgcagctga tccacgacga cagcctgacc 12241 tttaaagagg acatccagaa agcccaggtg tccggccagg gcgatagcct gcacgagcac 12301 attgccaatc tggccggcag ccccgccatt aagaagggca tcctgcagac agtgaaggtg 12361 gtggacgagc tcgtgaaagt gatgggccgg cacaagcccg agaacatcgt gatcgaaatg 12421 gccagagaga accagaccac ccagaaggga cagaagaaca gccgcgagag aatgaagcgg 12481 atcgaagagg gcatcaaaga gctgggcagc cagatcctga aagaacaccc cgtggaaaac 12541 acccagctgc agaacgagaa gctgtacctg tactacctgc agaatgggcg ggatatgtac 12601 gtggaccagg aactggacat caaccggctg tccgactacg atgtggacgc tatcgtgcct 12661 cagagctttc tgaaggacga ctccatcgat aacaaagtgc tgactcggag cgacaagaac 12721 cggggcaaga gcgacaacgt gccctccgaa gaggtcgtga agaagatgaa gaactactgg 12781 cgccagctgc tgaatgccaa gctgattacc cagaggaagt tcgacaatct gaccaaggcc 12841 gagagaggcg gcctgagcga actggataag gccggcttca tcaagagaca gctggtggaa 12901 acccggcaga tcacaaagca cgtggcacag atcctggact cccggatgaa cactaagtac 12961 gacgagaacg acaaactgat ccgggaagtg aaagtgatca ccctgaagtc caagctggtg 13021 tccgatttcc ggaaggattt ccagttttac aaagtgcgcg agatcaacaa ctaccaccac 13081 gcccacgacg cctacctgaa cgccgtcgtg ggaaccgccc tgatcaaaaa gtaccctaag 13141 ctggaaagcg agttcgtgta cggcgactac aaggtgtacg acgtgcggaa gatgatcgcc 13201 aagagcgagc aggaaatcgg caaggctacc gccaagtact tcttctacag caacatcatg 13261 aactttttca agaccgagat taccctggcc aacggcgaga tccggaagcg gcctctgatc 13321 gagacaaacg gcgaaacagg cgagatcgtg tgggataagg gccgggactt tgccaccgtg 13381 cggaaagtgc tgtctatgcc ccaagtgaat atcgtgaaaa agaccgaggt gcagacaggc 13441 ggcttcagca aagagtctat cctgcccaag aggaacagcg acaagctgat cgccagaaag 13501 aaggactggg accctaagaa gtacggcggc ttcgacagcc ccaccgtggc ctattctgtg 13561 ctggtggtgg ccaaagtgga aaagggcaag tccaagaaac tgaagagtgt gaaagagctg 13621 ctggggatca ccatcatgga aagaagcagc ttcgagaaga atcccatcga ctttctggaa 13681 gccaagggct acaaagaagt gaaaaaggac ctgatcatca agctgcctaa gtactccctg 13741 ttcgagctgg aaaacggccg gaagagaatg ctggcctctg ccggcgaact gcagaaggga 13801 aacgaactgg ccctgccctc caaatatgtg aacttcctgt acctggccag ccactatgag

```
13861   aagctgaagg gctcccccga ggataatgag cagaaacagc tgtttgtgga acagcacaaa
13921   cactacctgg acgagatcat cgagcagatc agcgagttct ccaagagagt gatcctggcc
13981   gacgctaatc tggacaaggt gctgagcgcc tacaacaagc acagagacaa gcctatcaga
14041   gagcaggccg agaatatcat ccacctgttt accctgacca atctgggagc ccctgccgcc
14101   ttcaagtact ttgacaccac catcgaccgg aagaggtaca ccagcaccaa agaggtgctg
14161   gacgccaccc tgatccacca gagcatcacc ggcctgtacg agacacggat cgacctgtct
14221   cagctgggag gcgacaagcg acctgccgcc
```

AXCM LCV2 puro IDUA No-spacer gibson (SEQ ID NO: 39)

```
LOCUS             Exported 14230 bp ds-DNA circular
DEFINITION        synthetic circular DNA
KEYWORDS          AXCM_LCV2_puro_IDUA_No-spacer_gibson
SOURCE            synthetic DNA construct
ORGANISM          synthetic DNA construct
REFERENCE         1 (bases 1 to 14230)
FEATURES          Location/Qualifiers
source            1 . . . 14230
                  /organism = "synthetic DNA construct"
                  /mol_type = "other DNA"
LTR               828 . . . 1016
                  /note = "5' LTR (R and U5 portions; U3 was replaced by the
                  CMV promoter)"
misc_feature      1067 . . . 1204
                  /note = "Psi"
misc_feature      1124 . . . 1127
                  /note = "SD; splice donor"
misc_feature      1171 . . . 1535
                  /note = "gag"
misc_feature      1681 . . . 1922
                  /note = "RRE"
misc_feature      2440 . . . 2557
                  /note = "CPPT; central polypurine tract"
promoter          2608 . . . 2856
                  /note = "Human U6"
misc_feature      2857 . . . 2942
                  /note = "sgRNA scaffold"
misc_feature      2943 . . . 2948
                  /note = "Linker"
promoter          3001 . . . 3256
                  /note = "EFS-NS"
CDS               3280 . . . 4419
                  /codon_start = 1
                  /note = "ADARB1_Catalytic Domain" (SEQ ID NO: 40)

/translation = "MLADAVSRLVLGKFGDLTDNFSSPHARRKVLAGVVMTTGTDVKDAKVIS
VSTGTKCINGEYMSDRGLALNDCHAEIISRRSLLRFLYTQLELYLNNKDDQKRSIFQKSE
RGGFRLKENVQFHLYISTSPCGDARIFSPHEPILEEPADRHPNRKARGQLRTKIESGQGTIP
VRSNASIQTWDGVLQGERLLTMSCSDKIARWNVVGIQGSLLSIFVEPIYFSSIILGSLYHG
DHLSRAMYQRISNIEDLPPLYTLNKPLLSGISNAEARQPGKAPNFSVNWTVGDSAIEVIN
ATTGKDELGRASRLCKHALYCRWMRVHGKVPSHLLRSKITKPNVYHESKLAAKEYQA
AKARLFTAFIKAGLGAWVEKPTEQDQFSLTP"
```

```
misc_feature          3280 . . . 3282
                      /note = "hSpCas9"

CDS                   4420 . . . 4467
                      /codon_start = 1
                      /note = "XTEN"
                      /translation = "SGSETPGTSESATPES" (SEQ ID NO: 41)

CDS                   4468 . . . 8571
                      /codon_start = 1
                      /product = "catalytically dead mutant of the Cas9
                      endonuclease from the Streptococcus pyogenes Type II
                      CRISPR/Cas system"
                      /note = "dCas9"
                      /note = "RNA-guided DNA-binding protein that lacks
                      endonuclease activity due to the D10A mutation in the RuvC
                      catalytic domain and the H840A mutation in the HNH
                      catalytic domain" (SEQ ID NO: 42)

/translation = "MDKKYSIGLAIGTNSVGWAVITDEYKVPSKKFKVLGNTDRHSIKKNLIGAL
LFDSGETAEATRLKRTARRRYTRRKNRICYLQEIFSNEMAKVDDSFFHRLEESFLVEEDK
KHERHPIFGNIVDEVAYHEKYPTIYHLRKKLVDSTDKADLRLIYLALAHMIKFRGHFLIE
GDLNPDNSDVDKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQIGDQYADLF
LAAKNLSDAILLSDILRVNTEITKAPLSASMIKRYDEHHQDLTLLKALVRQQLPEKYKEIF
FDQSKNGYAGYIDGGASQEEFYKFIKPILEKMDGTEELLVKLNREDLLRKQRTFDNGSIP
HQIHLGELHAILRRQEDFYPFLKDNREKIEKILTFRIPYYVGPLARGNSRFAWMTRKSEET
ITPWNFEEVVDKGASAQSFIERMTNFDKNLPNEKVLPKHSLLYEYFTVYNELTKVKYVT
EGMRKPAFLSGEQKKAIVDLLFKTNRKVTVKQLKEDYFKKIECFDSVEISGVEDRFNAS
LGTYHDLLKIIKDKDFLDNEENEDILEDIVLTLTLFEDREMIEERLKTYAHLFDDKVMKQ
LKRRRYTGWGRLSRKLINGIRDKQSGKTILDFLKSDGFANRNFMQLIHDDSLTFKEDIQK
AQVSGQGDSLHEHIANLAGSPAIKKGILQTVKVVDELVKVMGRHKPENIVIEMARENQT
TQKGQKNSRERMKRIEEGIKELGSQILKEHPVENTQLQNEKLYLYYLQNGRDMYVDQE
LDINRLSDYDVDAIVPQSFLKDDSIDNKVLTRSDKNRGKSDNVPSEEVVKKMKNYWRQ
LLNAKLITQRKFDNLTKAERGGLSELDKAGFIKRQLVETRQITKHVAQILDSRMNTKYD
ENDKLIREVKVITLKSKLVSDFRKDFQFYKVREINNYHHAHDAYLNAVVGTALIKKYPK
LESEFVYGDYKVYDVRKMIAKSEQEIGKATAKYFFYSNIMNFFKTEITLANGEIRKRPLIE
TNGETGEIVWDKGRDFATVRKVLSMPQVNIVKKTEVQTGGFSKESILPKRNSDKLIARK
KDWDPKKYGGFDSPTVAYSVLVVAKVEKGKSKKLKSVKELLGITIMERSSFEKNPIDFL
EAKGYKEVKKDLIIKLPKYSLFELENGRKRMLASAGELQKGNELALPSKYVNFLYLASH
YEKLKGSPEDNEQKQLFVEQHKHYLDEIIEQISEFSKRVILADANLDKVLSAYNKHRDKP
IREQAENIIHLFTLTNLGAPAAFKYFDTTIDRKRYTSTKEVLDATLIHQSITGLYETRIDLS
QLGGD"

misc_feature          8572 . . . 8619
                      /note = "NLS"

CDS                   8572
                      /codon_start = 1
                      /product = "catalytically dead mutant of the Cas9
                      endonuclease from the Streptococcus pyogenes Type II
                      CRISPR/Cas system"
                      /note = "dCas9"
                      /note = "RNA-guided DNA-binding protein that lacks
                      endonuclease activity due to the D10A mutation in the RuvC
                      catalytic domain and the H840A mutation in the HNH
                      catalytic domain"
                      /translation=""

misc_feature          8620 . . . 8643
                      /note = "FLAG"

misc_feature          8644 . . . 8709
                      /note = "P2A"

CDS                   8710 . . . 9306
                      /note = "Puro"

misc_binding          9322 . . . 9910
                      /note = "WPRE"

LTR                   9981 . . . 10216
                      /note = "3' LTR"

rep_origin            12665 . . . 12890
                      /note = "ColE1"
```

```
misc_feature            13102 . . . 13908
                        /note = "AmpR"

ORIGIN (SEQ ID NO: 39)
     1  gtcgacggat cgggagatct cccgatcccc tatggtgcac tctcagtaca atctgctctg
    61  atgccgcata gttaagccag tatctgctcc ctgcttgtgt gttggaggtc gctgagtagt
   121  gcgcgagcaa aatttaagct acaacaaggc aaggcttgac cgacaattgc atgaagaatc
   181  tgcttagggt taggcgtttt gcgctgcttc gcgatgtacg ggccagatat acgcgttgac
   241  attgattatt gactagttat taatagtaat caattacggg gtcattagtt catagcccat
   301  atatggagtt ccgcgttaca taacttacgg taaatggccc gcctggctga ccgcccaacg
   361  acccccgccc attgacgtca ataatgacgt atgttcccat agtaacgcca atagggactt
   421  tccattgacg tcaatgggtg gagtatttac ggtaaactgc ccacttggca gtacatcaag
   481  tgtatcatat gccaagtacg ccccctattg acgtcaatga cggtaaatgg cccgcctggc
   541  attatgccca gtacatgacc ttatgggact ttcctacttg gcagtacatc tacgtattag
   601  tcatcgctat taccatggtg atgcggtttt ggcagtacat caatgggcgt ggatagcggt
   661  ttgactcacg gggatttcca agtctccacc ccattgacgt caatgggagt ttgttttggc
   721  accaaaatca acgggacttt ccaaaatgtc gtaacaactc cgccccattg acgcaaatgg
   781  gcggtaggcg tgtacggtgg gaggtctata taagcagcgc gttttgcctg tactgggtct
   841  ctctggttag accagatctg agcctgggag ctctctggct aactagggaa cccactgctt
   901  aagcctcaat aaagcttgcc ttgagtgctt caagtagtgt gtgcccgtct gttgtgtgac
   961  tctggtaact agagatccct cagacccttt tagtcagtgt ggaaaatctc tagcagtggc
  1021  gcccgaacag ggacttgaaa gcgaaaggga aaccagagga gctctctcga cgcaggactc
  1081  ggcttgctga agcgcgcacg gcaagaggcg aggggcggcg actggtgagt acgccaaaaa
  1141  ttttgactag cggaggctag aaggagagag atgggtgcga gagcgtcagt attaagcggg
  1201  ggagaattag atcgcgatgg gaaaaaattc ggttaaggcc agggggaaag aaaaaatata
  1261  aattaaaaca tatagtatgg gcaagcaggg agctagaacg attcgcagtt aatcctggcc
  1321  tgttagaaac atcagaaggc tgtagacaaa tactgggaca gctacaacca tcccttcaga
  1381  caggatcaga agaacttaga tcattatata atacagtagc aaccctctat tgtgtgcatc
  1441  aaaggataga gataaaagac accaaggaag ctttagacaa gatagaggaa gagcaaaaca
  1501  aaagtaagac caccgcacag caagcggccg ctgatcttca gacctggagg aggagatatg
  1561  agggacaatt ggagaagtga attatataaa tataaagtag taaaaattga accattagga
  1621  gtagcaccca ccaaggcaaa gagaagagtg gtgcagagag aaaaaagagc agtgggaata
  1681  ggagctttgt tccttgggtt cttgggagca gcaggaagca ctatgggcgc agcgtcaatg
  1741  acgctgacgg tacaggccag acaattattg tctggtatag tgcagcagca gaacaatttg
  1801  ctgagggcta ttgaggcgca acagcatctg ttgcaactca cagtctgggg catcaagcag
  1861  ctccaggcaa gaatcctggc tgtggaaaga tacctaaagg atcaacagct cctggggatt
  1921  tggggttgct ctggaaaact catttgcacc actgctgtgc cttggaatgc tagttggagt
  1981  aataaatctc tggaacagat ttggaatcac acgacctgga tggagtggga cagagaaatt
  2041  aacaattaca caagcttaat acactcctta attgaagaat cgcaaaacca gcaagaaaag
  2101  aatgaacaag aattattgga attagataaa tgggcaagtt tgtggaattg gtttaacata
  2161  acaaattggc tgtggtatat aaaattattc ataatgatag taggaggctt ggtaggttta
```

-continued 2221 agaatagttt ttgctgtact ttctatagtg aatagagtta ggcagggata ttcaccatta 2281 tcgtttcaga cccacctccc aaccccgagg ggacccgaca ggcccgaagg aatagaagaa 2341 gaaggtggag agagagacag agacagatcc attcgattag tgaacggatc ggcactgcgt 2401 gcgccaattc tgcagacaaa tggcagtatt catccacaat tttaaaagaa aaggggggat 2461 tggggggtac agtgcagggg aaagaatagt agacataata gcaacagaca tacaaactaa 2521 agaattacaa aaacaaatta caaaaattca aaattttcgg gtttattaca gggacagcag 2581 agatccagtt tggttaatta aggtaccgag ggcctatttc ccatgattcc ttcatatttg 2641 catatacgat acaaggctgt tagagagata attagaatta atttgactgt aaacacaaag 2701 atattagtac aaaatacgtg acgtagaaag taataatttc ttgggtagtt tgcagtttta 2761 aaattatgtt ttaaaatgga ctatcatatg cttaccgtaa ettgaaagta tttcgatttc 2821 ttggctttat atatcttgtg gaaaggacga aacaccgttt aagagctatg ctggaaacag 2881 catagcaagt ttaaataagg ctagtccgtt atcaacttga aaaagtggca ccgagtcggt 2941 gcttcattac ttcggcccag agctgctcct tttttcctg cagcccggga attcgctagc 3001 taggtcttga aaggagtggg aattggctcc ggtgcccgtc agtgggcaga gcgcacatcg 3061 cccacagtcc ccgagaagtt ggggggaggg gtcggcaatt gatccggtgc ctagagaagg 3121 tggcgcgggg taaactggga aagtgatgtc gtgtactggc tccgcctttt tcccgagggt 3181 gggggagaac cgtatataag tgcagtagtc gccgtgaacg ttcttttcg caacgggttt 3241 gccgccagaa cacaggaccg gttctagagc gctgccacca tgttagctga cgctgtctca 3301 cgcctggtcc tgggtaagtt tggtgacctg accgacaact tctcctcccc tcacgctcgc 3361 agaaaagtgc tggctggagt cgtcatgaca acaggcacag atgttaaaga tgccaaggtg 3421 ataagtgttt ctacaggaac aaaatgtatt aatggtgaat acatgagtga tcgtggcctt 3481 gcattaaatg actgccatgc agaaataata tctcggagat ccttgctcag atttctttat 3541 acacaacttg agctttactt aaataacaaa gatgatcaaa aaagatccat ctttcagaaa 3601 tcagagcgag gggggtttag gctgaaggag aatgtccagt ttcatctgta catcagcacc 3661 tctccctgtg gagatgccag aatcttctca ccacatgagc caatcctgga agaaccagca 3721 gatagacacc caaatcgtaa agcaagagga cagctacgga ccaaaataga gtctggtcag 3781 gggacgattc cagtgcgctc caatgcgagc atccaaacgt gggacggggt gctgcaaggg 3841 gagcggctgc tcaccatgtc ctgcagtgac aagattgcac gctggaacgt ggtgggcatc 3901 cagggatccc tgctcagcat tttcgtggag cccatttact tctcgagcat catcctgggc 3961 agcctttacc acggggacca cctttccagg gccatgtacc agcggatctc caacatagag 4021 gacctgccac ctctctacac cctcaacaag cctttgctca gtggcatcag caatgcagaa 4081 gcacggcagc cagggaaggc ccccaacttc agtgtcaact ggacggtagg cgactccgct 4141 attgaggtca tcaacgccac gactgggaag gatgagctgg gccgcgcgtc ccgcctgtgt 4201 aagcacgcgt tgtactgtcg ctggatgcgt gtgcacggca aggttccctc ccacttacta 4261 cgctccaaga ttaccaagcc caacgtgtac catgagtcca agctggcggc aaaggagtac 4321 caggccgcca aggcgcgtct gttcacagcc ttcatcaagg cggggctggg ggcctgggtg 4381 gagaagccca ccgagcagga ccagttctca ctcacgccca gtggaagtga gacaccggga 4441 acctcagaga gcgccacgcc agaaagcatg gacaagaagt acagcatcgg cctggccatc 4501 ggcaccaact ctgtgggctg ggccgtgatc accgacgagt acaaggtgcc cagcaagaaa 4561 ttcaaggtgc tgggcaacac cgaccggcac agcatcaaga agaacctgat cggcgccctg -continued

```
4621  ctgttcgaca gcggagaaac agccgaggcc acccggctga agagaaccgc cagaagaaga
4681  tacaccagac ggaagaaccg gatctgctat ctgcaagaga tcttcagcaa cgagatggcc
4741  aaggtggacg acagcttctt ccacagactg gaagagtcct tcctggtgga agaggataag
4801  aagcacgagc ggcaccccat cttcggcaac atcgtggacg aggtggccta ccacgagaag
4861  taccccacca tctaccacct gagaaagaaa ctggtggaca gcaccgacaa ggccgacctg
4921  cggctgatct atctggccct ggcccacatg atcaagttcc ggggccactt cctgatcgag
4981  ggcgacctga accccgacaa cagcgacgtg gacaagctgt tcatccagct ggtgcagacc
5041  tacaaccagc tgttcgagga aaaccccatc aacgccagcg gcgtggacgc caaggccatc
5101  ctgtctgcca gactgagcaa gagcagacgg ctggaaaatc tgatcgccca gctgcccggc
5161  gagaagaaga atggcctgtt cggcaacctg attgccctga gcctgggcct gacccccaac
5221  ttcaagagca acttcgacct ggccgaggat gccaaactgc agctgagcaa ggacacctac
5281  gacgacgacc tggacaacct gctggcccag atcggcgacc agtacgccga cctgtttctg
5341  gccgccaaga acctgtccga cgccatcctg ctgagcgaca tcctgagagt gaacaccgag
5401  atcaccaagg cccccctgag cgcctctatg atcaagagat acgacgagca ccaccaggac
5461  ctgaccctgc tgaaagctct cgtgcggcag cagctgcctg agaagtacaa agagattttc
5521  ttcgaccaga gcaagaacgg ctacgccggc tacatcgatg gcggagccag ccaggaagag
5581  ttctacaagt tcatcaagcc catcctggaa aagatggacg gcaccgagga actgctcgtg
5641  aagctgaaca gagaggacct gctgcggaag cagcggacct tcgacaacgg cagcatcccc
5701  caccagatcc acctgggaga gctgcacgcc attctgcggc ggcaggaaga tttttaccca
5761  ttcctgaagg acaaccggga aaagatcgag aagatcctga ccttccgcat cccctactac
5821  gtgggccctc tggccagggg aaacagcaga ttcgcctgga tgaccagaaa gagcgaggaa
5881  accatcaccc cctggaactt cgaggaagtg gtggacaagg gcgccagcgc ccagagcttc
5941  atcgagcgga tgaccaactt cgataagaac ctgcccaacg agaaggtgct gcccaagcac
6001  agcctgctgt acgagtactt caccgtgtac aacgagctga ccaaagtgaa atacgtgacc
6061  gagggaatga gaaagcccgc cttcctgagc ggcgagcaga aaaaagccat cgtggacctg
6121  ctgttcaaga ccaaccggaa agtgaccgtg aagcagctga aagaggacta cttcaagaaa
6181  atcgagtgct tcgactccgt ggaaatctcc ggcgtggaag atcggttcaa cgcctccctg
6241  ggcacatacc acgatctgct gaaaattatc aaggacaagg acttcctgga caatgaggaa
6301  aacgaggaca ttctggaaga tatcgtgctg accctgacac tgtttgagga cagagagatg
6361  atcgaggaac ggctgaaaac ctatgcccac ctgttcgacg acaaagtgat gaagcagctg
6421  aagcggcgga gatacaccgg ctggggcagg ctgagccgga agctgatcaa cggcatccgg
6481  gacaagcagt ccggcaagac aatcctggat ttcctgaagt ccgacggctt cgccaacaga
6541  aacttcatgc agctgatcca cgacgacagc ctgaccttta aagaggacat ccagaaagcc
6601  caggtgtccg gccagggcga tagcctgcac gagcacattg ccaatctggc cggcagcccc
6661  gccattaaga agggcatcct gcagacagtg aaggtggtgg acgagctcgt gaaagtgatg
6721  ggccggcaca agcccgagaa catcgtgatc gaaatggcca gagagaacca gaccacccag
6781  aagggacaga agaacagccg cgagagaatg aagcggatcg aagagggcat caaagagctg
6841  ggcagccaga tcctgaaaga acaccccgtg gaaaacaccc agctgcagaa cgagaagctg
6901  tacctgtact acctgcagaa tgggcgggat atgtacgtgg accaggaact ggacatcaac
```

```
6961  cggctgtccg actacgatgt ggacgctatc gtgcctcaga gctttctgaa ggacgactcc
7021  atcgataaca aagtgctgac tcggagcgac aagaaccggg gcaagagcga caacgtgccc
7081  tccgaagagg tcgtgaagaa gatgaagaac tactggcgcc agctgctgaa tgccaagctg
7141  attacccaga ggaagttcga caatctgacc aaggccgaga gaggcggcct gagcgaactg
7201  gataaggccg gcttcatcaa gagacagctg gtggaaaccc ggcagatcac aaagcacgtg
7261  gcacagatcc tggactcccg gatgaacact aagtacgacg agaacgacaa actgatccgg
7321  gaagtgaaag tgatcaccct gaagtccaag ctggtgtccg atttccggaa ggatttccag
7381  ttttacaaag tgcgcgagat caacaactac caccacgccc acgacgccta cctgaacgcc
7441  gtcgtgggaa ccgccctgat caaaaagtac cctaagctgg aaagcgagtt cgtgtacggc
7501  gactacaagg tgtacgacgt gcggaagatg atcgccaaga gcgagcagga aatcggcaag
7561  gctaccgcca agtacttctt ctacagcaac atcatgaact tttcaagac cgagattacc
7621  ctggccaacg gcgagatccg gaagcggcct ctgatcgaga caaacggcga aacaggcgag
7681  atcgtgtggg ataagggccg ggactttgcc accgtgcgga aagtgctgtc tatgccccaa
7741  gtgaatatcg tgaaaaagac cgaggtgcag acaggcggct tcagcaaaga gtctatcctg
7801  cccaagagga acagcgacaa gctgatcgcc agaaagaagg actgggaccc taagaagtac
7861  ggcggcttcg acagccccac cgtggcctat tctgtgctgg tggtggccaa agtggaaaag
7921  ggcaagtcca agaaactgaa gagtgtgaaa gagctgctgg ggatcaccat catggaaaga
7981  agcagcttcg agaagaatcc catcgacttt ctggaagcca agggctacaa agaagtgaaa
8041  aaggacctga tcatcaagct gcctaagtac tccctgttcg agctggaaaa cggccggaag
8101  agaatgctgg cctctgccgg cgaactgcag aagggaaacg aactggccct gccctccaaa
8161  tatgtgaact tcctgtacct ggccagccac tatgagaagc tgaagggctc cccgaggat
8221  aatgagcaga aacagctgtt tgtggaacag cacaaacact acctggacga gatcatcgag
8281  cagatcagcg agttctccaa gagagtgatc ctggccgacg ctaatctgga caaggtgctg
8341  agcgcctaca acaagcacag agacaagcct atcagagagc aggccgagaa tatcatccac
8401  ctgtttaccc tgaccaatct gggagcccct gccgccttca agtactttga caccaccatc
8461  gaccggaaga ggtacaccag caccaaagag gtgctggacg ccaccctgat ccaccagagc
8521  atcaccggcc tgtacgagac acggatcgac ctgtctcagc tgggaggcga caagcgacct
8581  gccgccacaa agaaggctgg acaggctaag aagaagaaag attacaaaga cgatgacgat
8641  aagggatccg gcgcaacaaa cttctctctg ctgaaacaag ccggagatgt cgaagagaat
8701  cctggaccga ccgagtacaa gcccacggtg cgcctcgcca cccgcgacga cgtccccagg
8761  gccgtacgca ccctcgccgc cgcgttcgcc gactaccccg ccacgcgcca caccgtcgat
8821  ccggaccgcc acatcgagcg ggtcaccgag ctgcaagaac tcttcctcac gcgcgtcggg
8881  ctcgacatcg gcaaggtgtg ggtcgcggac gacggcgccg cggtggcggt ctggaccacg
8941  ccggagagcg tcgaagcggg ggcggtgttc gccgagatcg gcccgcgcat ggccgagttg
9001  agcggttccc ggctggccgc gcagcaacag atggaaggcc tcctggcgcc gcaccggccc
9061  aaggagcccg cgtggttcct ggccaccgtc ggagtctcgc ccgaccacca gggcaagggt
9121  ctgggcagcg ccgtcgtgct ccccggagtg gaggcggccg agcgcgccgg ggtgcccgcc
9181  ttcctggaga cctccgcgcc ccgcaacctc cccttctacg agcggctcgg cttcaccgtc
9241  accgccgacg tcgaggtgcc cgaaggaccg cgcacctggt gcatgacccg caagcccggt
9301  gcctgaacgc gttaagtcga caatcaacct ctggattaca aaatttgtga aagattgact
```

-continued

```
9361  ggtattctta actatgttgc tccttttacg ctatgtggat acgctgcttt aatgcctttg
9421  tatcatgcta ttgcttcccg tatggctttc attttctcct ccttgtataa atcctggttg
9481  ctgtctcttt atgaggagtt gtggcccgtt gtcaggcaac gtggcgtggt gtgcactgtg
9541  tttgctgacg caacccccac tggttggggc attgccacca cctgtcagct cctttccggg
9601  actttcgctt tccccctccc tattgccacg gcggaactca tcgccgcctg ccttgcccgc
9661  tgctggacag gggctcggct gttgggcact gacaattccg tggtgttgtc ggggaaatca
9721  tcgtcctttc cttggctgct cgcctgtgtt gccacctgga ttctgcgcgg gacgtccttc
9781  tgctacgtcc cttcggccct caatccagcg gaccttcctt cccgcggcct gctgccggct
9841  ctgcggcctc ttccgcgtct tcgccttcgc cctcagacga gtcggatctc cctttgggcc
9901  gcctccccgc gtcgacttta agaccaatga cttacaaggc agctgtagat cttagccact
9961  ttttaaaaga aaagggggga ctggaagggc taattcactc ccaacgaaga caagatctgc
10021 tttttgcttg tactgggtct ctctggttag accagatctg agcctgggag ctctctggct
10081 aactagggaa cccactgctt aagcctcaat aaagcttgcc ttgagtgctt caagtagtgt
10141 gtgcccgtct gttgtgtgac tctggtaact agagatccct cagacccttt tagtcagtgt
10201 ggaaaatctc tagcagggcc cgtttaaacc cgctgatcag cctcgactgt gccttctagt
10261 tgccagccat ctgttgtttg cccctccccc gtgccttcct tgaccctgga aggtgccact
10321 cccactgtcc tttcctaata aaatgaggaa attgcatcgc attgtctgag taggtgtcat
10381 tctattctgg ggggtggggt ggggcaggac agcaaggggg aggattggga agacaatagc
10441 aggcatgctg gggatgcggt gggctctatg gcttctgagg cggaaagaac cagctggggc
10501 tctagggggt atccccacgc gccctgtagc ggcgcattaa gcgcggcggg tgtggtggtt
10561 acgcgcagcg tgaccgctac acttgccagc gccctagcgc ccgctccttt cgctttcttc
10621 ccttcctttc tcgccacgtt cgccggcttt ccccgtcaag ctctaaatcg ggggctccct
10681 ttagggttcc gatttagtgc tttacggcac ctcgacccca aaaaacttga ttagggtgat
10741 ggttcacgta gtgggccatc gccctgatag acggtttttc gccctttgac gttggagtcc
10801 acgttcttta atagtggact cttgttccaa actggaacaa cactcaaccc tatctcggtc
10861 tattcttttg atttataagg gattttgccg atttcggcct attggttaaa aaatgagctg
10921 atttaacaaa aatttaacgc gaattaattc tgtggaatgt gtgtcagtta gggtgtggaa
10981 agtccccagg ctccccagca ggcagaagta tgcaaagcat gcatctcaat tagtcagcaa
11041 ccaggtgtgg aaagtcccca ggctccccag caggcagaag tatgcaaagc atgcatctca
11101 attagtcagc aaccatagtc ccgcccctaa ctccgcccat cccgccccta actccgccca
11161 gttccgccca ttctccgccc catggctgac taattttttt tatttatgca gaggccgagg
11221 ccgcctctgc ctctgagcta ttccagaagt agtgaggagg cttttttgga ggcctaggct
11281 tttgcaaaaa gctcccggga gcttgtatat ccattttcgg atctgatcag cacgtgttga
11341 caattaatca tcggcatagt atatcggcat agtataatac gacaaggtga ggaactaaac
11401 catggccaag ttgaccagtg ccgttccggt gctcaccgcg cgcgacgtcg ccggagcggt
11461 cgagttctgg accgaccggc tcgggttctc ccgggacttc gtggaggacg acttcgccgg
11521 tgtggtccgg gacgacgtga ccctgttcat cagcgcggtc caggaccagg tggtgccgga
11581 caacaccctg gcctgggtgt gggtgcgcgg cctggacgag ctgtacgccg agtggtcgga
11641 ggtcgtgtcc acgaacttcc gggacgcctc cgggccggcc atgaccgaga tcggcgagca
```

```
11701  gccgtggggg cgggagttcg ccctgcgcga cccggccggc aactgcgtgc acttcgtggc
11761  cgaggagcag gactgacacg tgctacgaga tttcgattcc accgccgcct tctatgaaag
11821  gttgggcttc ggaatcgttt tccgggacgc cggctggatg atcctccagc gcggggatct
11881  catgctggag ttcttcgccc accccaactt gtttattgca gcttataatg gttacaaata
11941  aagcaatagc atcacaaatt tcacaaataa agcatttttt tcactgcatt ctagttgtgg
12001  tttgtccaaa ctcatcaatg tatcttatca tgtctgtata ccgtcgacct ctagctagag
12061  cttggcgtaa tcatggtcat agctgtttcc tgtgtgaaat tgttatccgc tcacaattcc
12121  acacaacata cgagccggaa gcataaagtg taaagcctgg ggtgcctaat gagtgagcta
12181  actcacatta attgcgttgc gctcactgcc cgctttccag tcgggaaacc tgtcgtgcca
12241  gctgcattaa tgaatcggcc aacgcgcggg gagaggcggt ttgcgtattg ggcgctcttc
12301  cgcttcctcg ctcactgact cgctgcgctc ggtcgttcgg ctgcggcgag cggtatcagc
12361  tcactcaaag gcggtaatac ggttatccac agaatcaggg gataacgcag gaaagaacat
12421  gtgagcaaaa ggccagcaaa aggccaggaa ccgtaaaaag gccgcgttgc tggcgttttt
12481  ccataggctc cgcccccctg acgagcatca caaaaatcga cgctcaagtc agaggtggcg
12541  aaacccgaca ggactataaa gataccaggc gtttccccct ggaagctccc tcgtgcgctc
12601  tcctgttccg accctgccgc ttaccggata cctgtccgcc tttctccctt cgggaagcgt
12661  ggcgctttct catagctcac gctgtaggta tctcagttcg gtgtaggtcg ttcgctccaa
12721  gctgggctgt gtgcacgaac cccccgttca gcccgaccgc tgcgccttat ccggtaacta
12781  tcgtcttgag tccaacccgg taagacacga cttatcgcca ctggcagcag ccactggtaa
12841  caggattagc agagcgaggt atgtaggcgg tgctacagag ttcttgaagt ggtggcctaa
12901  ctacggctac actagaagaa cagtatttgg tatctgcgct ctgctgaagc cagttacctt
12961  cggaaaaaga gttggtagct cttgatccgg caaacaaacc accgctggta gcggtggttt
13021  ttttgtttgc aagcagcaga ttacgcgcag aaaaaaagga tctcaagaag atcctttgat
13081  cttttctacg gggtctgacg ctcagtggaa cgaaaactca cgttaaggga ttttggtcat
13141  gagattatca aaaaggatct tcacctagat ccttttaaat taaaaatgaa gttttaaatc
13201  aatctaaagt atatatgagt aaacttggtc tgacagttac caatgcttaa tcagtgaggc
13261  acctatctca gcgatctgtc tatttcgttc atccatagtt gcctgactcc ccgtcgtgta
13321  gataactacg atacgggagg gcttaccatc tggccccagt gctgcaatga taccgcgaga
13381  cccacgctca ccggctccag atttatcagc aataaaccag ccagccggaa gggccgagcg
13441  cagaagtggt cctgcaactt tatccgcctc catccagtct attaattgtt gccgggaagc
13501  tagagtaagt agttcgccag ttaatagttt gcgcaacgtt gttgccattg ctacaggcat
13561  cgtggtgtca cgctcgtcgt ttggtatggc ttcattcagc tccggttccc aacgatcaag
13621  gcgagttaca tgatccccca tgttgtgcaa aaaagcggtt agctccttcg gtcctccgat
13681  cgttgtcaga agtaagttgg ccgcagtgtt atcactcatg gttatggcag cactgcataa
13741  ttctcttact gtcatgccat ccgtaagatg cttttctgtg actggtgagt actcaaccaa
13801  gtcattctga gaatagtgta tgcggcgacc gagttgctct tgcccggcgt caatacggga
13861  taataccgcg ccacatagca gaactttaaa agtgctcatc attggaaaac gttcttcggg
13921  gcgaaaactc tcaaggatct taccgctgtt gagatccagt tcgatgtaac ccactcgtgc
13981  acccaactga tcttcagcat cttttacttt caccagcgtt tctgggtgag caaaaacagg
14041  aaggcaaaat gccgcaaaaa agggaataag ggcgacacgg aaatgttgaa tactcatact
```

```
14101   cttccttttt caatattatt gaagcattta tcagggttat tgtctcatga gcggatacat

14161   atttgaatgt atttagaaaa ataaacaaat aggggttccg cgcacatttc cccgaaaagt

14221   gccacctgac
```

What is claimed is:

1. A method of selective RNA editing comprising administering a recombinant expression system for CRISPR/Cas-directed RNA editing of a target mRNA to a cell obtained from a subject, the recombinant expression system comprising:

(A) a nucleic acid sequence encoding a CRISPR/Cas RNA editing fusion protein comprising a nuclease-dead CRISPR associated endonuclease (dCas) fused to a catalytically active deaminase domain of Adenosine Deaminase acting on RNA 2 (ADAR2); and (B) a nucleic acid sequence encoding an extended single guide RNA (esgRNA) comprising: (i) a short extension sequence of homology to the target mRNA comprising a mismatch for a target adenosine, wherein the short extension sequence is 15 nucleotides to 60 nucleotides in length, and (ii) a dCas scaffold binding sequence.

2. The method of claim 1, further comprising administering an antisense synthetic oligonucleotide compound comprising a PAMmer sequence.

3. A method of characterizing the effects of directed cellular RNA editing on processing and dynamics comprising administering a recombinant expression system for CRISPR/Cas-directed RNA editing of a target mRNA to a cell sample and determining its effects, the recombinant expression system comprising:

(A) a nucleic acid sequence encoding a CRISPR/Cas RNA editing fusion protein comprising a nuclease-dead CRISPR associated endonuclease (dCas) fused to a catalytically active deaminase domain of Adenosine Deaminase acting on RNA 2 (ADAR2); and (B) a nucleic acid sequence encoding an extended single guide RNA (esgRNA) comprising: (i) a short extension sequence of homology to the target mRNA comprising a mismatch for a target adenosine, wherein the short extension sequence is 15 nucleotides to 60 nucleotides in length, and (ii) a dCas scaffold binding sequence.

4. The method of claim 3, wherein the cell sample is derived from a subject.

5. The method of claim 1, further comprising correction of a G to A mutation in the target mRNA.

6. The method of claim 1, wherein the target mRNA is selected from the group consisting of dysferlin mRNA, cystic fibrosis transmembrane conductance regulator (CTFR) mRNA, and alpha-L iduronidase (IDUA) mRNA.

7. The method of claim 1, wherein the target mRNA is associated with a disease selected from the group consisting of Hurler's syndrome, Cystic fibrosis, and muscular dystrophy.

8. The method of claim 3, further comprising administering an antisense synthetic oligonucleotide compound comprising a PAMmer sequence.

9. The method of claim 3, further comprising correction of a G to A mutation in the target mRNA.

10. The method of claim 3, wherein the target mRNA is selected from the group consisting of dysferlin mRNA, cystic fibrosis transmembrane conductance regulator (CTFR) mRNA, and alpha-L iduronidase (IDUA) mRNA.

11. The method of claim 3, wherein the target mRNA is associated with a disease selected from the group consisting of Hurler's syndrome, Cystic fibrosis, and muscular dystrophy.

* * * * *

UNITED STATES PATENT AND TRADEMARK OFFICE

CERTIFICATE OF CORRECTION

PATENT NO. : 12,163,148 B2
APPLICATION NO. : 17/811626
DATED : December 10, 2024
INVENTOR(S) : Eugene Yeo et al.

It is certified that error appears in the above-identified patent and that said Letters Patent is hereby corrected as shown below:

On the Title Page

Column 2 (item (56) Other Publications), Line 2, delete “sapiens], ”” and insert -- sapiens],” --.

In the Claims

Column 254, Line 33, in Claim 6, delete “(CTFR)” and insert -- (CFTR) --.

Column 254, Approximately Line 45, in Claim 10, delete “(CTFR)” and insert -- (CFTR) --.

Signed and Sealed this
Fourth Day of February, 2025

Coke Morgan Stewart
*Acting Director of the United States Patent and Trademark Office*

```
                              SEQUENCE LISTING

Sequence total quantity: 55
SEQ ID NO: 1           moltype = AA  length = 1368
FEATURE                Location/Qualifiers
source                 1..1368
                       mol_type = protein
                       organism = Streptococcus pyogenes
SEQUENCE: 1
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD             1368

SEQ ID NO: 2           moltype = AA  length = 1053
FEATURE                Location/Qualifiers
source                 1..1053
                       mol_type = protein
                       organism = Staphylococcus aureus
SEQUENCE: 2
MKRNYILGLD IGITSVGYGI IDYETRDVID AGVRLFKEAN VENNEGRRSK RGARRLKRRR  60
RHRIQRVKKL LFDYNLLTDH SELSGINPYE ARVKGLSQKL SEEEFSAALL HLAKRRGVHN  120
VNEVEEDTGN ELSTKEQISR NSKALEEKYV AELQLERLKK DGEVRGSINR FKTSDYVKEA  180
KQLLKVQKAY HQLDQSFIDT YIDLLETRRT YYEGPGEGSP FGWKDIKEWY EMLMGHCTYF  240
PEELRSVKYA YNADLYNALN DLNNLVITRD ENEKLEYYEK FQIIENVFKQ KKKPTLKQIA  300
KEILVNEEDI KGYRVTSTGK PEFTNLKVYH DIKDITARKE IIENAELLDQ IAKILTIYQS  360
SEDIQEELTN LNSELTQEEI EQISNLKGYT GTHNLSLKAI NLILDELWHT NDNQIAIFNR  420
LKLVPKKVDL SQQKEIPTTL VDDFILSPVV KRSFIQSIKV INAIIKKYGL PNDIIIELAR  480
EKNSKDAQKM INEMQKRNRQ TNERIEEIIR TTGKENAKYL IEKIKLHDMQ EGKCLYSLEA  540
IPLEDLLNNP FNYEVDHIIP RSVSFDNSFN NKVLVKQEEN SKKGNRTPFQ YLSSSDSKIS  600
YETFKKHILN LAKGKGRISK TKKEYLLEER DINRFSVQKD FINRNLVDTR YATRGLMNLL  660
RSYFRVNNLD VKVKSINGGF TSFLRRKWKF KKERNKGYKH HAEDALIIAN ADFIFKEWKK  720
LDKAKKVMEN QMFEEKQAES MPEIETEQEY KEIFITPHQI KHIKDFKDYK YSHRVDKKPN  780
RELINDTLYS TRKDDKGNTL IVNNLNGLYD KDNDKLKKLI NKSPEKLLMY HHDPQTYQKL  840
KLIMEQYGDE KNPLYKYYEE TGNYLTKYSK KDNGPVIKKI KYYGNKLNAH LDITDDYPNS  900
RNKVVKLSLK PYRFDVYLDN GVYKFVTVKN LDVIKKENYY EVNSKCYEEA KKLKKISNQA  960
EFIASFYNND LIKINGELYR VIGVNNDLLN RIEVNMIDIT YREYLENMND KRPPRIIKTI  1020
ASKTQSIKKY STDILGNLYE VKSKKHPQII KKG                              1053

SEQ ID NO: 3           moltype = AA  length = 1121
FEATURE                Location/Qualifiers
source                 1..1121
                       mol_type = protein
                       organism = Streptococcus thermophilus
SEQUENCE: 3
MSDLVLGLDI GIGSVGVGIL NKVTGEIIHK NSRIFPAAQA ENNLVRRTNR QGRRLARRKK  60
HRRVRLNRLF EESGLITDFT KISINLNPYQ LRVKGLTDEL SNEELFIALK NMVKHRGISY  120
LDDASDDGNS SVGDYAQIVK ENSKQLETKT PGQIQLERYQ TYGQLRGDFT VEKDGKKHRL  180
INVFPTSAYR SEALRILQTQ QEFNPQITDE FINRYLEILT GKRKYYHGPG NEKSRTDYGR  240
```

```
YRTSGETLDN IFGILIGKCT FYPDEFRAAK ASYTAQEFNL LNDLNNLTVP TETKKLSKEQ  300
KNQIINYVKN EKAMGPAKLF KYIAKLLSCD VADIKGYRID KSGKAEIHTF EAYRKMKTLE  360
TLDIEQMDRE TLDKLAYVLT LNTEREGIQE ALEHEFADGS FSQKQVDELV QFRKANSSIF  420
GKGWHNFSVK LMMELIPELY ETSEEQMTIL TRLGKQKTTS SSNKTKYIDE KLLTEEIYNP  480
VVAKSVRQAI KIVNAAIKEY GDFDNIVIEM ARETNEDDEK KAIQKIQKAN KDEKDAAMLK  540
AANQYNGKAE LPHSVFHGHK QLATKIRLWH QQGERCLYTG KTISIHDLIN NSNQFEVDHI  600
LPLSITFDDS LANKVLVYAT ANQEKGQRTP YQALDSMDDA WSFRELKAFV RESKTLSNKK  660
KEYLLTEEDI SKFDVRKKFI ERNLVDTRYA SRVVLNALQE HFRAHKIDTK VSVVRGQFTS  720
QLRRHWGIEK TRDTYHHHAV DALIIAASSQ LNLWKKQKNT LVSYSEDQLL DIETGELISD  780
DEYKESVFKA PYQHFVDTLK SKEFEDSILF SYQVDSKFNR KISDATIYAT RQAKVGKDKA  840
DETYVLGKIK DIYTQDGYDA FMKIYKKDKS KFLMYRHDPQ TFEKVIEPIL ENYPNKQIND  900
KGKEVPCNPF LKYKEEHGYI RKYSKKGNGP EIKSLKYYDS KLGNHIDITP KDSNNKVVLQ  960
SVSPWRADVY FNKTTGKYEI LGLKYADLQF DKGTGTYKIS QEKYNDIKKK EGVDSDSEFK  1020
FTLYKNDLLL VKDTETKEQQ LFRFLSRTMP KQKHYVELKP YDKQKFEGGE ALIKVLGNVA  1080
NSGQCKKGLG KSNISIYKVR TDVLGNQHII KNEGDKPKLD F                    1121

SEQ ID NO: 4            moltype = AA  length = 1082
FEATURE                 Location/Qualifiers
source                  1..1082
                        mol_type = protein
                        organism = Neisseria meningitidis
SEQUENCE: 4
MAAFKPNPIN YILGLDIGIA SVGWAMVEID EDENPICLID LGVRVFERAE VPKTGDSLAM  60
ARRLARSVRR LTRRRAHRLL RARRLLKREG VLQAADFDEN GLIKSLPNTP WQLRAAALDR  120
KLTPLEWSAV LLHLIKHRGY LSQRKNEGET ADKELGALLK GVADNAHALQ TGDFRTPAEL  180
ALNKFEKESG HIRNQRGDYS HTFSRKDLQA ELILLFEKQK EFGNPHVSGG LKEGIETLLM  240
TQRPALSGDA VQKMLGHCTF EPAEPKAAKN TYTAERFIWL TKLNNLRILE QGSERPLTDT  300
ERATLMDEPY RKSKLTYAQA RKLLGLEDTA FFKGLRYGKD NAEASTLMEM KAYHAISRAL  360
EKEGLKDKKS PLNLSPELQD EIGTAFSLFK TDEDITGRLK DRIQPEILEA LLKHISFDKF  420
VQISLKALRR IVPLMEQGKR YDEACAEIYG DHYGKKNTEE KIYLPPIPAD EIRNPVVLRA  480
LSQARKVING VVRRYGSPAR IHIETAREVG KSFKDRKEIE KRQEENRKDR EKAAAKFREY  540
FPNFVGEPKS KDILKLRLYE QQHGKCLYSG KEINLGRLNE KGYVEIDHAL PFSRTWDDSF  600
NNKVLVLGSE NQNKGNQTPY EYFNGKDNSR EWQEFKARVE TSRFPRSKKQ RILLQKFDED  660
GFKERNLNDT RYVNRFLCQF VADRMRLTGK GKKRVFASNG QITNLLRGFW GLRKVRAEND  720
RHHALDAVVV ACSTVAMQQK ITRFVRYKEM NAFDGKTIDK ETGEVLHQKT HFPQPWEFFA  780
QEVMIRVFGK PDGKPEFEEA DTPEKLRTLL AEKLSSRPEA VHEYVTPLFV SRAPNRKMSG  840
QGHMETVKSA KRLDEGVSVL RVPLTQLKLK DLEKMVNRER EPKLYEALKA RLEAHKDDPA  900
KAFAEPFYKY DKAGNRTQQV KAVRVEQVQK TGVWVRNHNG IADNATMVRV DVFEKGDKYY  960
LVPIYSWQVA KGILPDRAVV QGKDEEDWQL IDDSFNFKFS LHPNDLVEVI TKKARMFGYF  1020
ASCHRGTGNI NIRIHDLDHK IGKNGILEGI GVKTALSFQK YQIDELGKEI RPCRLKKRPP  1080
VR                                                               1082

SEQ ID NO: 5            moltype = AA  length = 1037
FEATURE                 Location/Qualifiers
source                  1..1037
                        mol_type = protein
                        organism = Parvibaculum lavamentivorans
SEQUENCE: 5
MERIFGFDIG TTSIGFSVID YSSTQSAGNI QRLGVRIFPE ARDPDGTPLN QQRRQKRMMR  60
RQLRRRRIRR KALNETLHEA GFLPAYGSAD WPVVMADEPY ELRRRGLEEG LSAYEFGRAI  120
YHLAQHRHFK GRELEESDTP DPDVDDEKEA ANERAATLKA LKNEQTTLGA WLARRPPSDR  180
KRGIHAHRNV VAEEFERLWE VQSKFHPALK SEEMRARISD TIFAQRPVFW RKNTLGECRF  240
MPGEPLCPKG SWLSQQRRML EKLNNLAIAG GNARPLDAEE RDAILSKLQQ QASMSWPGVR  300
SALKALYKQR GEPGAEKSLK FNLELGGESK LLGNALEAKL ADMFGPDWPA HPRKQEIRHA  360
VHERLWAADY GETPDKKRVI ILSEKDRKAH REAAANSFVA DFGITGEQAA QLQALKLPTG  420
WEPYSIPALN LFLAELEKGE RFGALVNGPD WEGWRRTNFP HRNQPTGEIL DKLPSPASKE  480
ERERISQLRN PTVVRTQNEL RKVVNNLIGL YGKPDRIRIE VGRDVGKSKR EREEIQSGIR  540
RNEKQRKKAT EDLIKNGIAN PSRDDVEKWI LWKEGQERCP YTGDQIGFNA LFREGRYEVE  600
HIWPRSRSFD NSPRNKTLCR KDVNIEKGNR MPFEAFGHDE DRWSAIQIRL QGMVSAKGGT  660
GMSPGKVKRF LAKTMPEDFA ARQLNDTRYA AKQILAQLKR LWPDMGPEAP VKVEAVTGQV  720
TAQLRKLWTL NNILADDGEK TRADHRHHAI DALTVACTHP GMTNKLSRYW QLRDDPRAEK  780
PALTPPWDTI RADAEKAVSE IVVSHRVRKK VSGPLHKETT YGDTGTDIKT KSGTYRQFVT  840
RKKIESLSKG ELDEIRDPRI KEIVAAHVAG RGGDPKKAFP PYPCVSPGGP EIRKVRLTSK  900
QQLNLMAQTG NGYADLGSNH HIAIYRLPDG KADFEIVSLF DASRRLAQRN PIVQRTRADG  960
ASFVMSLAAG EAIMIPEGSK KGIWIVQGVW ASGQVVLERD TDADHSTTTR PMPNPILKDD  1020
AKKVSIDPIG RVRPSND                                               1037

SEQ ID NO: 6            moltype = AA  length = 1084
FEATURE                 Location/Qualifiers
source                  1..1084
                        mol_type = protein
                        organism = Diphthera sp.
SEQUENCE: 6
MKYHVGIDVG TFSVGLAAIE VDDAGMPIKT LSLVSHIHDS GLDPDEIKSA VTRLASSGIA  60
RRTRRLYRRK RRRLQQLDKF IQRQGWPVIE LEDYSDPLYP WKVRAELAAS YIADEKERGE  120
KLSVALRHIA RHRGWRNPYA KVSSLYLPDG PSDAFKAIRE EIKRASGQPV PETATVGQMV  180
TLCELGTLKL RGEGGVLSAR LQQSDYAREI QEICRMQEIG QELYRKIIDV VFAAESPKGS  240
ASSRVGKDPL QPGKNRALKA SDAFQRYRIA ALIGNLRVRV DGEKRILSVE EKNLVFDHLV  300
NLTPKKEPEW VTIAEILGID RGQLIGTATM TDDGERAGAR PPTHDTNRSI VNSRIAPLVD  360
```

```
WWKTASALEQ HAMVKALSNA EVDDFDSPEG AKVQAFFADL DDDVHAKLDS LHLPVGRAAY  420
SEDTLVRLTR RMLSDGVDLY TARLQEFGIE PSWTPPTPRI GEPVGNPAVD RVLKTVSRWL  480
ESATKTWGAP ERVIIEHVRE GFVTEKRARE MDGDMRRRAA RNAKLFQEMQ EKLNVQGKPS  540
RADLWRYQSV QRQNCQCAYC GSPITFSNSE MDHIVPRAGQ GSTNTRENLV AVCHRCNQSK  600
GNTPFAIWAK NTSIEGVSVK EAVERTRHWV TDTGMRSTDF KKFTKAVVER FQRATMDEEI  660
DARSMESVAW MANELRSRVA QHFASHGTTV RVYRGSLTAE ARRASGISGK LKFFDGVGKS  720
RLDRRHHAID AAVIAFTSDY VAETLAVRSN LKQSQAHRQE APQWREFTGK DAEHRAAWRV  780
WCQKMEKLSA LLTEDLRDDR VVVMSNVRLR LGNGSAHKET IGKLSKVKLS SQLSVSDIDK  840
ASSEALWCAL TREPGFDPKE GLPANPERHI RVNGTHVYAG DNIGLFPVSA GSIALRGGYA  900
ELGSSFHHAR VYKITSGKKP AFAMLRVYTI DLLPYRNQDL FSVELKPQTM SMRQAEKKLR  960
DALATGNAEY LGWLVVDDEL VVDTSKIATD QVKAVEAELG TIRRWRVDGF FSPSKLRLRP  1020
LQMSKEGIKK ESAPELSKII DRPGWLPAVN KLFSDGNVTV VRRDSLGRVR LESTAHLPVT  1080
WKVQ                                                              1084

SEQ ID NO: 7          moltype = AA  length = 1130
FEATURE               Location/Qualifiers
source                1..1130
                      mol_type = protein
                      organism = Streptococcus bovis
SEQUENCE: 7
MTNGKILGLD IGIASVGVGI IEAKTGKVVH ANSRLFSAAN AENNAERRGF RGSRRLNRRK  60
KHRVKRVRDL FEKYGIVTDF RNLNLNPYEL RVKGLTEQLK NEELFAALRT ISKRRGISYL  120
DDAEDDSTGS TDYAKSIDEN RRLLKNKTPG QIQLERLEKY GQLRGNFTVY DENGEAHRLI  180
NVFSTSDYEK EARKILETQA DYNKKITAEF IDDYVEILTQ KRKYYHGPGN EKSRTDYGRF  240
RTDGTTLENI FGILIGKCNF YPDEYRASKA SYTAQEYNFL NDLNNLKVST ETGKLSTEQK  300
ESLVEFAKNT ATLGPAKLLK EIAKILDCKV DEIKGYREDD KGKPDLHTFE PYRKLKFNLE  360
SINIDDLSRE VIDKLADILT LNTEREGIED AIKRNLPNQF TEEQISEIIK VRKSQSTAFN  420
KGWHSFSAKL MNELIPELYA TSDEQMTILT RLEKFKVNKK SSKNTKTIDE KEVTDEIYNP  480
VVAKSVRQTI KIINAAVKKY GDFDKIVIEM PRDKNADDEK KFIDKRNKEN KKEKDDALKR  540
AAYLYNSSDK LPDEVFHGNK QLETKIRLWY QQGERCLYSG KPISIQELVH NSNNFEIDHI  600
LPLSLSFDDS LANKVLVYAW TNQEKGQKTP YQVIDSMDAA WSFREMKDYV LKQKGLGKKK  660
RDYLLTTENI DKIEVKKKFI ERNLVDTRYA SRVVLNSLQS ALRELGKDTK VSVVRGQFTS  720
QLRRKWKIDK SRETYHHHAV DALIIAASSQ LKLWEKQDNP MFVDYGKNQV VDKQTGEILS  780
VSDDEYKELV FQPPYQGFVN TISSKGFEDE ILFSYQVDSK YNRKVSDATI YSTRKAKIGK  840
DKKEETYVLG KIKDIYSQNG FDTFIKKYNK DKTQFLMYQK DSLTWENVIE VILRDYPTTK  900
KSEDGKNDVK CNPFEEYRRE NGLICKYSKK GKGTPIKSLK YYDKKLGNCI DITPEESRNK  960
VILQSINPWR ADVYFNPETL KYELMGLKYS DLSFEKGTGN YHISQEKYDA IKEKEGIGKK  1020
SEFKFTLYRN DLILIKDIAS GEQEIYRFLS RTMPNVNHYV ELKPYDKEKF DNVQELVEAL  1080
GEADKVGRCI KGLNKPNISI YKVRTDVLGN KYFVKKKGDK PKLDFKNNKK            1130

SEQ ID NO: 8          moltype = AA  length = 1082
FEATURE               Location/Qualifiers
source                1..1082
                      mol_type = protein
                      organism = Neisseria cinerea
SEQUENCE: 8
MAAFKPNPMN YILGLDIGIA SVGWAIVEID EEENPIRLID LGVRVFERAE VPKTGDSLAA  60
ARRLARSVRR LTRRRAHRLL RARRLLKREG VLQAADFDEN GLIKSLPNTP WQLRAAALDR  120
KLTPLEWSAV LLHLIKHRGY LSQRKNEGET ADKELGALLK GVADNTHALQ TGDFRTPAEL  180
ALNKFEKESG HIRNQRGDYS HTFNRKDLQA ELNLLFEKQK EFGNPHVSDG LKEGIETLLM  240
TQRPALSGDA VQKMLGHCTF EPTEPKAAKN TYTAERFVWL TKLNNLRILE QGSERPLTDT  300
ERATLMDEPY RKSKLTYAQA RKLLDLDDTA FFKGLRYGKD NAEASTLMEM KAYHAISRAL  360
EKEGLKDKKS PLNLSPELQD EIGTAFSLFK TDEDITGRLK DRVQPEILEA LLKHISFDKF  420
VQISLKALRR IVPLMEQGNR YDEACTEIYG DHYGKKNTEE KIYLPPIPAD EIRNPVVLRA  480
LSQARKVING VVRRYGSPAR IHIETAREVG KSFKDRKEIE KRQEENRKDR EKSAAKFREY  540
FPNFVGEPKS KDILKLRLYE QQHGKCLYSG KEINLGRLNE KGYVEIDHAL PFSRTWDDSF  600
NNKVLALGSE NQNKGNQTPY EYFNGKDNSR EWQEFKARVE TSRFPRSKKQ RILLQKFDED  660
GFKERNLNDT RYINRFLCQF VADHMLLTGK GKRRVFASNG QITNLLRGFW GLRKVRAEND  720
RHHALDAVVV ACSTIAMQQK ITRFVRYKEM NAFDGKTIDK ETGEVLHQKA HFPQPWEFFA  780
QEVMIRVFGK PDGKPEFEEA DTPEKLRTLL AEKLSSRPEA VHKYVTPLFI SRAPNRKMSG  840
QGHMETVKSA KRLDEGISVL RVPLTQLKLK DLEKMVNRER EPKLYEALKA RLEAHKDDPA  900
KAFAEPFYKY DKAGNRTQQV KAVRVEQVQK TGVWVHNHNG IADNATIVRV DVFEKGGKYY  960
LVPIYSWQVA KGILPDRAVV QGKDEEDWTV MDDSFEFKFV LYANDLIKLT AKKNEFLGYF  1020
VSLNRATGAI DIRTHDTDST KGKNGIFQSV GVKTALSFQK YQIDELGKEI RPCRLKKRPP  1080
VR                                                                1082

SEQ ID NO: 9          moltype = AA  length = 1003
FEATURE               Location/Qualifiers
source                1..1003
                      mol_type = protein
                      organism = Campylobacter lari
SEQUENCE: 9
MRILGFDIGI NSIGWAFVEN DELKDCGVRI FTKAENPKNK ESLALPRRNA RSSRRRLKRR  60
KARLIAIKRI LAKELKLNYK DYVAADGELP KAYEGSLASV YELRYKALTQ NLETKDLARV  120
ILHIAKHRGY MNKNEKKSND AKKGKILSAL KNNALKLENY QSVGEYFYKE FFQKYKKNTK  180
NFIKIRNTKD NYNNCVLSSD LEKELKLILE KQKEFGYNYS EDFINEILKV AFFQRPLKDF  240
SHLVGACTFF EEEKRACKNS YSAWEFVALT KIINEIKSLE KISGEIVPTQ TINEVLNLIL  300
DKGSITYKKF RSCINLHESI SFKSLKYDKE NAENAKLIDF RKLVEFKKAL GVHSLSRQEL  360
DQISTHITLI KDNVKLKTVL EKYNLSNEQI NNLLEIEFND YINLSFKALG MILPLMREGK  420
```

```
RYDEACEIAN LKPKTVDEKK DFLPAFCDSI FAHELSNPVV NRAISEYRKV LNALLKKYGK  480
VHKIHLELAR DVGLSKKARE KIEKEQKENQ AVNAWALKEC ENIGLKASAK NILKLKLWKE  540
QKEICIYSGN KISIEHLKDE KALEVDHIYP YSRSFDDSFI NKVLVFTKEN QEKLNKTPFE  600
AFGKNIEKWS KIQTLAQNLP YKKKNKILDE NFKDKQQEDF ISRNLNDTRY IATLIAKYTK  660
EYLNFLLLSE NENANLKSGE KGSKIHVQTI SGMLTSVLRH TWGFDKKDRN NHLHHALDAI  720
IVAYSTNSII KAFSDFRKNQ ELLKARFYAK ELTSDNYKHQ VKFFEPFKSF REKILSKIDE  780
IFVSKPPRKR ARRALHKDTF HSENKIIDKC SYNSKEGLQI ALSCGRVRKI GTKYVENDTI  840
VRVDIFKKQN KFYAIPIYAM DFALGILPNK IVITGKDKNN NPKQWQTIDE SYEFCFSLYK  900
NDLILLQKKN MQEPEFAYYN DFSISTSSIC VEKHDNKFEN LTSNQKLLFS NAKEGSVKVE  960
SLGIQNLKVF EKYIITPLGD KIKADFQPRE NISLKTSKKY GLR                   1003

SEQ ID NO: 10          moltype = AA  length = 1395
FEATURE                Location/Qualifiers
source                 1..1395
                       mol_type = protein
                       organism = Treponema denticola
SEQUENCE: 10
MKKEIKDYFL GLDVGTGSVG WAVTDTDYKL LKANRKDLWG MRCFETAETA EVRRLHRGAR  60
RRIERRKKRI KLLQELFSQE IAKTDEGFFQ RMKESPFYAE DKTILQENTL FNDKDFADKT  120
YHKAYPTINH LIKAWIENKV KPDPRLLYLA CHNIIKKRGH FLFEGDFDSE NQFDTSIQAL  180
FEYLREDMEV DIDADSQKVK EILKDSSLKN SEKQSRLNKI LGLKPSDKQK KAITNLISGN  240
KINFADLYDN PDLKDAEKNS ISFSKDDFDA LSDDLASILG DSFELLLKAK AVYNCSVLSK  300
VIGDEQYLSF AKVKIYEKHK TDLTKLKNVI KKHFPKDYKK VFGYNKNEKN NNNYSGYVGV  360
CKTKSKKLII NNSVNQEDFY KFLKTILSAK SEIKEVNDIL TEIETGTFLP KQISKSNAEI  420
PYQLRKMELE KILSNAEKHF SFLKQKDEKG LSHSEKIIML LTFKIPYYIG PINDNHKKFF  480
PDRCWVVKKE KSPSGKTTPW NFFDHIDKEK TAEAFITSRT NFCTYLVGES VLPKSSLLYS  540
EYTVLNEINN LQIIIDGKNI CDIKLKQKIY EDLFKKYKKI TQKQISTFIK HEGICNKTDE  600
VIILGIDKEC TSSLKSYIEL KNIFGKQVDE ISTKNMLEEI IRWATIYDEG EGKTILKTKI  660
KAEYGKYCSD EQIKKILNLK FSGWGRLSRK FLETVTSEMP GFSEPVNIIT AMRETQNNLM  720
ELLSSEFTFT ENIKKINSGF EDAEKQFSYD GLVKPLFLSP SVKKMLWQTL KLVKEISHIT  780
QAPPKKIFIE MAKGAELEPA RTKTRLKILQ DLYNNCKNDA DAFSSEIKDL SGKIENEDNL  840
RLRSDKLYLY YTQLGKCMYC GKPIEIGHVF DTSNYDIDHI YPQSKIKDDS ISNRVLVCSS  900
CNKNKEDKYP LKSEIQSKQR GFWNFLQRNN FISLEKLNRL TRATPISDDE TAKFIARQLV  960
ETRQATKVAA KVLEKMFPET KIVYSKAETV SMFRNKFDIV KCREINDFHH AHDAYLNIVV  1020
GNVYNTKFTN NPWNFIKEKR DNPKIADTYN YYKVFDYDVK RNNITAWEKG KTIITVKDML  1080
KRNTPIYTRQ AACKKGELFN QTIMKKGLGQ HPLKKEGPFS NISKYGGYNK VSAAYYTLIE  1140
YEEKGNKIRS LETIPLYLVK DIQKDQDVLK SYLTDLLGKK EFKILVPKIK INSLLKINGF  1200
PCHITGKTND SFLLRPAVQF CCSNNEVLYF KKIIRFSEIR SQREKIGKTI SPYEDLSFRS  1260
YIKENLWKKT KNDEIGEKEF YDLLQKKNLE IYDMLLTKHK DTIYKKRPNS ATIDILVKGK  1320
EKFKSLIIEN QFEVILEILK LFSATRNVSD LQHIGGSKYS GVAKIGNKIS SLDNCILIYQ  1380
SITGIFEKRI DLLKV                                                  1395

SEQ ID NO: 11          moltype = AA  length = 1345
FEATURE                Location/Qualifiers
source                 1..1345
                       mol_type = protein
                       organism = Streptococcus mutans
SEQUENCE: 11
MKKPYSIGLD IGTNSVGWAV VTDDYKVPAK KMKVLGNTDK SHIEKNLLGA LLFDSGNTAE  60
DRRLKRTARR RYTRRRNRIL YLQEIFSEEM GKVDDSFFHR LEDSFLVTED KRGERHPIFG  120
NLEEEVKYHE NFPTIYHLRQ YLADNPEKVD LRLVYLALAH IIKFRGHFLI EGKFDTRNND  180
VQRLFQEFLA VYDNTFENSS LQEQNVQVEE ILTDKISKSA KKDRVLKLFP NEKSNGRFAE  240
FLKLIVGNQA DFKKHFELEE KAPLQFSKDT YEEELEVLLA QIGDNYAELF LSAKKLYDSI  300
LLSGILTVTD VGTKAPLSAS MIQRYNEHQM DLAQLKQFIR QKLSDKYNEV FSDVSKDGYA  360
GYIDGKTNQE AFYKYLKGLL NKIEGSGYFL DKIEREDFLR KQRTFDNGSI PHQIHLQEMR  420
AIIRRQAEFY PFLADNQDRI EKLLTFRIPY YVGPLARGKS DFAWLSRKSA DKITPWNFDE  480
IVDKESSAEA FINRMTNYDL YLPNQKVLPK HSLLYEKFTV YNELTKVKYK TEQGKTAFFD  540
ANMKQEIFDG VFKVYRKVTK DKLMDFLEKE FDEFRIVDLT GLDKENKVFN ASYGTYHDLC  600
KILDKDFLDN SKNEKILEDI VLTLTLFEDR EMIRKRLENY SDLLTKEQVK KLERRHYTGW  660
GRLSAELIHG IRNKESRKTI LDYLIDDGNS NRNFMQLIND DALSFKEEIA KAQVIGETDN  720
LNQVVSDIAG SPAIKKGILQ SLKIVDELVK IMGHQPENIV VEMARENQFT NQGRRNSQQR  780
LKGLTDSIKE FGSQILKEHP VENSQLQNDR LFLYYLQNGR DMYTGEELDI DYLSQYDIDH  840
IIPQAFIKDN SIDNRVLTSS KENRGKSDDV PSKDVVRKMK SYWSKLLSAK LITQRKFDNL  900
TKAERGGLTD DDKAGFIKRQ LVETRQITKH VARILDERFN TETDENNKKI RQVKIVTLKS  960
NLVSNFRKEF ELYKVREIND YHHAHDAYLN AVIGKALLGV YPQLEPEFVY GDYPHFHGHK  1020
ENKATAKKFF YSNIMNFFKK DDVRTDKNGE IIWKKDEHIS NIKKVLSYPQ VNIVKKVEEQ  1080
TGGFSKESIL PKGNSDKLIP RKTKKFYWDT KKYGGFDSPI VAYSILVIAD IEKGKSKKLK  1140
TVKALVGVTI MEKMTFERDP VAFLERKGYR NVQEENIIKL PKYSLFKLEN GRKRLLASAR  1200
ELQKGNEIVL PNHLGTLLYH AKNIHKVDEP KHLDYVDKHK DEFKELLDVV SNFSKKYTLA  1260
EGNLEKIKEL YAQNNGEDLK ELASSFINLL TFTAIGAPAT FKFFDKNIDR KRYTSTTEIL  1320
NATLIHQSIT GLYETRIDLN KLGGD                                       1345

SEQ ID NO: 12          moltype = AA  length = 1388
FEATURE                Location/Qualifiers
source                 1..1388
                       mol_type = protein
                       organism = Streptococcus thermophilus
SEQUENCE: 12
MTKPYSIGLD IGTNSVGWAV TTDNYKVPSK KMKVLGNTSK KYIKKNLLGV LLFDSGITAE  60
```

```
GRRLKRTARR RYTRRRNRIL YLQEIFSTEM ATLDDAFFQR LDDSFLVPDD KRDSKYPIFG  120
NLVEEKAYHD EFPTIYHLRK YLADSTKKAD LRLVYLALAH MIKYRGHFLI EGEFNSKNND  180
IQKNFQDFLD TYNAIFESDL SLENSKQLEE IVKDKISKLE KKDRILKLFP GEKNSGIFSE  240
FLKLIVGNQA DFRKCFNLDE KASLHFSKES YDEDLETLLG YIGDDYSDVF LKAKKLYDAI  300
LLSGFLTVTD NETEAPLSSA MIKRYNEHKE DLALLKEYIR NISLKTYNEV FKDDTKNGYA  360
GYIDGKTNQE DFYVYLKKLL AEFEGADYFL EKIDREDFLR KQRTFDNGSI PYQIHLQEMR  420
AILDKQAKFY PFLAKNKERI EKILTFRIPY YVGPLARGNS DFAWSIRKRN EKITPWNFED  480
VIDKESSAEA FINRMTSFDL YLPEEKVLPK HSLLYETFNV YNELTKVRFI AESMRDYQFL  540
DSKQKKDIVR LYFKDKRKVT DKDIIEYLHA IYGYDGIELK GIEKQFNSSL STYHDLLNII  600
NDKEFLDDSS NEAIIEEIIH TLTIFEDREM IKQRLSKFEN IFDKSVLKKL SRRHYTGWGK  660
LSAKLINGIR DEKSGNTILD YLIDDGISNR NFMQLIHDDA LSFKKKIQKA QIIGDEDKGN  720
IKEVVKSLPG SPAIKKGILQ SIKIVDELVK VMGGRKPESI VVEMARENQY TNQGKSNSQQ  780
RLKRLEKSLK ELGSKILKEN IPAKLSKIDN NALQNDRLYL YYLQNGKDMY TGDDLDIDRL  840
SNYDIDHIIP QAFLKDNSID NKVLVSSASN RGKSDDVPSL EVVKKRKTFW YQLLKSKLIS  900
QRKFDNLTKA ERGGLSPEDK AGFIQRQLVE TRQITKHVAR LLDEKFNNKK DENNRAVRTV  960
KIITLKSTLV SQFRKDFELY KVREINDFHH AHDAYLNAVV ASALLKKYPK LEPEFVYGDY  1020
PKYNSFRERK SATEKVYFYS NIMNIFKKSI SLADGRVIER PLIEVNEETG ESVWNKESDL  1080
ATVRRVLSYP QVNVVKKVEE QNHGLDRGKP KGLFNANLSS KPKPNSNENL VGAKEYLDPK  1140
KYGGYAGISN SFTVLVKGTI EKGAKKKITN VLEFQGISIL DRINYRKDKL NFLLEKGYKD  1200
IELIIELPKY SLFELSDGSR RMLASILSTN NKRGEIHKGN QIFLSQKFVK LLYHAKRISN  1260
TINENHRKYV ENHKKEFEEL FYYILEFNEN YVGAKKNGKL LNSAFQSWQN HSIDELCSSF  1320
IGPTGSERKG LFELTSRGSA ADFEFLGVKI PRYRDYTPSS LLKDATLIHQ SVTGLYETRI  1380
DLAKLGEG                                                           1388

SEQ ID NO: 13           moltype = AA  length = 984
FEATURE                 Location/Qualifiers
source                  1..984
                        mol_type = protein
                        organism = Campylobacter jejuni
SEQUENCE: 13
MARILAFDIG ISSIGWAFSE NDELKDCGVR IFTKVENPKT GESLALPRRL ARSARKRLAR  60
RKARLNHLKH LIANEFKLNY EDYQSFDESL AKAYKGSLIS PYELRFRALN ELLSKQDFAR  120
VILHIAKRRG YDDIKNSDDK EKGAILKAIK QNEEKLANYQ SVGEYLYKEY FQKFKENSKE  180
FTNVRNKKES YERCIAQSFL KDELKLIFKK QREFGFSFSK KFEEEVLSVA FYKRALKDFS  240
HLVGNCSFFT DEKRAPKNSP LAFMFVALTR IINLLNNLKN TEGILYTKDD LNALLNEVLK  300
NGTLTYKQTK KLLGLSDDYE FKGEKGTYFI EFKKYKEFIK ALGEHNLSQD DLNEIAKDIT  360
LIKDEIKLKK ALAKYDLNQN QIDSLSKLEF KDHLNISFKA LKLVTPLMLE GKKYDEACNE  420
LNLKVAINED KKDFLPAFNE TYYKDEVTNP VVLRAIKEYR KVLNALLKKY GKVHKINIEL  480
AREVGKNHSQ RAKIEKEQNE NYKAKKDAEL ECEKLGLKIN SKNILKLRLF KEQKEFCAYS  540
GEKIKISDLQ DEKMLEIDHI YPYSRSFDDS YMNKVLVFTK QNQEKLNQTP FEAFGNDSAK  600
WQKIEVLAKN LPTKKQKRIL DKNYKDKEQK NFKDRNLNDT RYIARLVLNY TKDYLDFLPL  660
SDDENTKLND TQKGSKVHVE AKSGMLTSAL RHTWGFSAKD RNNHLHHAID AVIIAYANNS  720
IVKAFSDFKK EQESNSAELY AKKISELDYK NKRKFFEPFS GFRQKVLDKI DEIFVSKPER  780
KKPSGALHEE TFRKEEEFYQ SYGGKEGVLK ALELGKIRKV NGKIVKNGDM FRVDIFKHKK  840
TNKFYAVPIY TMDFALKVLP NKAVARSKKG EIKDWILMDE NYEFCFSLYK DSLILIQTKD  900
MQEPEFVYYN AFTSSTVSLI VSKHDNKFET LSKNQKILFK NANEKEVIAK SIGIQNLKVF  960
EKYIVSALGE VTKAEFRQRE DFKK                                         984

SEQ ID NO: 14           moltype = AA  length = 1056
FEATURE                 Location/Qualifiers
source                  1..1056
                        mol_type = protein
                        organism = Pasteurella multocida
SEQUENCE: 14
MQTTNLSYIL GLDLGIASVG WAVVEINENE DPIGLIDVGV RIFERAEVPK TGESLALSRR  60
LARSTRRLIR RRAHRLLLAK RFLKREGILS TIDLEKGLPN QAWELRVAGL ERRLSAIEWG  120
AVLLHLIKHR GYLSKRKNES QTNNKELGAL LSGVAQNHQL LQSDDYRTPA ELALKKFAKE  180
EGHIRNQRGA YTHTFNRLDL LAELNLLFAQ QHQFGNPHCK EHIQQYMTEL LMWQKPALSG  240
EAILKMLGKC THEKNEFKAA KHTYSAERFV WLTKLNNLRI LEDGAERALN EEERQLLINH  300
PYEKSKLTYA QVRKLLGLSE QAIFKHLRYS KENAESATFM ELKAWHAIRK ALENQGLKDT  360
WQDLAKKPDL LDEIGTAFSL YKTDEDIQQY LTNKVPNSVI NALLVSLNFD KFIELSLKSL  420
RKILPLMEQG KRYDQACREI YGHHYGEANQ KTSQLLPAIP AQEIRNPVVL RTLSQARKVI  480
NAIIRQYGSP ARVHIETGRE LGKSFKERRE IQKQQEDNRT KRESAVQKFK ELFSDFSSEP  540
KSKDILKFRL YEQQHGKCLY SGKEINIHRL NEKGYVEIDH ALPFSRTWDD SFNNKVLVLA  600
SENQNKGNQT PYEWLQGKIN SERWKNFVAL VLGSQCSAAK KQRLLTQVID DNKFIDRNLN  660
DTRYIARFLS NYIQENLLLV GKNKKNVFTP NGQITALLRS RWGLIKAREN NNRHHALDAI  720
VVACATPSMQ QKITRFIRFK EVHPYKIENR YEMVDQESGE IISPHFPEPW AYFRQEVNIR  780
VFDNHPDTVL KEMLPDRPQA NHQFVQPLFV SRAPTRKMSG QGHMETIKSA KRLAEGISVL  840
RIPLTQLKPN LLENMVNKER EPALYAGLKA RLAEFNQDPA KAFATPFYKQ GGQQVKAIRV  900
EQVQKSGVLV RENNGVADNA SIVRTDVFIK NNKFFLVPIY TWQVAKGILP NKAIVAHKNE  960
DEWEEMDEGA KFKFSLFPND LVELKTKKEY FFGYYIGLDR ATGNISLKEH DGEISKGKDG  1020
VYRVGVKLAL SFEKYQVDEL GKNRQICRPQ QRQPVR                            1056

SEQ ID NO: 15           moltype = AA  length = 1629
FEATURE                 Location/Qualifiers
source                  1..1629
                        mol_type = protein
                        organism = Francisella sp.
SEQUENCE: 15
```

-continued

```
MNFKILPIAI DLGVKNTGVF SAFYQKGTSL ERLDNKNGKV YELSKDSYTL LMNNRTARRH  60
QRRGIDRKQL VKRLFKLIWT EQLNLEWDKD TQQAISFLFN RRGFSFITDG YSPEYLNIVP  120
EQVKAILMDI FDDYNGEDDL DSYLKLATEQ ESKISEIYNK LMQKILEFKL MKLCTDIKDD  180
KVSTKTLKEI TSYEFELLAD YLANYSESLK TQKFSYTDKQ GNLKELSYYH HDKYNIQEFL  240
KRHATINDRI LDTLLTDDLD IWNFNFEKFD FDKNEEKLQN QEDKDHIQAH LHHFVFAVNK  300
IKSEMASGGR HRSQYFQEIT NVLDENNHQE GYLKNFCENL HNKKYSNLSV KNLVNLIGNL  360
SNLELKPLRK YFNDKIHAKA DHWDEQKFTE TYCHWILGEW RVGVKDQDKK DGAKYSYKDL  420
CNELKQKVTK AGLVDFLLEL DPCRTIPPYL DNNNRKPPKC QSLILNPKFL DNQYPNWQQY  480
LQELKKLQSI QNYLDSFETD LKVLKSSKDQ PYFVEYKSSN QQIASGQRDY KDLDARILQF  540
IFDRVKASDE LLLNEIYFQA KKLKQKASSE LEKLESSKKL DEVIANSQLS QILKSQHTNG  600
IFEQGTFLHL VCKYYKQRQR ARDSRLYIMP EYRYDKKLHK YNNTGRFDDD NQLLTYCNHK  660
PRQKRYQLLN DLAGVLQVSP NFLKDKIGSD DDLFISKWLV EHIRGFKKAC EDSLKIQKDN  720
RGLLNHKINI ARNTKGKCEK EIFNLICKIE GSEDKKGNYK HGLAYELGVL LFGEPNEASK  780
PEFDRKIKKF NSIYSFAQIQ QIAFAERKGN ANTCAVCSAD NAHRMQQIKI TEPVEDNKDK  840
IILSAKAQRL PAIPTRIVDG AVKKMATILA KNIVDDNWQN IKQVLSAKHQ LHIPIITESN  900
AFEFEPALAD VKGKSLKDRR KKALERISPE NIFKDKNNRI KEFAKGISAY SGANLTDGDF  960
DGAKEELDHI IPRSHKKYGT LNDEANLICV TRGDNKNKGN RIFCLRDLAD NYKLKQFETT  1020
DDLEIEKKIA DTIWDANKKD FKFGNYRSFI NLTPQEQKAF RHALFLADEN PIKQAVIRAI  1080
NNRNRTFVNG TQRYFAEVLA NNIYLRAKKE NLNTDKISFD YFGIPTIGNG RGIAEIRQLY  1140
EKVDSDIQAY AKGDKPQASY SHLIDAMLAF CIAADEHRND GSIGLEIDKN YSLYPLDKNT  1200
GEVFTKDIFS QIKITDNEFS DKKLVRKKAI EGFNTHRQMT RDGIYAENYL PILIHKELNE  1260
VRKGYTWKNS EEIKIFKGKK YDIQQLNNLV YCLKFVDKPI SIDIQISTLE ELRNILTTNN  1320
IAATAEYYYI NLKTQKLHEY YIENYNTALG YKKYSKEMEF LRSLAYRSER VKIKSIDDVK  1380
QVLDKDSNFI IGKITLPFKK EWQRLYREWQ NTTIKDDYEF LKSFFNVKSI TKLHKKVRKD  1440
FSLPISTNEG KFLVKRKTWD NNFIYQILND SDSRADGTKP FIPAFDISKN EIVEAIIDSF  1500
TSKNIFWLPK NIELQKVDNK NIFAIDTSKW FEVETPSDLR DIGIATIQYK IDNNSRPKVR  1560
VKLDYVIDDD SKINYFMNHS LLKSRYPDKV LEILKQSTII EFESSGFNKT IKEMLGMKLA  1620
GIYNETSNN                                                          1629

SEQ ID NO: 16          moltype = AA  length = 1371
FEATURE                Location/Qualifiers
source                 1..1371
                       mol_type = protein
                       organism = Lactobacillus buchneri
SEQUENCE: 16
MKVNNYHIGL DIGTSSIGWV AIGKDGKPLR VKGKTAIGAR LFQEGNPAAD RRMFRTTRRR  60
LSRRKWRLKL LEEIFDPYIT PVDSTFFARL KQSNLSPKDS RKEFKGSMLF PDLTDMQYHK  120
NYPTIYHLRH ALMTQDKKFD IRMVYLAIHH IVKYRGNFLN STPVDSFKAS KVDFVDQFKK  180
LNELYAAINP EESFKINLAN SEDIGHQFLD PSIRKFDKKK QIPKIVPVMM NDKVTDRLNG  240
KIASEIIHAI LGYKAKLDVV LQCTPVDSKP WALKFDDEDI DAKLEKILPE MDENQQSIVA  300
ILQNLYSQVT LNQIVPNGMS LSESMIEKYN DHHDHLKLYK KLIDQLADPK KKAVLKKAYS  360
QYVGDDGKVI EQAEFWSSVK KNLDDSELSK QIMDLIDAEK FMPKQRTSQN GVIPHQLHQR  420
ELDEIIEHQS KYYPWLVEIN PNKHDLHLAK YKIEQLVAFR VPYYVGPMIT PKDQAESAET  480
VFSWMERKGT ETGQITPWNF DEKVDRKASA NRFIKRMTTK DTYLIGEDVL PDESLLYEKF  540
KVLNELNMVR VNGKLLKVAD KQAIFQDLFE NYKHVSVKKL QNYIKAKTGL PSDPEISGLS  600
DPEHFNNSLG TYNDFKKLFG SKVDEPDLQD DFEKIVEWST VFEDKKILRE KLNEITWLSD  660
QQKDVLESSR YQGWGRLSKK LLTGIVNDQG ERIIDKLWNT NKNFMQIQSD DDFAKRIHEA  720
NADQMQAVDV EDVLADAYTS PQNKKAIRQV VKVVDDIQKA MGGVAPKYIS IEFTRSEDRN  780
PRRTISRQRQ LENTLKDTAK SLAKSINPEL LSELDNAAKS KKGLTDRLYL YFTQLGKDIY  840
TGEPINIDEL NKYDIDHILP QAFIKDNSLD NRVLVLTAVN NGKSDNVPLR MFGAKMGHFW  900
KQLAEAGLIS KRKLKNLQTD PDTISKYAMH GFIRRQLVET SQVIKLVANI LGDKYRNDDT  960
KIIEITARMN HQMRDEFGFI KNREINDYHH AFDAYLTAFL GRYLYHRYIK LRPYFVYGDF  1020
KKFREDKVTM RNFNFLHDLT DDTQEKIADA ETGEVIWDRE NSIQQLKDVY HYKFMLISHE  1080
VYTLRGAMFN QTVYPASDAG KRKLIPVKAD RPVNVYGGYS GSADAYMAIV RIHNKKGDKY  1140
RVVGVPMRAL DRLDAAKNVS DADFDRALKD VLAPQLTKTK KSRKTGEITQ VIEDFEIVLG  1200
KVMYRQLMID GDKKFMLGSS TYQYNAKQLV LSDQSVKTLA SKGRLDPLQE SMDYNNVYTE  1260
ILDKVNQYFS LYDMNKFRHK LNLGFSKFIS FPNHNVLDGN TKVSSGKREI LQEILNGLHA  1320
NPTFGNLKDV GITTPFGQLQ QPNGILLSDE TKIRYQSPTG LFERTVSLKD L           1371

SEQ ID NO: 17          moltype = AA  length = 1334
FEATURE                Location/Qualifiers
source                 1..1334
                       mol_type = protein
                       organism = Listeria innocua
SEQUENCE: 17
MKKPYTIGLD IGTNSVGWAV LTDQYDLVKR KMKIAGDSEK KQIKKNFWGV RLFDEGQTAA  60
DRRMARTARR RIERRRNRIS YLQGIFAEEM SKTDANFFCR LSDSFYVDNE KRNSRHPFFA  120
TIEEEVEYHK NYPTIYHLRE ELVNSSEKAD LRLVYLALAH IIKYRGNFLI EGALDTQNTS  180
VDGIYKQFIQ TYNQVFASGI EDGSLKKLED NKDVAKILVE KVTRKEKLER ILKLYPGEKS  240
AGMFAQFISL IVGSKGNFQK PFDLIEKSDI ECAKDSYEED LESLLALIGD EYAELFVAAK  300
NAYSAVVLSS IITVAETETN AKLSASMIER FDTHEEDLGE LKAFIKLHLP KHYEEIFSNT  360
EKHGYAGYID GKTKQADFYK YMKMTLENIE GADYFIAKIE KENFLRKQRT FDNGAIPHQL  420
HLEELEAILH QQAKYYPFLK ENYDKIKSLV TFRIPYFVGP LANGQSEFAW LTRKADGEIR  480
PWNIEEKVDF GKSAVDFIEK MTNKDTYLPK ENVLPKHSLC YQKYLVYNEL TKVRYINDQG  540
KTSYFSGQEK EQIFNDLFKQ KRKVKKKDLE LFLRNMSHVE SPTIEGLEDS FNSSYSTYHD  600
LLKVGIKQEI LDNPVNTEML ENIVKILTVF EDKRMIKEQL QQFSDVLDGV VLKKLERRHY  660
TGWGRLSAKL LMGIRDKQSH LTILDYLMND DGLNRNLMQL INDSNLSFKS IIEKEQVTTA  720
DKDIQSIVAD LAGSPAIKKG ILQSLKIVDE LVSVMGYPPQ TIVVEMAREN QTTGKGKNNS  780
RPRYKSLEKA IKEFGSQILK EHPTDNQELR NNRLYLYYLQ NGKDMYTGQD LDIHNLSNYD  840
```

```
IDHIVPQSFI TDNSIDNLVL TSSAGNREKG DDVPPLEIVR KRKVFWEKLY QGNLMSKRKF  900
DYLTKAERGG LTEADKARFI HRQLVETRQI TKNVANILHQ RFNYEKDDHG NTMKQVRIVT  960
LKSALVSQFR KQFQLYKVRD VNDYHHAHDA YLNGVVANTL LKVYPQLEPE FVYGDYHQFD  1020
WFKANKATAK KQFYTNIMLF FAQKDRIIDE NGEILWDKKY LDTVKKVMSY RQMNIVKKTE  1080
IQKGEFSKAT IKPKGNSSKL IPRKTNWDPM KYGGLDSPNM AYAVVIEYAK GKNKLVFEKK  1140
IIRVTIMERK AFEKDEKAFL EEQGYRQPKV LAKLPKYTLY ECEEGRRRML ASANEAQKGN  1200
QQVLPNHLVT LLHHAANCEV SDGKSLDYIE SNREMFAELL AHVSEFAKRY TLAEANLNKI  1260
NQLFEQNKEG DIKAIAQSFV DLMAFNAMGA PASFKFFETT IERKRYNNLK ELLNSTIIYQ  1320
SITGLYESRK RLDD                                                   1334

SEQ ID NO: 18          moltype = AA  length = 1372
FEATURE                Location/Qualifiers
source                 1..1372
                       mol_type = protein
                       organism = Legionella pneumophila
SEQUENCE: 18
MESSQILSPI GIDLGGKFTG VCLSHLEAFA ELPNHANTKY SVILIDHNNF QLSQAQRRAT  60
RHRVRNKKRN QFVKRVALQL FQHILSRDLN AKEETALCHY LNNRGYTYVD TDLDEYIKDE  120
TTINLLKELL PSESEHNFID WFLQKMQSSE FRKILVSKVE EKKDDKELKN AVKNIKNFIT  180
GFEKNSVEGH RHRKVYFENI KSDITKDNQL DSIKKKIPSV CLSNLLGHLS NLQWKNLHRY  240
LAKNPKQFDE QTFGNEFLRM LKNFRHLKGS QESLAVRNLI QQLEQSQDYI SILEKTPPEI  300
TIPPYEARTN TGMEKDQSLL LNPEKLNNLY PNWRNLIPGI IDAHPFLEKD LEHTKLRDRK  360
RIISPSKQDE KRDSYILQRY LDLNKKIDKF KIKKQLSFLG QGKQLPANLI ETQKEMETHF  420
NSSLVSVLIQ IASAYNKERE DAAQGIWFDN AFSLCELSNI NPPRKQKILP LLVGAILSED  480
FINNKDKWAK FKIFWNTHKI GRTSLKSKCK EIEEARKNSG NAFKIDYEEA LNHPEHSNNK  540
ALIKIIQTIP DIIQAIQSHL GHNDSQALIY HNPFSLSQLY TILETKRDGF HKNCVAVTCE  600
NYWRSQKTEI DPEISYASRL PADSVRPFDG VLARMMQRLA YEIAMAKWEQ IKHIPDNSSL  660
LIPIYLEQNR FEFEESFKKI KGSSSDKTLE QAIEKQNIQW EEKFQRIINA SMNICPYKGA  720
SIGGQGEIDH IYPRSLSKKH FGVIFNSEVN LIYCSSQGNR EKKEEHYLLE HLSPLYLKHQ  780
FGTDNVSDIK NFISQNVANI KKYISFHLLT PEQQKAARHA LFLDYDDEAF KTITKFLMSQ  840
QKARVNGTQK FLGKQIMEFL STLADSKQLQ LEFSIKQITA EEVHDHRELL SKQEPKLVKS  900
RQQSFPSHAI DATLTMSIGL KEFPQFSQEL DNSWFINHLM PDEVHLNPVR SKEKYNKPNI  960
SSTPLFKDSL YAERFIPVWV KGETFAIGFS EKDLFEIKPS NKEKLFTLLK TYSTKNPGES  1020
LQELQAKSKA KWLYFPINKT LALEFLHHYF HKEIVTPDDT TVCHFINSLR YYTKKESITV  1080
KILKEPMPVL SVKFESSKKN VLGSFKHTIA LPATKDWERL FNHPNFLALK ANPAPNPKEF  1140
NEFIRKYFLS DNNPNSDIPN NGHNIKPQKH KAVRKVFSLP VIPGNAGTMM RIRRKDNKGQ  1200
PLYQLQTIDD TPSMGIQINE DRLVKQEVLM DAYKTRNLST IDGINNSEGQ AYATFDNWLT  1260
LPVSTFKPEI IKLEMKPHSK TRRYIRITQS LADFIKTIDE ALMIKPSDSI DDPLNMPNEI  1320
VCKNKLFGNE LKPRDGKMKI VSTGKIVTYE FESDSTPQWI QTLYVTQLKK QP         1372

SEQ ID NO: 19          moltype = AA  length = 1082
FEATURE                Location/Qualifiers
source                 1..1082
                       mol_type = protein
                       organism = Neisseria lactamica
SEQUENCE: 19
MAAFKPNPMN YILGLDIGIA SVGWAMVEVD EEENPIRLID LGVRVFERAE VPKTGDSLAM  60
ARRLARSVRR LTRRRAHRLL RARRLLKREG VLQDADFDEN GLVKSLPNTP WQLRAAALDR  120
KLTCLEWSAV LLHLVKHRGY LSQRKNEGET ADKELGALLK GVADNAHALQ TGDFRTPAEL  180
ALNKFEKESG HIRNQRGDYS HTFSRKDLQA ELNLLFEKQK EFGNPHVSDG LKEDIETLLM  240
AQRPALSGDA VQKMLGHCTF EPAEPKAAKN TYTAERFIWL TKLNNLRILE QGSERPLTDT  300
ERATLMDEPY RKSKLTYAQA RKLLGLEDTA FFKGLRYGKD NAEASTLMEM KAYHAISRAL  360
EKEGLKDKKS PLNLSTELQD EIGTAFSLFK TDKDITGRLK DRVQPEILEA LLKHISFDKF  420
VQISLKALRR IVPLMEQGKR YDEACAEIYG DHYCKKNAEE KIYLPPIPAD EIRNPVVLRA  480
LSQARKVINC VVRRYGSPAR IHIETAREVG KSFKDRKEIE KRQEENRKDR EKAAAKFREY  540
FPNFVGEPKS KDILKLRLYE QQHGKCLYSG KEINLVRLNE KGYVEIDHAL PFSRTWDDSF  600
NNKVLVLGSE NQNKGNQTPY EYFNGKDNSR EWQEFKARVE TSRFPRSKKQ RILLQKFDEE  660
GFKERNLNDT RYVNRFLCQF VADHILLTGK GKRRVFASNG QITNLLRGFW GLRKVRTEND  720
RHHALDAVVV ACSTVAMQQK ITRFVRYKEM NAFDGKTIDK ETGEVLHQKA HFPQPWEFFA  780
QEVMIRVFGK PDGKPEFEEA DTPEKLRTLL AEKLSSRPEA VHEYVTPLFV SRAPNRKMSG  840
QGHMETVKSA KRLDEGISVL RVPLTQLKLK GLEKMVNRER EPKLYDALKA QLETHKDDPA  900
KAFAEPFYKY DKAGSRTQQV KAVRIEQVQK TGVWVRNHNG IADNATMVRV DVFEKGGKYY  960
LVPIYSWQVA KGILPDRAVV AFKDEEDWTV MDDSFEFRFV LYANDLIKLT AKKNEFLGYF  1020
VSLNRATGAI DIRTHDTDST KGKNGIFQSV GVKTALSFQK NQIDELGKEI RPCRLKKRPP  1080
VR                                                                1082

SEQ ID NO: 20          moltype = AA  length = 1082
FEATURE                Location/Qualifiers
source                 1..1082
                       mol_type = protein
                       organism = Neisseria meningitidis
SEQUENCE: 20
MAAFKPNPIN YILGLDIGIA SVGWAMVEID EDENPICLID LGVRVFERAE VPKTGDSLAM  60
ARRLARSVRR LTRRRAHRLL RARRLLKREG VLQAADFDEN GLIKSLPNTP WQLRAAALDR  120
KLTPLEWSAV LLHLIKHRGY LSQRKNEGET ADKELGALLK GVADNAHALQ TGDFRTPAEL  180
ALNKFEKESG HIRNQRGDYS HTFSRKDLQA ELILLFEKQK EFGNPHVSGG LKEGIETLLM  240
TQRPALSGDA VQKMLGHCTF EPAEPKAAKN TYTAERFIWL TKLNNLRILE QGSERPLTDT  300
ERATLMDEPY RKSKLTYAQA RKLLGLEDTA FFKGLRYGKD NAEASTLMEM KAYHAISRAL  360
EKEGLKDKKS PLNLSPELQD EIGTAFSLFK TDEDITGRLK DRIQPEILEA LLKHISFDKF  420
```

```
VQISLKALRR IVPLMEQGKR YDEACAEIYG DHYGKKNTEE KIYLPPIPAD EIRNPVVLRA  480
LSQARKVING VVRRYGSPAR IHIETAREVG KSFKDRKEIE KRQEENRKDR EKAAAKFREY  540
FPNFVGEPKS KDILKLRLYE QQHGKCLYSG KEINLGRLNE KGYVEIDHAL PFSRTWDDSF  600
NNKVLVLGSE NQNKGNQTPY EYFNGKDNSR EWQEFKARVE TSRFPRSKKQ RILLQKFDED  660
GFKERNLNDT RYVNRFLCQF VADRMRLTGK GKKRVFASNG QITNLLRGFW GLRKVRAEND  720
RHHALDAVVV ACSTVAMQQK ITRFVRYKEM NAFDGKTIDK ETGEVLHQKT HFPQPWEFFA  780
QEVMIRVFGK PDGKPEFEEA DTPEKLRTLL AEKLSSRPEA VHEYVTPLFV SRAPNRKMSG  840
QGHMETVKSA KRLDEGVSVL RVPLTQLKLK DLEKMVNRER EPKLYEALKA RLEAHKDDPA  900
KAFAEPFYKY DKAGNRTQQV KAVRVEQVQK TGVWVRNHNG IADNATMVRV DVFEKGDKYY  960
LVPIYSWQVA KGILPDRAVV QGKDEEDWQL IDDSFNFKFS LHPNDLVEVI TKKARMFGYF  1020
ASCHRGTGNI NIRIHDLDHK IGKNGILEGI GVKTALSFQK YQIDELGKEI RPCRLKKRPP  1080
VR                                                                1082

SEQ ID NO: 21          moltype = AA  length = 1187
FEATURE                Location/Qualifiers
source                 1..1187
                       mol_type = protein
                       organism = Bifidobacterium longum
SEQUENCE: 21
MLSRQLLGAS HLARPVSYSY NVQDNDVHCS YGERCFMRGK RYRIGIDVGL NSVGLAAVEV  60
SDENSPVRLL NAQSVIHDGG VDPQKNKEAI TRKNMSGVAR RTRRMRRRKR ERLHKLDMLL  120
GKFGYPVIEP ESLDKPFEEW HVRAELATRY IEDDELRRES ISIALRHMAR HRGWRNPYRQ  180
VDSLISDNPY SKQYGELKEK AKAYNDDATA AEEESTPAQL VVAMLDAGYA EAPRLRWRTG  240
SKKPDAEGYL PVRLMQEDNA NELKQIFRVQ RVPADEWKPL FRSVFYAVSP KGSAEQRVGQ  300
DPLAPEQARA LKASLAFQEY RIANVITNLR IKDASAELRK LTVDEKQSIY DQLVSPSSED  360
ITWSDLCDFL GFKRSQLKGV GSLTEDGEER ISSRPPRLTS VQRIYESDNK IRKPLVAWWK  420
SASDNEHEAM IRLLSNTVDI DKVREDVAYA SAIEFIDGLD DDALTKLDSV DLPSGRAAYS  480
VETLQKLTRQ MLTTDDDLHE ARKTLFNVTD SWRPPADPIG EPLGNPSVDR VLKNVNRYLM  540
NCQQRWGNPV SVNIEHVRSS FSSVAFARKD KREYEKNNEK RSIFRSSLSE QLRADEQMEK  600
VRESDLRRLE AIQRQNGQCL YCGRTITFRT CEMDHIVPRK GVGSTNTRTN FAAVCAECNR  660
MKSNTPFAIW ARSEDAQTRG VSLAEAKKRV TMFTFNPKSY APREVKAFKQ AVIARLQQTE  720
DDAAIDNRSI ESVAWMADEL HRRIDWYFNA KQYVNSASID DAEAETMKTT VSVFQGRVTA  780
SARRAAGIEG KIHFIGQQSK TRLDRRHHAV DASVIAMMNT AAAQTLMERE SLRESQRLIG  840
LMPGERSWKE YPYEGTSRYE SFHLWLDNMD VLLELLNDAL DNDRIAVMQS QRYVLGNSIA  900
HDATIHPLEK VPLGSAMSAD LIRRASTPAL WCALTRLPDY DEKEGLPEDS HREIRVHDTR  960
YSADDEMGFF ASQAAQIAVQ EGSADIGSAI HHARVYRCWK TNAKGVRKYF YGMIRVFQTD  1020
LLRACHDDLF TVPLPPQSIS MRYGEPRVVQ ALQSGNAQYL GSLVVGDEIE MDFSSLDVDG  1080
QIGEYLQFFS QFSGGNLAWK HWVVDGFFNQ TQLRIRPRYL AAEGLAKAFS DDVVPDGVQK  1140
IVTKQGWLPP VNTASKTAVR IVRRNAFGEP RLSSAHHMPC SWQWRHE                1187

SEQ ID NO: 22          moltype = AA  length = 1101
FEATURE                Location/Qualifiers
source                 1..1101
                       mol_type = protein
                       organism = Akkermansia muciniphila
SEQUENCE: 22
MSRSLTFSFD IGYASIGWAV IASASHDDAD PSVCGCGTVL FPKDDCQAFK RREYRRLRRN  60
IRSRRVRIER IGRLLVQAQI ITPEMKETSG HPAPFYLASE ALKGHRTLAP IELWHVLRWY  120
AHNRGYDNNA SWSNSLSEDG GNGEDTERVK HAQDLMDKHG TATMAETICR ELKLEEGKAD  180
APMEVSTPAY KNLNTAFPRL IVEKEVRRIL ELSAPLIPGL TAEIIELIAQ HHPLTTEQRG  240
VLLQHGIKLA RRYRGSLLFG QLIPRFDNRI ISRCPVTWAQ VYEAELKKGN SEQSARERAE  300
KLSKVPTANC PEFYEYRMAR ILCNIRADGE PLSAEIRREL MNQARQEGKL TKASLEKAIS  360
SRLGKETETN VSNYFTLHPD SEEALYLNPA VEVLQRSGIG QILSPSVYRI AANRLRRGKS  420
VTPNYLLNLL KSRGESGEAL EKKIEKESKK KEADYADTPL KPKYATGRAP YARTVLKKVV  480
EEILDGEDPT RPARGEAHPD GELKAHDGCL YCLLDTDSSV NQHQKERRLD TMTNNHLVRH  540
RMLILDRLLK DLIQDFADGQ KDRISRVCVE VGKELTTFSA MDSKKIQREL TLRQKSHTDA  600
VNRLKRKLPG KALSANLIRK CRIAMDMNWT CPFTGATYGD HELENLELEH IVPHSFRQSN  660
ALSSLVLTWP GVNRMKGQRT GYDFVEQEQE NPVPDKPNLH ICSLNNYREL VEKLDDKKGH  720
EDDRRRKKKR KALLMVRGLS HKHQSQNHEA MKEIGMTEGM MTQSSHLMKL ACKSIKTSLP  780
DAHIDMIPGA VTAEVRKAWD VFGVFKELCP EAADPDSGKI LKENLRSLTH LHHALDACVL  840
GLIPYIIPAH HNGLLRRVLA MRRIPEKLIP QVRPVANQRH YVLNDDGRMM LRDLSASLKE  900
NIREQLMEQR VIQHVPADMG GALLKETMQR VLSVDGSGED AMVSLSKKKD GKKEKNQVKA  960
SKLVGVFPEG PSKLKALKAA IEIDGNYGVA LDPKPVVIRH IKVFKRIMAL KEQNGGKPVR  1020
ILKKGMLIHL TSSKDPKHAG VWRIESIQDS KGGVKLDLQR AHCAVPKNKT HECNWREVDL  1080
ISLLKKYQMK RYPTSYTGTP R                                            1101

SEQ ID NO: 23          moltype = AA  length = 1498
FEATURE                Location/Qualifiers
source                 1..1498
                       mol_type = protein
                       organism = Odoribacter laneus
SEQUENCE: 23
METTLGIDLG TNSIGLALVD QEEHQILYSG VRIFPEGINK DTIGLGEKEE SRNATRRAKR  60
QMRRQYFRKK LRKAKLLELL IAYDMCPLKP EDVRRWKNWD KQQKSTVRQF PDTPAFREWL  120
KQNPYELRKQ AVTEDVTRPE LGRILYQMIQ RRGFLSSRKG KEEGKIFTGK DRMVGIDETR  180
KNLQKQTLGA YLYDIAPKNG EKYRFRTERV RARYTLRDMY IREFEIIWQR QAGHLGLAHE  240
QATRKKNIFL EGSATNVRNS KLITHLQAKY GRGHVLIEDT RITVTFQLPL KEVLGGKIEI  300
EEEQLKFKSN ESVLFWQRPL RSQKSLLSKC VFEGRNFYDP VHQKWIIAGP TPAPLSHPEF  360
EEFRAYQFIN NIIYGKNEHL TAIQREAVFE LMCTESKDFN FEKIPKHLKL FEKFNFDDTT  420
```

```
KVPACTTISQ LRKLFPHPVW EEKREEIWHC FYFYDDNTLL FEKLQKDYAL QTNDLEKIKK  480
IRLSESYGNV SLKAIRRINP YLKKGYAYST AVLLGGIRNS FGKRFEYFKE YEPEIEKAVC  540
RILKEKNAEG EVIRKIKDYL VHNRFGFAKN DRAFQKLYHH SQAITTQAQK ERLPETGNLR  600
NPIVQQGLNE LRRTVNKLLA TCREKYGPSF KFDHIHVEMG RELRSSKTER EKQSRQIREN  660
EKKNEAAKVK LAEYGLKAYR DNIQKYLLYK EIEEKGGTVC CPYTGKTLNI SHTLGSDNSV  720
QIEHIIPYSI SLDDSLANKT LCDATFNREK GELTPYDFYQ KDPSPEKWGA SSWEEIEDRA  780
FRLLPYAKAQ RFIRRKPQES NEFISRQLND TRYISKKAVE YLSAICSDVK AFPGQLTAEL  840
RHLWGLNNIL QSAPDITFPL PVSATENHRE YYVITNEQNE VIRLFPKQGE TPRTEKGELL  900
LTGEVERKVF RCKGMQEFQT DVSDGKYWRR IKLSSSVTWS PLFAPKPISA DGQIVLKGRI  960
EKGVFVCNQL KQKLKTGLPD GSYWISLPVI SQTFKEGESV NNSKLTSQQV QLFGRVREGI  1020
FRCHNYQCPA SGADGNFWCT LDTDTAQPAF TPIKNAPPGV GGGQIILTGD VDDKGIFHAD  1080
DDLHYELPAS LPKGKYYGIF TVESCDPTLI PIELSAPKTS KGENLIEGNI WVDEHTGEVR  1140
FDPKKNREDQ RHHAIDAIVI ALSSQSLFQR LSTYNARREN KKRGLDSTEH FPSPWPGFAQ  1200
DVRQSVVPLL VSYKQNPKTL CKISKTLYKD GKKIHSCGNA VRGQLHKETV YGQRTAPGAT  1260
EKSYHIRKDI RELKTSKHIG KVVDITIRQM LLKHLQENYH IDITQEFNIP SNAFFKEGVY  1320
RIFLPNKHGE PVPIKKIRMK EELGNAERLK DNINQYVNPR NNHHVMIYQD ADGNLKEEIV  1380
SFWSVIERQN QGQPIYQLPR EGRNIVSILQ INDTFLIGLK EEEPEVYRND LSTLSKHLYR  1440
VQKLSGMYYT FRHHLASTLN NEREEFRIQS LEAWKRANPV KVQIDEIGRI TFLNGPLC    1498

SEQ ID NO: 24          moltype = AA  length = 931
FEATURE                Location/Qualifiers
source                 1..931
                       mol_type = protein
                       organism = Homo sapiens
SEQUENCE: 24
MAEIKEKICD YLFNVSDSSA LNLAKNIGLT KARDINAVLI DMERQGDVYR QGTTPPIWHL  60
TDKKRERMQI KRNTNSVPET APAAIPETKR NAEFLTCNIP TSNASNNMVT TEKVENGQEP  120
VIKLENRQEA RPEPARLKPP VHYNGPSKAG YVDFENGQWA TDDIPDDLNS IRAAPGEFRA  180
IMEMPSFYSH GLPRCSPYKK LTECQLKNPI SGLLEYAQFA SQTCEFNMIE QSGPPHEPRF  240
KFQVVINGRE FPPAEAGSKK VAKQDAAMKA MTILLEEAKA KDSGKSEESS HYSTEKESEK  300
TAESQTPTPS ATSFFSGKSP VTTLLECMHK LGNSCEFRLL SKEGPAHEPK FQYCVAVGAQ  360
TFPSVSAPSK KVAKQMAAEE AMKALHGEAT NSMASDNQPE GMISESLDNL ESMMPNKVRK  420
IGELVRYLNT NPVGGLLEYA RSHGFAAEFK LVDQSGPPHE PKFVYQAKVG GRWFPAVCAH  480
SKKQGKQEAA DAALRVLIGE NEKAERMGFT EVTPVTGASL RRTMLLLSRS PEAQPKTLPL  540
TGSTFHDQIA MLSHRCFNTL TNSFQPSLLG RKILAAIIMK KDSEDMGVVV SLGTGNRCVK  600
GDSLSLKGET VNDCHAEIIS RRGFIRFLYS ELMKYNSQTA KDSIFEPAKG GEKLQIKKTV  660
SFHLYISTAP CGDGALFDKS CSDRAMESTE SRHYPVFENP KQGKLRTKVE NGEGTIPVES  720
SDIVPTWDGI RLGERLRTMS CSDKILRWNV LGLQGALLTH FLQPIYLKSV TLGYLFSQGH  780
LTRAICCRVT RDGSAFEDGL RHPFIVNHPK VGRVSIYDSK RQSGKTKETS VNWCLADGYD  840
LEILDGTRGT VDGPRNELSR VSKKNIFLLF KKLCSFRYRR DLLRLSYGEA KKAARDYETA  900
KNYFKKGLKD MGYGNWISKP QEEKNFYLCP V                                 931

SEQ ID NO: 25          moltype = AA  length = 701
FEATURE                Location/Qualifiers
source                 1..701
                       mol_type = protein
                       organism = Homo sapiens
SEQUENCE: 25
MDIEDEENMS SSSTDVKENR NLDNVSPKDG STPGPGEGSQ LSNGGGGGPG RKRPLEEGSN  60
GHSKYRLKKR RKTPGPVLPK NALMQLNEIK PGLQYTLLSQ TGPVHAPLFV MSVEVNGQVF  120
EGSGPTKKKA KLHAAEKALR SFVQFPNASE AHLAMGRTLS VNTDFTSDQA DFPDTLFNGF  180
ETPDKAEPPF YVGSNGDDSF SSSGDLSLSA SPVPASLAQP PLPVLPPFPP PSGKNPVMIL  240
NELRPGLKYD FLSESGESHA KSFVMSVVVD GQFFEGSGRN KKLAKARAAQ SALAAIFNLH  300
LDQTPSRQPI PSEGLQLHLP QVLADAVSRL VLGKFGDLTD NFSSPHARRK VLAGVVMTTG  360
TDVKDAKVIS VSTGTKCING EYMSDRGLAL NDCHAEIISR RSLLRFLYTQ LELYLNNKDD  420
QKRSIFQKSE RGGFRLKENV QFHLYISTSP CGDARIFSPH EPILEEPADR HPNRKARGQL  480
RTKIESGEGT IPVRSNASIQ TWDGVLQGER LLTMSCSDKI ARWNVVGIQG SLLSIFVEPI  540
YFSSIILGSL YHGDHLSRAM YQRISNIEDL PPLYTLNKPL LSGISNAEAR QPGKAPNFSV  600
NWTVGDSAIE VINATTGKDE LGRASRLCKH ALYCRWMRVH GKVPSHLLRS KITKPNVYHE  660
SKLAAKEYQA AKARLFTAFI KAGLGAWVEK PTEQDQFSLT P                      701

SEQ ID NO: 26          moltype = AA  length = 739
FEATURE                Location/Qualifiers
source                 1..739
                       mol_type = protein
                       organism = Homo sapiens
SEQUENCE: 26
MASVLGSGRG SGGLSSQLKC KSKRRRRRRS KRKDKVSILS TFLAPFKHLS PGITNTEDDD  60
TLSTSSAEVK ENRNVGNLAA RPPPSGDRAR GGAPGAKRKR PLEEGNGGHL CKLQLVWKKL  120
SWSVAPKNAL VQLHELRPGL QYRTVSQTGP VHAPVFAVAV EVNGLTFEGT GPTKKKAKMR  180
AAELALRSFV QFPNACQAHL AMGGGPGPGT DFTSDQADFP DTLFQEFEPP APRPGLAGGR  240
PGDAALLSAA YGRRRLLCRA LDLVGPTPAT PAAPGERNPV VLLNRLRAGL RYVCLAEPAE  300
RRARSFVMAV SVDGRTFEGS GRSKKLARGQ AAQAALQELF DIQMPGHAPG RARRTPMPQE  360
FADSISQLVT QKFREVTTDL TPMHARHKAL AGIVMTKGLD ARQAQVVALS SGTKCISGEH  420
LSDQGLVVND CHAEVVARRA FLHFLYTQLE LHLSKRREDS ERSIFVRLKE GGYRLRENIL  480
FHLYVSTSPC GDARLHSPYE ITTDLHSSKH LVRKFRGHLR TKIESGEGTV PVRGPSAVQT  540
WDGVLLGEQL ITMSCTDKIA RWNVLGLQGA LLSHFVEPVY LQSIVVGSLH HTGHLARVMS  600
HRMEGVGQLP ASYRHNRPLL SGVSDAEARQ PGKSPPFSMN WVVGSADLEI INATTGRRSC  660
GGPSRLCKHV LSARWARLYG RLSTRTPSPG DTPSMYCEAK LGAHTYQSVK QQLFKAFQKA  720
```

```
GLGTWVRKPP EQQQFLLTL                                               739

SEQ ID NO: 27          moltype = DNA  length = 10826
FEATURE                Location/Qualifiers
misc_feature           1..10826
                       note = Description of Artificial Sequence:
                        Syntheticpolynucleotide
source                 1..10826
                       mol_type = other DNA
                       organism = synthetic construct
SEQUENCE: 27
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gtttaaacgg gccctctaga ctcgagcggc cgccactgtg ctggatatct gcagagaacc  960
atgttagctg acgctgtctc acgcctggtc ctgggtaagt ttggtgacct gaccgacaac  1020
ttctcctccc ctcacgctcg cagaaaagtg ctggctggag tcgtcatgac aacaggcaca  1080
gatgttaaag atgccaaggt gataagtgtt tctacaggaa caaaatgtat taatggtgaa  1140
tacatgagtg atcgtggcct tgcattaaat gactgccatg cagaaataat atctcggaga  1200
tccttgctca gatttcttta tacacaactt gagctttact taaataacaa agatgatcaa  1260
aaaagatcca tctttcagaa atcagagcga gggggtttta ggctgaagga gaatgtccag  1320
tttcatctgt acatcagcac ctctccctgt ggagatgcca gaatcttctc accacatgag  1380
ccaatcctgg aagaaccagc agatagacac ccaaatcgta aagcaagagg acagctacgg  1440
accaaaatag agtctggtga ggggacgatt ccagtgcgct ccaatgcgag catccaaacg  1500
tgggacgggg tgctgcaagg ggagcggctg ctcaccatgt cctgcagtga caagattgca  1560
cgctggaacg tggtgggcat ccagggatcc ctgctcagca ttttcgtgga gcccatttac  1620
ttctcgagca tcatcctggg cagcctttac cacggggacc acctttccag ggccatgtac  1680
cagcggatct ccaacataga ggacctgcca cctctctaca ccctcaacaa gcctttgctc  1740
agtggcatca gcaatgcaga agcacggcag ccagggaagg cccccaactt cagtgtcaac  1800
tggacggtag gcgactccgc tattgaggtc atcaacgcca cgactgggaa ggatgagctg  1860
ggccgcgcgt cccgcctgtg taagcacgcg ttgtactgtc gctggatgcg tgtgcacggc  1920
aaggttccct cccacttact acgctccaag attaccaagc ccaacgtgta ccatgagtcc  1980
aagctggcgg caaaggagta ccaggccgcc aaggcgcgtc tgttcacagc cttcatcaag  2040
gcggggctgg gggcctgggt ggagaagccc accgagcagg accagttctc actcacgccc  2100
agtggaagtg agacaccggg aacctcagag agcgccacgc cagaaagcat ggacaagaag  2160
tacagcatcg gcctggccat cggcaccaac tctgtgggct gggccgtgat caccgacgag  2220
tacaaggtgc ccagcaagaa attcaaggtg ctgggcaaca ccgaccggca cagcatcaag  2280
aagaacctga tcggcgccct gctgttcgac agcggagaaa cagccgaggc cacccggctg  2340
aagagaaccg ccagaagaag atacaccaga cggaagaacc ggatctgcta tctgcaagag  2400
atcttcagca acgagatggc caaggtggac gacagcttct tccacagact ggaagagtcc  2460
ttcctggtgg aagaggataa gaagcacgag cggcacccca tcttcggcaa catcgtggac  2520
gaggtggcct accacgagaa gtaccccacc atctaccacc tgagaaagaa actggtggac  2580
agcaccgaca aggccgacct gcggctgatc tatctggccc tggcccacat gatcaagttc  2640
cggggccact tcctgatcga gggcgacctg aaccccgaca acagcgacgt ggacaagctg  2700
ttcatccagc tggtgcagac ctacaaccag ctgttcgagg aaaaccccat caacgccagc  2760
ggcgtggacg ccaaggccat cctgtctgcc agactgagca agagcagacg gctggaaaat  2820
ctgatcgccc agctgcccgg cgagaagaag aatggcctgt tcggcaacct gattgccctg  2880
agcctgggcc tgacccccaa cttcaagagc aacttcgacc tggccgagga tgccaaactg  2940
cagctgagca aggacaccta cgacgacgac ctggacaacc tgctggccca gatcggcgac  3000
cagtacgccg acctgtttct ggccgccaag aacctgtccg acgccatcct gctgagcgac  3060
atcctgagag tgaacaccga gatcaccaag gcccccctga gcgcctctat gatcaagaga  3120
tacgacgagc accaccagga cctgaccctg ctgaaagctc tcgtgcggca gcagctgcct  3180
gagaagtaca aagagatttt cttcgaccag agcaagaacg gctacgccgg ctacatcgat  3240
ggcggagcca gccaggaaga gttctacaag ttcatcaagc ccatcctgga aaagatggac  3300
ggcaccgagg aactgctcgt gaagctgaac agagaggacc tgctgcggaa gcagcggacc  3360
ttcgacaacg gcagcatccc ccaccagatc cacctgggag agctgcacgc cattctgcgg  3420
cggcaggaag atttttaccc attcctgaag gacaaccggg aaaagatcga gaagatcctg  3480
accttccgca tcccctacta cgtgggccct ctggccaggg gaaacagcag attcgcctgg  3540
atgaccagaa agagcgagga aaccatcacc ccctggaact tcgaggaagt ggtggacaag  3600
ggcgccagcg cccagagctt catcgagcgg atgaccaact tcgataagaa cctgcccaac  3660
gagaaggtgc tgcccaagca cagcctgctg tacgagtact tcaccgtgta caacgagctg  3720
accaaagtga aatacgtgac cgagggaatg agaaagcccg ccttcctgag cggcgagcag  3780
aaaaaagcca tcgtggacct gctgttcaag accaaccgga aagtgaccgt gaagcagctg  3840
aaagaggact acttcaagaa aatcgagtgc ttcgactccg tggaaatctc cggcgtggaa  3900
gatcggttca acgcctccct gggcacatac cacgatctgc tgaaaattat caaggacaag  3960
gacttcctgg acaatgagga aaacgaggac attctggaag atatcgtgct gaccctgaca  4020
ctgtttgagg acagagagat gatcgaggaa cggctgaaaa cctatgccca cctgttcgac  4080
```

```
gacaaagtga tgaagcagct gaagcggcgg agatacaccg gctggggcag gctgagccgg  4140
aagctgatca acggcatccg ggacaagcag tccggcaaga caatcctgga tttcctgaag  4200
tccgacggct tcgccaacag aaacttcatg cagctgatcc acgacgacag cctgaccttt  4260
aaagaggaca tccagaaagc ccaggtgtcc ggccagggcg atagcctgca cgagcacatt  4320
gccaatctgg ccggcagccc cgccattaag aagggcatcc tgcagacagt gaaggtggtg  4380
gacgagctcg tgaaagtgat gggccggcac aagcccgaga acatcgtgat cgaaatggcc  4440
agagagaacc agaccaccca gaagggacag aagaacagcc gcgagagaat gaagcggatc  4500
gaagagggca tcaaagagct gggcagccag atcctgaaag aacaccccgt ggaaaacacc  4560
cagctgcaga acgagaagct gtacctgtac tacctgcaga atgggcggga tatgtacgtg  4620
gaccaggaac tggacatcaa ccggctgtcc gactacgatg tggacgctat cgtgcctcag  4680
agctttctga aggacgactc catcgataac aaagtgctga ctcggagcga caagaaccgg  4740
ggcaagagcg acaacgtgcc ctccgaagag gtcgtgaaga agatgaagaa ctactggcgc  4800
cagctgctga atgccaagct gattacccag aggaagttcg acaatctgac caaggccgag  4860
agaggcggcc tgagcgaact ggataaggcc ggcttcatca agagacagct ggtggaaacc  4920
cggcagatca caaagcacgt ggcacagatc ctggactccc ggatgaacac taagtacgac  4980
gagaacgaca aactgatccg ggaagtgaaa gtgatcaccc tgaagtccaa gctggtgtcc  5040
gatttccgga aggatttcca gtttacaaa gtgcgcgaga tcaacaacta ccaccacgcc  5100
cacgacgcct acctgaacgc cgtcgtggga accgccctga tcaaaaagta ccctaagctg  5160
gaaagcgagt tcgtgtacgg cgactacaag gtgtacgacg tgcggaagat gatcgccaag  5220
agcgagcagg aaatcggcaa ggctaccgcc aagtacttct tctacagcaa catcatgaac  5280
tttttcaaga ccgagattac cctggccaac ggcgagatcc ggaagcggcc tctgatcgag  5340
acaaacggcg aaacaggcga gatcgtgtgg gataagggcc gggactttgc caccgtgcgg  5400
aaagtgctgt ctatgcccca agtgaatatc gtgaaaaaga ccgaggtgca gacaggcggc  5460
ttcagcaaag agtctatcct gcccaagagg aacagcgaca agctgatcgc cagaaagaag  5520
gactgggacc ctaagaagta cggcggcttc gacagcccca ccgtggccta ttctgtgctg  5580
gtggtggcca aagtggaaaa gggcaagtcc aagaaactga agagtgtgaa agagctgctg  5640
gggatcacca tcatggaaag aagcagcttc gagaagaatc ccatcgactt tctggaagcc  5700
aagggctaca aagaagtgaa aaaggacctg atcatcaagc tgcctaagta ctccctgttc  5760
gagctggaaa acggccggaa gagaatgctg gcctctgccg gcgaactgca gaagggaaac  5820
gaactggccc tgccctccaa atatgtgaac ttcctgtacc tggccagcca ctatgagaag  5880
ctgaagggct cccccgagga taatgagcag aaacagctgt ttgtggaaca gcacaaacac  5940
tacctggacg agatcatcga gcagatcagc gagttctcca agagagtgat cctggccgac  6000
gctaatctgg acaaggtgct gagcgcctac aacaagcaca gagacaagcc tatcagagag  6060
caggccgaga atatcatcca cctgtttacc ctgaccaatc tgggagcccc tgccgccttc  6120
aagtactttg acaccaccat cgaccggaag aggtacacca gcaccaaaga ggtgctggac  6180
gccaccctga tccaccagag catcaccggc ctgtacgaga cacggatcga cctgtctcag  6240
ctgggaggcg acgcctatcc ctatgacgtg cccgattatg ccagcctggg cagcggctcc  6300
cccaagaaaa aacgcaaggt ggaagatcct aagaaaaagc ggaaagtgga cgtgtaacca  6360
ccacactgga ctagtggatc cgagctcggt accaagctta agtttaaacc gctgatcagc  6420
ctcgactgtg ccttctagtt gccagccatc tgttgtttgc ccctcccccg tgccttcctt  6480
gaccctggaa ggtgccactc ccactgtcct ttcctaataa aatgaggaaa ttgcatcgca  6540
ttgtctgagt aggtgtcatt ctattctggg gggtggggtg gggcaggaca gcaaggggga  6600
ggattgggaa gacaatagca ggcatgctgg ggatgcggtg ggctctatgg cttctgaggc  6660
ggaaagaacc agctggggct ctagggggta tccccacgcg ccctgtagcg gcgcattaag  6720
cgcggcgggt gtggtggtta cgcgcagcgt gaccgctaca cttgccagcg ccctagcgcc  6780
cgctcctttc gctttcttcc cttcctttct cgccacgttc gccggctttc cccgtcaagc  6840
tctaaatcgg gggctccctt tagggttccg atttagtgct ttacggcacc tcgaccccaa  6900
aaaacttgat tagggtgatg gttcacgtag tgggccatcg ccctgataga cggtttttcg  6960
ccctttgacg ttggagtcca cgttctttaa tagtggactc ttgttccaaa ctggaacaac  7020
actcaaccct atctcggtct attcttttga tttataaggg attttgccga tttcggccta  7080
ttggttaaaa aatgagctga tttaacaaaa atttaacgcg aattaattct gtggaatgtg  7140
tgtcagttag ggtgtggaaa gtccccaggc tccccagcag gcagaagtat gcaaagcatg  7200
catctcaatt agtcagcaac caggtgtgga aagtccccag gctccccagc aggcagaagt  7260
atgcaaagca tgcatctcaa ttagtcagca accatagtcc cgcccctaac tccgcccatc  7320
ccgcccctaa ctccgcccag ttccgcccat tctccgcccc atggctgact aattttttt  7380
atttatgcag aggccgaggc cgcctctgcc tctgagctat tccagaagta gtgaggaggc  7440
ttttttggag gcctaggctt ttgcaaaaag ctcccgggag cttgtatatc cattttcgga  7500
tctgatcaag agacaggatg aggatcgttt cgcatgattg aacaagatgg attgcacgca  7560
ggttctccgg ccgcttgggt ggagaggcta ttcggctatg actgggcaca acagacaatc  7620
ggctgctctg atgccgccgt gttccggctg tcagcgcagg ggcgcccggt tctttttgtc  7680
aagaccgacc tgtccggtgc cctgaatgaa ctgcaggacg aggcagcgcg gctatcgtgg  7740
ctggccacga cgggcgttcc ttgcgcagct gtgctcgacg ttgtcactga agcgggaagg  7800
gactggctgc tattgggcga agtgccgggg caggatctcc tgtcatctca ccttgctcct  7860
gccgagaaag tatccatcat ggctgatgca atgcggcggc tgcatacgct tgatccggct  7920
acctgcccat tcgaccacca agcgaaacat cgcatcgagc gagcacgtac tcggatggaa  7980
gccggtcttg tcgatcagga tgatctggac gaagagcatc aggggctcgc gccagccgaa  8040
ctgttcgcca ggctcaaggc gcgcatgccc gacggcgagg atctcgtcgt gacccatggc  8100
gatgcctgct tgccgaatat catggtggaa aatggccgct tttctggatt catcgactgt  8160
ggccggctgg gtgtggcgga ccgctatcag gacatagcgt tggctacccg tgatattgct  8220
gaagagcttg gcggcgaatg ggctgaccgc ttcctcgtgc tttacggtat cgccgctccc  8280
gattcgcagc gcatcgcctt ctatcgcctt cttgacgagt tcttctgagc gggactctgg  8340
ggttcgaaat gaccgaccaa gcgacgccca acctgccatc acgagatttc gattccaccg  8400
ccgccttcta tgaaaggttg ggcttcggaa tcgttttccg ggacgccggc tggatgatcc  8460
tccagcgcgg ggatctcatg ctggagttct tcgcccaccc caacttgttt attgcagctt  8520
ataatggtta caaataaagc aatagcatca caaatttcac aaataaagca tttttttcac  8580
tgcattctag ttgtggtttg tccaaactca tcaatgtatc ttatcatgtc tgtataccgt  8640
cgacctctag ctagagcttg gcgtaatcat ggtcatagct gtttcctgtg tgaaattgtt  8700
atccgctcac aattccacac aacatacgag ccggaagcat aaagtgtaaa gcctggggtg  8760
cctaatgagt gagctaactc acattaattg cgttgcgctc actgcccgct ttccagtcgg  8820
```

```
gaaacctgtc gtgccagctg cattaatgaa tcggccaacg cgcggggaga ggcggtttgc  8880
gtattgggcg ctcttccgct tcctcgctca ctgactcgct gcgctcggtc gttcggctgc  8940
ggcgagcggt atcagctcac tcaaaggcgg taatacggtt atccacagaa tcaggggata  9000
acgcaggaaa gaacatgtga gcaaaaggcc agcaaaaggc caggaaccgt aaaaaggccg  9060
cgttgctggc gtttttccat aggctccgcc cccctgacga gcatcacaaa aatcgacgct  9120
caagtcagag gtggcgaaac ccgacaggac tataaagata ccaggcgttt ccccctggaa  9180
gctccctcgt gcgctctcct gttccgaccc tgccgcttac cggatacctg tccgcctttc  9240
tcccttcggg aagcgtggcg ctttctcata gctcacgctg taggtatctc agttcggtgt  9300
aggtcgttcg ctccaagctg ggctgtgtgc acgaaccccc cgttcagccc gaccgctgcg  9360
ccttatccgg taactatcgt cttgagtcca acccggtaag acacgactta tcgccactgg  9420
cagcagccac tggtaacagg attagcagag cgaggtatgt aggcggtgct acagagttct  9480
tgaagtggtg gcctaactac ggctacacta gaagaacagt atttggtatc tgcgctctgc  9540
tgaagccagt taccttcgga aaaagagttg gtagctcttg atccggcaaa caaaccaccg  9600
ctggtagcgg tttttttgtt tgcaagcagc agattacgcg cagaaaaaaa ggatctcaag  9660
aagatccttt gatcttttct acggggtctg acgctcagtg gaacgaaaac tcacgttaag  9720
ggattttggt catgagatta tcaaaaagga tcttcaccta gatcctttta aattaaaaat  9780
gaagttttaa atcaatctaa agtatatatg agtaaacttg gtctgacagt taccaatgct  9840
taatcagtga ggcacctatc tcagcgatct gtctatttcg ttcatccata gttgcctgac  9900
tccccgtcgt gtagataact acgatacggg agggcttacc atctggcccc agtgctgcaa  9960
tgataccgcg agacccacgc tcaccggctc cagatttatc agcaataaac cagccagccg  10020
gaagggccga gcgcagaagt ggtcctgcaa ctttatccgc ctccatccag tctattaatt  10080
gttgccggga agctagagta agtagttcgc cagttaatag tttgcgcaac gttgttgcca  10140
ttgctacagg catcgtggtg tcacgctcgt cgtttggtat ggcttcattc agctccggtt  10200
cccaacgatc aaggcgagtt acatgatccc ccatgttgtg caaaaaagcg gttagctcct  10260
tcggtcctcc gatcgttgtc agaagtaagt tggccgcagt gttatcactc atggttatgg  10320
cagcactgca taattctctt actgtcatgc catccgtaag atgcttttct gtgactggtg  10380
agtactcaac caagtcattc tgagaatagt gtatgcggcg accgagttgc tcttgcccgg  10440
cgtcaatacg ggataatacc gcgccacata gcagaacttt aaaagtgctc atcattggaa  10500
aacgttcttc ggggcgaaaa ctctcaagga tcttaccgct gttgagatcc agttcgatgt  10560
aacccactcg tgcacccaac tgatcttcag catcttttac tttcaccagc gtttctgggt  10620
gagcaaaaac aggaaggcaa aatgccgcaa aaaagggaat aagggcgaca cggaaatgtt  10680
gaatactcat actcttcctt tttcaatatt attgaagcat ttatcagggt tattgtctca  10740
tgagcggata catatttgaa tgtatttaga aaaataaaca aataggggtt ccgcgcacat  10800
ttccccgaaa agtgccacct gacgtc                                     10826

SEQ ID NO: 28          moltype = DNA  length = 6722
FEATURE                Location/Qualifiers
misc_feature           1..6722
                       note = Description of Artificial Sequence:
                        Syntheticpolynucleotide
source                 1..6722
                       mol_type = other DNA
                       organism = synthetic construct
SEQUENCE: 28
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gtttaaacgg gccctctaga ctcgagcggc cgccactgtg ctggatatct gcagagaacc  960
atgttagctg acgctgtctc acgcctggtc ctgggtaagt ttggtgacct gaccgacaac  1020
ttctcctccc ctcacgctcg cagaaaagtg ctggctggag tcgtcatgac aacaggcaca  1080
gatgttaaag atgccaaggt gataagtgtt tctacaggaa caaaatgtat taatggtgaa  1140
tacatgagtg atcgtggcct tgcattaaat gactgccatg cagaaataat atctcggaga  1200
tccttgctca gatttcttta tacacaactt gagctttact taaataacaa agatgatcaa  1260
aaaagatcca tctttcagaa atcagagcga gggggtttta ggctgaagga gaatgtccag  1320
tttcatctgt acatcagcac ctctccctgt ggagatgcca gaatcttctc accacatgag  1380
ccaatcctgg aagaaccagc agatagacac ccaaatcgta aagcaagagg acagctacgg  1440
accaaaatag agtctggtga ggggacgatt ccagtgcgct ccaatgcgag catccaaacg  1500
tgggacgggg tgctgcaagg ggagcggctg ctcaccatgt cctgcagtga caagattgca  1560
cgctggaacg tggtgggcat ccagggatcc ctgctcagca ttttcgtgga gcccatttac  1620
ttctcgagca tcatcctggg cagcctttac cacggggacc acctttccag ggccatgtac  1680
cagcggatct ccaacataga ggacctgcca cctctctaca ccctcaacaa gcctttgctc  1740
agtggcatca gcaatgcaga agcacggcag ccagggaagg cccccaactt cagtgtcaac  1800
tggacggtag gcgactccgc tattgaggtc atcaacgcca cgactgggaa ggatgagctg  1860
ggccgcgcgt cccgcctgtg taagcacgcg ttgtactgtc gctggatgcg tgtgcacggc  1920
aaggttccct cccacttact acgctccaag attaccaagc ccaacgtgta ccatgagtcc  1980
aagctggcgg caaaggagta ccaggccgcc aaggcgcgtc tgttcacagc cttcatcaag  2040
gcggggctgg gggcctgggt ggagaagccc accgagcagg accagttctc actcacgccc  2100
```

-continued

```
agtggaagtg agacaccggg aacctcagag agcgccacgc cagaaagcgc ctatccctat  2160
gacgtgcccg attatgccag cctgggcagc ggctccccca agaaaaaacg caaggtggaa  2220
gatcctaaga aaaagcggaa agtggacgtg taaccaccac actggactag tggatccgag  2280
ctcggtacca agcttaagtt taaaccgctg atcagcctcg actgtgcctt ctagttgcca  2340
gccatctgtt gtttgcccct cccccgtgcc ttccttgacc ctggaaggtg ccactcccac  2400
tgtcctttcc taataaaatg aggaaattgc atcgcattgt ctgagtaggt gtcattctat  2460
tctggggggt ggggtggggc aggacagcaa gggggaggat tgggaagaca atagcaggca  2520
tgctggggat gcggtgggct ctatggcttc tgaggcggaa agaaccagct ggggctctag  2580
ggggtatccc cacgcgccct gtagcggcgc attaagcgcg gcgggtgtgg tggttacgcg  2640
cagcgtgacc gctacacttg ccagcgccct agcgcccgct cctttcgctt tcttcccttc  2700
ctttctcgcc acgttcgccg gctttccccg tcaagctcta aatcgggggc tccctttagg  2760
gttccgattt agtgctttac ggcacctcga ccccaaaaaa cttgattagg gtgatggttc  2820
acgtagtggg ccatcgccct gatagacggt ttttcgccct ttgacgttgg agtccacgtt  2880
ctttaatagt ggactcttgt tccaaactgg aacaacactc aaccctatct cggtctattc  2940
ttttgattta taagggattt tgccgatttc ggcctattgg ttaaaaaatg agctgattta  3000
acaaaaattt aacgcgaatt aattctgtgg aatgtgtgtc agttagggtg tggaaagtcc  3060
ccaggctccc cagcaggcag aagtatgcaa agcatgcatc tcaattagtc agcaaccagg  3120
tgtggaaagt ccccaggctc cccagcaggc agaagtatgc aaagcatgca tctcaattag  3180
tcagcaacca tagtcccgcc cctaactccg cccatcccgc ccctaactcc gcccagttcc  3240
gcccattctc cgccccatgg ctgactaatt ttttttattt atgcagaggc cgaggccgcc  3300
tctgcctctg agctattcca gaagtagtga ggaggctttt ttggaggcct aggcttttgc  3360
aaaaagctcc cgggagcttg tatatccatt ttcggatctg atcaagagac aggatgagga  3420
tcgtttcgca tgattgaaca agatggattg cacgcaggtt ctccggccgc ttgggtggag  3480
aggctattcg gctatgactg ggcacaacag acaatcggct gctctgatgc cgccgtgttc  3540
cggctgtcag cgcaggggcg cccggttctt tttgtcaaga ccgacctgtc cggtgccctg  3600
aatgaactgc aggacgaggc agcgcggcta tcgtggctgg ccacgacggg cgttccttgc  3660
gcagctgtgc tcgacgttgt cactgaagcg ggaagggact ggctgctatt gggcgaagtg  3720
ccggggcagg atctcctgtc atctcacctt gctcctgccg agaaagtatc catcatggct  3780
gatgcaatgc ggcggctgca tacgcttgat ccggctacct gcccattcga ccaccaagcg  3840
aaacatcgca tcgagcgagc acgtactcgg atggaagccg gtcttgtcga tcaggatgat  3900
ctggacgaag agcatcaggg gctcgcgcca gccgaactgt tcgccaggct caaggcgcgc  3960
atgcccgacg gcgaggatct cgtcgtgacc catggcgatg cctgcttgcc gaatatcatg  4020
gtggaaaatg gccgcttttc tggattcatc gactgtggcc ggctgggtgt ggcggaccgc  4080
tatcaggaca tagcgttggc tacccgtgat attgctgaag agcttggcgg cgaatgggct  4140
gaccgcttcc tcgtgcttta cggtatcgcc gctcccgatt cgcagcgcat cgccttctat  4200
cgccttcttg acgagttctt ctgagcggga ctctggggtt cgaaatgacc gaccaagcga  4260
cgcccaacct gccatcacga gatttcgatt ccaccgccgc cttctatgaa aggttgggct  4320
tcggaatcgt tttccgggac gccggctgga tgatcctcca gcgcggggat ctcatgctgg  4380
agttcttcgc ccaccccaac ttgtttattg cagcttataa tggttacaaa taaagcaata  4440
gcatcacaaa tttcacaaat aaagcatttt tttcactgca ttctagttgt ggtttgtcca  4500
aactcatcaa tgtatcttat catgtctgta taccgtcgac ctctagctag agcttggcgt  4560
aatcatggtc atagctgttt cctgtgtgaa attgttatcc gctcacaatt ccacacaaca  4620
tacgagccgg aagcataaag tgtaaagcct ggggtgccta atgagtgagc taactcacat  4680
taattgcgtt gcgctcactg cccgctttcc agtcgggaaa cctgtcgtgc cagctgcatt  4740
aatgaatcgg ccaacgcgcg gggagaggcg gtttgcgtat tgggcgctct tccgcttcct  4800
cgctcactga ctcgctgcgc tcggtcgttc ggctgcggcg agcggtatca gctcactcaa  4860
aggcggtaat acggttatcc acagaatcag gggataacgc aggaaagaac atgtgagcaa  4920
aaggccagca aaaggccagg aaccgtaaaa aggccgcgtt gctggcgttt ttccataggc  4980
tccgcccccc tgacgagcat cacaaaaatc gacgctcaag tcagaggtgg cgaaacccga  5040
caggactata aagataccag gcgtttcccc ctggaagctc cctcgtgcgc tctcctgttc  5100
cgaccctgcc gcttaccgga tacctgtccg cctttctccc ttcgggaagc gtggcgcttt  5160
ctcatagctc acgctgtagg tatctcagtt cggtgtaggt cgttcgctcc aagctgggct  5220
gtgtgcacga accccccgtt cagcccgacc gctgcgcctt atccggtaac tatcgtcttg  5280
agtccaaccc ggtaagacac gacttatcgc cactggcagc agccactggt aacaggatta  5340
gcagagcgag gtatgtaggc ggtgctacag agttcttgaa gtggtggcct aactacggct  5400
acactagaag aacagtattt ggtatctgcg ctctgctgaa gccagttacc ttcggaaaaa  5460
gagttggtag ctcttgatcc ggcaaacaaa ccaccgctgg tagcggtttt tttgtttgca  5520
agcagcagat tacgcgcaga aaaaaaggat ctcaagaaga tcctttgatc ttttctacgg  5580
ggtctgacgc tcagtggaac gaaaactcac gttaagggat tttggtcatg agattatcaa  5640
aaaggatctt cacctagatc cttttaaatt aaaaatgaag ttttaaatca atctaaagta  5700
tatatgagta aacttggtct gacagttacc aatgcttaat cagtgaggca cctatctcag  5760
cgatctgtct atttcgttca tccatagttg cctgactccc cgtcgtgtag ataactacga  5820
tacgggaggg cttaccatct ggccccagtg ctgcaatgat accgcgagac ccacgctcac  5880
cggctccaga tttatcagca ataaaccagc cagccggaag ggccgagcgc agaagtggtc  5940
ctgcaacttt atccgcctcc atccagtcta ttaattgttg ccgggaagct agagtaagta  6000
gttcgccagt taatagtttg cgcaacgttg ttgccattgc tacaggcatc gtggtgtcac  6060
gctcgtcgtt tggtatggct tcattcagct ccggttccca acgatcaagg cgagttacat  6120
gatcccccat gttgtgcaaa aaagcggtta gctccttcgg tcctccgatc gttgtcagaa  6180
gtaagttggc cgcagtgtta tcactcatgg ttatggcagc actgcataat tctcttactg  6240
tcatgccatc cgtaagatgc ttttctgtga ctggtgagta ctcaaccaag tcattctgag  6300
aatagtgtat gcggcgaccg agttgctctt gcccggcgtc aatacgggat aataccgcgc  6360
cacatagcag aactttaaaa gtgctcatca ttggaaaacg ttcttcgggg cgaaaactct  6420
caaggatctt accgctgttg agatccagtt cgatgtaacc cactcgtgca cccaactgat  6480
cttcagcatc ttttactttc accagcgttt ctgggtgagc aaaaacagga aggcaaaatg  6540
ccgcaaaaaa gggaataagg gcgacacgga aatgttgaat actcatactc ttcctttttc  6600
aatattattg aagcatttat cagggttatt gtctcatgag cggatacata tttgaatgta  6660
tttagaaaaa taaacaaata ggggttccgc gcacatttcc ccgaaaagtg ccacctgacg  6720
tc                                                                 6722
```

```
SEQ ID NO: 29          moltype = DNA  length = 10826
FEATURE                Location/Qualifiers
misc_feature           1..10826
                       note = Description of Artificial Sequence:
                        Syntheticpolynucleotide
source                 1..10826
                       mol_type = other DNA
                       organism = synthetic construct
SEQUENCE: 29
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tggggacttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gtttaaacgg gccctctaga ctcgagcggc cgccactgtg ctggatatct gcagagaacc  960
atgttagctg acgctgtctc acgcctggtc ctgggtaagt ttggtgacct gaccgacaac  1020
ttctcctccc ctcacgctcg cagaaaagtg ctggctggag tcgtcatgac aacaggcaca  1080
gatgttaaag atgccaaggt gataagtgtt tctacaggaa caaaatgtat taatggtgaa  1140
tacatgagtg atcgtggcct tgcattaaat gactgccatg cagaaataat atctcggaga  1200
tccttgctca gatttcttta tacacaactt gagctttact taaataacaa agatgatcaa  1260
aaaagatcca tctttcagaa atcagagcga gggggtttta ggctgaagga gaatgtccag  1320
tttcatctgt acatcagcac ctctccctgt ggagatgcca gaatcttctc accacatgag  1380
ccaatcctgg aagaaccagc agatagacac ccaaatcgta aagcaagagg acagctacgg  1440
accaaaatag agtctggtca ggggacgatt ccagtgcgct ccaatgcgag catccaaacg  1500
tgggacgggg tgctgcaagg ggagcggctg ctcaccatgt cctgcagtga caagattgca  1560
cgctggaacg tggtgggcat ccagggatcc ctgctcagca ttttcgtgga gcccatttac  1620
ttctcgagca tcatcctggg cagcctttac cacggggacc acctttccag ggccatgtac  1680
cagcggatct ccaacataga ggacctgcca cctctctaca ccctcaacaa gcctttgctc  1740
agtggcatca gcaatgcaga agcacggcag ccagggaagg cccccaactt cagtgtcaac  1800
tggacggtag gcgactccgc tattgaggtc atcaacgcca cgactgggaa ggatgagctg  1860
ggccgcgcgt cccgcctgtg taagcacgcg ttgtactgtc gctggatgcg tgtgcacggc  1920
aaggttccct cccacttact acgctccaag attaccaagc ccaacgtgta ccatgagtcc  1980
aagctggcgg caaaggagta ccaggccgcc aaggcgcgtc tgttcacagc cttcatcaag  2040
gcggggctgg gggcctgggt ggagaagccc accgagcagg accagttctc actcacgccc  2100
agtggaagtg agacaccggg aacctcagag agcgccacgc cagaaagcat ggacaagaag  2160
tacagcatcg gcctggccat cggcaccaac tctgtgggct gggccgtgat caccgacgag  2220
tacaaggtgc ccagcaagaa attcaaggtg ctgggcaaca ccgaccggca cagcatcaag  2280
aagaacctga tcggcgccct gctgttcgac agcggagaaa cagccgaggc cacccggctg  2340
aagagaaccg ccagaagaag atacaccaga cggaagaacc ggatctgcta tctgcaagag  2400
atcttcagca acgagatggc caaggtggac gacagcttct tccacagact ggaagagtcc  2460
ttcctggtgg aagaggataa gaagcacgag cggcacccca tcttcggcaa catcgtggac  2520
gaggtggcct accacgagaa gtaccccacc atctaccacc tgagaaagaa actggtggac  2580
agcaccgaca aggccgacct gcggctgatc tatctggccc tggcccacat gatcaagttc  2640
cggggccact tcctgatcga gggcgacctg aaccccgaca acagcgacgt ggacaagctg  2700
ttcatccagc tggtgcagac ctacaaccag ctgttcgagg aaaaccccat caacgccagc  2760
ggcgtggacg ccaaggccat cctgtctgcc agactgagca agagcagacg gctggaaaat  2820
ctgatcgccc agctgcccgg cgagaagaag aatggcctgt tcggcaacct gattgccctg  2880
agcctgggcc tgacccccaa cttcaagagc aacttcgacc tggccgagga tgccaaactg  2940
cagctgagca aggacaccta cgacgacgac ctggacaacc tgctggccca gatcggcgac  3000
cagtacgccg acctgtttct ggccgccaag aacctgtccg acgccatcct gctgagcgac  3060
atcctgagag tgaacaccga gatcaccaag gccccccctga gcgcctctat gatcaagaga  3120
tacgacgagc accaccagga cctgaccctg ctgaaagctc tcgtgcggca gcagctgcct  3180
gagaagtaca aagagatttt cttcgaccag agcaagaacg gctacgccgg ctacatcgat  3240
ggcggagcca gccaggaaga gttctacaag ttcatcaagc ccatcctgga aaagatggac  3300
ggcaccgagg aactgctcgt gaagctgaac agagaggacc tgctgcggaa gcagcggacc  3360
ttcgacaacg gcagcatccc ccaccagatc cacctgggag agctgcacgc cattctgcgg  3420
cggcaggaag atttttaccc attcctgaag gacaaccggg aaaagatcga gaagatcctg  3480
accttccgca tcccctacta cgtgggccct ctggccaggg gaaacagcag attcgcctgg  3540
atgaccagaa agagcgagga aaccatcacc ccctggaact tcgaggaagt ggtggacaag  3600
ggcgccagcg cccagagctt catcgagcgg atgaccaact tcgataagaa cctgcccaac  3660
gagaaggtgc tgcccaagca cagcctgctg tacgagtact tcaccgtgta caacgagctg  3720
accaaagtga aatacgtgac cgagggaatg agaaagcccg ccttcctgag cggcgagcag  3780
aaaaaagcca tcgtggacct gctgttcaag accaaccgga aagtgaccgt gaagcagctg  3840
aaagaggact acttcaagaa aatcgagtgc ttcgactccg tggaaatctc cggcgtggaa  3900
gatcggttca acgcctccct gggcacatac cacgatctgc tgaaaattat caaggacaag  3960
gacttcctgg acaatgagga aaacgaggac attctggaag atatcgtgct gaccctgaca  4020
ctgtttgagg acagagagat gatcgaggaa cggctgaaaa cctatgccca cctgttcgac  4080
gacaaagtga tgaagcagct gaagcggcgg agatacaccg gctggggcag gctgagccgg  4140
aagctgatca acggcatccg ggacaagcag tccggcaaga caatcctgga tttcctgaag  4200
```

-continued

```
tccgacggct tcgccaacag aaacttcatg cagctgatcc acgacgacag cctgaccttt  4260
aaagaggaca tccagaaagc ccaggtgtcc ggccagggcg atagcctgca cgagcacatt  4320
gccaatctgg ccggcagccc cgccattaag aagggcatcc tgcagacagt gaaggtggtg  4380
gacgagctcg tgaaagtgat gggccggcac aagcccgaga acatcgtgat cgaaatggcc  4440
agagagaacc agaccaccca gaagggacag aagaacagcc gcgagagaat gaagcggatc  4500
gaagagggca tcaaagagct gggcagccag atcctgaaag aacaccccgt ggaaaacacc  4560
cagctgcaga acgagaagct gtacctgtac tacctgcaga atgggcggga tatgtacgtg  4620
gaccaggaac tggacatcaa ccggctgtcc gactacgatg tggacgctat cgtgcctcag  4680
agctttctga aggacgactc catcgataac aaagtgctga ctcggagcga caagaaccgg  4740
ggcaagagcg acaacgtgcc ctccgaagag gtcgtgaaga agatgaagaa ctactggcgc  4800
cagctgctga atgccaagct gattacccag aggaagttcg acaatctgac caaggccgag  4860
agaggcggcc tgagcgaact ggataaggcc ggcttcatca agagacagct ggtggaaacc  4920
cggcagatca caaagcacgt ggcacagatc ctggactccc ggatgaacac taagtacgac  4980
gagaacgaca aactgatccg ggaagtgaaa gtgatcaccc tgaagtccaa gctggtgtcc  5040
gatttccgga aggatttcca gttttacaaa gtgcgcgaga tcaacaacta ccaccacgcc  5100
cacgacgcct acctgaacgc cgtcgtggga accgccctga tcaaaaagta ccctaagctg  5160
gaaagcgagt tcgtgtacgg cgactacaag gtgtacgacg tgcggaagat gatcgccaag  5220
agcgagcagg aaatcggcaa ggctaccgcc aagtacttct tctacagcaa catcatgaac  5280
tttttcaaga ccgagattac cctggccaac ggcgagatcc ggaagcggcc tctgatcgag  5340
acaaacggcg aaacaggcga gatcgtgtgg gataagggcc gggactttgc caccgtgcgg  5400
aaagtgctgt ctatgcccca agtgaatatc gtgaaaaaga ccgaggtgca gacaggcggc  5460
ttcagcaaag agtctatcct gcccaagagg aacagcgaca agctgatcgc cagaaagaag  5520
gactgggacc ctaagaagta cggcggcttc gacagcccca ccgtggccta ttctgtgctg  5580
gtggtggcca aagtggaaaa gggcaagtcc aagaaactga agagtgtgaa agagctgctg  5640
gggatcacca tcatggaaag aagcagcttc gagaagaatc ccatcgactt tctggaagcc  5700
aagggctaca aagaagtgaa aaaggacctg atcatcaagc tgcctaagta ctccctgttc  5760
gagctggaaa acggccggaa gagaatgctg gcctctgccg gcgaactgca gaagggaaac  5820
gaactggccc tgccctccaa atatgtgaac ttcctgtacc tggccagcca ctatgagaag  5880
ctgaagggct cccccgagga taatgagcag aaacagctgt ttgtggaaca gcacaaacac  5940
tacctggacg agatcatcga gcagatcagc gagttctcca agagagtgat cctggccgac  6000
gctaatctgg acaaggtgct gagcgcctac aacaagcaca gagacaagcc tatcagagag  6060
caggccgaga atatcatcca cctgtttacc ctgaccaatc tgggagcccc tgccgccttc  6120
aagtactttg acaccaccat cgaccggaag aggtacacca gcaccaaaga ggtgctggac  6180
gccaccctga tccaccagag catcaccggc ctgtacgaga cacggatcga cctgtctcag  6240
ctgggaggcg acgcctatcc ctatgacgtg cccgattatg ccagcctggg cagcggctcc  6300
cccaagaaaa aacgcaaggt ggaagatcct aagaaaaagc ggaaagtgga cgtgtaacca  6360
ccacactgga ctagtggatc cgagctcggt accaagctta agtttaaacc gctgatcagc  6420
ctcgactgtg ccttctagtt gccagccatc tgttgtttgc ccctcccccg tgccttcctt  6480
gaccctggaa ggtgccactc ccactgtcct ttcctaataa aatgaggaaa ttgcatcgca  6540
ttgtctgagt aggtgtcatt ctattctggg gggtggggtg gggcaggaca gcaaggggga  6600
ggattgggaa gacaatagca ggcatgctgg ggatgcggtg ggctctatgg cttctgaggc  6660
ggaaagaacc agctggggct ctagggggta tccccacgcg ccctgtagcg gcgcattaag  6720
cgcggcgggt gtggtggtta cgcgcagcgt gaccgctaca cttgccagcg ccctagcgcc  6780
cgctcctttc gctttcttcc cttcctttct cgccacgttc gccggctttc cccgtcaagc  6840
tctaaatcgg gggctccctt tagggttccg atttagtgct ttacggcacc tcgaccccaa  6900
aaaacttgat tagggtgatg gttcacgtag tgggccatcg ccctgataga cggtttttcg  6960
ccctttgacg ttggagtcca cgttctttaa tagtggactc ttgttccaaa ctggaacaac  7020
actcaaccct atctcggtct attcttttga tttataaggg attttgccga tttcggccta  7080
ttggttaaaa aatgagctga tttaacaaaa atttaacgcg aattaattct gtggaatgtg  7140
tgtcagttag ggtgtggaaa gtccccaggc tccccagcag gcagaagtat gcaaagcatg  7200
catctcaatt agtcagcaac caggtgtgga aagtccccag gctccccagc aggcagaagt  7260
atgcaaagca tgcatctcaa ttagtcagca accatagtcc cgcccctaac tccgcccatc  7320
ccgcccctaa ctccgcccag ttccgcccat tctccgcccc atggctgact aattttttt  7380
atttatgcag aggccgaggc cgcctctgcc tctgagctat tccagaagta gtgaggaggc  7440
ttttttggag gcctaggctt ttgcaaaaag ctcccgggag cttgtatatc cattttcgga  7500
tctgatcaag agacaggatg aggatcgttt cgcatgattg aacaagatgg attgcacgca  7560
ggttctccgg ccgcttgggt ggagaggcta ttcggctatg actgggcaca acagacaatc  7620
ggctgctctg atgccgccgt gttccggctg tcagcgcagg ggcgcccggt tctttttgtc  7680
aagaccgacc tgtccggtgc cctgaatgaa ctgcaggacg aggcagcgcg gctatcgtgg  7740
ctggccacga cgggcgttcc ttgcgcagct gtgctcgacg ttgtcactga agcgggaagg  7800
gactggctgc tattgggcga agtgccgggg caggatctcc tgtcatctca ccttgctcct  7860
gccgagaaag tatccatcat ggctgatgca atgcggcggc tgcatacgct tgatccggct  7920
acctgcccat tcgaccacca agcgaaacat cgcatcgagc gagcacgtac tcggatggaa  7980
gccggtcttg tcgatcagga tgatctggac gaagagcatc aggggctcgc gccagccgaa  8040
ctgttcgcca ggctcaaggc gcgcatgccc gacggcgagg atctcgtcgt gacccatggc  8100
gatgcctgct tgccgaatat catggtggaa aatggccgct tttctggatt catcgactgt  8160
ggccggctgg gtgtggcgga ccgctatcag gacatagcgt tggctacccg tgatattgct  8220
gaagagcttg gcggcgaatg ggctgaccgc ttcctcgtgc tttacggtat cgccgctccc  8280
gattcgcagc gcatcgcctt ctatcgcctt cttgacgagt tcttctgagc gggactctgg  8340
ggttcgaaat gaccgaccaa gcgacgccca acctgccatc acgagatttc gattccaccg  8400
ccgccttcta tgaaaggttg ggcttcggaa tcgttttccg ggacgccggc tggatgatcc  8460
tccagcgcgg ggatctcatg ctggagttct tcgcccaccc caacttgttt attgcagctt  8520
ataatggtta caaataaagc aatagcatca caaatttcac aaataaagca tttttttcac  8580
tgcattctag ttgtggtttg tccaaactca tcaatgtatc ttatcatgtc tgtataccgt  8640
cgacctctag ctagagcttg gcgtaatcat ggtcatagct gtttcctgtg tgaaattgtt  8700
atccgctcac aattccacac aacatacgag ccggaagcat aaagtgtaaa gcctggggtg  8760
cctaatgagt gagctaactc acattaattg cgttgcgctc actgcccgct ttccagtcgg  8820
gaaacctgtc gtgccagctg cattaatgaa tcggccaacg cgcggggaga ggcggtttgc  8880
gtattgggcg ctcttccgct tcctcgctca ctgactcgct gcgctcggtc gttcggctgc  8940
```

```
ggcgagcggt atcagctcac tcaaaggcgg taatacggtt atccacagaa tcaggggata  9000
acgcaggaaa gaacatgtga gcaaaaggcc agcaaaaggc caggaaccgt aaaaaggccg  9060
cgttgctggc gtttttccat aggctccgcc cccctgacga gcatcacaaa aatcgacgct  9120
caagtcagag gtggcgaaac ccgacaggac tataaagata ccaggcgttt ccccctggaa  9180
gctccctcgt gcgctctcct gttccgaccc tgccgcttac cggatacctg tccgcctttc  9240
tcccttcggg aagcgtggcg ctttctcata gctcacgctg taggtatctc agttcggtgt  9300
aggtcgttcg ctccaagctg ggctgtgtgc acgaaccccc cgttcagccc gaccgctgcg  9360
ccttatccgg taactatcgt cttgagtcca acccggtaag acacgactta tcgccactgg  9420
cagcagccac tggtaacagg attagcagag cgaggtatgt aggcggtgct acagagttct  9480
tgaagtggtg gcctaactac ggctacacta gaagaacagt atttggtatc tgcgctctgc  9540
tgaagccagt taccttcgga aaaagagttg gtagctcttg atccggcaaa caaaccaccg  9600
ctggtagcgg tttttttgtt tgcaagcagc agattacgcg cagaaaaaaa ggatctcaag  9660
aagatccttt gatcttttct acggggtctg acgctcagtg gaacgaaaac tcacgttaag  9720
ggattttggt catgagatta tcaaaaagga tcttcaccta gatcctttta aattaaaaat  9780
gaagttttaa atcaatctaa agtatatatg agtaaacttg gtctgacagt taccaatgct  9840
taatcagtga ggcacctatc tcagcgatct gtctatttcg ttcatccata gttgcctgac  9900
tccccgtcgt gtagataact acgatacggg agggcttacc atctggcccc agtgctgcaa  9960
tgataccgcg agacccacgc tcaccggctc cagatttatc agcaataaac cagccagccg  10020
gaagggccga gcgcagaagt ggtcctgcaa ctttatccgc ctccatccag tctattaatt  10080
gttgccggga agctagagta agtagttcgc cagttaatag tttgcgcaac gttgttgcca  10140
ttgctacagg catcgtggtg tcacgctcgt cgtttggtat ggcttcattc agctccggtt  10200
cccaacgatc aaggcgagtt acatgatccc ccatgttgtg caaaaaagcg gttagctcct  10260
tcggtcctcc gatcgttgtc agaagtaagt tggccgcagt gttatcactc atggttatgg  10320
cagcactgca taattctctt actgtcatgc catccgtaag atgcttttct gtgactggtg  10380
agtactcaac caagtcattc tgagaatagt gtatgcggcg accgagttgc tcttgcccgg  10440
cgtcaatacg ggataatacc gcgccacata gcagaacttt aaaagtgctc atcattggaa  10500
aacgttcttc ggggcgaaaa ctctcaagga tcttaccgct gttgagatcc agttcgatgt  10560
aacccactcg tgcacccaac tgatcttcag catcttttac tttcaccagc gtttctgggt  10620
gagcaaaaac aggaaggcaa aatgccgcaa aaaagggaat aagggcgaca cggaaatgtt  10680
gaatactcat actcttcctt tttcaatatt attgaagcat ttatcagggt tattgtctca  10740
tgagcggata catatttgaa tgtatttaga aaaataaaca aataggggtt ccgcgcacat  10800
ttccccgaaa agtgccacct gacgtc                                      10826

SEQ ID NO: 30          moltype = DNA  length = 6722
FEATURE                Location/Qualifiers
misc_feature           1..6722
                       note = Description of Artificial Sequence:
                        Syntheticpolynucleotide
source                 1..6722
                       mol_type = other DNA
                       organism = synthetic construct
SEQUENCE: 30
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gtttaaacgg gccctctaga ctcgagcggc cgccactgtg ctggatatct gcagagaacc  960
atgttagctg acgctgtctc acgcctgttc ctgggtaagt ttggtgacct gaccgacaac  1020
ttctcctccc ctcacgctcg cagaaaagtg ctggctggag tcgtcatgac aacaggcaca  1080
gatgttaaag atgccaaggt gataagtgtt tctacaggaa caaaatgtat taatggtgaa  1140
tacatgagtg atcgtggcct tgcattaaat gactgccatg cagaaataat atctcggaga  1200
tccttgctca gatttcttta tacacaactt gagctttact taaataacaa agatgatcaa  1260
aaaagatcca tctttcagaa atcagagcga gggggggttta ggctgaagga gaatgtccag  1320
tttcatctgt acatcagcac ctctccctgt ggagatgcca gaatcttctc accacatgag  1380
ccaatcctgg aagaaccagc agatagacac ccaaatcgta aagcaagagg acagctacgg  1440
accaaaatag agtctggtca ggggacgatt ccagtgcgct ccaatgcgag catccaaacg  1500
tgggacgggg tgctgcaagg ggagcggctg ctcaccatgt cctgcagtga caagattgca  1560
cgctggaacg tggtgggcat ccagggatcc ctgctcagca ttttcgtgga gcccatttac  1620
ttctcgagca tcatcctggg cagcctttac cacggggacc acctttccag ggccatgtac  1680
cagcggatct ccaacataga ggacctgcca cctctctaca ccctcaacaa gcctttgctc  1740
agtggcatca gcaatgcaga agcacggcag ccagggaagg cccccaactt cagtgtcaac  1800
tggacggtag gcgactccgc tattgaggtc atcaacgcca cgactgggaa ggatgagctg  1860
ggccgcgcgt cccgcctgtg taagcacgcg ttgtactgtc gctggatgcg tgtgcacggc  1920
aaggttccct cccacttact acgctccaag attaccaagc ccaacgtgta ccatgagtcc  1980
aagctggcgg caaaggagta ccaggccgcc aaggcgcgtc tgttcacagc cttcatcaag  2040
gcggggctgg gggcctgggt ggagaagccc accgagcagg accagttctc actcacgccc  2100
agtggaagtg agacaccggg aacctcagag agcgccacgc cagaaagcgc ctatccctat  2160
gacgtgcccg attatgccag cctgggcagc ggctccccca agaaaaaacg caaggtggaa  2220
```

```
gatcctaaga aaaagcggaa agtggacgtg taaccaccac actggactag tggatccgag  2280
ctcggtacca agcttaagtt taaaccgctg atcagcctcg actgtgcctt ctagttgcca  2340
gccatctgtt gtttgcccct cccccgtgcc ttccttgacc ctggaaggtg ccactcccac  2400
tgtcctttcc taataaaatg aggaaattgc atcgcattgt ctgagtaggt gtcattctat  2460
tctggggggt ggggtggggc aggacagcaa gggggaggat tgggaagaca atagcaggca  2520
tgctggggat gcggtgggct ctatggcttc tgaggcggaa agaaccagct ggggctctag  2580
ggggtatccc cacgcgccct gtagcggcgc attaagcgcg gcgggtgtgg tggttacgcg  2640
cagcgtgacc gctacacttg ccagcgccct agcgcccgct cctttcgctt tcttcccttc  2700
ctttctcgcc acgttcgccg gctttccccg tcaagctcta aatcgggggc tccctttagg  2760
gttccgattt agtgctttac ggcacctcga ccccaaaaaa cttgattagg gtgatggttc  2820
acgtagtggg ccatcgccct gatagacggt ttttcgccct ttgacgttgg agtccacgtt  2880
ctttaatagt ggactcttgt tccaaactgg aacaacactc aaccctatct cggtctattc  2940
ttttgattta taagggattt tgccgatttc ggcctattgg ttaaaaaatg agctgattta  3000
acaaaaattt aacgcgaatt aattctgtgg aatgtgtgtc agttagggtg tggaaagtcc  3060
ccaggctccc cagcaggcag aagtatgcaa agcatgcatc tcaattagtc agcaaccagg  3120
tgtggaaagt ccccaggctc cccagcaggc agaagtatgc aaagcatgca tctcaattag  3180
tcagcaacca tagtcccgcc cctaactccg cccatcccgc ccctaactcc gcccagttcc  3240
gcccattctc cgccccatgg ctgactaatt ttttttattt atgcagaggc cgaggccgcc  3300
tctgcctctg agctattcca gaagtagtga ggaggctttt ttggaggcct aggcttttgc  3360
aaaaagctcc cgggagcttg tatatccatt ttcggatctg atcaagagac aggatgagga  3420
tcgtttcgca tgattgaaca agatggattg cacgcaggtt ctccggccgc ttgggtggag  3480
aggctattcg gctatgactg ggcacaacag acaatcggct gctctgatgc cgccgtgttc  3540
cggctgtcag cgcaggggcg cccggttctt tttgtcaaga ccgacctgtc cggtgccctg  3600
aatgaactgc aggacgaggc agcgcggcta tcgtggctgg ccacgacggg cgttccttgc  3660
gcagctgtgc tcgacgttgt cactgaagcg ggaagggact ggctgctatt gggcgaagtg  3720
ccggggcagg atctcctgtc atctcacctt gctcctgccg agaaagtatc catcatggct  3780
gatgcaatgc ggcggctgca tacgcttgat ccggctacct gcccattcga ccaccaagcg  3840
aaacatcgca tcgagcgagc acgtactcgg atggaagccg gtcttgtcga tcaggatgat  3900
ctggacgaag agcatcaggg gctcgcgcca gccgaactgt tcgccaggct caaggcgcgc  3960
atgcccgacg gcgaggatct cgtcgtgacc catggcgatg cctgcttgcc gaatatcatg  4020
gtggaaaatg gccgcttttc tggattcatc gactgtggcc ggctgggtgt ggcggaccgc  4080
tatcaggaca tagcgttggc tacccgtgat attgctgaag agcttggcgg cgaatgggct  4140
gaccgcttcc tcgtgcttta cggtatcgcc gctcccgatt cgcagcgcat cgccttctat  4200
cgccttcttg acgagttctt ctgagcggga ctctggggtt cgaaatgacc gaccaagcga  4260
cgcccaacct gccatcacga gatttcgatt ccaccgccgc cttctatgaa aggttgggct  4320
tcggaatcgt tttccgggac gccggctgga tgatcctcca gcgcggggat ctcatgctgg  4380
agttcttcgc ccaccccaac ttgtttattg cagcttataa tggttacaaa taaagcaata  4440
gcatcacaaa tttcacaaat aaagcatttt tttcactgca ttctagttgt ggtttgtcca  4500
aactcatcaa tgtatcttat catgtctgta taccgtcgac ctctagctag agcttggcgt  4560
aatcatggtc atagctgttt cctgtgtgaa attgttatcc gctcacaatt ccacacaaca  4620
tacgagccgg aagcataaag tgtaaagcct ggggtgccta atgagtgagc taactcacat  4680
taattgcgtt gcgctcactg cccgctttcc agtcgggaaa cctgtcgtgc cagctgcatt  4740
aatgaatcgg ccaacgcgcg gggagaggcg gtttgcgtat tgggcgctct tccgcttcct  4800
cgctcactga ctcgctgcgc tcggtcgttc ggctgcggcg agcggtatca gctcactcaa  4860
aggcggtaat acggttatcc acagaatcag gggataacgc aggaaagaac atgtgagcaa  4920
aaggccagca aaaggccagg aaccgtaaaa aggccgcgtt gctggcgttt ttccataggc  4980
tccgcccccc tgacgagcat cacaaaaatc gacgctcaag tcagaggtgg cgaaacccga  5040
caggactata aagataccag gcgtttcccc ctggaagctc cctcgtgcgc tctcctgttc  5100
cgaccctgcc gcttaccgga tacctgtccg cctttctccc ttcgggaagc gtggcgcttt  5160
ctcatagctc acgctgtagg tatctcagtt cggtgtaggt cgttcgctcc aagctgggct  5220
gtgtgcacga accccccgtt cagcccgacc gctgcgcctt atccggtaac tatcgtcttg  5280
agtccaaccc ggtaagacac gacttatcgc cactggcagc agccactggt aacaggatta  5340
gcagagcgag gtatgtaggc ggtgctacag agttcttgaa gtggtggcct aactacggct  5400
acactagaag aacagtattt ggtatctgcg ctctgctgaa gccagttacc ttcggaaaaa  5460
gagttggtag ctcttgatcc ggcaaacaaa ccaccgctgg tagcggtttt tttgtttgca  5520
agcagcagat tacgcgcaga aaaaaaggat ctcaagaaga tcctttgatc ttttctacgg  5580
ggtctgacgc tcagtggaac gaaaactcac gttaagggat tttggtcatg agattatcaa  5640
aaaggatctt cacctagatc cttttaaatt aaaaatgaag ttttaaatca atctaaagta  5700
tatatgagta aacttggtct gacagttacc aatgcttaat cagtgaggca cctatctcag  5760
cgatctgtct atttcgttca tccatagttg cctgactccc cgtcgtgtag ataactacga  5820
tacgggaggg cttaccatct ggccccagtg ctgcaatgat accgcgagac ccacgctcac  5880
cggctccaga tttatcagca ataaaccagc cagccggaag ggccgagcgc agaagtggtc  5940
ctgcaacttt atccgcctcc atccagtcta ttaattgttg ccgggaagct agagtaagta  6000
gttcgccagt taatagtttg cgcaacgttg ttgccattgc tacaggcatc gtggtgtcac  6060
gctcgtcgtt tggtatggct tcattcagct ccggttccca acgatcaagg cgagttacat  6120
gatcccccat gttgtgcaaa aaagcggtta gctccttcgg tcctccgatc gttgtcagaa  6180
gtaagttggc cgcagtgtta tcactcatgg ttatggcagc actgcataat tctcttactg  6240
tcatgccatc cgtaagatgc ttttctgtga ctggtgagta ctcaaccaag tcattctgag  6300
aatagtgtat gcggcgaccg agttgctctt gcccggcgtc aatacgggat aataccgcgc  6360
cacatagcag aactttaaaa gtgctcatca ttggaaaacg ttcttcgggg cgaaaactct  6420
caaggatctt accgctgttg agatccagtt cgatgtaacc cactcgtgca cccaactgat  6480
cttcagcatc ttttactttc accagcgttt ctgggtgagc aaaaacagga aggcaaaatg  6540
ccgcaaaaaa gggaataagg gcgacacgga aatgttgaat actcatactc ttcctttttc  6600
aatattattg aagcatttat cagggttatt gtctcatgag cggatacata tttgaatgta  6660
tttagaaaaa taaacaaata ggggttccgc gcacatttcc ccgaaaagtg ccacctgacg  6720
tc                                                                 6722

SEQ ID NO: 31          moltype = DNA  length = 4951
FEATURE                Location/Qualifiers
```

```
misc_feature            1..4951
                        note = Description of Artificial Sequence:
                         Syntheticpolynucleotide
source                  1..4951
                        mol_type = other DNA
                        organism = synthetic construct
SEQUENCE: 31
tttttttcct gcagcccggg aaggatctgc gatcgctccg gtgcccgtca gtgggcagag  60
cgcacatcgc ccacagtccc cgagaagttg gggggagggg tcggcaattg aacgggtgcc  120
tagagaaggt ggcgcggggt aaactgggaa agtgatgtcg tgtactggct ccgccttttt  180
cccgagggtg ggggagaacc gtatataagt gcagtagtcg ccgtgaacgt tctttttcgc  240
aacgggtttg ccgccagaac acagctgaag cttcgagggg ctcgcatctc tccttcacgc  300
gcccgccgcc ctacctgagg ccgccatcca cgccggttga gtcgcgttct gccgcctccc  360
gcctgtggtg cctcctgaac tgcgtccgcc gtctaggtaa gtttaaagct caggtcgaga  420
ccgggccttt gtccggcgct cccttggagc ctacctagac tcagccggct ctccacgctt  480
tgcctgaccc tgcttgctca actctacgtc tttgtttcgt tttctgttct gcgccgttac  540
agatccaagc tgtgaccggc gcctacgcta gatggtgagc aagggcgagg aggataacat  600
ggccatcatc aaggagttca tgcgcttcaa ggtgcacatg gagggctccg tgaacggcca  660
cgagttcgag atcgagggcg agggcgaggg ccgcccctac gagggcaccc agaccgccaa  720
gctgaaggtg accaagggtg gcccccctgcc cttcgcctgg gacatcctgt cccctcagtt  780
catgtacggc tccaaggcct acgtgaagca ccccgccgac atccccgact acttgaagct  840
gtccttcccc gagggcttca agtgggagcg cgtgatgaac ttcgaggacg gcggcgtggt  900
gaccgtgacc caggactcct ccctgcagga cggcgagttc atctacaagg tgaagctgcg  960
cggcaccaac ttcccctccg acggccccgt aatgcagaag aagaccatgg gctgggaggc  1020
ctcctccgag cggatgtacc ccgaggacgg cgccctgaag ggcgagatca agcagaggct  1080
gaagctgaag gacggcggcc actacgacgc tgaggtcaag accacctaca aggccaagaa  1140
gcccgtgcag ctgcccggcg cctacaacgt caacatcaag ttggacatca cctcccacaa  1200
cgaggactac accatcgtgg aacagtacga acgcgccgag ggccgccact ccaccggcgg  1260
catggacgag ctgtacaagt aatccgagct cggtaccaag cttaagttta aaccgctgat  1320
cagcctcgac tgtgccttct agttgccagc catctgttgt ttgcccctcc cccgtgcctt  1380
ccttgaccct ggaaggtgcc actcccactg tcctttccta ataaaatgag gaaattgcat  1440
cgcattgtct gagtaggtgt cattctattc tggggggtgg ggtggggcag gacagcaagg  1500
gggaggattg ggaagacaat agcaggcatg ctggggatgc ggtgggctct atggggggatc  1560
cactagttct agagcggccg ccaccgcggt ggagctccag cttttgttcc ctttagtgag  1620
ggttaattgc gcgcttggcg taatcatggt catagctgtt tcctgtgtga aattgttatc  1680
cgctcacaat tccacacaac atacgagccg gaagcataaa gtgtaaagcc tggggtgcct  1740
aatgagtgag ctaactcaca ttaattgcgt tgcgctcact gcccgctttc cagtcgggaa  1800
acctgtcgtg ccagctgcat taatgaatcg gccaacgcgc ggggagaggc ggtttgcgta  1860
ttgggcgctc ttccgcttcc tcgctcactg actcgctgcg ctcggtcgtt cggctgcggc  1920
gagcggtatc agctcactca aaggcggtaa tacggttatc cacagaatca ggggataacg  1980
caggaaagaa catgtgagca aaaggccagc aaaaggccag gaaccgtaaa aaggccgcgt  2040
tgctggcgtt tttccatagg ctccgccccc ctgacgagca tcacaaaaat cgacgctcaa  2100
gtcagaggtg gcgaaacccg acaggactat aaagatacca ggcgtttccc cctggaagct  2160
ccctcgtgcg ctctcctgtt ccgaccctgc cgcttaccgg atacctgtcc gcctttctcc  2220
cttcgggaag cgtggcgctt tctcatagct cacgctgtag gtatctcagt tcggtgtagg  2280
tcgttcgctc caagctgggc tgtgtgcacg aacccccgt tcagcccgac cgctgcgcct  2340
tatccggtaa ctatcgtctt gagtccaacc cggtaagaca cgacttatcg ccactggcag  2400
cagccactgg taacaggatt agcagagcga ggtatgtagg cggtgctaca gagttcttga  2460
agtggtggcc taactacggc tacactagaa ggacagtatt tggtatctgc gctctgctga  2520
agccagttac cttcggaaaa agagttggta gctcttgatc cggcaaacaa accaccgctg  2580
gtagcggtgg tttttttgtt tgcaagcagc agattacgcg cagaaaaaaa ggatctcaag  2640
aagatccttt gatcttttct acggggtctg acgctcagtg gaacgaaaac tcacgttaag  2700
ggattttggt catgagatta tcaaaaagga tcttcaccta gatcctttta aattaaaaat  2760
gaagttttaa atcaatctaa agtatatatg agtaaacttg gtctgacagt taccaatgct  2820
taatcagtga ggcacctatc tcagcgatct gtctatttcg ttcatccata gttgcctgac  2880
tccccgtcgt gtagataact acgatacggg agggcttacc atctggcccc agtgctgcaa  2940
tgataccgcg agacccacgc tcaccggctc cagatttatc agcaataaac cagccagccg  3000
gaagggccga gcgcagaagt ggtcctgcaa ctttatccgc ctccatccag tctattaatt  3060
gttgccggga agctagagta agtagttcgc cagttaatag tttgcgcaac gttgttgcca  3120
ttgctacagg catcgtggtg tcacgctcgt cgtttggtat ggcttcattc agctccggtt  3180
cccaacgatc aaggcgagtt acatgatccc ccatgttgtg caaaaaagcg gttagctcct  3240
tcggtcctcc gatcgttgtc agaagtaagt tggccgcagt gttatcactc atggttatgg  3300
cagcactgca taattctctt actgtcatgc catccgtaag atgcttttct gtgactggtg  3360
agtactcaac caagtcattc tgagaatagt gtatgcggcg accgagttgc tcttgcccgg  3420
cgtcaatacg ggataatacc gcgccacata gcagaacttt aaaagtgctc atcattggaa  3480
aacgttcttc ggggcgaaaa ctctcaagga tcttaccgct gttgagatcc agttcgatgt  3540
aacccactcg tgcacccaac tgatcttcag catcttttac tttcaccagc gtttctgggt  3600
gagcaaaaac aggaaggcaa aatgccgcaa aaaagggaat aagggcgaca cggaaatgtt  3660
gaatactcat actcttcctt tttcaatatt attgaagcat ttatcagggt tattgtctca  3720
tgagcggata catatttgaa tgtatttaga aaaataaaca aataggggtt ccgcgcacat  3780
ttccccgaaa agtgccacct aaattgtaag cgttaatatt ttgttaaaat tcgcgttaaa  3840
tttttgttaa atcagctcat tttttaacca ataggccgaa atcggcaaaa tcccttataa  3900
atcaaaagaa tagaccgaga tagggttgag tgttgttcca gtttggaaca agagtccact  3960
attaaagaac gtggactcca acgtcaaagg gcgaaaaacc gtctatcagg gcgatggccc  4020
actacgtgaa ccatcaccct aatcaagttt tttggggtcg aggtgccgta aagcactaaa  4080
tcggaaccct aaagggagcc cccgatttag agcttgacgg ggaaagccgg cgaacgtggc  4140
gagaaaggaa gggaagaaag cgaaaggagc gggcgctagg gcgctggcaa gtgtagcggt  4200
cacgctgcgc gtaaccacca cacccgccgc gcttaatgcg ccgctacagg gcgcgtccca  4260
ttcgccattc aggctgcgca actgttggga agggcgatcg gtgcgggcct cttcgctatt  4320
```

```
acgccagctg gcgaaagggg gatgtgctgc aaggcgatta agttgggtaa cgccagggtt  4380
ttcccagtca cgacgttgta aaacgacggc cagtgagcgc gcgtaatacg actcactata  4440
gggcgaattg ggtaccgggc ccccctcga ggtcgacggt atcgataagc ttgatatcgt  4500
gtacaaaaaa gcaggcttta aaggaaccaa ttcagtcgac tggatccggt accaaggtcg  4560
ggcaggaaga gggcctattt cccatgattc cttcatattt gcatatacga tacaaggctg  4620
ttagagagat aattagaatt aatttgactg taaacacaaa gatattagta caaaatacgt  4680
gacgtagaaa gtaataattt cttgggtagt ttgcagtttt aaaattatgt tttaaaatgg  4740
actatcatat gcttaccgta acttgaaagt atttcgattt cttggcttta tatatcttgt  4800
ggaaaggacg aaacaccgaa gtcatgccgt ttcatgtggt ttaagagcta tgctggaaac  4860
agcatagcaa gtttaaataa ggctagtccg ttatcaactt gaaaaagtgg caccgagtcg  4920
gtgcttcatt gtgtcggcca cggaacaggc a                                 4951

SEQ ID NO: 32           moltype = DNA  length = 4930
FEATURE                 Location/Qualifiers
misc_feature            1..4930
                        note = Description of Artificial Sequence:
                         Syntheticpolynucleotide
source                  1..4930
                        mol_type = other DNA
                        organism = synthetic construct
SEQUENCE: 32
ctaaattgta agcgttaata ttttgttaaa attcgcgtta aatttttgtt aaatcagctc  60
atttttaac caataggccg aaatcggcaa aatcccttat aaatcaaaag aatagaccga  120
gatagggttg agtgttgttc cagtttggaa caagagtcca ctattaaaga acgtggactc  180
caacgtcaaa gggcgaaaaa ccgtctatca gggcgatggc ccactacgtg aaccatcacc  240
ctaatcaagt tttttggggt cgaggtgccg taaagcacta aatcggaacc ctaaagggag  300
cccccgattt agagcttgac ggggaaagcc ggcgaacgtg gcgagaaagg aagggaagaa  360
agcgaaagga gcgggcgcta gggcgctggc aagtgtagcg gtcacgctgc gcgtaaccac  420
cacacccgcc gcgcttaatg cgccgctaca gggcgcgtcc cattcgccat tcaggctgcg  480
caactgttgg gaagggcgat cggtgcgggc ctcttcgcta ttacgccagc tggcgaaagg  540
gggatgtgct gcaaggcgat taagttgggt aacgccaggg ttttcccagt cacgacgttg  600
taaaacgacg gccagtgagc gcgcgtaata cgactcacta tagggcgaat tgggtaccgg  660
gcccccctc gaggtcgacg gtatcgataa gcttgatatc gtgtacaaaa aagcaggctt  720
taaaggaacc aattcagtcg actggatccg gtaccaaggt cgggcaggaa gagggcctat  780
ttcccatgat tccttcatat ttgcatatac gatacaaggc tgttagagag ataattagaa  840
ttaatttgac tgtaaacaca aagatattag tacaaaatac gtgacgtaga aagtaataat  900
ttcttgggta gtttgcagtt ttaaaattat gttttaaaat ggactatcat atgcttaccg  960
taacttgaaa gtatttcgat ttcttggctt tatatatctt gtggaaagga cgaaacaccg  1020
tttaagagct atgctggaaa cagcatagca agtttaaata aggctagtcc gttatcaact  1080
tgaaaaagtg gcaccgagtc ggtgcttcat tgtgtcggcc acggaacagg cattttttc  1140
ctgcagcccg ggaaggatct gcgatcgctc cggtgcccgt cagtgggcag agcgcacatc  1200
gcccacagtc cccgagaagt tggggggagg ggtcggcaat tgaacgggtg cctagagaag  1260
gtggcgcggg gtaaactggg aaagtgatgt cgtgtactgg ctccgccttt ttcccgaggg  1320
tgggggagaa ccgtatataa gtgcagtagt cgccgtgaac gttcttttc gcaacgggtt  1380
tgccgccaga acacagctga agcttcgagg ggctcgcatc tctccttcac gcgcccgccg  1440
ccctacctga ggccgccatc cacgccggtt gagtcgcgtt ctgccgcctc ccgcctgtgg  1500
tgcctcctga actgcgtccg ccgtctaggt aagtttaaag ctcaggtcga gaccgggcct  1560
ttgtccggcg ctcccttgga gcctacctag actcagccgg ctctccacgc tttgcctgac  1620
cctgcttgct caactctacg tctttgtttc gttttctgtt ctgcgccgtt acagatccaa  1680
gctgtgaccg gcgcctacgc tagatggtga gcaagggcga ggaggataac atggccatca  1740
tcaaggagtt catgcgcttc aaggtgcaca tggagggctc cgtgaacggc cacgagttcg  1800
agatcgaggg cgagggcgag ggccgcccct acgagggcac ccagaccgcc aagctgaagg  1860
tgaccaaggg tggccccctg cccttcgcct gggacatcct gtcccctcag ttcatgtacg  1920
gctccaaggc ctacgtgaag caccccgccg acatccccga ctacttgaag ctgtccttcc  1980
ccgagggctt caagtgggag cgcgtgatga acttcgagga cggcggcgtg gtgaccgtga  2040
cccaggactc ctccctgcag gacggcgagt tcatctacaa ggtgaagctg cgcggcacca  2100
acttccccctc cgacggcccc gtaatgcaga agaagaccat gggctgggag gcctcctccg  2160
agcggatgta ccccgaggac ggcgccctga agggcgagat caagcagagg ctgaagctga  2220
aggacggcgg ccactacgac gctgaggtca agaccaccta caaggccaag aagcccgtgc  2280
agctgcccgg cgcctacaac gtcaacatca agttggacat cacctcccac aacgaggact  2340
acaccatcgt ggaacagtac gaacgcgccg agggccgcca ctccaccggc ggcatggacg  2400
agctgtacaa gtaatccgag ctcggtacca agcttaagtt taaaccgctg atcagcctcg  2460
actgtgcctt ctagttgcca gccatctgtt gtttgcccct cccccgtgcc ttccttgacc  2520
ctggaaggtg ccactcccac tgtcctttcc taataaaatg aggaaattgc atcgcattgt  2580
ctgagtaggt gtcattctat tctggggggt ggggtggggc aggacagcaa gggggaggat  2640
tgggaagaca atagcaggca tgctggggat gcggtgggct ctatggggga tccactagtt  2700
ctagagcggc cgccaccgcg gtggagctcc agcttttgtt ccctttagtg agggttaatt  2760
gcgcgcttgg cgtaatcatg gtcatagctg tttcctgtgt gaaattgtta tccgctcaca  2820
attccacaca acatacgagc cggaagcata aagtgtaaag cctggggtgc ctaatgagtg  2880
agctaactca cattaattgc gttgcgctca ctgcccgctt tccagtcggg aaacctgtcg  2940
tgccagctgc attaatgaat cggccaacgc gcggggagag gcggtttgcg tattgggcgc  3000
tcttccgctt cctcgctcac tgactcgctg cgctcggtcg ttcggctgcg gcgagcggta  3060
tcagctcact caaaggcggt aatacggtta tccacagaat caggggataa cgcaggaaag  3120
aacatgtgag caaaaggcca gcaaaaggcc aggaaccgta aaaaggccgc gttgctggcg  3180
tttttccata ggctccgccc ccctgacgag catcacaaaa atcgacgctc aagtcagagg  3240
tggcgaaacc cgacaggact ataaagatac caggcgtttc cccctggaag ctccctcgtg  3300
cgctctcctg ttccgaccct gccgcttacc ggatacctgt ccgcctttct cccttcggga  3360
agcgtggcgc tttctcatag ctcacgctgt aggtatctca gttcggtgta ggtcgttcgc  3420
tccaagctgg gctgtgtgca cgaacccccc gttcagcccg accgctgcgc cttatccggt  3480
```

```
aactatcgtc ttgagtccaa cccggtaaga cacgacttat cgccactggc agcagccact  3540
ggtaacagga ttagcagagc gaggtatgta ggcggtgcta cagagttctt gaagtggtgg  3600
cctaactacg gctacactag aaggacagta tttggtatct gcgctctgct gaagccagtt  3660
accttcggaa aaagagttgg tagctcttga tccggcaaac aaaccaccgc tggtagcggt  3720
ggtttttttg tttgcaagca gcagattacg cgcagaaaaa aaggatctca agaagatcct  3780
ttgatctttt ctacggggtc tgacgctcag tggaacgaaa actcacgtta agggattttg  3840
gtcatgagat tatcaaaaag gatcttcacc tagatccttt taaattaaaa atgaagtttt  3900
aaatcaatct aaagtatata tgagtaaact tggtctgaca gttaccaatg cttaatcagt  3960
gaggcaccta tctcagcgat ctgtctattt cgttcatcca tagttgcctg actccccgtc  4020
gtgtagataa ctacgatacg ggagggctta ccatctggcc ccagtgctgc aatgataccg  4080
cgagacccac gctcaccggc tccagattta tcagcaataa accagccagc cggaagggcc  4140
gagcgcagaa gtggtcctgc aactttatcc gcctccatcc agtctattaa ttgttgccgg  4200
gaagctagag taagtagttc gccagttaat agtttgcgca acgttgttgc cattgctaca  4260
ggcatcgtgg tgtcacgctc gtcgtttggt atggcttcat tcagctccgg ttcccaacga  4320
tcaaggcgag ttacatgatc ccccatgttg tgcaaaaaag cggttagctc cttcggtcct  4380
ccgatcgttg tcagaagtaa gttggccgca gtgttatcac tcatggttat ggcagcactg  4440
cataattctc ttactgtcat gccatccgta agatgctttt ctgtgactgg tgagtactca  4500
accaagtcat tctgagaata gtgtatgcgg cgaccgagtt gctcttgccc ggcgtcaata  4560
cgggataata ccgcgccaca tagcagaact ttaaaagtgc tcatcattgg aaaacgttct  4620
tcggggcgaa aactctcaag gatcttaccg ctgttgagat ccagttcgat gtaacccact  4680
cgtgcaccca actgatcttc agcatctttt actttcacca gcgtttctgg gtgagcaaaa  4740
acaggaaggc aaaatgccgc aaaaaaggga ataagggcga cacggaaatg ttgaatactc  4800
atactcttcc tttttcaata ttattgaagc atttatcagg gttattgtct catgagcgga  4860
tacatatttg aatgtattta gaaaaataaa caaatagggg ttccgcgcac atttccccga  4920
aaagtgccac                                                         4930

SEQ ID NO: 33           moltype = DNA  length = 4930
FEATURE                 Location/Qualifiers
misc_feature            1..4930
                        note = Description of Artificial Sequence:
                         Syntheticpolynucleotide
source                  1..4930
                        mol_type = other DNA
                        organism = synthetic construct
SEQUENCE: 33
tttttttcct gcagcccggg aaggatctgc gatcgctccg gtgcccgtca gtgggcagag  60
cgcacatcgc ccacagtccc cgagaagttg gggggagggg tcggcaattg aacgggtgcc  120
tagagaaggt ggcgcggggt aaactgggaa agtgatgtcg tgtactggct ccgccttttt  180
cccgagggtg ggggagaacc gtatataagt gcagtagtcg ccgtgaacgt tctttttcgc  240
aacgggtttg ccgccagaac acagctgaag cttcgagggg ctcgcatctc tccttcacgc  300
gcccgccgcc ctacctgagg ccgccatcca cgccggttga gtcgcgttct gccgcctccc  360
gcctgtggtg cctcctgaac tgcgtccgcc gtctaggtaa gtttaaagct caggtcgaga  420
ccgggccttt gtccggcgct cccttggagc ctacctagac tcagccggct ctccacgctt  480
tgcctgaccc tgcttgctca actctacgtc tttgtttcgt tttctgttct gcgccgttac  540
agatccaagc tgtgaccggc gcctacgcta gatggtgagc aagggcgagg aggataacat  600
ggccatcatc aaggagttca tgcgcttcaa ggtgcacatg gagggctccg tgaacggcca  660
cgagttcgag atcgagggcg agggcgaggg ccgcccctac gagggcaccc agaccgccaa  720
gctgaaggtg accaagggtg gccccctgcc cttcgcctgg gacatcctgt cccctcagtt  780
catgtacggc tccaaggcct acgtgaagca ccccgccgac atccccgact acttgaagct  840
gtccttcccc gagggcttca agtgggagcg cgtgatgaac ttcgaggacg gcggcgtggt  900
gaccgtgacc caggactcct ccctgcagga cggcgagttc atctacaagg tgaagctgcg  960
cggcaccaac ttcccctccg acggccccgt aatgcagaag aagaccatgg gctgggaggc  1020
ctcctccgag cggatgtacc ccgaggacgg cgccctgaag ggcgagatca agcagaggct  1080
gaagctgaag gacggcggcc actacgacgc tgaggtcaag accacctaca aggccaagaa  1140
gcccgtgcag ctgcccggcg cctacaacgt caacatcaag ttggacatca cctcccacaa  1200
cgaggactac accatcgtgg aacagtacga acgcgccgag ggccgccact ccaccggcgg  1260
catggacgag ctgtacaagt aatccgagct cggtaccaag cttaagttta aaccgctgat  1320
cagcctcgac tgtgccttct agttgccagc catctgttgt ttgcccctcc cccgtgcctt  1380
ccttgaccct ggaaggtgcc actcccactg tcctttccta ataaaatgag gaaattgcat  1440
cgcattgtct gagtaggtgt cattctattc tggggggtgg ggtggggcag gacagcaagg  1500
gggaggattg ggaagacaat agcaggcatg ctggggatgc ggtgggctct atggggggatc  1560
cactagttct agagcggccg ccaccgcggt ggagctccag cttttgttcc ctttagtgag  1620
ggttaattgc gcgcttggcg taatcatggt catagctgtt tcctgtgtga aattgttatc  1680
cgctcacaat tccacacaac atacgagccg gaagcataaa gtgtaaagcc tggggtgcct  1740
aatgagtgag ctaactcaca ttaattgcgt tgcgctcact gcccgctttc cagtcgggaa  1800
acctgtcgtg ccagctgcat taatgaatcg gccaacgcgc ggggagaggc ggtttgcgta  1860
ttgggcgctc ttccgcttcc tcgctcactg actcgctgcg ctcggtcgtt cggctgcggc  1920
gagcggtatc agctcactca aaggcggtaa tacggttatc cacagaatca ggggataacg  1980
caggaaagaa catgtgagca aaaggccagc aaaaggccag gaaccgtaaa aaggccgcgt  2040
tgctggcgtt tttccatagg ctccgccccc ctgacgagca tcacaaaaat cgacgctcaa  2100
gtcagaggtg gcgaaacccg acaggactat aaagatacca ggcgtttccc cctggaagct  2160
ccctcgtgcg ctctcctgtt ccgaccctgc cgcttaccgg atacctgtcc gcctttctcc  2220
cttcgggaag cgtggcgctt tctcatagct cacgctgtag gtatctcagt tcggtgtagg  2280
tcgttcgctc caagctgggc tgtgtgcacg aaccccccgt tcagcccgac cgctgcgcct  2340
tatccggtaa ctatcgtctt gagtccaacc cggtaagaca cgacttatcg ccactggcag  2400
cagccactgg taacaggatt agcagagcga ggtatgtagg cggtgctaca gagttcttga  2460
agtggtggcc taactacggc tacactagaa ggacagtatt tggtatctgc gctctgctga  2520
agccagttac cttcggaaaa agagttggta gctcttgatc cggcaaacaa accaccgctg  2580
gtagcggtgg tttttttgtt tgcaagcagc agattacgcg cagaaaaaaa ggatctcaag  2640
```

```
aagatccttt gatcttttct acggggtctg acgctcagtg gaacgaaaac tcacgttaag  2700
ggattttggt catgagatta tcaaaaagga tcttcaccta gatcctttta aattaaaaat  2760
gaagttttaa atcaatctaa agtatatatg agtaaacttg gtctgacagt taccaatgct  2820
taatcagtga ggcacctatc tcagcgatct gtctatttcg ttcatccata gttgcctgac  2880
tccccgtcgt gtagataact acgatacggg agggcttacc atctggcccc agtgctgcaa  2940
tgataccgcg agacccacgc tcaccggctc cagatttatc agcaataaac cagccagccg  3000
gaagggccga gcgcagaagt ggtcctgcaa ctttatccgc ctccatccag tctattaatt  3060
gttgccggga agctagagta agtagttcgc cagttaatag tttgcgcaac gttgttgcca  3120
ttgctacagg catcgtggtg tcacgctcgt cgtttggtat ggcttcattc agctccggtt  3180
cccaacgatc aaggcgagtt acatgatccc ccatgttgtg caaaaaagcg gttagctcct  3240
tcggtcctcc gatcgttgtc agaagtaagt tggccgcagt gttatcactc atggttatgg  3300
cagcactgca taattctctt actgtcatgc catccgtaag atgcttttct gtgactggtg  3360
agtactcaac caagtcattc tgagaatagt gtatgcggcg accgagttgc tcttgcccgg  3420
cgtcaatacg ggataatacc gcgccacata gcagaacttt aaaagtgctc atcattggaa  3480
aacgttcttc ggggcgaaaa ctctcaagga tcttaccgct gttgagatcc agttcgatgt  3540
aacccactcg tgcacccaac tgatcttcag catcttttac tttcaccagc gtttctgggt  3600
gagcaaaaac aggaaggcaa aatgccgcaa aaaagggaat aagggcgaca cggaaatgtt  3660
gaatactcat actcttcctt tttcaatatt attgaagcat ttatcagggt tattgtctca  3720
tgagcggata catatttgaa tgtatttaga aaaataaaca aataggggtt ccgcgcacat  3780
ttccccgaaa agtgccacct aaattgtaag cgttaatatt ttgttaaaat tcgcgttaaa  3840
tttttgttaa atcagctcat tttttaacca ataggccgaa atcggcaaaa tcccttataa  3900
atcaaaagaa tagaccgaga tagggttgag tgttgttcca gtttggaaca agagtccact  3960
attaaagaac gtggactcca acgtcaaagg gcgaaaaacc gtctatcagg gcgatggccc  4020
actacgtgaa ccatcaccct aatcaagttt tttggggtcg aggtgccgta aagcactaaa  4080
tcggaaccct aaagggagcc cccgatttag agcttgacgg ggaaagccgg cgaacgtggc  4140
gagaaaggaa gggaagaaag cgaaaggagc gggcgctagg gcgctggcaa gtgtagcggt  4200
cacgctgcgc gtaaccacca cacccgccgc gcttaatgcg ccgctacagg gcgcgtccca  4260
ttcgccattc aggctgcgca actgttggga agggcgatcg gtgcgggcct cttcgctatt  4320
acgccagctg gcgaaagggg gatgtgctgc aaggcgatta agttgggtaa cgccagggtt  4380
ttcccagtca cgacgttgta aaacgacggc cagtgagcgc gcgtaatacg actcactata  4440
gggcgaattg ggtaccgggc ccccctcga ggtcgacggt atcgataagc ttgatatcgt   4500
gtacaaaaaa gcaggcttta aaggaaccaa ttcagtcgac tggatccggt accaaggtcg  4560
ggcaggaaga gggcctattt cccatgattc cttcatattt gcatatacga tacaaggctg  4620
ttagagagat aattagaatt aatttgactg taaacacaaa gatattagta caaaatacgt  4680
gacgtagaaa gtaataattt cttgggtagt ttgcagtttt aaaattatgt tttaaaatgg  4740
actatcatat gcttaccgta acttgaaagt atttcgattt cttggcttta tatatcttgt  4800
ggaaaggacg aaacaccgtt taagagctat gctggaaaca gcatagcaag tttaaataag  4860
gctagtccgt tatcaacttg aaaaagtggc accgagtcgg tgcttcattt gcctgttccg  4920
tggccgacac                                                         4930
```

```
SEQ ID NO: 34          moltype = DNA  length = 3388
FEATURE                Location/Qualifiers
misc_feature           1..3388
                       note = Description of Artificial Sequence:
                        Syntheticpolynucleotide
source                 1..3388
                       mol_type = other DNA
                       organism = synthetic construct
SEQUENCE: 34
ctaaattgta agcgttaata ttttgttaaa attcgcgtta aatttttgtt aaatcagctc  60
atttttttaac caataggccg aaatcggcaa aatcccttat aaatcaaaag aatagaccga  120
gatagggttg agtgttgttc cagtttggaa caagagtcca ctattaaaga acgtggactc  180
caacgtcaaa gggcgaaaaa ccgtctatca gggcgatggc ccactacgtg aaccatcacc  240
ctaatcaagt tttttggggt cgaggtgccg taaagcacta aatcggaacc ctaaagggag  300
cccccgattt agagcttgac ggggaaagcc ggcgaacgtg gcgagaaagg aagggaagaa  360
agcgaaagga gcgggcgcta gggcgctggc aagtgtagcg gtcacgctgc gcgtaaccac  420
cacacccgcc gcgcttaatg cgccgctaca gggcgcgtcc cattcgccat tcaggctgcg  480
caactgttgg gaagggcgat cggtgcgggc ctcttcgcta ttacgccagc tggcgaaagg  540
gggatgtgct gcaaggcgat taagttgggt aacgccaggg ttttcccagt cacgacgttg  600
taaaacgacg gccagtgagc gcgcgtaata cgactcacta tagggcgaat tgggtaccgg  660
gccccccctc gaggtcgacg gtatcgataa gcttgatatc gtgtacaaaa aagcaggctt  720
taaaggaacc aattcagtcg actggatccg gtaccaaggt cgggcaggaa gagggcctat  780
ttcccatgat tccttcatat ttgcatatac gatacaaggc tgttagagag ataattagaa  840
ttaatttgac tgtaaacaca aagatattag tacaaaatac gtgacgtaga aagtaataat  900
ttcttgggta gtttgcagtt ttaaaattat gttttaaaat ggactatcat atgcttaccg  960
taacttgaaa gtatttcgat ttcttggctt tatatatctt gtggaaagga cgaaacaccg  1020
tgataagtgg aatgccatgg tttaagagct atgctggaaa cagcatagca agtttaaata  1080
aggctagtcc gttatcaact tgaaaaagtg gcaccgagtc ggtgcttttt ttcctgcagc  1140
ccgggggatc cactagttct agagcggccg ccaccgcggt ggagctccag cttttgttcc  1200
ctttagtgag ggttaattgc gcgcttggcg taatcatggt catagctgtt tcctgtgtga  1260
aattgttatc cgctcacaat tccacacaac atacgagccg gaagcataaa gtgtaaagcc  1320
tggggtgcct aatgagtgag ctaactcaca ttaattgcgt tgcgctcact gcccgctttc  1380
cagtcgggaa acctgtcgtg ccagctgcat taatgaatcg gccaacgcgc ggggagaggc  1440
ggtttgcgta ttgggcgctc ttccgcttcc tcgctcactg actcgctgcg ctcggtcgtt  1500
cggctgcggc gagcggtatc agctcactca aaggcggtaa tacggttatc cacagaatca  1560
ggggataacg caggaaagaa catgtgagca aaaggccagc aaaaggccag gaaccgtaaa  1620
aaggccgcgt tgctggcgtt tttccatagg ctccgccccc ctgacgagca tcacaaaaat  1680
cgacgctcaa gtcagaggtg gcgaaacccg acaggactat aaagatacca ggcgtttccc  1740
cctggaagct ccctcgtgcg ctctcctgtt ccgaccctgc cgcttaccgg atacctgtcc  1800
```

```
gcctttctcc cttcgggaag cgtggcgctt tctcatagct cacgctgtag gtatctcagt  1860
tcggtgtagg tcgttcgctc caagctgggc tgtgtgcacg aaccccccgt tcagcccgac  1920
cgctgcgcct tatccggtaa ctatcgtctt gagtccaacc cggtaagaca cgacttatcg  1980
ccactggcag cagccactgg taacaggatt agcagagcga ggtatgtagg cggtgctaca  2040
gagttcttga agtggtggcc taactacggc tacactagaa ggacagtatt tggtatctgc  2100
gctctgctga agccagttac cttcggaaaa agagttggta gctcttgatc cggcaaacaa  2160
accaccgctg gtagcggtgg tttttttgtt tgcaagcagc agattacgcg cagaaaaaaa  2220
ggatctcaag aagatccttt gatcttttct acggggtctg acgctcagtg gaacgaaaac  2280
tcacgttaag ggattttggt catgagatta tcaaaaagga tcttcaccta gatcctttta  2340
aattaaaaat gaagttttaa atcaatctaa agtatatatg agtaaacttg gtctgacagt  2400
taccaatgct taatcagtga ggcacctatc tcagcgatct gtctatttcg ttcatccata  2460
gttgcctgac tccccgtcgt gtagataact acgatacggg agggcttacc atctggcccc  2520
agtgctgcaa tgataccgcg agacccacgc tcaccggctc cagatttatc agcaataaac  2580
cagccagccg gaagggccga gcgcagaagt ggtcctgcaa ctttatccgc ctccatccag  2640
tctattaatt gttgccggga agctagagta agtagttcgc cagttaatag tttgcgcaac  2700
gttgttgcca ttgctacagg catcgtggtg tcacgctcgt cgtttggtat ggcttcattc  2760
agctccggtt cccaacgatc aaggcgagtt acatgatccc ccatgttgtg caaaaaagcg  2820
gttagctcct tcggtcctcc gatcgttgtc agaagtaagt tggccgcagt gttatcactc  2880
atggttatgg cagcactgca taattctctt actgtcatgc catccgtaag atgcttttct  2940
gtgactggtg agtactcaac caagtcattc tgagaatagt gtatgcggcg accgagttgc  3000
tcttgcccgg cgtcaatacg ggataatacc gcgccacata gcagaacttt aaaagtgctc  3060
atcattggaa aacgttcttc ggggcgaaaa ctctcaagga tcttaccgct gttgagatcc  3120
agttcgatgt aacccactcg tgcacccaac tgatcttcag catcttttac tttcaccagc  3180
gtttctgggt gagcaaaaac aggaaggcaa aatgccgcaa aaaagggaat aagggcgaca  3240
cggaaatgtt gaatactcat actcttcctt tttcaatatt attgaagcat ttatcagggt  3300
tattgtctca tgagcggata catatttgaa tgtatttaga aaaataaaca aataggggtt  3360
ccgcgcacat ttccccgaaa agtgccac                                      3388

SEQ ID NO: 35          moltype = DNA  length = 14250
FEATURE                Location/Qualifiers
misc_feature           1..14250
                       note = Description of Artificial Sequence:
                        Syntheticpolynucleotide
source                 1..14250
                       mol_type = other DNA
                       organism = synthetic construct
SEQUENCE: 35
acaaagaagg ctggacaggc taagaagaag aaagattaca aagacgatga cgataaggga  60
tccggcgcaa caaacttctc tctgctgaaa caagccggag atgtcgaaga gaatcctgga  120
ccgaccgagt acaagcccac ggtgcgcctc gccacccgcg acgacgtccc cagggccgta  180
cgcaccctcg ccgccgcgtt cgccgactac cccgccacgc gccacaccgt cgatccggac  240
cgccacatcg agcgggtcac cgagctgcaa gaactcttcc tcacgcgcgt cgggctcgac  300
atcggcaagg tgtgggtcgc ggacgacggc gccgcggtgg cggtctggac cacgccggag  360
agcgtcgaag cgggggcggt gttcgccgag atcggcccgc gcatggccga gttgagcggt  420
tcccggctgg ccgcgcagca acagatggaa ggcctcctgg cgccgcaccg gcccaaggag  480
cccgcgtggt tcctggccac cgtcggagtc tcgcccgacc accagggcaa gggtctgggc  540
agcgccgtcg tgctccccgg agtggaggcg gccgagcgcg ccggggtgcc cgccttcctg  600
gagacctccg cgccccgcaa cctccccttc tacgagcggc tcggcttcac cgtcaccgcc  660
gacgtcgagg tgcccgaagg accgcgcacc tggtgcatga cccgcaagcc cggtgcctga  720
acgcgttaag tcgacaatca acctctggat tacaaaattt gtgaaagatt gactggtatt  780
cttaactatg ttgctccttt tacgctatgt ggatacgctg ctttaatgcc tttgtatcat  840
gctattgctt cccgtatggc tttcattttc tcctccttgt ataaatcctg gttgctgtct  900
ctttatgagg agttgtggcc cgttgtcagg caacgtggcg tggtgtgcac tgtgtttgct  960
gacgcaaccc ccactggttg gggcattgcc accacctgtc agctcctttc cgggactttc  1020
gctttccccc tccctattgc cacggcggaa ctcatcgccg cctgccttgc ccgctgctgg  1080
acaggggctc ggctgttggg cactgacaat tccgtggtgt tgtcggggaa atcatcgtcc  1140
tttccttggc tgctcgcctg tgttgccacc tggattctgc gcgggacgtc cttctgctac  1200
gtcccttcgg ccctcaatcc agcggacctt ccttcccgcg gcctgctgcc ggctctgcgg  1260
cctcttccgc gtcttcgcct tcgccctcag acgagtcgga tctccctttg ggccgcctcc  1320
ccgcgtcgac tttaagacca atgacttaca aggcagctgt agatcttagc cactttttaa  1380
aagaaaaggg gggactggaa gggctaattc actcccaacg aagacaagat ctgctttttg  1440
cttgtactgg gtctctctgg ttagaccaga tctgagcctg ggagctctct ggctaactag  1500
ggaacccact gcttaagcct caataaagct tgccttgagt gcttcaagta gtgtgtgccc  1560
gtctgttgtg tgactctggt aactagagat ccctcagacc cttttagtca gtgtggaaaa  1620
tctctagcag ggcccgttta aacccgctga tcagcctcga ctgtgccttc tagttgccag  1680
ccatctgttg tttgcccctc ccccgtgcct tccttgaccc tggaaggtgc cactcccact  1740
gtcctttcct aataaaatga ggaaattgca tcgcattgtc tgagtaggtg tcattctatt  1800
ctggggggtg gggtggggca ggacagcaag ggggaggatt gggaagacaa tagcaggcat  1860
gctggggatg cggtgggctc tatggcttct gaggcggaaa gaaccagctg gggctctagg  1920
gggtatcccc acgcgccctg tagcggcgca ttaagcgcgg cgggtgtggt ggttacgcgc  1980
agcgtgaccg ctacacttgc cagcgcccta gcgcccgctc ctttcgcttt cttcccttcc  2040
tttctcgcca cgttcgccgg ctttccccgt caagctctaa atcgggggct ccctttaggg  2100
ttccgattta gtgctttacg gcacctcgac cccaaaaaac ttgattaggg tgatggttca  2160
cgtagtgggc catcgccctg atagacggtt tttcgccctt tgacgttgga gtccacgttc  2220
tttaatagtg gactcttgtt ccaaactgga acaacactca accctatctc ggtctattct  2280
tttgatttat aagggatttt gccgatttcg gcctattggt taaaaaatga gctgatttaa  2340
caaaaattta acgcgaatta attctgtgga atgtgtgtca gttagggtgt ggaaagtccc  2400
caggctcccc agcaggcaga agtatgcaaa gcatgcatct caattagtca gcaaccaggt  2460
gtggaaagtc cccaggctcc ccagcaggca gaagtatgca aagcatgcat ctcaattagt  2520
```

-continued

```
cagcaaccat agtcccgccc ctaactccgc ccatcccgcc cctaactccg cccagttccg  2580
cccattctcc gccccatggc tgactaattt tttttattta tgcagaggcc gaggccgcct  2640
ctgcctctga gctattccag aagtagtgag gaggcttttt tggaggccta ggcttttgca  2700
aaaagctccc gggagcttgt atatccattt tcggatctga tcagcacgtg ttgacaatta  2760
atcatcggca tagtatatcg gcatagtata atacgacaag gtgaggaact aaaccatggc  2820
caagttgacc agtgccgttc cggtgctcac cgcgcgcgac gtcgccggag cggtcgagtt  2880
ctggaccgac cggctcgggt tctcccggga cttcgtggag gacgacttcg ccggtgtggt  2940
ccgggacgac gtgaccctgt tcatcagcgc ggtccaggac caggtggtgc cggacaacac  3000
cctggcctgg gtgtgggtgc gcggcctgga cgagctgtac gccgagtggt cggaggtcgt  3060
gtccacgaac ttccgggacg cctccgggcc ggccatgacc gagatcggcg agcagccgtg  3120
ggggcgggag ttcgccctgc gcgacccggc cggcaactgc gtgcacttcg tggccgagga  3180
gcaggactga cacgtgctac gagatttcga ttccaccgcc gccttctatg aaaggttggg  3240
cttcggaatc gttttccggg acgccggctg gatgatcctc cagcgcgggg atctcatgct  3300
ggagttcttc gcccacccca acttgtttat tgcagcttat aatggttaca aataaagcaa  3360
tagcatcaca aatttcacaa ataaagcatt tttttcactg cattctagtt gtggtttgtc  3420
caaactcatc aatgtatctt atcatgtctg tataccgtcg acctctagct agagcttggc  3480
gtaatcatgg tcatagctgt ttcctgtgtg aaattgttat ccgctcacaa ttccacacaa  3540
catacgagcc ggaagcataa agtgtaaagc ctggggtgcc taatgagtga gctaactcac  3600
attaattgcg ttgcgctcac tgcccgcttt ccagtcggga aacctgtcgt gccagctgca  3660
ttaatgaatc ggccaacgcg cggggagagg cggtttgcgt attgggcgct cttccgcttc  3720
ctcgctcact gactcgctgc gctcggtcgt tcggctgcgg cgagcggtat cagctcactc  3780
aaaggcggta atacggttat ccacagaatc aggggataac gcaggaaaga acatgtgagc  3840
aaaaggccag caaaaggcca ggaaccgtaa aaaggccgcg ttgctggcgt ttttccatag  3900
gctccgcccc cctgacgagc atcacaaaaa tcgacgctca agtcagaggt ggcgaaaccc  3960
gacaggacta taaagatacc aggcgtttcc ccctggaagc tccctcgtgc gctctcctgt  4020
tccgaccctg ccgcttaccg gatacctgtc cgcctttctc ccttcgggaa gcgtggcgct  4080
ttctcatagc tcacgctgta ggtatctcag ttcggtgtag gtcgttcgct ccaagctggg  4140
ctgtgtgcac gaaccccccg ttcagcccga ccgctgcgcc ttatccggta actatcgtct  4200
tgagtccaac ccggtaagac acgacttatc gccactggca gcagccactg gtaacaggat  4260
tagcagagcg aggtatgtag gcggtgctac agagttcttg aagtggtggc ctaactacgg  4320
ctacactaga agaacagtat ttggtatctg cgctctgctg aagccagtta ccttcggaaa  4380
aagagttggt agctcttgat ccggcaaaca aaccaccgct ggtagcggtg gtttttttgt  4440
ttgcaagcag cagattacgc gcagaaaaaa aggatctcaa gaagatcctt tgatcttttc  4500
tacggggtct gacgctcagt ggaacgaaaa ctcacgttaa gggattttgg tcatgagatt  4560
atcaaaaagg atcttcacct agatcctttt aaattaaaaa tgaagtttta aatcaatcta  4620
aagtatatat gagtaaactt ggtctgacag ttaccaatgc ttaatcagtg aggcacctat  4680
ctcagcgatc tgtctatttc gttcatccat agttgcctga ctccccgtcg tgtagataac  4740
tacgatacgg gagggcttac catctggccc cagtgctgca atgataccgc gagacccacg  4800
ctcaccggct ccagatttat cagcaataaa ccagccagcc ggaagggccg agcgcagaag  4860
tggtcctgca actttatccg cctccatcca gtctattaat tgttgccggg aagctagagt  4920
aagtagttcg ccagttaata gtttgcgcaa cgttgttgcc attgctacag gcatcgtggt  4980
gtcacgctcg tcgtttggta tggcttcatt cagctccggt tcccaacgat caaggcgagt  5040
tacatgatcc cccatgttgt gcaaaaaagc ggttagctcc ttcggtcctc cgatcgttgt  5100
cagaagtaag ttggccgcag tgttatcact catggttatg gcagcactgc ataattctct  5160
tactgtcatg ccatccgtaa gatgcttttc tgtgactggt gagtactcaa ccaagtcatt  5220
ctgagaatag tgtatgcggc gaccgagttg ctcttgcccg gcgtcaatac gggataatac  5280
cgcgccacat agcagaactt taaaagtgct catcattgga aaacgttctt cggggcgaaa  5340
actctcaagg atcttaccgc tgttgagatc cagttcgatg taacccactc gtgcacccaa  5400
ctgatcttca gcatctttta ctttcaccag cgtttctggg tgagcaaaaa caggaaggca  5460
aaatgccgca aaaaagggaa taagggcgac acggaaatgt tgaatactca tactcttcct  5520
ttttcaatat tattgaagca tttatcaggg ttattgtctc atgagcggat acatatttga  5580
atgtatttag aaaaataaac aaataggggt tccgcgcaca tttccccgaa aagtgccacc  5640
tgacgtcgac ggatcgggag atctcccgat cccctatggt gcactctcag tacaatctgc  5700
tctgatgccg catagttaag ccagtatctg ctccctgctt gtgtgttgga ggtcgctgag  5760
tagtgcgcga gcaaaattta agctacaaca aggcaaggct tgaccgacaa ttgcatgaag  5820
aatctgctta gggttaggcg ttttgcgctg cttcgcgatg tacgggccag atatacgcgt  5880
tgacattgat tattgactag ttattaatag taatcaatta cggggtcatt agttcatagc  5940
ccatatatgg agttccgcgt tacataactt acggtaaatg gcccgcctgg ctgaccgccc  6000
aacgaccccc gcccattgac gtcaataatg acgtatgttc ccatagtaac gccaataggg  6060
actttccatt gacgtcaatg ggtggagtat ttacggtaaa ctgcccactt ggcagtacat  6120
caagtgtatc atatgccaag tacgccccct attgacgtca atgacggtaa atggcccgcc  6180
tggcattatg cccagtacat gaccttatgg gactttccta cttggcagta catctacgta  6240
ttagtcatcg ctattaccat ggtgatgcgg ttttggcagt acatcaatgg gcgtggatag  6300
cggtttgact cacggggatt tccaagtctc caccccattg acgtcaatgg gagtttgttt  6360
tggcaccaaa atcaacggga ctttccaaaa tgtcgtaaca actccgcccc attgacgcaa  6420
atgggcggta ggcgtgtacg gtgggaggtc tatataagca gcgcgttttg cctgtactgg  6480
gtctctctgg ttagaccaga tctgagcctg ggagctctct ggctaactag ggaacccact  6540
gcttaagcct caataaagct tgccttgagt gcttcaagta gtgtgtgccc gtctgttgtg  6600
tgactctggt aactagagat ccctcagacc cttttagtca gtgtggaaaa tctctagcag  6660
tggcgcccga acagggactt gaaagcgaaa gggaaaccag aggagctctc tcgacgcagg  6720
actcggcttg ctgaagcgcg cacggcaaga ggcgaggggc ggcgactggt gagtacgcca  6780
aaaattttga ctagcggagg ctagaaggag agagatgggt gcgagagcgt cagtattaag  6840
cgggggagaa ttagatcgcg atgggaaaaa attcggttaa ggccaggggg aaagaaaaaa  6900
tataaattaa aacatatagt atgggcaagc agggagctag aacgattcgc agttaatcct  6960
ggcctgttag aaacatcaga aggctgtaga caaatactgg gacagctaca accatccctt  7020
cagacaggat cagaagaact tagatcatta tataatacag tagcaaccct ctattgtgtg  7080
catcaaagga tagagataaa agacaccaag gaagctttag acaagataga ggaagagcaa  7140
aacaaaagta agaccaccgc acagcaagcg gccgctgatc ttcagacctg gaggaggaga  7200
tatgagggac aattggagaa gtgaattata taaatataaa gtagtaaaaa ttgaaccatt  7260
```

-continued

```
aggagtagca cccaccaagg caaagagaag agtggtgcag agagaaaaaa gagcagtggg  7320
aataggagct ttgttccttg ggttcttggg agcagcagga agcactatgg gcgcagcgtc  7380
aatgacgctg acggtacagg ccagacaatt attgtctggt atagtgcagc agcagaacaa  7440
tttgctgagg gctattgagg cgcaacagca tctgttgcaa ctcacagtct ggggcatcaa  7500
gcagctccag gcaagaatcc tggctgtgga aagataccta aaggatcaac agctcctggg  7560
gatttggggt tgctctggaa aactcatttg caccactgct gtgccttgga atgctagttg  7620
gagtaataaa tctctggaac agatttggaa tcacacgacc tggatggagt gggacagaga  7680
aattaacaat tacacaagct taatacactc cttaattgaa gaatcgcaaa accagcaaga  7740
aaagaatgaa caagaattat tggaattaga taaatgggca agtttgtgga attggtttaa  7800
cataacaaat tggctgtggt atataaaatt attcataatg atagtaggag gcttggtagg  7860
tttaagaata gtttttgctg tactttctat agtgaataga gttaggcagg gatattcacc  7920
attatcgttt cagacccacc tcccaacccc gaggggaccc gacaggcccg aaggaataga  7980
agaagaaggt ggagagagag acagagacag atccattcga ttagtgaacg gatcggcact  8040
gcgtgcgcca attctgcaga caaatggcag tattcatcca caattttaaa agaaaagggg  8100
ggattggggg gtacagtgca ggggaaagaa tagtagacat aatagcaaca gacatacaaa  8160
ctaaagaatt acaaaaacaa attacaaaaa ttcaaaattt tcgggtttat tacagggaca  8220
gcagagatcc agtttggtta attaaggtac cgagggccta tttcccatga ttccttcata  8280
tttgcatata cgatacaagg ctgttagaga gataattaga attaatttga ctgtaaacac  8340
aaagatatta gtacaaaata cgtgacgtag aaagtaataa tttcttgggt agtttgcagt  8400
tttaaaatta tgttttaaaa tggactatca tatgcttacc gtaacttgaa agtatttcga  8460
tttcttggct ttatatatct tgtggaaagg acgaaacacc gttcataggg atccaagttt  8520
tgtttaagag ctatgctgga aacagcatag caagtttaaa taaggctagt ccgttatcaa  8580
cttgaaaaag tggcaccgag tcggtgcttc atttttcctc cactgttgca aagttttttt  8640
cctgcagccc gggaattcgc tagctaggtc ttgaaaggag tgggaattgg ctccggtgcc  8700
cgtcagtggg cagagcgcac atcgcccaca gtccccgaga agttgggggg aggggtcggc  8760
aattgatccg gtgcctagag aaggtggcgc ggggtaaact gggaaagtga tgtcgtgtac  8820
tggctccgcc tttttcccga gggtggggga gaaccgtata taagtgcagt agtcgccgtg  8880
aacgttcttt ttcgcaacgg gtttgccgcc agaacacagg accggttcta gagcgctgcc  8940
accatgttag ctgacgctgt ctcacgcctg gtcctgggta agtttggtga cctgaccgac  9000
aacttctcct cccctcacgc tcgcagaaaa gtgctggctg gagtcgtcat gacaacaggc  9060
acagatgtta aagatgccaa ggtgataagt gtttctacag gaacaaaatg tattaatggt  9120
gaatacatga gtgatcgtgg ccttgcatta aatgactgcc atgcagaaat aatatctcgg  9180
agatccttgc tcagatttct ttatacacaa cttgagcttt acttaaataa caaagatgat  9240
caaaaaagat ccatctttca gaaatcagag cgaggggggt ttaggctgaa ggagaatgtc  9300
cagtttcatc tgtacatcag cacctctccc tgtggagatg ccagaatctt ctcaccacat  9360
gagccaatcc tggaagaacc agcagataga cacccaaatc gtaaagcaag aggacagcta  9420
cggaccaaaa tagagtctgg tcaggggacg attccagtgc gctccaatgc gagcatccaa  9480
acgtgggacg gggtgctgca aggggagcgg ctgctcacca tgtcctgcag tgacaagatt  9540
gcacgctgga acgtggtggg catccaggga tccctgctca gcattttcgt ggagcccatt  9600
tacttctcga gcatcatcct gggcagcctt taccacgggg accacctttc cagggccatg  9660
taccagcgga tctccaacat agaggacctg ccacctctct acaccctcaa caagcctttg  9720
ctcagtggca tcagcaatgc agaagcacgg cagccaggga aggcccccaa cttcagtgtc  9780
aactggacgg taggcgactc cgctattgag gtcatcaacg ccacgactgg gaaggatgag  9840
ctgggccgcg cgtcccgcct gtgtaagcac gcgttgtact gtcgctggat gcgtgtgcac  9900
ggcaaggttc cctcccactt actacgctcc aagattacca agcccaacgt gtaccatgag  9960
tccaagctgg cggcaaagga gtaccaggcc gccaaggcgc gtctgttcac agccttcatc  10020
aaggcggggc tgggggcctg ggtggagaag cccaccgagc aggaccagtt ctcactcacg  10080
cccagtggaa gtgagacacc gggaacctca gagagcgcca cgccagaaag catggacaag  10140
aagtacagca tcggcctggc catcggcacc aactctgtgg gctgggccgt gatcaccgac  10200
gagtacaagg tgcccagcaa gaaattcaag gtgctgggca acaccgaccg gcacagcatc  10260
aagaagaacc tgatcggcgc cctgctgttc gacagcggag aaacagccga ggccacccgg  10320
ctgaagagaa ccgccagaag aagatacacc agacggaaga accggatctg ctatctgcaa  10380
gagatcttca gcaacgagat ggccaaggtg gacgacagct tcttccacag actggaagag  10440
tccttcctgg tggaagagga taagaagcac gagcggcacc ccatcttcgg caacatcgtg  10500
gacgaggtgg cctaccacga gaagtacccc accatctacc acctgagaaa gaaactggtg  10560
gacagcaccg acaaggccga cctgcggctg atctatctgg ccctggccca catgatcaag  10620
ttccggggcc acttcctgat cgagggcgac ctgaaccccg acaacagcga cgtggacaag  10680
ctgttcatcc agctggtgca gacctacaac cagctgttcg aggaaaaccc catcaacgcc  10740
agcggcgtgg acgccaaggc catcctgtct gccagactga gcaagagcag acggctggaa  10800
aatctgatcg cccagctgcc cggcgagaag aagaatggcc tgttcggcaa cctgattgcc  10860
ctgagcctgg gcctgacccc caacttcaag agcaacttcg acctggccga ggatgccaaa  10920
ctgcagctga gcaaggacac ctacgacgac gacctggaca acctgctggc ccagatcggc  10980
gaccagtacg ccgacctgtt tctggccgcc aagaacctgt ccgacgccat cctgctgagc  11040
gacatcctga gagtgaacac cgagatcacc aaggcccccc tgagcgcctc tatgatcaag  11100
agatacgacg agcaccacca ggacctgacc ctgctgaaag ctctcgtgcg gcagcagctg  11160
cctgagaagt acaaagagat tttcttcgac cagagcaaga acggctacgc cggctacatc  11220
gatggcggag ccagccagga agagttctac aagttcatca agcccatcct ggaaaagatg  11280
gacggcaccg aggaactgct cgtgaagctg aacagagagg acctgctgcg gaagcagcgg  11340
accttcgaca acggcagcat cccccaccag atccacctgg gagagctgca cgccattctg  11400
cggcggcagg aagattttta cccattcctg aaggacaacc gggaaaagat cgagaagatc  11460
ctgaccttcc gcatccccta ctacgtgggc cctctggcca ggggaaacag cagattcgcc  11520
tggatgacca gaaagagcga ggaaaccatc accccctgga acttcgagga agtggtggac  11580
aagggcgcca gcgcccagag cttcatcgag cggatgacca acttcgataa gaacctgccc  11640
aacgagaagg tgctgcccaa gcacagcctg ctgtacgagt acttcaccgt gtacaacgag  11700
ctgaccaaag tgaaatacgt gaccgaggga atgagaaagc ccgccttcct gagcggcgag  11760
cagaaaaaag ccatcgtgga cctgctgttc aagaccaacc ggaaagtgac cgtgaagcag  11820
ctgaaagagg actacttcaa gaaaatcgag tgcttcgact ccgtggaaat ctccggcgtg  11880
gaagatcggt tcaacgcctc cctgggcaca taccacgatc tgctgaaaat tatcaaggac  11940
aaggacttcc tggacaatga ggaaaacgag gacattctgg aagatatcgt gctgaccctg  12000
```

```
acactgtttg aggacagaga gatgatcgag gaacggctga aaacctatgc ccacctgttc  12060
gacgacaaag tgatgaagca gctgaagcgg cggagataca ccggctgggg caggctgagc  12120
cggaagctga tcaacggcat ccgggacaag cagtccggca agacaatcct ggatttcctg  12180
aagtccgacg gcttcgccaa cagaaacttc atgcagctga tccacgacga cagcctgacc  12240
tttaaagagg acatccagaa agcccaggtg tccggccagg gcgatagcct gcacgagcac  12300
attgccaatc tggccggcag ccccgccatt aagaagggca tcctgcagac agtgaaggtg  12360
gtggacgagc tcgtgaaagt gatgggccgg cacaagcccg agaacatcgt gatcgaaatg  12420
gccagagaga accagaccac ccagaaggga cagaagaaca gccgcgagag aatgaagcgg  12480
atcgaagagg gcatcaaaga gctgggcagc cagatcctga aagaacaccc cgtggaaaac  12540
acccagctgc agaacgagaa gctgtacctg tactacctgc agaatgggcg ggatatgtac  12600
gtggaccagg aactggacat caaccggctg tccgactacg atgtggacgc tatcgtgcct  12660
cagagctttc tgaaggacga ctccatcgat aacaaagtgc tgactcggag cgacaagaac  12720
cggggcaaga gcgacaacgt gccctccgaa gaggtcgtga agaagatgaa gaactactgg  12780
cgccagctgc tgaatgccaa gctgattacc cagaggaagt tcgacaatct gaccaaggcc  12840
gagagaggcg gcctgagcga actggataag gccggcttca tcaagagaca gctggtggaa  12900
acccggcaga tcacaaagca cgtggcacag atcctggact cccggatgaa cactaagtac  12960
gacgagaacg acaaactgat ccgggaagtg aaagtgatca ccctgaagtc caagctggtg  13020
tccgatttcc ggaaggattt ccagttttac aaagtgcgcg agatcaacaa ctaccaccac  13080
gcccacgacg cctacctgaa cgccgtcgtg ggaaccgccc tgatcaaaaa gtaccctaag  13140
ctggaaagcg agttcgtgta cggcgactac aaggtgtacg acgtgcggaa gatgatcgcc  13200
aagagcgagc aggaaatcgg caaggctacc gccaagtact tcttctacag caacatcatg  13260
aactttttca agaccgagat taccctggcc aacggcgaga tccggaagcg gcctctgatc  13320
gagacaaacg gcgaaacagg cgagatcgtg tgggataagg gccgggactt tgccaccgtg  13380
cggaaagtgc tgtctatgcc ccaagtgaat atcgtgaaaa agaccgaggt gcagacaggc  13440
ggcttcagca aagagtctat cctgcccaag aggaacagcg acaagctgat cgccagaaag  13500
aaggactggg accctaagaa gtacggcggc ttcgacagcc ccaccgtggc ctattctgtg  13560
ctggtggtgg ccaaagtgga aaagggcaag tccaagaaac tgaagagtgt gaaagagctg  13620
ctggggatca ccatcatgga aagaagcagc ttcgagaaga atcccatcga ctttctggaa  13680
gccaagggct acaaagaagt gaaaaaggac ctgatcatca agctgcctaa gtactccctg  13740
ttcgagctgg aaaacggccg gaagagaatg ctggcctctg ccggcgaact gcagaaggga  13800
aacgaactgg ccctgccctc caaatatgtg aacttcctgt acctggccag ccactatgag  13860
aagctgaagg gctcccccga ggataatgag cagaaacagc tgtttgtgga acagcacaaa  13920
cactacctgg acgagatcat cgagcagatc agcgagttct ccaagagagt gatcctggcc  13980
gacgctaatc tggacaaggt gctgagcgcc tacaacaagc acagagacaa gcctatcaga  14040
gagcaggccg agaatatcat ccacctgttt accctgacca atctgggagc ccctgccgcc  14100
ttcaagtact ttgacaccac catcgaccgg aagaggtaca ccagcaccaa agaggtgctg  14160
gacgccaccc tgatccacca gagcatcacc ggcctgtacg agacacggat cgacctgtct  14220
cagctgggag gcgacaagcg acctgccgcc                                  14250
```

```
SEQ ID NO: 36           moltype = AA  length = 380
FEATURE                 Location/Qualifiers
REGION                  1..380
                        note = Description of Artificial Sequence:
                         Syntheticpolypeptide
source                  1..380
                        mol_type = protein
                        organism = synthetic construct
SEQUENCE: 36
MLADAVSRLV LGKFGDLTDN FSSPHARRKV LAGVVMTTGT DVKDAKVISV STGTKCINGE  60
YMSDRGLALN DCHAEIISRR SLLRFLYTQL ELYLNNKDDQ KRSIFQKSER GGFRLKENVQ  120
FHLYISTSPC GDARIFSPHE PILEEPADRH PNRKARGQLR TKIESGQGTI PVRSNASIQT  180
WDGVLQGERL LTMSCSDKIA RWNVVGIQGS LLSIFVEPIY FSSIILGSLY HGDHLSRAMY  240
QRISNIEDLP PLYTLNKPLL SGISNAEARQ PGKAPNFSVN WTVGDSAIEV INATTGKDEL  300
GRASRLCKHA LYCRWMRVHG KVPSHLLRSK ITKPNVYHES KLAAKEYQAA KARLFTAFIK  360
AGLGAWVEKP TEQDQFSLTP                                             380
```

```
SEQ ID NO: 37           moltype = AA  length = 16
FEATURE                 Location/Qualifiers
REGION                  1..16
                        note = Description of Artificial Sequence: Syntheticpeptide
source                  1..16
                        mol_type = protein
                        organism = synthetic construct
SEQUENCE: 37
SGSETPGTSE SATPES                                                 16
```

```
SEQ ID NO: 38           moltype = AA  length = 1368
FEATURE                 Location/Qualifiers
REGION                  1..1368
                        note = Description of Artificial Sequence:
                         Syntheticpolypeptide
source                  1..1368
                        mol_type = protein
                        organism = synthetic construct
SEQUENCE: 38
MDKKYSIGLA IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
```

```
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDA  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 39          moltype = DNA  length = 14230
FEATURE                Location/Qualifiers
misc_feature           1..14230
                       note = Description of Artificial Sequence:
                        Syntheticpolynucleotide
source                 1..14230
                       mol_type = other DNA
                       organism = synthetic construct
SEQUENCE: 39
gtcgacggat cgggagatct cccgatcccc tatggtgcac tctcagtaca atctgctctg  60
atgccgcata gttaagccag tatctgctcc ctgcttgtgt gttggaggtc gctgagtagt  120
gcgcgagcaa aatttaagct acaacaaggc aaggcttgac cgacaattgc atgaagaatc  180
tgcttagggt taggcgtttt gcgctgcttc gcgatgtacg ggccagatat acgcgttgac  240
attgattatt gactagttat taatagtaat caattacggg gtcattagtt catagcccat  300
atatggagtt ccgcgttaca taacttacgg taaatggccc gcctggctga ccgcccaacg  360
acccccgccc attgacgtca ataatgacgt atgttcccat agtaacgcca atagggactt  420
tccattgacg tcaatgggtg gagtatttac ggtaaactgc ccacttggca gtacatcaag  480
tgtatcatat gccaagtacg ccccctattg acgtcaatga cggtaaatgg cccgcctggc  540
attatgccca gtacatgacc ttatgggact ttcctacttg gcagtacatc tacgtattag  600
tcatcgctat taccatggtg atgcggtttt ggcagtacat caatgggcgt ggatagcggt  660
ttgactcacg gggatttcca agtctccacc ccattgacgt caatgggagt ttgttttggc  720
accaaaatca acgggacttt ccaaaatgtc gtaacaactc cgccccattg acgcaaatgg  780
gcggtaggcg tgtacggtgg gaggtctata taagcagcgc gttttgcctg tactgggtct  840
ctctggttag accagatctg agcctgggag ctctctggct aactagggaa cccactgctt  900
aagcctcaat aaagcttgcc ttgagtgctt caagtagtgt gtgcccgtct gttgtgtgac  960
tctggtaact agagatccct cagacccttt tagtcagtgt ggaaaatctc tagcagtggc  1020
gcccgaacag ggacttgaaa gcgaaaggga aaccagagga gctctctcga cgcaggactc  1080
ggcttgctga agcgcgcacg gcaagaggcg aggggcggcg actggtgagt acgccaaaaa  1140
ttttgactag cggaggctag aaggagagag atgggtgcga gagcgtcagt attaagcggg  1200
ggagaattag atcgcgatgg gaaaaaattc ggttaaggcc agggggaaag aaaaaatata  1260
aattaaaaca tatagtatgg gcaagcaggg agctagaacg attcgcagtt aatcctggcc  1320
tgttagaaac atcagaaggc tgtagacaaa tactgggaca gctacaacca tcccttcaga  1380
caggatcaga agaacttaga tcattatata atacagtagc aaccctctat tgtgtgcatc  1440
aaaggataga gataaaagac accaaggaag ctttagacaa gatagaggaa gagcaaaaca  1500
aaagtaagac caccgcacag caagcggccg ctgatcttca gacctggagg aggagatatg  1560
agggacaatt ggagaagtga attatataaa tataaagtag taaaaattga accattagga  1620
gtagcaccca ccaaggcaaa gagaagagtg gtgcagagag aaaaaagagc agtgggaata  1680
ggagctttgt tccttgggtt cttgggagca gcaggaagca ctatgggcgc agcgtcaatg  1740
acgctgacgg tacaggccag acaattattg tctggtatag tgcagcagca gaacaatttg  1800
ctgagggcta ttgaggcgca acagcatctg ttgcaactca cagtctgggg catcaagcag  1860
ctccaggcaa gaatcctggc tgtggaaaga tacctaaagg atcaacagct cctggggatt  1920
tggggttgct ctggaaaact catttgcacc actgctgtgc cttggaatgc tagttggagt  1980
aataaatctc tggaacagat ttggaatcac acgacctgga tggagtggga cagagaaatt  2040
aacaattaca caagcttaat acactcctta attgaagaat cgcaaaacca gcaagaaaag  2100
aatgaacaag aattattgga attagataaa tgggcaagtt tgtggaattg gtttaacata  2160
acaaattggc tgtggtatat aaaattattc ataatgatag taggaggctt ggtaggttta  2220
agaatagttt ttgctgtact ttctatagtg aatagagtta ggcagggata ttcaccatta  2280
tcgtttcaga cccacctccc aaccccgagg ggacccgaca ggcccgaagg aatagaagaa  2340
gaaggtggag agagagacag agacagatcc attcgattag tgaacggatc ggcactgcgt  2400
gcgccaattc tgcagacaaa tggcagtatt catccacaat tttaaaagaa aaggggggat  2460
tggggggtac agtgcagggg aaagaatagt agacataata gcaacagaca tacaaactaa  2520
agaattacaa aaacaaatta caaaaattca aaattttcgg gtttattaca gggacagcag  2580
agatccagtt tggttaatta aggtaccgag ggcctatttc ccatgattcc ttcatatttg  2640
catatacgat acaaggctgt tagagagata attagaatta atttgactgt aaacacaaag  2700
atattagtac aaaatacgtg acgtagaaag taataatttc ttgggtagtt tgcagtttta  2760
aaattatgtt ttaaaatgga ctatcatatg cttaccgtaa cttgaaagta tttcgatttc  2820
ttggctttat atatcttgtg gaaaggacga aacaccgttt aagagctatg ctggaaacag  2880
catagcaagt ttaaataagg ctagtccgtt atcaacttga aaagtggcaa ccgagtcggt  2940
gcttcattac ttcggcccag agctgctcct ttttttcctg cagcccggga attcgctagc  3000
```

```
taggtcttga aaggagtggg aattggctcc ggtgcccgtc agtgggcaga gcgcacatcg  3060
cccacagtcc ccgagaagtt ggggggaggg gtcggcaatt gatccggtgc ctagagaagg  3120
tggcgcgggg taaactggga aagtgatgtc gtgtactggc tccgcctttt tcccgagggt  3180
gggggagaac cgtatataag tgcagtagtc gccgtgaacg ttcttttttcg caacgggttt  3240
gccgccagaa cacaggaccg gttctagagc gctgccacca tgttagctga cgctgtctca  3300
cgcctggtcc tgggtaagtt tggtgacctg accgacaact tctcctcccc tcacgctcgc  3360
agaaaagtgc tggctggagt cgtcatgaca acaggcacag atgttaaaga tgccaaggtg  3420
ataagtgttt ctacaggaac aaaatgtatt aatggtgaat acatgagtga tcgtggcctt  3480
gcattaaatg actgccatgc agaaataata tctcggagat ccttgctcag atttctttat  3540
acacaacttg agctttactt aaataacaaa gatgatcaaa aaagatccat ctttcagaaa  3600
tcagagcgag gggggtttag gctgaaggag aatgtccagt ttcatctgta catcagcacc  3660
tctccctgtg gagatgccag aatcttctca ccacatgagc caatcctgga agaaccagca  3720
gatagacacc caaatcgtaa agcaagagga cagctacgga ccaaaataga gtctggtcag  3780
gggacgattc cagtgcgctc caatgcgagc atccaaacgt gggacggggt gctgcaaggg  3840
gagcggctgc tcaccatgtc ctgcagtgac aagattgcac gctggaacgt ggtgggcatc  3900
cagggatccc tgctcagcat tttcgtggag cccatttact tctcgagcat catcctgggc  3960
agcctttacc acggggacca cctttccagg gccatgtacc agcggatctc caacatagag  4020
gacctgccac ctctctacac cctcaacaag cctttgctca gtggcatcag caatgcagaa  4080
gcacggcagc cagggaaggc cccaacttc agtgtcaact ggacggtagg cgactccgct  4140
attgaggtca tcaacgccac gactgggaag gatgagctgg gccgcgcgtc ccgcctgtgt  4200
aagcacgcgt tgtactgtcg ctggatgcgt gtgcacggca aggttccctc ccacttacta  4260
cgctccaaga ttaccaagcc caacgtgtac catgagtcca agctggcggc aaaggagtac  4320
caggccgcca aggcgcgtct gttcacagcc ttcatcaagg cggggctggg ggcctgggtg  4380
gagaagccca ccgagcagga ccagttctca ctcacgccca gtggaagtga gacaccggga  4440
acctcagaga gcgccacgcc agaaagcatg gacaagaagt acagcatcgg cctggccatc  4500
ggcaccaact ctgtgggctg ggccgtgatc accgacgagt acaaggtgcc cagcaagaaa  4560
ttcaaggtgc tgggcaacac cgaccggcac agcatcaaga agaacctgat cggcgccctg  4620
ctgttcgaca gcggagaaac agccgaggcc acccggctga agagaaccgc cagaagaaga  4680
tacaccagac ggaagaaccg gatctgctat ctgcaagaga tcttcagcaa cgagatggcc  4740
aaggtggacg acagcttctt ccacagactg gaagagtcct tcctggtgga agaggataag  4800
aagcacgagc ggcaccccat cttcggcaac atcgtggacg aggtggccta ccacgagaag  4860
taccccacca tctaccacct gagaaagaaa ctggtggaca gcaccgacaa ggccgacctg  4920
cggctgatct atctggccct ggcccacatg atcaagttcc ggggccactt cctgatcgag  4980
ggcgacctga accccgacaa cagcgacgtg gacaagctgt tcatccagct ggtgcagacc  5040
tacaaccagc tgttcgagga aaaccccatc aacgccagcg gcgtggacgc caaggccatc  5100
ctgtctgcca gactgagcaa gagcagacgg ctggaaaatc tgatcgccca gctgcccggc  5160
gagaagaaga atggcctgtt cggcaacctg attgccctga gcctgggcct gacccccaac  5220
ttcaagagca acttcgacct ggccgaggat gccaaactgc agctgagcaa ggacacctac  5280
gacgacgacc tggacaacct gctggcccag atcggcgacc agtacgccga cctgtttctg  5340
gccgccaaga acctgtccga cgccatcctg ctgagcgaca tcctgagagt gaacaccgag  5400
atcaccaagg cccccctgag cgcctctatg atcaagagat acgacgagca ccaccaggac  5460
ctgaccctgc tgaaagctct cgtgcggcag cagctgcctg agaagtacaa agagattttc  5520
ttcgaccaga gcaagaacgg ctacgccggc tacatcgatg gcggagccag ccaggaagag  5580
ttctacaagt tcatcaagcc catcctggaa aagatggacg gcaccgagga actgctcgtg  5640
aagctgaaca gagaggacct gctgcggaag cagcggacct tcgacaacgg cagcatcccc  5700
caccagatcc acctgggaga gctgcacgcc attctgcggc ggcaggaaga tttttaccca  5760
ttcctgaagg acaaccggga aaagatcgag aagatcctga ccttccgcat cccctactac  5820
gtgggccctc tggccagggg aaacagcaga ttcgcctgga tgaccagaaa gagcgaggaa  5880
accatcaccc cctggaactt cgaggaagtg gtggacaagg gcgccagcgc ccagagcttc  5940
atcgagcgga tgaccaactt cgataagaac ctgcccaacg agaaggtgct gcccaagcac  6000
agcctgctgt acgagtactt caccgtgtac aacgagctga ccaaagtgaa atacgtgacc  6060
gagggaatga gaaagcccgc cttcctgagc ggcgagcaga aaaaagccat cgtggacctg  6120
ctgttcaaga ccaaccggaa agtgaccgtg aagcagctga aagaggacta cttcaagaaa  6180
atcgagtgct tcgactccgt ggaaatctcc ggcgtggaag atcggttcaa cgcctccctg  6240
ggcacatacc acgatctgct gaaaattatc aaggacaagg acttcctgga caatgaggaa  6300
aacgaggaca ttctggaaga tatcgtgctg accctgacac tgtttgagga cagagagatg  6360
atcgaggaac ggctgaaaac ctatgcccac ctgttcgacg acaaagtgat gaagcagctg  6420
aagcggcgga gatacaccgg ctggggcagg ctgagccgga agctgatcaa cggcatccgg  6480
gacaagcagt ccggcaagac aatcctggat ttcctgaagt ccgacggctt cgccaacaga  6540
aacttcatgc agctgatcca cgacgacagc ctgaccttta aagaggacat ccagaaagcc  6600
caggtgtccg gccagggcga tagcctgcac gagcacattg ccaatctggc cggcagcccc  6660
gccattaaga agggcatcct gcagacagtg aaggtggtgg acgagctcgt gaaagtgatg  6720
ggccggcaca agcccgagaa catcgtgatc gaaatggcca gagagaacca gaccacccag  6780
aagggacaga agaacagccg cgagagaatg aagcggatcg aagagggcat caaagagctg  6840
ggcagccaga tcctgaaaga acaccccgtg gaaaacaccc agctgcagaa cgagaagctg  6900
tacctgtact acctgcagaa tggcgggat atgtacgtgg accaggaact ggacatcaac  6960
cggctgtccg actacgatgt ggacgctatc gtgcctcaga gctttctgaa ggacgactcc  7020
atcgataaca aagtgctgac tcggagcgac aagaaccggg gcaagagcga caacgtgccc  7080
tccgaagagg tcgtgaagaa gatgaagaac tactggcgcc agctgctgaa tgccaagctg  7140
attacccaga ggaagttcga caatctgacc aaggccgaga gaggcggcct gagcgaactg  7200
gataaggccg gcttcatcaa gagacagctg gtggaaaccc ggcagatcac aaagcacgtg  7260
gcacagatcc tggactcccg gatgaacact aagtacgacg agaacgacaa actgatccgg  7320
gaagtgaaag tgatcaccct gaagtccaag ctggtgtccg atttccggaa ggatttccag  7380
ttttacaaag tgcgcgagat caacaactac caccacgccc acgacgccta cctgaacgcc  7440
gtcgtgggaa ccgccctgat caaaaagtac cctaagctgg aaagcgagtt cgtgtacggc  7500
gactacaagg tgtacgacgt gcggaagatg atcgccaaga gcgagcagga aatcggcaag  7560
gctaccgcca agtacttctt ctacagcaac atcatgaact tttcaagac cgagattacc  7620
ctggccaacg gcgagatccg gaagcggcct ctgatcgaga caaacggcga aacaggcgag  7680
atcgtgtggg ataagggccg ggactttgcc accgtgcgga aagtgctgtc tatgccccaa  7740
```

```
gtgaatatcg tgaaaaagac cgaggtgcag acaggcggct tcagcaaaga gtctatcctg  7800
cccaagagga acagcgacaa gctgatcgcc agaaagaagg actgggaccc taagaagtac  7860
ggcggcttcg acagccccac cgtggcctat tctgtgctgg tggtggccaa agtggaaaag  7920
ggcaagtcca agaaactgaa gagtgtgaaa gagctgctgg ggatcaccat catggaaaga  7980
agcagcttcg agaagaatcc catcgacttt ctggaagcca agggctacaa agaagtgaaa  8040
aaggacctga tcatcaagct gcctaagtac tccctgttcg agctggaaaa cggccggaag  8100
agaatgctgg cctctgccgg cgaactgcag aagggaaacg aactggccct gccctccaaa  8160
tatgtgaact tcctgtacct ggccagccac tatgagaagc tgaagggctc ccccgaggat  8220
aatgagcaga aacagctgtt tgtggaacag cacaaacact acctggacga gatcatcgag  8280
cagatcagcg agttctccaa gagagtgatc ctggccgacg ctaatctgga caaggtgctg  8340
agcgcctaca acaagcacag agacaagcct atcagagagc aggccgagaa tatcatccac  8400
ctgtttaccc tgaccaatct gggagcccct gccgccttca agtactttga caccaccatc  8460
gaccggaaga ggtacaccag caccaaagag gtgctggacg ccaccctgat ccaccagagc  8520
atcaccggcc tgtacgagac acggatcgac ctgtctcagc tgggaggcga caagcgacct  8580
gccgccacaa agaaggctgg acaggctaag aagaagaaag attacaaaga cgatgacgat  8640
aagggatccg gcgcaacaaa cttctctctg ctgaaacaag ccggagatgt cgaagagaat  8700
cctggaccga ccgagtacaa gcccacggtg cgcctcgcca cccgcgacga cgtccccagg  8760
gccgtacgca ccctcgccgc cgcgttcgcc gactaccccg ccacgcgcca caccgtcgat  8820
ccggaccgcc acatcgagcg ggtcaccgag ctgcaagaac tcttcctcac gcgcgtcggg  8880
ctcgacatcg gcaaggtgtg ggtcgcggac gacggcgccg cggtggcggt ctggaccacg  8940
ccggagagcg tcgaagcggg ggcggtgttc gccgagatcg gcccgcgcat ggccgagttg  9000
agcggttccc ggctggccgc gcagcaacag atggaaggcc tcctggcgcc gcaccggccc  9060
aaggagcccg cgtggttcct ggccaccgtc ggagtctcgc ccgaccacca gggcaagggt  9120
ctgggcagcg ccgtcgtgct ccccggagtg gaggcggccg agcgcgccgg ggtgcccgcc  9180
ttcctggaga cctccgcgcc ccgcaacctc cccttctacg agcggctcgg cttcaccgtc  9240
accgccgacg tcgaggtgcc cgaaggaccg cgcacctggt gcatgacccg caagcccggt  9300
gcctgaacgc gttaagtcga caatcaacct ctggattaca aaatttgtga aagattgact  9360
ggtattctta actatgttgc tccttttacg ctatgtggat acgctgcttt aatgcctttg  9420
tatcatgcta ttgcttcccg tatggctttc attttctcct ccttgtataa atcctggttg  9480
ctgtctcttt atgaggagtt gtggcccgtt gtcaggcaac gtggcgtggt gtgcactgtg  9540
tttgctgacg caacccccac tggttggggc attgccacca cctgtcagct cctttccggg  9600
actttcgctt tccccctccc tattgccacg gcggaactca tcgccgcctg ccttgcccgc  9660
tgctggacag gggctcggct gttgggcact gacaattccg tggtgttgtc ggggaaatca  9720
tcgtcctttc cttggctgct cgcctgtgtt gccacctgga ttctgcgcgg gacgtccttc  9780
tgctacgtcc cttcggccct caatccagcg gaccttcctt cccgcggcct gctgccggct  9840
ctgcggcctc ttccgcgtct tcgccttcgc cctcagacga gtcggatctc cctttgggcc  9900
gcctccccgc gtcgacttta agaccaatga cttacaaggc agctgtagat cttagccact  9960
ttttaaaaga aaaggggga ctggaagggc taattcactc ccaacgaaga caagatctgc  10020
tttttgcttg tactgggtct ctctggttag accagatctg agcctgggag ctctctggct  10080
aactagggaa cccactgctt aagcctcaat aaagcttgcc ttgagtgctt caagtagtgt  10140
gtgcccgtct gttgtgtgac tctggtaact agagatccct cagacccttt tagtcagtgt  10200
ggaaaatctc tagcagggcc cgtttaaacc cgctgatcag cctcgactgt gccttctagt  10260
tgccagccat ctgttgtttg cccctccccc gtgccttcct tgaccctgga aggtgccact  10320
cccactgtcc tttcctaata aaatgaggaa attgcatcgc attgtctgag taggtgtcat  10380
tctattctgg ggggtggggt ggggcaggac agcaaggggg aggattggga agacaatagc  10440
aggcatgctg gggatgcggt gggctctatg gcttctgagg cggaaagaac cagctggggc  10500
tctagggggt atccccacgc gccctgtagc ggcgcattaa gcgcggcggg tgtggtggtt  10560
acgcgcagcg tgaccgctac acttgccagc gccctagcgc ccgctccttt cgctttcttc  10620
ccttcctttc tcgccacgtt cgccggcttt ccccgtcaag ctctaaatcg ggggctccct  10680
ttagggttcc gatttagtgc tttacggcac ctcgacccca aaaaacttga ttagggtgat  10740
ggttcacgta gtgggccatc gccctgatag acggtttttc gccctttgac gttggagtcc  10800
acgttcttta atagtggact cttgttccaa actggaacaa cactcaaccc tatctcggtc  10860
tattcttttg atttataagg gattttgccg atttcggcct attggttaaa aaatgagctg  10920
atttaacaaa aatttaacgc gaattaattc tgtggaatgt gtgtcagtta gggtgtggaa  10980
agtccccagg ctccccagca ggcagaagta tgcaaagcat gcatctcaat tagtcagcaa  11040
ccaggtgtgg aaagtcccca ggctccccag caggcagaag tatgcaaagc atgcatctca  11100
attagtcagc aaccatagtc ccgcccctaa ctccgcccat cccgccccta actccgccca  11160
gttccgccca ttctccgccc catggctgac taattttttt tatttatgca gaggccgagg  11220
ccgcctctgc ctctgagcta ttccagaagt agtgaggagg cttttttgga ggcctaggct  11280
tttgcaaaaa gctcccggga gcttgtatat ccattttcgg atctgatcag cacgtgttga  11340
caattaatca tcggcatagt atatcggcat agtataatac gacaaggtga ggaactaaac  11400
catggccaag ttgaccagtg ccgttccggt gctcaccgcg cgcgacgtcg ccggagcggt  11460
cgagttctgg accgaccggc tcgggttctc ccgggacttc gtggaggacg acttcgccgg  11520
tgtggtccgg gacgacgtga ccctgttcat cagcgcggtc caggaccagg tggtgccgga  11580
caacaccctg gcctgggtgt gggtgcgcgg cctggacgag ctgtacgccg agtggtcgga  11640
ggtcgtgtcc acgaacttcc gggacgcctc cgggccggcc atgaccgaga tcggcgagca  11700
gccgtggggg cgggagttcg ccctgcgcga cccggccggc aactgcgtgc acttcgtggc  11760
cgaggagcag gactgacacg tgctacgaga tttcgattcc accgccgcct tctatgaaag  11820
gttgggcttc ggaatcgttt tccgggacgc cggctggatg atcctccagc gcggggatct  11880
catgctggag ttcttcgccc accccaactt gtttattgca gcttataatg gttacaaata  11940
aagcaatagc atcacaaatt tcacaaataa agcatttttt tcactgcatt ctagttgtgg  12000
tttgtccaaa ctcatcaatg tatcttatca tgtctgtata ccgtcgacct ctagctagag  12060
cttggcgtaa tcatggtcat agctgtttcc tgtgtgaaat tgttatccgc tcacaattcc  12120
acacaacata cgagccggaa gcataaagtg taaagcctgg ggtgcctaat gagtgagcta  12180
actcacatta attgcgttgc gctcactgcc cgctttccag tcgggaaacc tgtcgtgcca  12240
gctgcattaa tgaatcggcc aacgcgcggg gagaggcggt ttgcgtattg ggcgctcttc  12300
cgcttcctcg ctcactgact cgctgcgctc ggtcgttcgg ctgcggcgag cggtatcagc  12360
tcactcaaag gcggtaatac ggttatccac agaatcaggg gataacgcag gaaagaacat  12420
gtgagcaaaa ggccagcaaa aggccaggaa ccgtaaaaag gccgcgttgc tggcgttttt  12480
```

```
ccataggctc cgcccccctg acgagcatca caaaaatcga cgctcaagtc agaggtggcg  12540
aaacccgaca ggactataaa gataccaggc gtttccccct ggaagctccc tcgtgcgctc  12600
tcctgttccg accctgccgc ttaccggata cctgtccgcc tttctccctt cgggaagcgt  12660
ggcgctttct catagctcac gctgtaggta tctcagttcg gtgtaggtcg ttcgctccaa  12720
gctgggctgt gtgcacgaac cccccgttca gcccgaccgc tgcgccttat ccggtaacta  12780
tcgtcttgag tccaacccgg taagacacga cttatcgcca ctggcagcag ccactggtaa  12840
caggattagc agagcgaggt atgtaggcgg tgctacagag ttcttgaagt ggtggcctaa  12900
ctacggctac actagaagaa cagtatttgg tatctgcgct ctgctgaagc cagttacctt  12960
cggaaaaaga gttggtagct cttgatccgg caaacaaacc accgctggta gcggtggttt  13020
ttttgtttgc aagcagcaga ttacgcgcag aaaaaaagga tctcaagaag atcctttgat  13080
cttttctacg gggtctgacg ctcagtggaa cgaaaactca cgttaaggga ttttggtcat  13140
gagattatca aaaaggatct tcacctagat ccttttaaat taaaaatgaa gttttaaatc  13200
aatctaaagt atatatgagt aaacttggtc tgacagttac caatgcttaa tcagtgaggc  13260
acctatctca gcgatctgtc tatttcgttc atccatagtt gcctgactcc ccgtcgtgta  13320
gataactacg atacgggagg gcttaccatc tggccccagt gctgcaatga taccgcgaga  13380
cccacgctca ccggctccag atttatcagc aataaaccag ccagccggaa gggccgagcg  13440
cagaagtggt cctgcaactt tatccgcctc catccagtct attaattgtt gccgggaagc  13500
tagagtaagt agttcgccag ttaatagttt gcgcaacgtt gttgccattg ctacaggcat  13560
cgtggtgtca cgctcgtcgt ttggtatggc ttcattcagc tccggttccc aacgatcaag  13620
gcgagttaca tgatccccca tgttgtgcaa aaaagcggtt agctccttcg gtcctccgat  13680
cgttgtcaga agtaagttgg ccgcagtgtt atcactcatg gttatggcag cactgcataa  13740
ttctcttact gtcatgccat ccgtaagatg cttttctgtg actggtgagt actcaaccaa  13800
gtcattctga gaatagtgta tgcggcgacc gagttgctct tgcccggcgt caatacggga  13860
taataccgcg ccacatagca gaactttaaa agtgctcatc attggaaaac gttcttcggg  13920
gcgaaaactc tcaaggatct taccgctgtt gagatccagt tcgatgtaac ccactcgtgc  13980
acccaactga tcttcagcat cttttacttt caccagcgtt tctgggtgag caaaaacagg  14040
aaggcaaaat gccgcaaaaa agggaataag ggcgacacgg aaatgttgaa tactcatact  14100
cttccttttt caatattatt gaagcattta tcagggttat tgtctcatga gcggatacat  14160
atttgaatgt atttagaaaa ataaacaaat aggggttccg cgcacatttc cccgaaaagt  14220
gccacctgac                                                         14230

SEQ ID NO: 40          moltype = AA  length = 380
FEATURE                Location/Qualifiers
REGION                 1..380
                       note = Description of Artificial Sequence:
                        Syntheticpolypeptide
source                 1..380
                       mol_type = protein
                       organism = synthetic construct
SEQUENCE: 40
MLADAVSRLV LGKFGDLTDN FSSPHARRKV LAGVVMTTGT DVKDAKVISV STGTKCINGE  60
YMSDRGLALN DCHAEIISRR SLLRFLYTQL ELYLNNKDDQ KRSIFQKSER GGFRLKENVQ  120
FHLYISTSPC GDARIFSPHE PILEEPADRH PNRKARGQLR TKIESGQGTI PVRSNASIQT  180
WDGVLQGERL LTMSCSDKIA RWNVVGIQGS LLSIFVEPIY FSSIILGSLY HGDHLSRAMY  240
QRISNIEDLP PLYTLNKPLL SGISNAEARQ PGKAPNFSVN WTVGDSAIEV INATTGKDEL  300
GRASRLCKHA LYCRWMRVHG KVPSHLLRSK ITKPNVYHES KLAAKEYQAA KARLFTAFIK  360
AGLGAWVEKP TEQDQFSLTP                                              380

SEQ ID NO: 41          moltype = AA  length = 16
FEATURE                Location/Qualifiers
REGION                 1..16
                       note = Description of Artificial Sequence: Syntheticpeptide
source                 1..16
                       mol_type = protein
                       organism = synthetic construct
SEQUENCE: 41
SGSETPGTSE SATPES                                                  16

SEQ ID NO: 42          moltype = AA  length = 1368
FEATURE                Location/Qualifiers
REGION                 1..1368
                       note = Description of Artificial Sequence:
                        Syntheticpolypeptide
source                 1..1368
                       mol_type = protein
                       organism = synthetic construct
SEQUENCE: 42
MDKKYSIGLA IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
```

```
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDA  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 43          moltype = DNA  length = 21
FEATURE                Location/Qualifiers
misc_feature           1..21
                       note = Description of Artificial Sequence:
                        Syntheticoligonucleotide
source                 1..21
                       mol_type = other DNA
                       organism = synthetic construct
SEQUENCE: 43
gttcataggg atccaagttt t                                            21

SEQ ID NO: 44          moltype = DNA  length = 20
FEATURE                Location/Qualifiers
misc_feature           1..20
                       note = Description of Artificial Sequence:
                        Syntheticoligonucleotide
source                 1..20
                       mol_type = other DNA
                       organism = synthetic construct
SEQUENCE: 44
tttcctccac tgttgcaaag                                              20

SEQ ID NO: 45          moltype = DNA  length = 20
FEATURE                Location/Qualifiers
misc_feature           1..20
                       note = Description of Artificial Sequence:
                        Syntheticoligonucleotide
source                 1..20
                       mol_type = other DNA
                       organism = synthetic construct
SEQUENCE: 45
ccagcgccca ccgcccccag                                              20

SEQ ID NO: 46          moltype = DNA  length = 21
FEATURE                Location/Qualifiers
misc_feature           1..21
                       note = Description of Artificial Sequence:
                        Syntheticoligonucleotide
source                 1..21
                       mol_type = other DNA
                       organism = synthetic construct
SEQUENCE: 46
acttcggccc agagctgctc c                                            21

SEQ ID NO: 47          moltype = DNA  length = 4921
FEATURE                Location/Qualifiers
misc_feature           1..4921
                       note = Description of Artificial Sequence:
                        Syntheticpolynucleotide
source                 1..4921
                       mol_type = other DNA
                       organism = synthetic construct
SEQUENCE: 47
ttttttcct gcagcccggg aaggatctgc gatcgctccg gtgcccgtca gtgggcagag  60
cgcacatcgc ccacagtccc cgagaagttg gggggagggg tcggcaattg aacgggtgcc  120
tagagaaggt ggcgcggggt aaactgggaa agtgatgtcg tgtactggct ccgccttttt  180
cccgagggtg ggggagaacc gtatataagt gcagtagtcg ccgtgaacgt tctttttcgc  240
aacgggtttg ccgccagaac acagctgaag cttcgagggg ctcgcatctc tccttcacgc  300
gcccgccgcc ctacctgagg ccgccatcca cgccggttga gtcgcgttct gccgcctccc  360
gcctgtggtg cctcctgaac tgcgtccgcc gtctaggtaa gtttaaagct caggtcgaga  420
ccgggccttt gtccggcgct cccttggagc ctacctagac tcagccggct ctccacgctt  480
tgcctgaccc tgcttgctca actctacgtc tttgtttcgt ttctgttct gcgccgttac  540
agatccaagc tgtgaccggc gcctacgcta aaggcgaagg aggataacat  600
ggccatcatc aaggagttca tgcgcttcaa ggtgcacatg gagggctccg tgaacggcca  660
cgagttcgag atcgagggcg agggcgaggg ccgcccctac gagggcaccc agaccgccaa  720
gctgaaggtg accaagggtg gcccccctgcc cttcgcctgg gacatcctgt cccctcagtt  780
catgtacggc tccaaggcct acgtgaagca ccccgccgac atccccgact acttgaagct  840
```

```
gtccttcccc gagggcttca agtgggagcg cgtgatgaac ttcgaggacg gcggcgtggt  900
gaccgtgacc caggactcct ccctgcagga cggcgagttc atctacaagg tgaagctgcg  960
cggcaccaac ttcccctccg acggccccgt aatgcagaag aagaccatgg gctgggaggc  1020
ctcctccgag cggatgtacc ccgaggacgg cgccctgaag ggcgagatca agcagaggct  1080
gaagctgaag gacggcggcc actacgacgc tgaggtcaag accacctaca aggccaagaa  1140
gcccgtgcag ctgcccggcg cctacaacgt caacatcaag ttggacatca cctcccacaa  1200
cgaggactac accatcgtgg aacagtacga acgcgccgag ggccgccact ccaccggcgg  1260
catggacgag ctgtacaagt aatccgagct cggtaccaag cttaagttta aaccgctgat  1320
cagcctcgac tgtgccttct agttgccagc catctgttgt ttgcccctcc cccgtgcctt  1380
ccttgaccct ggaaggtgcc actcccactg tcctttccta ataaaatgag gaaattgcat  1440
cgcattgtct gagtaggtgt cattctattc tggggggtgg ggtggggcag gacagcaagg  1500
gggaggattg ggaagacaat agcaggcatg ctggggatgc ggtgggctct atggggggatc  1560
cactagttct agagcggccg ccaccgcggt ggagctccag cttttgttcc ctttagtgag  1620
ggttaattgc gcgcttggcg taatcatggt catagctgtt tcctgtgtga aattgttatc  1680
cgctcacaat tccacacaac atacgagccg gaagcataaa gtgtaaagcc tggggtgcct  1740
aatgagtgag ctaactcaca ttaattgcgt tgcgctcact gcccgctttc cagtcgggaa  1800
acctgtcgtg ccagctgcat taatgaatcg gccaacgcgc ggggagaggc ggtttgcgta  1860
ttgggcgctc ttccgcttcc tcgctcactg actcgctgcg ctcggtcgtt cggctgcggc  1920
gagcggtatc agctcactca aaggcggtaa tacggttatc cacagaatca ggggataacg  1980
caggaaagaa catgtgagca aaaggccagc aaaaggccag gaaccgtaaa aaggccgcgt  2040
tgctggcgtt tttccatagg ctccgccccc ctgacgagca tcacaaaaat cgacgctcaa  2100
gtcagaggtg gcgaaacccg acaggactat aaagatacca ggcgtttccc cctggaagct  2160
ccctcgtgcg ctctcctgtt ccgaccctgc cgcttaccgg atacctgtcc gcctttctcc  2220
cttcgggaag cgtggcgctt tctcatagct cacgctgtag gtatctcagt tcggtgtagg  2280
tcgttcgctc caagctgggc tgtgtgcacg aaccccccgt tcagcccgac cgctgcgcct  2340
tatccggtaa ctatcgtctt gagtccaacc cggtaagaca cgacttatcg ccactggcag  2400
cagccactgg taacaggatt agcagagcga ggtatgtagg cggtgctaca gagttcttga  2460
agtggtggcc taactacggc tacactagaa ggacagtatt tggtatctgc gctctgctga  2520
agccagttac cttcggaaaa agagttggta gctcttgatc cggcaaacaa accaccgctg  2580
gtagcggtgg tttttttgtt tgcaagcagc agattacgcg cagaaaaaaa ggatctcaag  2640
aagatccttt gatcttttct acggggtctg acgctcagtg gaacgaaaac tcacgttaag  2700
ggattttggt catgagatta tcaaaaagga tcttcaccta gatcctttta aattaaaaat  2760
gaagttttaa atcaatctaa agtatatatg agtaaacttg gtctgacagt taccaatgct  2820
taatcagtga ggcacctatc tcagcgatct gtctatttcg ttcatccata gttgcctgac  2880
tccccgtcgt gtagataact acgatacggg agggcttacc atctggcccc agtgctgcaa  2940
tgataccgcg agacccacgc tcaccggctc cagatttatc agcaataaac cagccagccg  3000
gaagggccga gcgcagaagt ggtcctgcaa ctttatccgc ctccatccag tctattaatt  3060
gttgccggga agctagagta agtagttcgc cagttaatag tttgcgcaac gttgttgcca  3120
ttgctacagg catcgtggtg tcacgctcgt cgtttggtat ggcttcattc agctccggtt  3180
cccaacgatc aaggcgagtt acatgatccc ccatgttgtg caaaaaagcg gttagctcct  3240
tcggtcctcc gatcgttgtc agaagtaagt tggccgcagt gttatcactc atggttatgg  3300
cagcactgca taattctctt actgtcatgc catccgtaag atgcttttct gtgactggtg  3360
agtactcaac caagtcattc tgagaatagt gtatgcggcg accgagttgc tcttgcccgg  3420
cgtcaatacg ggataatacc gcgccacata gcagaacttt aaaagtgctc atcattggaa  3480
aacgttcttc ggggcgaaaa ctctcaagga tcttaccgct gttgagatcc agttcgatgt  3540
aacccactcg tgcacccaac tgatcttcag catcttttac tttcaccagc gtttctgggt  3600
gagcaaaaac aggaaggcaa aatgccgcaa aaaagggaat aagggcgaca cggaaatgtt  3660
gaatactcat actcttcctt tttcaatatt attgaagcat ttatcagggt tattgtctca  3720
tgagcggata catatttgaa tgtatttaga aaaataaaca aataggggtt ccgcgcacat  3780
ttccccgaaa agtgccacct aaattgtaag cgttaatatt ttgttaaaat tcgcgttaaa  3840
tttttgttaa atcagctcat tttttaacca ataggccgaa atcggcaaaa tcccttataa  3900
atcaaaagaa tagaccgaga tagggttgag tgttgttcca gtttggaaca agagtccact  3960
attaaagaac gtggactcca acgtcaaagg gcgaaaaacc gtctatcagg gcgatggccc  4020
actacgtgaa ccatcaccct aatcaagttt tttggggtcg aggtgccgta aagcactaaa  4080
tcggaaccct aaagggagcc cccgatttag agcttgacgg ggaaagccgg cgaacgtggc  4140
gagaaaggaa gggaagaaag cgaaaggagc gggcgctagg gcgctggcaa gtgtagcggt  4200
cacgctgcgc gtaaccacca cacccgccgc gcttaatgcg ccgctacagg gcgcgtccca  4260
ttcgccattc aggctgcgca actgttggga agggcgatcg gtgcgggcct cttcgctatt  4320
acgccagctg gcgaaagggg gatgtgctgc aaggcgatta agttgggtaa cgccagggtt  4380
ttcccagtca cgacgttgta aaacgacggc cagtgagcgc gcgtaatacg actcactata  4440
gggcgaattg ggtaccgggc ccccccctcga ggtcgacggt atcgataagc ttgatatcgt  4500
gtacaaaaaa gcaggcttta aaggaaccaa ttcagtcgac tggatccggt accaaggtcg  4560
ggcaggaaga gggcctattt cccatgattc cttcatattt gcatatacga tacaaggctg  4620
ttagagagat aattagaatt aatttgactg taaacacaaa gatattagta caaaatacgt  4680
gacgtagaaa gtaataattt cttgggtagt ttgcagtttt aaaattatgt tttaaaatgg  4740
actatcatat gcttaccgta acttgaaagt atttcgattt cttggcttta tatatcttgt  4800
ggaaaggacg aaacaccggt tatagtactc tggaaacaga atctactata acaaggcaaa  4860
atgccgtgtt tatctcgtca acttgttggc gagattcatt gtgtcggcca cggaacaggc  4920
a                                                                  4921
```

```
SEQ ID NO: 48          moltype = DNA  length = 9842
FEATURE                Location/Qualifiers
misc_feature           1..9842
                       note = Description of Artificial Sequence:
                        Syntheticpolynucleotide
source                 1..9842
                       mol_type = other DNA
                       organism = synthetic construct
SEQUENCE: 48
```

-continued gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
gtttaaacgg gccctctaga ctcgagcggc cgccactgtg ctggatatct gcagagaacc 960
atgttagctg acgctgtctc acgcctggtc ctgggtaagt ttggtgacct gaccgacaac 1020
ttctcctccc ctcacgctcg cagaaaagtg ctggctggag tcgtcatgac aacaggcaca 1080
gatgttaaag atgccaaggt gataagtgtt tctacaggaa caaaatgtat taatggtgaa 1140
tacatgagtg atcgtggcct tgcattaaat gactgccatg cagaaataat atctcggaga 1200
tccttgctca gatttcttta tacacaactt gagctttact taaataacaa agatgatcaa 1260
aaaagatcca tctttcagaa atcagagcga ggggggttta ggctgaagga gaatgtccag 1320
tttcatctgt acatcagcac ctctccctgt ggagatgcca gaatcttctc accacatgag 1380
ccaatcctgg aagaaccagc agatagacac ccaaatcgta aagcaagagg acagctacgg 1440
accaaaatag agtctggtca ggggacgatt ccagtgcgct ccaatgcgag catccaaacg 1500
tgggacgggg tgctgcaagg ggagcggctg ctcaccatgt cctgcagtga caagattgca 1560
cgctggaacg tggtgggcat ccagggatcc ctgctcagca ttttcgtgga gcccatttac 1620
ttctcgagca tcatcctggg cagcctttac cacggggacc acctttccag ggccatgtac 1680
cagcggatct ccaacataga ggacctgcca cctctctaca ccctcaacaa gcctttgctc 1740
agtggcatca gcaatgcaga agcacggcag ccagggaagg cccccaactt cagtgtcaac 1800
tggacggtag gcgactccgc tattgaggtc atcaacgcca cgactgggaa ggatgagctg 1860
ggccgcgcgt cccgcctgtg taagcacgcg ttgtactgtc gctggatgcg tgtgcacggc 1920
aaggttccct cccacttact acgctccaag attaccaagc ccaacgtgta ccatgagtcc 1980
aagctggcgg caaaggagta ccaggccgcc aaggcgcgtc tgttcacagc cttcatcaag 2040
gcggggctgg gggcctgggt ggagaagccc accgagcagg accagttctc actcacgccc 2100
ggatccggat ccaagcggaa ctacatcctg ggcctggcca tcggcatcac cagcgtgggc 2160
tacggcatca tcgactacga gacacgggac gtgatcgatg ccggcgtgcg gctgttcaaa 2220
gaggccaacg tggaaaacaa cgagggcagg cggagcaaga gaggcgccag aaggctgaag 2280
cggcggaggc ggcatagaat ccagagagtg aagaagctgc tgttcgacta caacctgctg 2340
accgaccaca gcgagctgag cggcatcaac ccctacgagg ccagagtgaa gggcctgagc 2400
cagaagctga gcgaggaaga gttctctgcc gccctgctgc acctggccaa gagaagaggc 2460
gtgcacaacg tgaacgaggt ggaagaggac accggcaacg agctgtccac caaagagcag 2520
atcagccgga acagcaaggc cctggaagag aaatacgtgg ccgaactgca gctggaacgg 2580
ctgaagaaag acggcgaagt gcggggcagc atcaacagat tcaagaccag cgactacgtg 2640
aaagaagcca aacagctgct gaaggtgcag aaggcctacc accagctgga ccagagcttc 2700
atcgacacct acatcgacct gctggaaacc cggcggacct actatgaggg acctggcgag 2760
ggcagcccct tcggctggaa ggacatcaaa gaatggtacg agatgctgat gggccactgc 2820
acctacttcc ccgaggaact gcggagcgtg aagtacgcct acaacgccga cctgtacaac 2880
gccctgaacg acctgaacaa tctcgtgatc accagggacg agaacgagaa gctggaatat 2940
tacgagaagt tccagatcat cgagaacgtg ttcaagcaga agaagaagcc caccctgaag 3000
cagatcgcca aagaaatcct cgtgaacgaa gaggatatta agggctacag agtgaccagc 3060
accggcaagc ccgagttcac caacctgaag gtgtaccacg acatcaagga cattaccgcc 3120
cggaaagaga ttattgagaa cgccgagctg ctggatcaga ttgccaagat cctgaccatc 3180
taccagagca gcgaggacat ccaggaagaa ctgaccaatc tgaactccga gctgacccag 3240
gaagagatcg agcagatctc taatctgaag ggctataccg gcacccacaa cctgagcctg 3300
aaggccatca acctgatcct ggacgagctg tggcacacca acgacaacca gatcgctatc 3360
ttcaaccggc tgaagctggt gcccaagaag gtggacctgt cccagcagaa agagatcccc 3420
accaccctgg tggacgactt catcctgagc cccgtcgtga agagaagctt catccagagc 3480
atcaaagtga tcaacgccat catcaagaag tacggcctgc ccaacgacat cattatcgag 3540
ctggcccgcg agaagaactc caaggacgcc cagaaaatga tcaacgagat gcagaagcgg 3600
aaccggcaga ccaacgagcg gatcgaggaa atcatccgga ccaccggcaa agagaacgcc 3660
aagtacctga tcgagaagat caagctgcac gacatgcagg aaggcaagtg cctgtacagc 3720
ctggaagcca tccctctgga agatctgctg aacaacccct tcaactatga ggtggaccac 3780
atcatcccca gaagcgtgtc cttcgacaac agcttcaaca acaaggtgct cgtgaagcag 3840
gaagaagcca gcaagaaggg caaccggacc ccattccagt acctgagcag cagcgacagc 3900
aagatcagct acgaaacctt caagaagcac atcctgaatc tggccaaggg caagggcaga 3960
atcagcaaga ccaagaaaga gtatctgctg gaagaacggg acatcaacag gttctccgtg 4020
cagaaagact tcatcaaccg gaacctggtg gataccagat acgccaccag aggcctgatg 4080
aacctgctgc ggagctactt cagagtgaac aacctggacg tgaaagtgaa gtccatcaat 4140
ggcggcttca ccagctttct gcggcggaag tggaagttta agaaagagcg gaacaagggg 4200
tacaagcacc acgccgagga cgccctgatc attgccaacg ccgatttcat cttcaaagag 4260
tggaagaaac tggacaaggc caaaaaagtg atggaaaacc agatgttcga ggaaaagcag 4320
gccgagagca tgcccgagat cgaaaccgag caggagtaca aagagatctt catcaccccc 4380
caccagatca agcacattaa ggacttcaag gactacaagt acagccaccg ggtggacaag 4440
aagcctaata gagagctgat taacgacacc ctgtactcca cccggaagga cgacaagggc 4500
aacaccctga tcgtgaacaa tctgaacggc ctgtacgaca aggacaatga caagctgaaa 4560
aagctgatca acaagagccc cgaaaagctg ctgatgtacc accacgaccc ccagacctac 4620
cagaaactga agctgattat ggaacagtac ggcgacgaga agaatcccct gtacaagtac 4680
tacgaggaaa ccgggaacta cctgaccaag tactccaaaa aggacaacgg ccccgtgatc 4740

-continued

```
aagaagatta agtattacgg caacaaactg aacgcccatc tggacatcac cgacgactac  4800
cccaacagca gaaacaaggt cgtgaagctg tccctgaagc cctacagatt cgacgtgtac  4860
ctggacaatg gcgtgtacaa gttcgtgacc gtgaagaatc tggatgtgat caaaaaagaa  4920
aactactacg aagtgaatag caagtgctat gaggaagcta agaagctgaa gaagatcagc  4980
aaccaggccg agtttatcgc ctccttctac aacaacgatc tgatcaagat caacggcgag  5040
ctgtatagag tgatcggcgt gaacaacgac ctgctgaacc ggatcgaagt gaacatgatc  5100
gacatcacct accgcgagta cctggaaaac atgaacgaca agaggccccc caggatcatt  5160
aagacaatcg cctccaagac ccagagcatt aagaagtaca gcacagacat tctgggcaac  5220
ctgtatgaag tgaaatctaa gaagcaccct cagatcatca aaaagggcgc ctatccctat  5280
gacgtgcccg attatgccag cctgggcagc ggctccccca agaaaaaacg caaggtggaa  5340
gatcctaaga aaaagcggaa agtggacgtg taaccaccac actggactag tggatccgag  5400
ctcggtacca agcttaagtt taaaccgctg atcagcctcg actgtgcctt ctagttgcca  5460
gccatctgtt gtttgcccct cccccgtgcc ttccttgacc ctggaaggtg ccactcccac  5520
tgtcctttcc taataaaatg aggaaattgc atcgcattgt ctgagtaggt gtcattctat  5580
tctggggggt ggggtggggc aggacagcaa gggggaggat tgggaagaca atagcaggca  5640
tgctggggat gcggtgggct ctatggcttc tgaggcggaa agaaccagct ggggctctag  5700
ggggtatccc cacgcgccct gtagcggcgc attaagcgcg gcgggtgtgg tggttacgcg  5760
cagcgtgacc gctacacttg ccagcgccct agcgcccgct cctttcgctt tcttcccttc  5820
ctttctcgcc acgttcgccg gctttccccg tcaagctcta aatcgggggc tccctttagg  5880
gttccgattt agtgctttac ggcacctcga ccccaaaaaa cttgattagg gtgatggttc  5940
acgtagtggg ccatcgccct gatagacggt ttttcgccct ttgacgttgg agtccacgtt  6000
ctttaatagt ggactcttgt tccaaactgg aacaacactc aaccctatct cggtctattc  6060
ttttgattta taagggattt tgccgatttc ggcctattgg ttaaaaaatg agctgattta  6120
acaaaaattt aacgcgaatt aattctgtgg aatgtgtgtc agttagggtg tggaaagtcc  6180
ccaggctccc cagcaggcag aagtatgcaa agcatgcatc tcaattagtc agcaaccagg  6240
tgtggaaagt ccccaggctc cccagcaggc agaagtatgc aaagcatgca tctcaattag  6300
tcagcaacca tagtcccgcc cctaactccg cccatcccgc ccctaactcc gcccagttcc  6360
gcccattctc cgccccatgg ctgactaatt ttttttattt atgcagaggc cgaggccgcc  6420
tctgcctctg agctattcca gaagtagtga ggaggctttt ttggaggcct aggcttttgc  6480
aaaaagctcc cgggagcttg tatatccatt ttcggatctg atcaagagac aggatgagga  6540
tcgtttcgca tgattgaaca agatggattg cacgcaggtt ctccggccgc ttgggtggag  6600
aggctattcg gctatgactg ggcacaacag acaatcggct gctctgatgc cgccgtgttc  6660
cggctgtcag cgcaggggcg cccggttctt tttgtcaaga ccgacctgtc cggtgccctg  6720
aatgaactgc aggacgaggc agcgcggcta tcgtggctgg ccacgacggg cgttccttgc  6780
gcagctgtgc tcgacgttgt cactgaagcg ggaagggact ggctgctatt gggcgaagtg  6840
ccggggcagg atctcctgtc atctcacctt gctcctgccg agaaagtatc catcatggct  6900
gatgcaatgc ggcggctgca tacgcttgat ccggctacct gcccattcga ccaccaagcg  6960
aaacatcgca tcgagcgagc acgtactcgg atggaagccg gtcttgtcga tcaggatgat  7020
ctggacgaag agcatcaggg gctcgcgcca gccgaactgt tcgccaggct caaggcgcgc  7080
atgcccgacg gcgaggatct cgtcgtgacc catggcgatg cctgcttgcc gaatatcatg  7140
gtggaaaatg gccgcttttc tggattcatc gactgtggcc ggctgggtgt ggcggaccgc  7200
tatcaggaca tagcgttggc tacccgtgat attgctgaag agcttggcgg cgaatgggct  7260
gaccgcttcc tcgtgcttta cggtatcgcc gctcccgatt cgcagcgcat cgccttctat  7320
cgccttcttg acgagttctt ctgagcggga ctctggggtt cgaaatgacc gaccaagcga  7380
cgcccaacct gccatcacga gatttcgatt ccaccgccgc cttctatgaa aggttgggct  7440
tcggaatcgt tttccgggac gccggctgga tgatcctcca gcgcggggat ctcatgctgg  7500
agttcttcgc ccaccccaac ttgtttattg cagcttataa tggttacaaa taaagcaata  7560
gcatcacaaa tttcacaaat aaagcatttt tttcactgca ttctagttgt ggtttgtcca  7620
aactcatcaa tgtatcttat catgtctgta taccgtcgac ctctagctag agcttggcgt  7680
aatcatggtc atagctgttt cctgtgtgaa attgttatcc gctcacaatt ccacacaaca  7740
tacgagccgg aagcataaag tgtaaagcct ggggtgccta atgagtgagc taactcacat  7800
taattgcgtt gcgctcactg cccgctttcc agtcgggaaa cctgtcgtgc cagctgcatt  7860
aatgaatcgg ccaacgcgcg gggagaggcg gtttgcgtat tgggcgctct tccgcttcct  7920
cgctcactga ctcgctgcgc tcggtcgttc ggctgcggcg agcggtatca gctcactcaa  7980
aggcggtaat acggttatcc acagaatcag gggataacgc aggaaagaac atgtgagcaa  8040
aaggccagca aaaggccagg aaccgtaaaa aggccgcgtt gctggcgttt ttccataggc  8100
tccgcccccc tgacgagcat cacaaaaatc gacgctcaag tcagaggtgg cgaaacccga  8160
caggactata aagataccag gcgtttcccc ctggaagctc cctcgtgcgc tctcctgttc  8220
cgaccctgcc gcttaccgga tacctgtccg cctttctccc ttcgggaagc gtggcgcttt  8280
ctcatagctc acgctgtagg tatctcagtt cggtgtaggt cgttcgctcc aagctgggct  8340
gtgtgcacga accccccgtt cagcccgacc gctgcgcctt atccggtaac tatcgtcttg  8400
agtccaaccc ggtaagacac gacttatcgc cactggcagc agccactggt aacaggatta  8460
gcagagcgag gtatgtaggc ggtgctacag agttcttgaa gtggtggcct aactacggct  8520
acactagaag aacagtattt ggtatctgcg ctctgctgaa gccagttacc ttcggaaaaa  8580
gagttggtag ctcttgatcc ggcaaacaaa ccaccgctgg tagcggtttt tttgtttgca  8640
agcagcagat tacgcgcaga aaaaaaggat ctcaagaaga tcctttgatc ttttctacgg  8700
ggtctgacgc tcagtggaac gaaaactcac gttaagggat tttggtcatg agattatcaa  8760
aaaggatctt cacctagatc cttttaaatt aaaaatgaag ttttaaatca atctaaagta  8820
tatatgagta aacttggtct gacagttacc aatgcttaat cagtgaggca cctatctcag  8880
cgatctgtct atttcgttca tccatagttg cctgactccc cgtcgtgtag ataactacga  8940
tacgggaggg cttaccatct ggccccagtg ctgcaatgat accgcgagac ccacgctcac  9000
cggctccaga tttatcagca ataaaccagc cagccggaag ggccgagcgc agaagtggtc  9060
ctgcaacttt atccgcctcc atccagtcta ttaattgttg ccgggaagct agagtaagta  9120
gttcgccagt taatagtttg cgcaacgttg ttgccattgc tacaggcatc gtggtgtcac  9180
gctcgtcgtt tggtatggct tcattcagct ccggttccca acgatcaagg cgagttacat  9240
gatcccccat gttgtgcaaa aaagcggtta gctccttcgg tcctccgatc gttgtcagaa  9300
gtaagttggc cgcagtgtta tcactcatgg ttatggcagc actgcataat tctcttactg  9360
tcatgccatc cgtaagatgc ttttctgtga ctggtgagta ctcaaccaag tcattctgag  9420
aatagtgtat gcggcgaccg agttgctctt gcccggcgtc aatacgggat aataccgcgc  9480
```

```
cacatagcag aactttaaaa gtgctcatca ttggaaaacg ttcttcgggg cgaaaactct  9540
caaggatctt accgctgttg agatccagtt cgatgtaacc cactcgtgca cccaactgat  9600
cttcagcatc ttttactttc accagcgttt ctgggtgagc aaaaacagga aggcaaaatg  9660
ccgcaaaaaa gggaataagg gcgacacgga aatgttgaat actcatactc ttcctttttc  9720
aatattattg aagcatttat cagggttatt gtctcatgag cggatacata tttgaatgta  9780
tttagaaaaa taaacaaata ggggttccgc gcacatttcc ccgaaaagtg ccacctgacg  9840
tc                                                                 9842

SEQ ID NO: 49          moltype = AA  length = 4
FEATURE                Location/Qualifiers
REGION                 1..4
                       note = Description of Artificial Sequence: Syntheticpeptide
source                 1..4
                       mol_type = protein
                       organism = synthetic construct
SEQUENCE: 49
GSGS                                                               4

SEQ ID NO: 50          moltype = AA  length = 380
FEATURE                Location/Qualifiers
REGION                 1..380
                       note = Description of Artificial Sequence:
                        Syntheticpolypeptide
source                 1..380
                       mol_type = protein
                       organism = synthetic construct
SEQUENCE: 50
MLADAVSRLV LGKFGDLTDN FSSPHARRKV LAGVVMTTGT DVKDAKVISV STGTKCINGE  60
YMSDRGLALN DCHAEIISRR SLLRFLYTQL ELYLNNKDDQ KRSIFQKSER GGFRLKENVQ  120
FHLYISTSPC GDARIFSPHE PILEEPADRH PNRKARGQLR TKIESGEGTI PVRSNASIQT  180
WDGVLQGERL LTMSCSDKIA RWNVVGIQGS LLSIFVEPIY FSSIILGSLY HGDHLSRAMY  240
QRISNIEDLP PLYTLNKPLL SGISNAEARQ PGKAPNFSVN WTVGDSAIEV INATTGKDEL  300
GRASRLCKHA LYCRWMRVHG KVPSHLLRSK ITKPNVYHES KLAAKEYQAA KARLFTAFIK  360
AGLGAWVEKP TEQDQFSLTP                                              380

SEQ ID NO: 51          moltype = AA  length = 9
FEATURE                Location/Qualifiers
REGION                 1..9
                       note = Description of Artificial Sequence: Syntheticpeptide
source                 1..9
                       mol_type = protein
                       organism = synthetic construct
SEQUENCE: 51
YPYDVPDYA                                                          9

SEQ ID NO: 52          moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 52
PKKKRKV                                                            7

SEQ ID NO: 53          moltype = AA  length = 264
FEATURE                Location/Qualifiers
REGION                 1..264
                       note = Description of Artificial Sequence:
                        Syntheticpolypeptide
source                 1..264
                       mol_type = protein
                       organism = synthetic construct
SEQUENCE: 53
MIEQDGLHAG SPAAWVERLF GYDWAQQTIG CSDAAVFRLS AQGRPVLFVK TDLSGALNEL  60
QDEAARLSWL ATTGVPCAAV LDVVTEAGRD WLLLGEVPGQ DLLSSHLAPA EKVSIMADAM  120
RRLHTLDPAT CPFDHQAKHR IERARTRMEA GLVDQDDLDE EHQGLAPAEL FARLKARMPD  180
GEDLVVTHGD ACLPNIMVEN GRFSGFIDCG RLGVADRYQD IALATRDIAE ELGGEWADRF  240
LVLYGIAAPD SQRIAFYRLL DEFF                                         264

SEQ ID NO: 54          moltype = AA  length = 286
FEATURE                Location/Qualifiers
REGION                 1..286
                       note = Description of Artificial Sequence:
                        Syntheticpolypeptide
source                 1..286
                       mol_type = protein
                       organism = synthetic construct
SEQUENCE: 54
```

-continued

```
MSIQHFRVAL IPFFAAFCLP VFAHPETLVK VKDAEDQLGA RVGYIELDLN SGKILESFRP  60
EERFPMMSTF KVLLCGAVLS RIDAGQEQLG RRIHYSQNDL VEYSPVTEKH LTDGMTVREL  120
CSAAITMSDN TAANLLLTTI GGPKELTAFL HNMGDHVTRL DRWEPELNEA IPNDERDTTM  180
PVAMATTLRK LLTGELLTLA SRQQLIDWME ADKVAGPLLR SALPAGWFIA DKSGAGERGS  240
RGIIAALGPD GKPSRIVVIY TTGSQATMDE RNRQIAEIGA SLIKHW                286

SEQ ID NO: 55           moltype = AA  length = 236
FEATURE                 Location/Qualifiers
REGION                  1..236
                        note = Description of Artificial Sequence:
                         Syntheticpolypeptide
source                  1..236
                        mol_type = protein
                        organism = synthetic construct
SEQUENCE: 55
MVSKGEEDNM AIIKEFMRFK VHMEGSVNGH EFEIEGEGEG RPYEGTQTAK LKVTKGGPLP  60
FAWDILSPQF MYGSKAYVKH PADIPDYLKL SFPEGFKWER VMNFEDGGVV TVTQDSSLQD  120
GEFIYKVKLR GTNFPSDGPV MQKKTMGWEA SSERMYPEDG ALKGEIKQRL KLKDGGHYDA  180
EVKTTYKAKK PVQLPGAYNV NIKLDITSHN EDYTIVEQYE RAEGRHSTGG MDELYK      236
```